United States Patent
Yan et al.

(10) Patent No.: US 6,706,511 B2
(45) Date of Patent: Mar. 16, 2004

(54) ISOLATED HUMAN KINASE PROTEINS

(75) Inventors: Chunhua Yan, Boyds, MD (US); Zhenya Li, Boyds, MD (US); Beena Neelam, Gaithersburg, MD (US); Valentina DiFrancesco, Rockville, MD (US); Ellen M. Beasley, Darnestown, MD (US)

(73) Assignee: Applera Corporation, Norwalk, CT (US)

( * ) Notice: Subject to any disclaimer, the term of this patent is extended or adjusted under 35 U.S.C. 154(b) by 6 days.

(21) Appl. No.: 10/274,194

(22) Filed: Oct. 21, 2002

(65) Prior Publication Data

US 2003/0232408 A1 Dec. 18, 2003

Related U.S. Application Data

(62) Division of application No. 09/984,890, filed on Oct. 31, 2001, now Pat. No. 6,492,156.

(51) Int. Cl.[7] .............................. C12N 9/12; C12N 1/20; C12N 15/00; C12N 5/00; C07K 1/00
(52) U.S. Cl. .................... 435/194; 530/350; 435/320.1; 435/325; 435/252.3; 435/6
(58) Field of Search .............................. 435/194, 320.1, 435/252.3, 325, 6; 530/350

(56) References Cited

FOREIGN PATENT DOCUMENTS

WO 9613592 * 5/1996

OTHER PUBLICATIONS

Drewes et al. "Mark, a Novel Family of Proteins Kinases that Phosphorylate Microtubule–Associated Proteins and Trigger Microtubule Disruption." Cell. Apr. 18, 1997. vol. 89, pp. 297–308.
International Search report dated Jul. 11, 2003.

* cited by examiner

*Primary Examiner*—Maryam Monshipouri
(74) *Attorney, Agent, or Firm*—Celera Genomics; Justin D. Karjala

(57) ABSTRACT

The present invention provides amino acid sequences of peptides that are encoded by genes within the human genome, the kinase peptides of the present invention. The present invention specifically provides isolated peptide and nucleic acid molecules, methods of identifying orthologs and paralogs of the kinase peptides, and methods of identifying modulators of the kinase peptides.

4 Claims, 50 Drawing Sheets

```
   1 ATGTCCAGCG CTCGGACCCC CCTACCCACG CTGAACGAGA GGGACACGGA
  51 GCAGCCCACC TTGGGACACC TTGACTCCAA GCCCAGCAGT AAGTCCAACA
 101 TGATTCGGGG CCGCAACTCA GCCACCTCTG CTGATGAGCA GCCCCACATT
 151 GGAAACTACC GGCTCCTCAA GACCATTGGC AAGGGTAATT TTGCCAAGGT
 201 GAAGTTGGCC CGACACATCC TGACTGGGAA AGAGGTAGCT GTGAAGATCA
 251 TTGACAAGAC TCAACTGAAC TCCTCCAGCC TCCAGAAACT ATTCCGCGAA
 301 GTAAGAATAA TGAAGGTTTT GAATCATCCC AACATAGTTA AATTATTTGA
 351 AGTGATTGAG ACTGAGAAAA CGCTCTACCT TGTCATGGAG TACGCTAGTG
 401 GCGGAGAGGT ATTTGATTAC CTAGTGGCTC ATGGCAGGAT GAAAGAAAAA
 451 GAGGCTCGAG CCAAATTCCG CCAGGTAGTG TCTGCTGTGC AGTACTGTCA
 501 CCAGAAGTTT ATTGTCCATA GAGACTTAAA GGCAGAAAAC CTGCTCTTGG
 551 ATGCTGATAT GAACATCAAG ATTGCAGACT TTGGCTTCAG CAATGAATTC
 601 ACCTTTGGGA ACAAGCTGGA CACCTTCTGT GGCAGTCCCC CTTATGCTGC
 651 CCCAGAACTC TTCCAGGGCA AAAAATATGA TGGACCCGAG GTGGATGTGT
 701 GGAGCCTAGG AGTTATCCTC TATACACTGG TCAGCGGATC CCTGCCTTTT
 751 GATGGACAGA ACCTCAAGGA GCTGCGGGAA CGGGTACTGA GGGGAAAATA
 801 CCGTATTCCA TTCTACATGT CCACGGACTG TGAAAACCTG CTTAAGAAAT
 851 TTCTCATTCT TAATCCCAGC AAGAGAGGCA CTTTAGAGCA AATCATGAAA
 901 GATCGATGGA TGAATGTGGG TCACGAAGAT GATGAACTAA AGCCTTACGT
 951 GGAGCCACTC CCTGACTACA AGGACCCCCG GCGGACAGAG CTGATGGTGT
1001 CCATGGGTTA TACACGGGAA GAGATCCAGG ACTCGCTGGT GGGCCAGAGA
1051 TACAACGAGG TGATGGCCAC CTATCTGCTC CTGGGCTACA AGAGCTCCGA
1101 GCTGGAAGGC GACACCATCA CCCTGAAACC CCGGCCTTCA GCTGATCTGA
1151 CCAATAGCAG CGCCCCATCC CCATCCCACA AGGTACAGCG CAGCGTGTCG
1201 GCCAATCCCA GCAGCGGCG CTTCAGCGAC CAGGCTGGTC CTGCCATTCC
1251 CACCTCTAAT TCTTACTCTA AGAAGACTCA GAGTAACAAC GCAGAAAATA
1301 AGCGGCCTGA GGAGGACCGG GAGTCAGGGC GGAAAGCCAG CAGCACAGCC
1351 AAGGTGCCTG CCAGCCCCCT GCCCGGTCTG GAGAGGAAGA AGACCACCCC
1401 AACCCCCTCC ACGAACAGCG TCCTCTCCAC CAGCACAAAT CGAAGCAGGA
1451 ATTCCCCACT TTTGGAGCGG GCCAGCCTCG GCCAGGCCTC CATCCAGAAT
1501 GGCAAAGACA GCACAGCCCC CCAGCGTGTC CCTGTTGCCT CCCCATCCGC
1551 CCACAACATC AGCAGCAGTG GTGGAGCCCC AGACCGAACT AACTTCCCCC
1601 GGGGTGTGTC CAGCCGAAGC ACCTTCCATG CTGGGCAGCT CCGACAGGTG
1651 CGGGACCAGC AGAATTTGCC CTACGGTGTG ACCCCAGCCT CTCCCTCTGG
1701 CCACAGCCAG GGCCGGCGGG GGGCCTCTGG GAGCATCTTC AGCAAGTTCA
1751 CCTCCAAGTT TGTACGCAGG AACCTGAATG AACCTGAAAG CAAAGACCGA
1801 GTGGAGACGC TCAGACCTCA CGTGGTGGGC AGTGGCGGCA ACGACAAAGA
1851 AAAGGAAGAA TTTCGGGAGG CCAAGCCCCG CTCCCTCCGC TTCACGTGGA
1901 GTATGAAGAC CACGAGCTCC ATGGAGCCCA ACGAGATGAT GCGGGAGATC
1951 CGCAAGGTGC TGGACGCGAA CAGCTGCCAG AGCGAGCTGC ATGAGAAGTA
2001 CATGCTGCTG TGCATGCACG GCACGCCGGG CCACGAGGAC TTCGTGCAGT
2051 GGGAGATGGA GGTGTGCAAA CTGCCGCGGC TCTCTCTCAA CGGGGTTCGA
2101 TTTAAGCGGA TATCGGGCAC CTCCATGGCC TTCAAAAACA TTGCCTCCAA
2151 AATAGCCAAC GAGCTGAAGC TTTAA          (SEQ ID NO:1)
```

FIGURE 1A

FEATURES:
Start Codon: 1
Stop Codon: 2173

Homologous proteins:
Top 10 BLAST Hits

| | Score | E |
|---|---|---|
| CRA\|18000005076710 /altid=gi\|11067437 /def=ref\|NP_067731.1\| ser... | 1418 | 0.0 |
| CRA\|46000103792917 /altid=gi\|15042611 /def=gb\|AAK82368.1\|AF3876... | 1384 | 0.0 |
| CRA\|117000066864950 /altid=gi\|9845489 /def=ref\|NP_004945.2\| ELK... | 1379 | 0.0 |
| CRA\|18000005061736 /altid=gi\|9845487 /def=ref\|NP_059672.1\| ELKL... | 1339 | 0.0 |
| CRA\|88000001156998 /altid=gi\|7446398 /def=pir\|\|G01025 serine/th... | 1339 | 0.0 |
| CRA\|149000126080096 /altid=gi\|14250622 /def=gb\|AAH08771.1\|AAH08... | 1332 | 0.0 |
| CRA\|18000004939026 /altid=gi\|6679643 /def=ref\|NP_031954.1\| ELKL... | 1319 | 0.0 |
| CRA\|18000004906726 /altid=gi\|346945 /def=pir\|\|S31333 protein ki... | 1248 | 0.0 |
| CRA\|32000237666055 /altid=gi\|14764243 /def=ref\|XP_037764.1\| ELK... | 875 | 0.0 |
| CRA\|32000237666053 /altid=gi\|14764237 /def=ref\|XP_037763.1\| ELK... | 875 | 0.0 |

Blast hits to dbEST:

| CRA Number | gi Number | Score | | Expect |
|---|---|---|---|---|
| CRA\|56000140027815 | gi\|14649878 | 1604 bits | (809) | 0.0 |
| CRA\|113000033910976 | gi\|10216507 | 1463 bits | (738) | 0.0 |
| CRA\|160000136119317 | gi\|14173010 | 1417 bits | (715) | 0.0 |
| CRA\|113000033942433 | gi\|10219367 | 1417 bits | (715) | 0.0 |
| CRA\|107000020386558 | gi\|9343047 | 1255 bits | (633) | 0.0 |
| CRA\|158000041290072 | gi\|10994272 | 1223 bits | (617) | 0.0 |
| CRA\|11000545544945 | gi\|9155653 | 1187 bits | (599) | 0.0 |
| CRA\|225000001741704 | gi\|15755809 | 1158 bits | (584) | 0.0 |
| CRA\|160000136058139 | gi\|14169810 | 1152 bits | (581) | 0.0 |
| CRA\|1000491165793 | gi\|5452865 | 1130 bits | (570) | 0.0 |
| CRA\|11000545526171 | gi\|9153925 | 1059 bits | (534) | 0.0 |
| CRA\|78000106801247 | gi\|10390259 | 995 bits | (502) | 0.0 |
| CRA\|147000035349687 | gi\|12399257 | 979 bits | (494) | 0.0 |
| CRA\|112000056972111 | gi\|14374440 | 979 bits | (494) | 0.0 |
| CRA\|64000081152930 | gi\|15346261 | 948 bits | (478) | 0.0 |
| CRA\|11000545400890 | gi\|9142297 | 938 bits | (473) | 0.0 |
| CRA\|155000146359590 | gi\|13327757 | 922 bits | (465) | 0.0 |
| CRA\|11000545450274 | gi\|9146937 | 912 bits | (460) | 0.0 |
| CRA\|45000033524462 | gi\|8257100 | 910 bits | (459) | 0.0 |
| CRA\|47000019387182 | gi\|9775630 | 908 bits | (458) | 0.0 |
| CRA\|11000545400296 | gi\|9142242 | 890 bits | (449) | 0.0 |
| CRA\|118000028616173 | gi\|10901028 | 835 bits | (421) | 0.0 |
| CRA\|223000002472058 | gi\|15688546 | 690 bits | (348) | 0.0 |

FIGURE 1B

EXPRESSION INFORMATION FOR MODULATORY USE:
library source:

| gi Number | Organ | Tissue Type |
|---|---|---|
| gi|14649878 | brain | neuroblastoma |
| gi|10216507 | lung | small cell carcinoma |
| gi|14173010 | muscle | rhabdomyosarcoma |
| gi|10219367 | lung | small cell carcinoma |
| gi|9343047 | lymph | Burkitt lymphoma |
| gi|10994272 | (none) | ovary, tumor tissue |
| gi|9155653 | placenta | choriocarcinoma |
| gi|15755809 | pooled colon/kidney/stomach | |
| gi|14169810 | colon | adenocarcinoma cell line |
| gi|5452865 | colon | colon tumor, RER+ |
| gi|9153925 | placenta | choriocarcinoma |
| gi|10390259 | placenta | choriocarcinoma |
| gi|12399257 | placenta_normal | |
| gi|14374440 | colon | |
| gi|15346261 | pooled pancreas/spleen | |
| gi|9142297 | lymph | Burkitt lymphoma |
| gi|13327757 | kidney | renal cell adenocarcinoma |
| gi|9146937 | kidney | renal cell adenocarcinoma |
| gi|8257100 | breast_normal | |
| gi|9775630 | cervix | cervical carcinoma cell line |
| gi|9142242 | lymph | Burkitt lymphoma |
| gi|10901028 | uterus_tumor | |
| gi|15688546 | Pancreas | Purified pancreatic islet |

FIGURE 1C

```
  1 MSSARTPLPT LNERDTEQPT LGHLDSKPSS KSNMIRGRNS ATSADEQPHI
 51 GNYRLLKTIG KGNFAKVKLA RHILTGKEVA VKIIDKTQLN SSSLQKLFRE
101 VRIMKVLNHP NIVKLFEVIE TEKTLYLVME YASGGEVFDY LVAHGRMKEK
151 EARAKFRQVV SAVQYCHQKF IVHRDLKAEN LLLDADMNIK IADFGFSNEF
201 TFGNKLDTFC GSPPYAAPEL FQGKKYDGPE VDVWSLGVIL YTLVSGSLPF
251 DGQNLKELRE RVLRGKYRIP FYMSTDCENL LKKFLILNPS KRGTLEQIMK
301 DRWMNVGHED DELKPYVEPL PDYKDPRRTE LMVSMGYTRE EIQDSLVGQR
351 YNEVMATYLL LGYKSSELEG DTITLKPRPS ADLTNSSAPS PSHKVQRSVS
401 ANPKQRRFSD QAGPAIPTSN SYSKKTQSNN AENKRPEEDR ESGRKASSTA
451 KVPASPLPGL ERKKTTPTPS TNSVLSTSTN RSRNSPLLER ASLGQASIQN
501 GKDSTAPQRV PVASPSAHNI SSSGGAPDRT NFPRGVSSRS TFHAGQLRQV
551 RDQQNLPYGV TPASPSGHSQ GRRGASGSIF SKFTSKFVRR NLNEPESKDR
601 VETLRPHVVG SGGNDKEKEE FREAKPRSLR FTWSMKTTSS MEPNEMMREI
651 RKVLDANSCQ SELHEKYMLL CMHGTPGHED FVQWEMEVCK LPRLSLNGVR
701 FKRISGTSMA FKNIASKIAN ELKL   (SEQ ID NO:2)
```

FEATURES:
Functional domains and key regions:
Prosite results:
PDOC00001 PS00001 ASN_GLYCOSYLATION
N-glycosylation site
Number of matches: 4

| | | |
|---|---|---|
| 1 | 90-93 | NSSS |
| 2 | 385-388 | NSSA |
| 3 | 480-483 | NRSR |
| 4 | 519-522 | NISS |

PDOC00004 PS00004 CAMP_PHOSPHO_SITE
cAMP- and cGMP-dependent protein kinase phosphorylation site
Number of matches: 5

| | | |
|---|---|---|
| 1 | 291-294 | KRGT |
| 2 | 406-409 | RRFS |
| 3 | 444-447 | RKAS |
| 4 | 462-465 | RKKT |
| 5 | 702-705 | KRIS |

PDOC00005 PS00005 PKC_PHOSPHO_SITE
Protein kinase C phosphorylation site
Number of matches: 16

| | | |
|---|---|---|
| 1 | 3-5 | SAR |
| 2 | 29-31 | SSK |
| 3 | 75-77 | TGK |
| 4 | 121-123 | TEK |
| 5 | 290-292 | SKR |
| 6 | 374-376 | TLK |
| 7 | 392-394 | SHK |

FIGURE 2A

|   |         |     |
|---|---------|-----|
| 8  | 423-425 | SKK |
| 9  | 442-444 | SGR |
| 10 | 449-451 | TAK |
| 11 | 479-481 | TNR |
| 12 | 537-539 | SSR |
| 13 | 584-586 | TSK |
| 14 | 603-605 | TLR |
| 15 | 628-630 | SLR |
| 16 | 634-636 | SMK |

PDOC00006 PS00006 CK2_PHOSPHO_SITE
Casein kinase II phosphorylation site
Number of matches: 8

|   |         |      |
|---|---------|------|
| 1 | 10-13   | TLNE |
| 2 | 42-45   | TSAD |
| 3 | 75-78   | TGKE |
| 4 | 133-136 | SGGE |
| 5 | 275-278 | TDCE |
| 6 | 338-341 | TREE |
| 7 | 366-369 | SELE |
| 8 | 639-642 | SSME |

PDOC00008 PS00008 MYRISTYL
N-myristoylation site
Number of matches: 5

|   |         |       |
|---|---------|-------|
| 1 | 348-353 | GQRYNE |
| 2 | 559-564 | GVTPAS |
| 3 | 574-579 | GASGSI |
| 4 | 610-615 | GSGGND |
| 5 | 706-711 | GTSMAF |

PDOC00009 PS00009 AMIDATION
Amidation site
Number of matches: 3

|   |         |      |
|---|---------|------|
| 1 | 222-225 | QGKK |
| 2 | 442-445 | SGRK |
| 3 | 570-573 | QGRR |

PDOC00100 PS00107 PROTEIN_KINASE_ATP
Protein kinases ATP-binding region signature
         59-82         IGKGNFAKVKLARHILTGKEVAVK

FIGURE 2B

PDOC00100 PS00108 PROTEIN_KINASE_ST
Serine/Threonine protein kinases active-site signature
    171-183     IVHRDLKAENLLL Membrane spanning structure and domains:
  Helix Begin   End   Score Certainty
    1    231    251   1.431 Certain BLAST Alignment to Top Hit:
>CRA|18000005076710 /altid=gi|11067437 /def=ref|NP_067731.1|
          serine/threonine kinase [Rattus norvegicus] /org=Rattus
          norvegicus /taxon=10116 /dataset=nraa /length=722
          Length = 722

Score = 1418 bits (3629), Expect = 0.0
 Identities = 706/724 (97%), Positives = 715/724 (98%), Gaps = 2/724 (0%)
 Frame = +3

Query: 396   MSSARTPLPTLNERDTEQPTLGHLDSKPSSKSNMIRGRNSATSADEQPHIGNYRLLKTIG 575
             MSSARTPLPTLNERDTEQPTLGHLDSKPSSKSNM+RGRNSATSADEQPHIGNYRLLKTIG
Sbjct: 1     MSSARTPLPTLNERDTEQPTLGHLDSKPSSKSNMLRGRNSATSADEQPHIGNYRLLKTIG 60

Query: 576   KGNFAKVKLARHILTGKEVAVKIIDKTQLNSSSLQKLFREVRIMKVLNHPNIVKLFEVIE 749
             KGNFAKVKLARHILTGKEVAVKIIDKTQLNSSSLQKLFREVRIMKVLNHPNIVKLFEVIE
Sbjct: 61    KGNFAKVKLARHILTGKEVAVKIIDKTQLNSSSLQKLFREVRIMKVLNHPNIVKLFEVIE 120

Query: 750   TEKTLYLVMEYASGGEVFDYLVAHGRMKEKEARAKFRQVVSAVQYCHQKFIVHRDLKAEN 929
             TEKTLYLVMEYASGGEVFDYLVAHGRMKEKEARAKFRQ+VSAVQYCHQKFIVHRDLKAEN
Sbjct: 121   TEKTLYLVMEYASGGEVFDYLVAHGRMKEKEARAKFRQIVSAVQYCHQKFIVHRDLKAEN 180

Query: 930   LLLDADMNIKIADFGFSNEFTFGNKLDTFCGSPPYAAPELFQGKKYDGPEVDVWSLGVIL 1109
             LLLDADMNIKIADFGFSNEFTFGNKLDTFCGSPPYAAPELFQGKKYDGPEVDVWSLGVIL
Sbjct: 181   LLLDADMNIKIADFGFSNEFTFGNKLDTFCGSPPYAAPELFQGKKYDGPEVDVWSLGVIL 240

Query: 1110  YTLVSGSLPFDGQNLKELRERVLRGKYRIPFYMSTDCENLLKKFLILNPSKRGTLEQIMK 1289
             YTLVSGSLPFDGQNLKELRERVLRGKYRIPFYMSTDCENLLKKFLILNPSKRGTLEQIMK
Sbjct: 241   YTLVSGSLPFDGQNLKELRERVLRGKYRIPFYMSTDCENLLKKFLILNPSKRGTLEQIMK 300

Query: 1290  DRWMNVGHEDDELKPYVEPLPDYKDPRRTELMVSMGYTREEIQDSLVGQRYNEVMATYLL 1469
             DRWMNVGHEDDELKPYVEPLPDYKDPRRTELMVSMGYTREEIQDSLVGQRYNEVMATYLL
Sbjct: 301   DRWMNVGHEDDELKPYVEPLPDYKDPRRTELMVSMGYTREEIQDSLVGQRYNEVMATYLL 360

FIGURE 2C

```
Query: 1470 LGYKSSELEGDTITLKPRPSADLTNSSAPSPSHKVQRSVSANPKQRRFSDQAGPAIPTSN 1649
             LGYKSSELEGDTITLKPRPSADLTNSSAPSPSHKVQRSVSANPKQRR SDQA PAIPTSN
Sbjct:  361 LGYKSSELEGDTITLKPRPSADLTNSSAPSPSHKVQRSVSANPKQRRSSDQAVPAIPTSN 420

Query: 1650 SYSKKTQSNNAENKRPEEDRESGRKASSTAKVPASPLPGLERKKTTPTPSTNSVLSTSTN 1829
             SYSKKTQSNNAENKRPEE  E+GRKASSTAKVPASPLPGL+RKKTTPTPSTNSVLSTSTN
Sbjct:  421 SYSKKTQSNNAENKRPEE--ETGRKASSTAKVPASPLPGLDRKKTTPTPSTNSVLSTSTN 478

Query: 1830 RSRNSPLLERASLGQASIQNGKDSTAPQRVPVASPSAHNISSSGGAPDRTNFPRGVSSRS 2009
             RSRNSPLL+RASLGQASIQNGKDSTAPQRVPVASPSAHNISSS GAPDRTNFPRGVSSRS
Sbjct:  479 RSRNSPLLDRASLGQASIQNGKDSTAPQRVPVASPSAHNISSSSGAPDRTNFPRGVSSRS 538

Query: 2010 TFHAGQLRQVRDQQNLPYGVTPASPSGHSQGRRGASGSIFSKFTSKFVRRNLNEPESKDR 2189
             TFHAGQLRQVRDQQNLP+GVTPASPSGHSQGRRGASGSIFSKFTSKFVRRNLNEPESKDR
Sbjct:  539 TFHAGQLRQVRDQQNLPFGVTPASPSGHSQGRRGASGSIFSKFTSKFVRRNLNEPESKDR 598

Query: 2190 VETLRPHVVGSGGNDKEKEEFREAKPRSLRFTWSMKTTSSMEPNEMMREIRKVLDANSCQ 2369
             VETLRPHVVG GG DKEKEEFREAKPRSLRFTWSMKTTSSMEPNEMMREIRKVLDANSCQ
Sbjct:  599 VETLRPHVVGGGGTDKEKEEFREAKPRSLRFTWSMKTTSSMEPNEMMREIRKVLDANSCQ 658

Query: 2370 SELHEKYMLLCMHGTPGHEDFVQWEMEVCKLPRLSLNGVRFKRISGTSMAFKNIASKIAN 2549
             SELHE+YMLLC+HGTPGHE+FVQWEMEVCKLPRLSLNGVRFKRISGTSMAFKNIASKIAN
Sbjct:  659 SELHERYMLLCVHGTPGHENFVQWEMEVCKLPRLSLNGVRFKRISGTSMAFKNIASKIAN 718

Query: 2550 ELKL 2561
             ELKL
Sbjct:  719 ELKL 722   (SEQ ID NO:4)
```

Hmmer search results (Pfam):
Scores for sequence family classification (score includes all domains):

| Model | Description | Score | E-value | N |
|---|---|---|---|---|
| PF00069 | Eukaryotic protein kinase domain | 346.8 | 2.3e-100 | 1 |
| CE00022 | CE00022 MAGUK_subfamily_d | 59.5 | 1.8e-17 | 3 |
| CE00359 | E00359 bone_morphogenetic_protein_receptor | 19.6 | 7.5e-05 | 2 |
| CE00334 | E00334 urotrophin_receptor | 12.7 | 0.00057 | 2 |
| PF00627 | UBA domain | 12.5 | 0.096 | 1 |
| CE00031 | CE00031 VEGFR | 4.0 | 0.25 | 1 |
| CE00203 | CE00203 ERBB_RECEPTOR | 3.0 | 1.7 | 1 |
| CE00287 | CE00287 PTK_Eph_orphan_receptor | -16.2 | 3.4e-07 | 1 |
| CE00292 | CE00292 PTK_membrane_span | -21.5 | 6.9e-08 | 1 |
| CE00291 | CE00291 PTK_fgf_receptor | -35.7 | 1.2e-06 | 1 |
| CE00290 | CE00290 PTK_Trk_family | -65.9 | 5.2e-11 | 1 |
| CE00289 | CE00289 PTK_PDGF_receptor | -68.0 | 0.4 | 1 |
| CE00286 | E00286 PTK_EGF_receptor | -75.9 | 1.8e-06 | 1 |
| CE00016 | CE00016 GSK_glycogen_synthase_kinase | -179.5 | 1e-06 | 1 |

FIGURE 2D

CE00288  CE00288  PTK_Insulin_receptor                    -208.8      0.01    1

Parsed for domains:

| Model | Domain | seq-f | seq-t | hmm-f | hmm-t | score | E-value |
|---|---|---|---|---|---|---|---|
| CE00022 | 1/3 | 59 | 131 .. | 23 | 98 .. | 10.3 | 0.0061 |
| CE00359 | 1/2 | 54 | 141 .. | 142 | 233 .. | 5.7 | 0.64 |
| CE00289 | 1/1 | 52 | 155 .. | 1 | 109 [] | -68.0 | 0.4 |
| CE00022 | 2/3 | 157 | 183 .. | 128 | 154 .. | 14.5 | 0.00034 |
| CE00031 | 1/1 | 172 | 195 .. | 1068 | 1091 .. | 4.0 | 0.25 |
| CE00203 | 1/1 | 171 | 195 .. | 861 | 885 .. | 3.0 | 1.7 |
| CE00334 | 1/2 | 172 | 197 .. | 678 | 703 .. | 11.1 | 0.0018 |
| CE00359 | 2/2 | 171 | 201 .. | 272 | 302 .. | 14.5 | 0.002 |
| CE00334 | 2/2 | 230 | 240 .. | 738 | 748 .. | -0.3 | 7 |
| CE00288 | 1/1 | 55 | 281 .. | 1 | 269 [] | -208.8 | 0.01 |
| CE00022 | 3/3 | 211 | 292 .. | 188 | 271 .. | 34.3 | 4.9e-10 |
| CE00290 | 1/1 | 54 | 302 .. | 1 | 282 [] | -65.9 | 5.2e-11 |
| CE00291 | 1/1 | 53 | 302 .. | 1 | 285 [] | -35.7 | 1.2e-06 |
| CE00286 | 1/1 | 53 | 302 .. | 1 | 263 [] | -75.9 | 1.8e-06 |
| CE00292 | 1/1 | 53 | 302 .. | 1 | 288 [] | -21.5 | 6.9e-08 |
| CE00287 | 1/1 | 53 | 302 .. | 1 | 260 [] | -16.2 | 3.4e-07 |
| PF00069 | 1/1 | 53 | 304 .. | 1 | 278 [] | 346.8 | 2.3e-100 |
| PF00627 | 1/1 | 332 | 362 .. | 9 | 41 .] | 12.5 | 0.096 |
| CE00016 | 1/1 | 2 | 412 .. | 1 | 433 [] | -179.5 | 1e-06 |

FIGURE 2E

```
   1 TCTAGGCGGG GAGACAAGCT CAGCAGCCTT GTGCAAAGCT AGCAAGGAAG
  51 AGAAAGGATA GGTAGGGTAG GGGTTGGGGA TGAAGGTCAA AGGGCAGGGG
 101 TGAGGCAGGG GTTAGAGCTA GAGTGAGAAG CTTGGAGAAG ATGGAGTCTA
 151 TTTAGACGAG AGTGTGGACC AGGGAGAGAC TGCTGGAACA CCAACCACCA
 201 ACTGCTTCCT CTCTCTTTTC CCTGCTTTCC AGACCCTGGC ATTAGAGGTG
 251 ATACCAGGCA CAGGAATCAG CAACGTGTCT CCCTTTGGCC ACCAGAGGGC
 301 AGATGATTCT CAAGGATCGA ATTTGGGTTG GGGAGTGAGG TGTTCTCTGT
 351 CCTCCTCTTC TCTCTTTCCC TCACCTTCAT GGGTGTGCCT TCACCTTCTT
 401 CCTCAACGGT TGGGTGCCTG AATAGAGCTG GTATGGGGCA TGGGGAGCAG
 451 TGCTGAAGTC CCAGGATTTA CTAAGAGTGT AGTGATACCT GTTGCCTTAG
 501 GAAGTACTTT CATACCCTGG TAATTACATC TGCTCAGATG CCTATTTCTC
 551 TGATTGATGG GATGAAGGCT GGCTCAAGAT GCTGTAGCTG GGAGTTGGAG
 601 GTCAAGTAGC AGGGGTCCAA TCAGCAGTTT TCCCAATAAC TCCTGGAGCC
 651 TCTCTGCTCC TGTACCTTTG GAACCTGTT GCCTGAGTCT GGTTTCTGAC
 701 TCCTGCGGGG CCTCTGCCTC CTGCCCACCT TAAGCCACTG ATGGGAGGGT
 751 GTGGTTCCAA CGTGTTCCAG GTACTATGGG TGAGGACAGC TTGGCGCTGG
 801 GGAAATCAGC CCAGGATACT CCCTGTCCTT GGTAACGCAG TGTAAGGGGA
 851 AGTGAGGAAT GGACTGCAGT TGCCATACAG ACTTCCTGTT AGTCAAGGGC
 901 TCTCCAAAGC TGAGAAGGAC CTCCGAGTTC ATGAATCCAA TGGCTTCACT
 951 TTACTGATGG GGAAAATGAG GCCCAGAGGA GGAAAGAAAA GAAACTTTAA
1001 ATGCCTTATC TTGCAGAGGC ATTTTAAAAG GTAACTGGAA TTCAGAAATG
1051 TCATTTTGAA TGTCAACGCA GGAGCAAAGG CAAAGGAAAG AGGAGCCTAA
1101 ACTCAGTGAT GTTATGTGAT TTTTCCAAGA TCACGCAGCA TTGGCACTTG
1151 GCAGAGCTGG GGCTGAAATG CAGGGCCCTG ACGCTCCCG CATCCGGTGC
1201 AGAGGACGCT GCCCTGGGCC TGCCTGGGGC CTTGCCGAGC CCTGCGGACT
1251 AGATGCGGGA ATGCACGGAT GAATCCACAG AAGCCAAGAT AGACGGTGGC
1301 AGACAGGCAA TAGACTGATG CTGCATTTGA CAGGTATATT GATAGGCTAG
1351 ATGATAAAAA GAAGATGAAT TTTATGAGCT GACCGACAGA TGGACAGAAA
1401 TGCAGACAGG AAGCTGCTAT AGAACCAGAG GATGCCAATC ACAGGGACGG
1451 CTAACAATCT TGTTTTGTAT TTAGTCAAAT CACAAGCACA GACAGGTGAC
1501 CCACGCTTCC TGTTCAAGGT TTGAAAATGC CCGAAAACTG ACGGAAAGAC
1551 ACGAAGCGAA TCAGACTCCG AGAGCCACCC GGGGAAACGA CCGGGTGCTC
1601 GGAGGGCCTC GGGTGTTGCC GGAAATGGCC GACGACCGCC CTCGGCAGGG
1651 CTGTGGGAGG GGGCGTGGCC GGCTCAGCAC GCGGAGCAGC TTCGGGTATT
1701 TCCGGAAACT GCCGAAAGCC CCCTTGAAGT GGGCGGGGAA AGGCCGGTGG
1751 GCGTGGCTGG ATGGCCGTGG ACGGGGGCGG GGGTAGGCA CCCGGGGTCG
1801 CTTCGTGGAT TTCCGTAAAC AGAGCCGAAG CTTCGTCTTC GGAATCGAGG
1851 AGGAGAGCGC GTCCCCGGGG TTTACCTTCT TCGGCTGTTT CCGGAATTCA
1901 CCCGTAGTCT GTGGCCGGGA GGAGAAGGCG CGCCCCACCT CCCGTTTCTA
1951 GCCGCTTCGG ATGTTTCCGG CTGCTGCCGG CGAAAAGAGC CGAGGGCCGG
2001 CGGTGGTGGC GGCCATGTTG GGAGCAGCAG GTCCGGCGGC GGCTGCCTGT
2051 GTGCCGGGCG CGGAGCAGTG CCGCTGAGGG CAGGGAGGA GCGAGGCAGG
2101 CGGCCGGCTG CGGCGGCAGA GAGTAGGCGG AGCGGCGCGG CCCGGCCGAA
2151 AGGCGGCACA GCCCAGCCGG GGGTCGGGGG GGTGCGGTCC GGAGCCGCTC
2201 GGAGCCGGCG CGGCCTAGCC CGAGCGGCGC ATCCCCGGGC TGGCGTGAGC
2251 GGCTGCCCGG CCTCCCCGCA CCCCCGGCCG GGGCCCATGC GGCGGGTGCT
```

FIGURE 3A-1

```
2301 CCTGCTGTGA GAAGCCCCGC CCGGCCGGGC TCCGCGCCTT CCCTTCCCTC
2351 CCTTCCTCCA AGCTTCTCGG TTCCCTCCCC CGAGATACCG GCGCCATGTC
2401 CAGCGCTCGG ACCCCCCTAC CCACGCTGAA CGAGAGGGAC ACGGAGCAGG
2451 TAAGGAGCCC CGAGGGCTCC CCGAATTCTC TGGCTGGGCC CTTTGCACCT
2501 TGCGGAGCCT CCTCCCTCTT CTGCTCTCCT CGTGCCCCTG CTGCCATCCT
2551 GCAAGCCTCG GCTGCCCTGT CATCCGGCTC CTGGCTCCGG CTCCGCACAT
2601 CCCGCTTCCG AGTCCTGACC TGGGACCCAC CTCGTCCTGA CTCCAAGCTG
2651 CACACTTGTC TTTCTGCCAA CCCCCGTCTC CCCTCACCGC CCTCCTGCGC
2701 TCTTCCGTGT CACCCTCCCCA GCTTCCCTTT CTCTTCCCTT TTTCTCTCAG
2751 GGGCCTTTCT GGTCTTCCTC CACCCACGCT TAAAGCAGCC ACCCTCCCGC
2801 TCCTCGAATA GCAGCACCCC GCGATTTGCC ACAGATCGTT GTCCACCTCT
2851 CCCTTCGTCT CTCCTGCCTC GCTTCCCCTC CGCCCGCACC GGTTCTGCCA
2901 GTCTCTGGGT TATCACCCTC AGGGTCCTTG CCCTGGACTG CGCTCTCGAT
2951 CCCTGGCCCC TTGCAGTTCC CCCAGCTTTT TCTACCCTGC TTCTTCGTTT
3001 TCCAAATTGT GCTCTCCCTC TTGCTTGCAA CCCACCAGCT CCACCCTCAT
3051 CACCTTTCCA AATCCTTCGC CTACTCTTTG CTCATCACTT TCCCTTCTTT
3101 GCTCCAGGAG CTCCCTGGAT CCTGGCGCTG GCATTTGTCG CTTCCGTGTT
3151 TCCCCACAGC TGTCATGCGC ATAGTTTTCC CACAGGTTGC GTTTGGGGTT
3201 CCAATCATCA CTCCCTTCAG AGTCTTTGGA TCCCTCTTGT TCTCTTCCCC
3251 TCGGGTTTGG CTTTTAGGTC CCTGGGCCTC TTGTTTCTCT CTGTGAGTGT
3301 TCTACCAGCC TTCTACTGGG CTCTTTCTCC CAACCCAAAG ACACTTGGCC
3351 CCACCGTATT AACACAACCT GTTGCTCAGT CCTTTCCCAG ACCTCGCTGC
3401 ATCACAGTTT TTGCCTTTCT GTCTTCGTAC GCTGGAACAC AAACCATGAT
3451 GACTTTCTGT GTCTTCACTC CCGTGCCTGG CACTTAGAGT ATTTTCTTTC
3501 TTGCTTGTTG CCTTCCTGTT TCTCCACCCT CACCCCATCT TCCTTACTGT
3551 GCCTTTTAAT CAGCGTTGCC TTTCATCTCC GCATTAGTCT CCTGCCTTCT
3601 TCATGTCCTG TGTATCCCCA CACCGTGCTT GGATCCATTC TGTTCCTATT
3651 GGCTAAGTCT CTGTAATGCC CAGGAAGTCC AGGTGTTTTG CATGCTAGTT
3701 TCTTGAGCTA CACCTCAGCC TCACGACTCT ACACGGTCCC CCTCATCCTG
3751 GCAGTCACTG CTATGTTTTT CACCCAAGTC TTAGCCTTTC TGTGTCATCT
3801 CACTTTTGAT CCCAGAGACG TCCACTTTCC ACACCTCCCC TTTATTTCAC
3851 CATCTCTAGC GTCCTTTGCT GACTGCTCTG TGCAGAGTCC CCTGCCTGTC
3901 ATACCTTTCT TGGTGGAGAA CTTTACTAGG CCAAAAAAAC TTGACTTGAA
3951 AAAGAAGTGC TTCTGCCCCG GGGCTGCTGT GCTTTTTGCC TTCTTTCCCC
4001 TCCTTCCATC CTTTATGTTT CCCTCTTACT CCCTTCTTTC TTTGTAGCCC
4051 GGTAGAGCAG TTGTTGTATT CTCTTGCATG TGAACATTCT TCTTTGAAAA
4101 ATCTTACCTC CTTTCTTTTA CTGTGTTTTT CTATTTTGTT ACCCCCTGGC
4151 CCTCTGTCAC CTGGGCAGTT AGGAACTAAA GAGAAGTTCT AGGCAGAGTT
4201 TTTCTCTGCA GGGTTGACCC TTTTATTACT TGTGGATTAT TTGCTTCTGG
4251 GGGTGAAATA GGGGTTGAGA GGGAGGGATG GTTGATTTCC ATTTCATCAC
4301 TGGGTTTGGC AGCTGGTTCT GCATGGGACA GGGGTCTTTG GAGACAGAGG
4351 AGCATGTTCT GTGTCTCGCA GTCTTTCTCT CCCTTGCCTA CCGGCTGTTT
4401 CTCTCTCCTT ACTGGGAATT GCTTTCTCTG GGCCCTCTTG AGGTTGCTTA
4451 TTCCACCCAT TTTCCTCTCA CAACCTTTGT TTTAGCAGGT AAACCCTGCT
4501 TAACCAGAGA ACTTTCCCAG ACTGTTGATC GTGAGCTGGT AGGAGGAGGC
4551 CAAGTGACTG ACTGGCACCC TCAGGCATTT GGGGAGTGGC GATGGAGTGC
```

FIGURE 3A-2

```
4601 CTACTCTCAG TGAGGCTGGT GGGGGGCATT GTGTTCAGCA GAGCAGAGTA
4651 ACAGACTGCC TCAGTGTGGT TTCTTTGTGC TGCTTACTAC ATGTAAATGT
4701 ATTATTGCCA TGGTATTTTT CCTGTGATGT GTGTGTTGAT TTCCTTTCTT
4751 CCTTACATGC CTAGCATACT GCTGAGCATA TAGTAGGAAT TCCACCGTAG
4801 TGTGCATCCA CTGATTCCAT GATAGCAGCA ATCAGTGACC ATTTGGGAAT
4851 GTAAGTAAGC TCTTTGCTCT TTGATAACTT TGCCCAGAGC AGTAGCTGCA
4901 TACATTGTCA TCCTGTTAGG ATTATTAATT ACCCATCCTA TTTCTACTCT
4951 TTATGGACTT AGATTCTCCT TAGCCCCTTC ATACCTTCTA CTGTTGTTCT
5001 CAGGGTAGCC AGTCACTGTA TCGATTTAAT ATTAAGTCTC ATTCCAGTAA
5051 AAGCAGGGAC TTTGGAAAAC CTTGGATGCA CCTATTCCAG ACAGATTCCT
5101 GTATTCTTTT TTTTTTTTTT TTTTGAGATA GAGTCTCGTT CTGTCGCCAG
5151 GCTGGAGTGC AGTGGCACAA TCTTGGCTCA CTGCAATCTC CGCCTCCTGG
5201 GTTCAAGCGA TTCCCCTGCC TCAGCCTCCT GAGTAGCTGG GACTACAGGC
5251 ACACACCGCC ACGCCCGGCT AATTTTTTGG ATTTTAGTAG AGACAGCGTT
5301 TCACCATGTT GTCCAGGATG GTCTCAGTCT CCTGTCCTCG TGATCCGGCC
5351 TCCCAAAGTG CTGGGATTAC AGGTGTGAGC CACTGCGCCG GCCTGATTC
5401 CTGTATTCTT TAAAACGGGA AAAAAGACAA GCAGCAGCTC CTCAGGTCAC
5451 AAGGCCAGGT ATATCAAACA CTGGCCTCCG AGAATAGATC ATGCCACCAA
5501 GTGAAAGAAA CCTCTTCTTG GTCCTGTTGT GATTTTAGAT AAAGTAGTCA
5551 TGGAAGCTTG GTCATTACTA TAGTCTTAAT GTTATTTTTT TTAAAAAGGG
5601 GATTTAGTTG GGCTGATTTC CTCCCCTAAA GGTCCTCTGT CACCTTATTT
5651 AAATTTAAAA CTGGTTTTAC CAGAAAATAG GTAAACAAAC ACCACTGGTT
5701 GTCTCCAGTC TCTTTTCTTG CTCTTCCTCT CCCTCTTCTT TAAAAATGTG
5751 GCTGATGAGA ACCTGTTTCC AGGAGCCCTT TAATCACTCT GAAACACACA
5801 GACACTGAAA ATGTTGAAGC ATAAAAATAA ACCTTGCGTT ACAGGGAGAT
5851 TGCCTGTGTG CTGTCCACTT CGCTTATAAC AGTGAAAGTA GGAGATTAAA
5901 AAAAAAAAAA AGTTAAGCCC TGTCTTTAAG ATGGTTTTTG TGACACCTGA
5951 TTCCAGATGT GCTTTTTCAC AGCCATAGAC TTCCTGCTTT TGCAGAAGGA
6001 GGGTTCTAAT CTGGGGCTCG TAGCTTGGGG GATTCTTAGT TTGTGAGCTG
6051 AGCTTTTTGT TCACTTCTTT TCCAAATGAC TCTGCTGGCC TGAAGCTTGG
6101 CAGTTGTGAA AGCAATCAGC AAGATGACTG TTTGTCTTCC AGCCAGCAGC
6151 AGCAGTCACA GGCAAGCCTG GAGAAAGGTC CAGCTTCCAG AGTTCACCTG
6201 CTAGAGTTTT CCATAACACC TGGGGGAGAG GCTACTCCAT CTGGGACCTG
6251 CCCCACCTCT GGGCCTCAGA AACTATGAGA GAGGGATTGA GAGAAAACTT
6301 GCCCCACTTC TGCTGCAGTG GGAAGGGAGG GGGCTGCTGT CAGGCTTCTA
6351 GGCAGTGAGC GGCATTGTTT ATTCTCTCAG TTCTAGGAAG GGGAGTTTAG
6401 AAGTACTGGT GAAGAAAACA AAGTTACAAG ATCCTATAAG GAACAGCTGA
6451 ACTACTCCAA ACACTCTCAC TGGACCCCCA TTGTTGATTC TGGATAAAAA
6501 TATATATATA TATAAAACTC TTTTTTTTTT TGACACAGAG TCTTGCTCTG
6551 TCGCCCAGGC TGGAGTGTAG CGATGCGATC TCGGCTCACT GCAACCTCCG
6601 CCTCCCGGGT CAAGCGATTC TCCTGCCTCA GCCTCCTGGG AGTAGCTGGG
6651 ACTACAGGCG CCCACCACCA TGCTGGCTAA TTTTTGTATT TTTAGTAGAG
6701 ACGGGGTTTT GCCATATTGG CCAAGCTGGT CTCGATCTCC TGACCTCAGG
6751 TGATCTGCTG GATAAATATT TTTTTTTTGC TTTTGGTGTA ACTTAGGTAG
6801 ATTGGATCGG CTAGCTAGCA TCTCAGTCCA CACTCTGAGC TGTGCAGCAG
6851 TGTGCCCTGG TGCTAATTCT CACTCTGTCC TTTGATTCTG GCCAGGGGGT
```

FIGURE 3A-3

```
6901 CCTTGGTGGT GCTGCCTTCT GGTCAGGAAT GTGGGTGAAT GTCAGACCAA
6951 ATAGTGTCAC TTTCGGCTTG GCCCTAGAGA TCAGGAAGGA AGTGTTGTTA
7001 GAGCAAGGGC TTTGGGAGTC CTTGGAGTTC GTAACCTTTG AATCTGAAAA
7051 GTAACTGTAC CTAGTAAATT AGAATAATTT CTCTCTGGTC AGGCACCATG
7101 GCTCATGCCT GTAGTCCTAG CACTTTGGGA AGCCAAGGCA GGAGGATTGC
7151 TTGAGGCCAG GAGTTCAAGA CCAGCCTGAT CAATAAAGTG AGACTCCATC
7201 TCTACAAAAA AATTTTTTTA AATTTAGCTG GGCATGGTGG CACATGCCTG
7251 TGGTTGCAGC TACACAGAAG GCTGAGGCAG GAGGATGGCT TGAGCTGGGG
7301 AGGTCGAGAC TGCATTGAGC TGTGTTTGTG CCACTGCACT TCAGCCTGGG
7351 TGACAGAGCA AGACACTATC TCAGAAAAAA AAAATTACTT TTCTCCAATT
7401 TATGGACTTC GGAAAGTAGC TAAACAGATG GATATAAGAC AGTTGTTGAA
7451 ACTCGGCCTG CTGCAGATTA AAATAAAGTT TGCACAAGGA TAACTTAATC
7501 TTTCAGACCA ACCAAAGTTT GGGCTGGAGA TTTTTCTCAG CATAAATGTC
7551 CTAAGCAGAG TTGGTGCCTA TGAGGTAGGA AAAGATTGAG ACTTTGCTTG
7601 CCTAAGAGGT TTGCAGGGTT CGAGCTTTTG GGAGTCAGAA CTTCTCAGAC
7651 TAGATTGTTT CCCCTTTGGA CAGAACAACC CAATTCTCAG TGGGCATTTG
7701 ATCAGGACTA ACCCAGGCCT TCATGAACTC TTTCCCATTG AGCACTTAGC
7751 CACCTGGCTG GCATTTCTCT TCTCCCAGGA GCTTCCATGA GGTTCCTACT
7801 TATGTATTAT GTCGACTTGA ATGAATATTT TATGTCTAGA GTGCAGCCAA
7851 GCCTCAGACT TTGTGGCCCA TTATCGACAA ATGGGGTAGG GGGTGGGCGC
7901 CACCTTTGGC CCCGTGATAG CTTCTCTGCT AAATGGACTC CCCCCAGCAG
7951 CACTTTGAAG CCCATTAATG GATTGGAATG AAGTAACCTC AGCAGATGGA
8001 AAGGGTGAGG AGGGTGGTCA TCTTCCTTCC CTGAGACTGC CTGATGAGGC
8051 TTTCCTACAG TAACCAGGAC AAGCCCCTAT TCCCTCTGCT TGGTTAAGCT
8101 GTGGACTGGA GCTACTAGGC CTCTGCTTTG AGAGGAAGTA TAGAAAGGAT
8151 TTGATTCTCT TTTAGCCATG GTGGGGCCGC CAGTTTCCCC ACTTTCCCAT
8201 CAAAGCAAAA ATTGAGAAGG ATGTGGAAAG GGTGGGTGGA GTTTAAAGCT
8251 GGCCCTTCCT CCTTCAGTGG AAGTTCAGCA AAATGACAAA CCAGATAGGT
8301 GGCTAAATTT CCTTCTCTTG ATGGGAGATT CCAGTATTTG TACGTTTTGT
8351 GCTTGTAGCT TGGATTCTCC AGGCCTCCTC CCAGCTTTCA TCAAACATGA
8401 GTGAGTCACT GAAGTGTTGT CTATGCATTT TCTCCCTTCT GTCTCTGCAA
8451 AGGGAAGAGT AAGCCTTTAC AAACCTGTGG GGGAGGAAGT CACCCTCTTC
8501 CCACTGCTGG AGAGCCAGGC TATCCCCAGG TTAACCCTGA AAGTGCTAAC
8551 TCCTGAGCAG AATGTTACTG CCACCCGCCC CCTTCCTTTT TGTTATAGGC
8601 CATTGAAGGT CATTGCTCGT CTTTTTTTTT GAGACAGTCT TGCTCTGGTC
8651 ACCCAGGCTG GAGTGCAGTG GCAGGATCTC AGCTCACTGC AACCTCCACC
8701 TACTGGGTTC AAGCGATTCT CATGCCTCAG TCTTCCAAAT AACCAGGATT
8751 ACAGGTGCGC ACCTCCATGC CTGGCACTT TTTGTATTTT TAGTAGAGAT
8801 AGGGTTTCAC CATGTTGGCC AGGCTGGTCT TGAACTCCTG GACTCAAGTG
8851 ATCCGCCTGC CGTGGCCTCT CAAAGTACTG GGATTACAGG AGTGAGCCAC
8901 CGCGCCCGGC ATCATTGCTT ATCTTTTAGA CTGAGATAGT ACAGCTGATT
8951 CTAAACAGCA CCCAGAGAGA ATCTGGCCTC TTGATTTCCA GTTGTGTCTC
9001 AGAGGAGGAG GCATCCCAGT TCCTCCTCTT GCCCTCTAGA CATCTCCTCC
9051 TCTGATAAGT ATAAATAGGC TAGATCCCTT TATCTTCATA TCTGTTTTTG
9101 TCTGGAATGT TTCAAGTTTC TCAAGCTAGG TGTGGTGGCT CATATCTGTA
9151 ATCCCAGCAC TTCGGGAGGC CACGGCAGGA GGATCACTTG AGCCCAGGAG
```

FIGURE 3A-4

```
 9201 TTCAAGACCA GCCTGAGCAA CATAGTGAGA CCTCATTTCT ACAAAAAAAA
 9251 AATTTTTTTT TTGAGACAGT CTTGCTCTGG TCACCCAGGC TGGAGTGCAG
 9301 TGGCAGGATC TCAGCTCACT GCAACCTCCA CCTACTGGGT TCAAGCGATT
 9351 CTCATGCCTC AGTCTCCCAA ATAGCTGAGA TTACAGGTGT ACGCCACTAT
 9401 GCCTGGCTAA TTTTTGTATT TTTAGTAGAG ATGGGGTTTC ACCATGTTGG
 9451 TCAGGCTGGC CTTGAACTCA TGACCTCGTG ATCTGCCTCA GCCTCCCAAA
 9501 GTGCTAGGAT TATAGGCATG AGTCACCCCG CCTGGCCAAA AAAAATTTTT
 9551 TTTTTTTTTT TGAGACGTTG TCTTGCCCTG TCGCCCAGGC TGGAGTGCAG
 9601 TGGCACGATC TCGGCTCACT GCAAGGTCCG CCTCCCGGAT TCACGCCATT
 9651 CTCCTGCCTC AGCCTCCCGA GTAGCTGGGA CTACAGGTGC CCGCCACCAC
 9701 ACCCGGCTAA TTTTTTTGTA TTTTCAGTAG AGACGGGGTT TCACCTTGTT
 9751 AGCCAGGATG GTCTCGATCT TCTGACCTCG TGATCCACCC ACCTCGGCCT
 9801 CCCAAAGTGC TGGGATTACA GGCGGGAGCC ACCGCGCCCA GCCCAAAAAA
 9851 ATTTTTAAAA AGTTACCTGG GTGTGGTAGC ACATGCGTGT ATCCCACCTA
 9901 CTCAGAAGGC TGAGATGTGA GGATCACTTG AGCCTGGGAA GTTGAGGCTG
 9951 CAGTGAGCTG TGATCATGCC ACTGCATTCC AGCCTGGGCA ACAGAGTGAG
10001 ACCCCATCTC AAGATAAATA AGGTTTGTCA GTCCCTGTGG TGGTTCTTTC
10051 CGCAGATGTC TGTCTTTGGG TTGGCACTTA TTTCCCCCTA CTTGCAGTTA
10101 TTCCTTACAT TTCTCATTAG AAAATGGCAA AAAGGGCAAA AGTAAATTCA
10151 TTTCCTTTTT ACACCAAATC ATTAATTTTA GGCTTATAAA ACTAAATGAA
10201 CAGAAGATTT GGTAGGAGAG GAGGGGAGAT GGACACTGAT ACTGGTGGCT
10251 AGGTGATCCT GAGGGACAAC TGGTGCCTGG CAGAAAGAGA GGAGGGCTGT
10301 GTTCAGTGAC TGGCTCCCAG CCACCTTTTT GGCCTTTTTC TTTTTAACAT
10351 GAGGAAGGCG GAGCAGACCA GGGGCTTCTC TGTAGAACCA GTCAAGCTGG
10401 TTTTGGGCAG CCTTGGCCTA TTTTCTTGTG TGCTCTTTGG GAAGTTGGCA
10451 ATACAAAGGT CTGCCTCCTT TGGGGCTGTG TTCGTTGAGG CGAAAGTTTG
10501 GAAGACAACT ATCTGTCAAC AACCCCCTTC TCCCCAAACA CTGAATGGGT
10551 CTCTGAGCTG GTCCTTCACT CCAGGGAGGA GGCTTTCTCT CCACCCTATG
10601 CTGAACCTGA AGGCAGCTTT GCTTTATACA CCTTTCACTG AAAGCTCTAA
10651 GACATTAACT CCTTTTTTGG ACTCCCTTCC CAATTCACAA CTTGGTGAAA
10701 GACCCTCAGC CTAGCCAGGA GGAAGGGACT GGGTCTGCCT TTGGCTCCTC
10751 ATTTATGGGT CTGGGAGGGG ATCAGGACTC CTTACTGCTA TGATCTGGCT
10801 GCTAAATTCA GTGACATCCC AGGCCTTTTT TCGTCCACGC AATGGGACTG
10851 TCTGTCCAGG CCTGCTGGGA AAGAAAAGAG AGAAAAAATA GTTTTTGCTC
10901 TTTGGCAGCT TACAGGGACT TCAGCCATAG GAAACAACCT GTAGGAAAGG
10951 TGGGAGCTTC CGGTCACCAT GTGTGCTGAC ACTTCCTGCA ATAGCACTAG
11001 GGAGTCTTTC TCAGGGAGCA AGGCCAGCCA GGTAGGATTA TTTCCCAGTC
11051 TCCCAGCTAA GCAGGAAATG CCAAAATATG AACGTTTAGT AATTAGTGAG
11101 TGTAACTACC TGCTGACAGA GCTCCAGCCT AGACCTTGTC CTTGGGGGCT
11151 GGTTGCCCCT GTTGATACTA CAGTGAGCTA CTCATTGCTT CTGATTACCA
11201 TTTCAGTATG AGTTTTGCTT TGGTTTCTGA TATCCCATGT GCGGCTGCCT
11251 TTTTTCTCCA CCTTCTTTTT GTTGTGTCTT TTTGTTTTTT TGAGACGGAG
11301 TCTTGCTCTG TTGCCCAGGC TGGAGTACAG TGGCACAATC TCAGCTCACT
11351 GCAACCTCCG CTTCCCAGGT TCAAGCAATT CTGCCTTAGC CTCCCAAGTA
11401 GCTGGTACTA CAGGCATGTG CCAGCACACC CGGCTAATTT TTTTTTTTTT
11451 TTTTTTGAGA CAGGGTCTCG CTCTGTCGCC CAGGCTGGAG TGCAGTGGCG
```

FIGURE 3A-5

```
11501 CGATCTCAGC TCACTGCAAG CTCTGCCTCC CGGGTTCACA CCATTCTCCT
11551 GCCTCAGCCT CCCGAGTAGC TGGGACTTCA GGCGCCCACC ACCATGCCCA
11601 GCTAATTTTT TGTACTTTTT TTTTTTTTAA AGTAGAGATG AGGTTTCACC
11651 ATGTTAGCCA GGATGGTCTC AATCTCCTGA CCTCATGATC CACCCACCTC
11701 GGCCTCCCAA AGTGCTGGGA TTACAGGCGT GAGCCACCGT GCCCGGCTGT
11751 AACACCTGGC TAATTTTTGT ATTTTTAGTA GAGATGGGAT TTCACCATGT
11801 TGGCCAGGAT GGTCTCGATC TCCTGACCTC GTGATCCGCC CGCCTCGGCT
11851 TCCCAAAGTG CTGAGATTGC AGGCGTGAGC CACCGCGCCT GACCTTGTTG
11901 GTGTTTTTAA GAGACAGGGT CTCACCCTGT CACCCAGGCT AGTATGCAGT
11951 GGTGTGATCA TAGCCCACTG CGGCCTCAAA TAGCTCCTAG GCTCAAGTGA
12001 TTCTCCCACC TTAGCTTCCA GAGTACTGGG ACTACAGGTC ACACCTGGCC
12051 CCCTCAACCT TCTGGACTTT TCACTCACCC CATCACTCCC TACTTCTCCG
12101 CCACAGAAGA CTGTCATTGG CTATCTTTGC AAGTAGTATT GAAGCCACTC
12151 GGAGATTGTT GCTTTGTCTT TTTGCTCATG AAAGTTTGAA TTACTGGTTC
12201 TCCAGTCACA GGAAGTGGGG CTCCTTAGGC CAGCTCCATC TCACGTAGTG
12251 TACTGATTAT GTTGAGCTTA TGGCACAGCT GAGAGGAGAG TCCAAACTTT
12301 TTGAACACTT TTTGACTTCC AATAAGTGGT TCCACTATGG TTAAGAGCAG
12351 GTTTGGTGGG CCGGGCGCGG TGGCTCATGC CTGTAATCCC AGCACTTTGG
12401 GAGGCCAAGG CAGGCGGATC ACCTGAGGTC AGGAGTTCGA GACCAGCCTG
12451 ACCAACATGG TAAAACCCTA TCTCAACTGG AAATACAAAA ATTAGCCCGG
12501 TGTGGTGTTG TACACCTATA GTCCCAGCTA CTCGGAAGGC TGAGGCACAA
12551 GAATCACTTG AATCTGGGAG GTGGAGGTTG CAGTGAACAG AGATCATGCC
12601 ACTGCACTCC AGCCTGGGCA ACAAAGCAAG ACTTTGTCTC AAACAAACAA
12651 TAAGAGCAGG TTTTGCGGCT AGATTTCCTG TATTGGAATC CTGGATCATC
12701 CTCTCCTGTG ATCTTAGGTT CCCTCTGTGT CTGTTTGCTC ATCTGTAAAA
12751 TGGGAGAAGA ATAGTACCCA TCTTATAGGT ATAGCTGTTA TGAGTATTAA
12801 AAGAGTTAAT GAATAGAAAG CATTTAGAAT AGCGCCTGGC ACAGCAGAAT
12851 GATCATTGTC ATTATTGTTC CAGTTGAACA ACACAGTGAA TTTTATCTGA
12901 GCACCACACA ACTCTAGGTC AGTATAAGGG GTGATGTTTG GGATTTCTCT
12951 GTAATCAGTT GAAAAAATCT TGTTCTGGCA TCTTCAAGCC ACTGGGGTCC
13001 TATAGGTGCT TTTTCTAACA TTTCTGTTTT TTTGTTTGTT TGTTTGTTTT
13051 TTTGAGATGG AGTCTTGCTC TTGTTACCCA GGCTGGAGTG CAGTAGCACC
13101 ATCTTGGCTC ACTGTGACCT CCACCTCCCA GGTTCAAGCG ATTCTCCTGC
13151 CTCAGCCTCC CAAGTAGCTG GGATTACAGG CACCTGCCAC CATACCTGGC
13201 TAATTTTTTT TTTTTTTTTT TTTTTTTTG TATTTTTAGT AGAGATGGGG
13251 TTTCACCATG TTGACCAGGC TGGTCTTGAA CTCCTGACCT CATGATCTGC
13301 CCACCTCGGC CTCCCAAAGT GCTGGGATTA CAGGCGTGAG CCACTGCACC
13351 CGCCCTAGTT TGCTTTTTTA CCAATCACCT ATCTGAAAAA AAATGGAATG
13401 CTACTGGAGA GATTCATGTA CTTCTGAGAA CACTTTTAGC TCATTTTTTA
13451 TAAGGCATCA ATATTAGATA GTTTTCTTGA TTAAAGAAAA AAAAACACCA
13501 CCCACTGCCT GCCTATATTT CTGGGTTGCA AATGATGGCG GTGGATGTGC
13551 AGCCTCATCC GTGGCTAGAA GGCCAAATCC AAAGTCACCA GAGCTTGAGT
13601 TTTTTGAGAG TTGAGATCTG TGTGTCAAAG GGGAAGCCCT AGGGTGGTTC
13651 TCTGCAGCAC CAAGAGCAGG GATTCATACC ATCATGTTCC TTTCTTTTTT
13701 CTTTTCTCGT CTTTTCTTTC TTCCTTTCTT TTTGTTCTCA TGAGTTCTCA
13751 CTGTGTTGCC CAGGCTGGTC TTGAATATTT GGCCTCAAGT GATCCTCCCG
```

FIGURE 3A-6

```
13801 CATTGGCCTC CCCAAGTGCT GGGATTACAC ACTCAGCCAT GTTCCTTTCT
13851 TCAAGTACGG TATTGACCCT TTGGCCACAG GAGAACGTGC CCAGTTTTTC
13901 TTAAAGACCA CGTGGGAACT CAGCAGCCCA TGATTGTAGG TTCCTTTTTC
13951 CCTCATAGAG TGGCCTTCAA GGGCAGGTTC TTGTTATCTG CGTTTCAGAG
14001 ACCCAAAGGG ACACAGGCAT TTCTGCTCCT GGGAATTTGC GGACTTTGAA
14051 TCTTGAGCTC AGATTTTGGT CTCTGTTGGT TGCTTGTTTA TCTTCATCTC
14101 TTGTCATTTC TGGAGCCTGC ATGCCTTCTC AGAGCAGCAG GTAAGTTGCT
14151 TAGTTTTTTC ACATTGAAGC TGTGGCTGGG GGAAGGTAAC AGTGTCCCCT
14201 CAGAACTCAT GGAGATGCCA GGCATAGTGG AGGCTGAGGC AGGAGGGTCA
14251 CTTGAGGCTG GAGGATTGCT TGAGGCCAGC CTGGGCAACA TGGTGAGAGC
14301 TCATCTCTAA AAAATTTTTT TAAAAATAAC TCATCAGGGG CTATTTCTTT
14351 CATTGTATTT TCCTCTTCCT TTTGAACCCC TCTGCTGACT TGTTTCACTT
14401 TCTTTTTTTC TGTTTGGTTT CTTTGAACTC CCTTTCTTCA TTATCATGTC
14451 CTCATTCCCG TCCATCTTAG GTTTTTCATT TCCTTGTTCC ACTCTCCCTA
14501 ACCTGTTTCT GTGCCCTGTT TATGGCATGG CTCAGGATAT GAATTTTGAT
14551 CTCCGTCTGA GATCTCCTTC AGGTATAGAA TCCCAGACCA CCTGGTCCTT
14601 TTGTTCTCTC ATTCCTCTGA TTTCTGTACA TTTAAGGATT CACTGCTTTA
14651 GAAAACTTTT TTTTTTTTTC TTGTTTCTGG AGCCACCTCT CTCAGTAAAG
14701 CCAGGCTTGG CAACTTATTA GGGACAGCAT TCTGGTTTCC CTGGTGACAG
14751 GGTTTAAGCT GATTCTAGGC TGTTGCCTCT AACCCATCAG GAATGCCATA
14801 AGTATAGACC CTGTCTTGGG AGAGATCTGG AGAGATACTT GAGAATTTTG
14851 GACACTGTAA TATTGAATTT GGTTCTAATT GTGATCTAGA GACCCTCAGA
14901 CTCTTTCAGG TGATGCACGA AGTCAAAATT CTGTTCATAG TAACGTTAAC
14951 ACAGTGTTGC TTTTTCACTC TCATTCCCTC ACCAGTATAC AGTGGCATTT
15001 TCCAGAGGCT AAATGATGTG TGGTAACATC ACATTCTTCT GGCTAATGAA
15051 ATGTGTAATT CTGTATTCTT GTGTTTTCTA TAATTTTTAA GGTAGTACTT
15101 TAAGGTAAAA ATATGGAAGT TTTCATTGAT GGACTCAGTT TGTTCTTAGT
15151 ACTTCTGTGC TCTTACTAGG TTTCTTCAGT TATAACTGCT ATCATCTTTT
15201 TGTACACTTC ATTACTGTCT AATAAATCCT TATTTTGAAA TCCCAGCATT
15251 TTCCTGGAAC CTTTGAGAAA ATATAAGAAG TAAGTACTAC TTGTAAAACT
15301 TGCTTGTAAA AACTTTTGGG AAAACTCCTA ATTTTAAAAA TTTTATTGAC
15351 AACTTATTTT AGCACTTTAT TCTAAAATAG AAAAAAATTT ATATTATTTC
15401 TCTTATATGT AAGGGTGGAT TGTTGGCTTA AAAAAGGGAG ATTAGAAGAC
15451 TTGCTTTTTC AACCCATAGC TGCAACTTGT ATGTTAAAAA TACTGAAGTG
15501 GACATACCAA CAAGTATAAA GGAGGACTTT AAAGAATCTG GGCAGAACTG
15551 TAAATAAGAA CTAAAAAAAA AAAAAAGAA AAGAAATGAA AGTGTAATGA
15601 AAGCTACCTT CTCAGTTTCA TAAATGTTCA TAATGTACCT TACTGCGTCT
15651 TATGCGACAG AACATTTTCA TGTAGTATTA TGGTACCAGT TAAGTTGTGG
15701 CATTCTTTCA AGATCATTTA GAGTTTAAAG AAAAAGGAAT TGCATATTTT
15751 ATGCGTACGT ACTATGAGCT CTTTAAAAGC CAAAATTTCT TCCAGTTTTT
15801 AAACTAGAAA TAAAAAAGTC ACTGAAGCCT CTATCTAACA GGATAAGTTG
15851 CCACATTGCT TTGGCTGGAA AAGCCCACAC AGAAACTGAG AGACGAATGA
15901 AGTCTTGAAC AGCTGACATT CCTGAATGCC CACTGGATGA AAAGTCAGTA
15951 AAATTCAAGG CAGTGCCGCT TTAAATGTTA CCAGGATTCA TTAAATTAAA
16001 GATTTAGCCA GGCGCGGTGG CTCATGCCTG TAATCCCAGC AGTTTGGGAG
16051 ACCGAGGCAG GTGGATCACC TGAGGTCAGG AGTTTGAGAC CAGCCTGGCC
```

FIGURE 3A-7

```
16101 AACATGGTGA AACTCCTTCT CTACTAAAAA TACAAAAATT AGCCAGGCGT
16151 GGTGGCGCAT GCCTGTAATC CCAGCTACTC GGGAGGCTGA GGCAGGAGAA
16201 TCGTTTGAAC CCAAGAGATG GAGGTTGCAG TGAGCCGAGA TCGTGCCATT
16251 GCACTCCAGC CTGGGCGACA AGAGCGAAAC TAAAAAAAAA AAAAAAGATG
16301 TAGCTGCACA CATGAAGACC AAGTTAATAT CTTATTTACA GAATTTTACT
16351 TTCACCTTAC AAATGAGCAA ATCTATAGAT GTGGCTCGAC TTGCTGTATC
16401 AGCACCAACT GCTCATCAAA GAATAATTTA TTTTATGTGA ATGCTCAGCA
16451 GCAGATACAA ATGGTGATAA ATATTCAAAG GGTTGAATAA CTTCCTGAAT
16501 CTCATGACTT ATCCTGGAAC AACTTTATTT CCATTTGCAC CCTTGGTGCA
16551 GAAGCAGTGG TGGAGAAAAC TGCTGACGCC GTAACATGGA TCAAGGAAGT
16601 GGCACTAAGC TCTACTAGTG GTCATTGTCA TGGTCTTCTT TCCCACCACA
16651 AACTTGTGGT TGAAAAATAA AAGCCATTTT TACTTGAGAA TGTCTTGAAT
16701 GAAGGATTAA AGACTATCAT TTTTTTTATT TACTTATTTA TTTATTTATT
16751 TATTTTAATT TTTATCTATT TATTTTTTTG AAACAGAGTC TCACTCTGTC
16801 TCCTAGGCTG AAGTGCAATG GCGTGATCTG TGCTCACTGC CACCTCTGCC
16851 TCCTGGGTTC AAGTGATTCT CCTGCCTCAG CCTCCCAAGT TGCTGGGATT
16901 ACAGGCACCT GCCACCACGC CTGGCTAATT TTTGTATTTT TAGTAGAGAC
16951 AGGGTTTCGC CACGTTGGCC GGGCTGGTCT GGAATTCCTG ACCTCAGGTG
17001 ATCCACCTGC CTCGGCCTCC CAAAGTGCTG GGATTACAGG CATGAGCCAC
17051 CATGCCTGGC CAAGACTATT AATTCTGTGT GTGTGTGTGT GTGTGTGTGT
17101 GTGTGTGTGT GTGAGGTCTC ACTGTGTCAC TTAGGCTGGA GTGCATTGGT
17151 GCAACCTCCG CCCACTGCAA CCTCTGCCTC CCGGGTTCAA GTGTTTCTC
17201 ACCTCAGCAT CCCCAGTAGC TGGTACTACA GTGGGGATAC TCCACCCCAG
17251 GAGTGAAGCA TATAACCCAG TTCCNNNNNN NNNNNNNNNN NNNNNNNNNN
17301 NNNNNNNNNN NNNNNNNNNN NNNNNNNNNN NNNNNNNNNN NNNNNNNNNN
17351 NNNNNNNNNN NNNNNNNNNN NNNNNNNNNN NNNNNNNNNN NNNNNNNNNN
17401 NNNNNNNNNN NNNNNNNNNN NNNNNNNNNN NNNNNNNNNN NNNNNNNNNN
17451 NNNNNNNNNN NNNNNNNNNN NNNNNNNNNN NNNNNNNNNN NNNNNNNNNN
17501 NNNNNNNNNN NNNNNNNNNN NNNNNNNNNN NNNNNNNNNN NNNNNNNNNN
17551 NNNNNNNNNN NNNNNNNNNN NNNNNNNNNN NNNNNNNNNN NNNNNNNNNN
17601 NNNNNNNNNN NNNNNNNNNN NNNNNNNNNN NNNNNNNNNN NNNNNNNNNN
17651 NNNNNNNNNN NNNNNNNNNN NNNNNNNNNN NNNNNNNNNN NNNNNNNNNN
17701 NNNNNNNNNN NNNNNNNNNN NNNNNNNNNN NNNNNNNNNN NNNNNNNNNN
17751 NNNNNNNNNN NNNNNNNNNN NNNNNNNNNN NNNNNNNNNN NNNNNNNNNN
17801 NNNNNNNNNN NNNNNNNNNN NNNNNNNNNN NNNNNNNNNN NNNNNNNNNN
17851 NNNNNNNNNN NNNNNNNNNN NNNNNNNNNN NNNNNNNNNN NNNNNNNNNN
17901 NNNNNNNNNN NNNNNNNNNN NNNNNNNNNN NNNNNNNNNN NNNNNNNNNN
17951 NNNNNNNNNN NNNNNNNNNN NNNNNNNNNN NNNNNNNNNN NNNNNNNNNN
18001 NNNNNNNNNN NNNNNNNNNN NNNNNNNNNN NNNNNNNNNN NNNNNNNNNN
18051 NNNNNNNNNN NNNNNNNNNN NNNNNNNNNN NNNNNNNNNN NNNNNNNNNN
18101 NNNNNNNNNN NNNNNNNNNN NNNNNNNNNN NNNNNNNNNN NNNNNNNNNN
18151 NNNNNNNNNN NNNNNNNNNN NNNNNNNNNN NNNNNNNNNN NNNNNNNNNN
18201 NNNNNNNNNN NNNNNNNNNN NNNNNNNNNN NNNNNNNNNN NNNNNNNNNN
18251 NNNNNNNNNN NNNNNNNNNN NNNNNNNNNN NNNNNNNNNN NNNNNNNNNN
18301 NNNNNNNNNN NNNNNNNNNN NNNNNNNNNN NNNNNNNNNN NNNNNNNNNN
18351 NNNNNNNNNN NNNNNNNNNN NNNNNNNNNN NNNNNNNNNN NNNNNNNNNN
```

FIGURE 3A-8

18401 NNNNNNNNNN NNNNNNNNNN NNNNNNNNNN NNNNNNNNNN NNNNNNNNNN
18451 NNNNNNNNNN NNNNNNNNNN NNNNNNNNNN NNNNNNNNNN NNNNNNNNNN
18501 NNNNNNNNNN NNNNNNNNNN NNNNNNNNNN NNNNNNNNNN NNNNNNNNNN
18551 NNNNNNNNNN NNNNNNNNNN NNNNNNNNNN NNNNNNNNNN NNNNNNNNNN
18601 NNNNNNNNNN NNNNNNNNNN NNNNNNNNNN NNNNNNNNNN NNNNNNNNNN
18651 NNNNNNNNNN NNNNNNNNNN NNNNNNNNNN NNNNNNNNNN NNNNNNNNNN
18701 NNNNNNNNNN NNNNNNNNNN NNNNNNNNNN NNNNNNNNNN NNNNNNNNNN
18751 NNNNNNNNNN NNNNNNNNNN NNNNNNNNNN NNNNNNNNNN NNNNNNNNNN
18801 NNNNNNNNNN NNNNNNNNNN NNNNNNNNNN NNNNNNNNNN NNNNNNNNNN
18851 NNNNNNNNNN NNNNNNNNNN NNNNNNNNNN NNNNNNNNNN NNNNNNNNNN
18901 NNNNNNNNNN NNNNNNNNNN NNNNNNNNNN NNNNNNNNNN NNNNNNNNNN
18951 NNNNNNNNNN NNNNNNNNNN NNNNNNNNNN NNNNNNNNNN NNNNNNNNNN
19001 NNNNNNNNNN NNNNNNNNNN NNNNNNNNNN NNNNNNNNNN NNNNNNNNNN
19051 NNNNNNNNNN NNNNNNNNNN NNNNNNNNNN NNNNNNNNNN NNNNNNNNNN
19101 NNNNNNNNNN NNNNNNNNNN NNNNNNNNNN NNNNNNNNNN NNNNNNNNNN
19151 NNNNNNNNNN NNNNNNNNNN NNNNNNNNNN NNNNNNNNNN NNNNNNNNNN
19201 NNNNNNNNNN NNNNNNNNNN NNNNNNNNNN NNNNNNNNNN NNNNNNNNNN
19251 NNNNNNNNNN NNNNNNNNNN NNNNNNNNNN NNNNNNNNNN NNNNNNNNNN
19301 NNNNNNNNNN NNNNNNNNNN NNNNNNNNNN NNNNNNNNNN NNNNNNNNNN
19351 NNNNNNNNNN NNNNNNNNNN NNNNNNNNNN NNNNNNNNNN NNNNNNNNNN
19401 NNNNNNNNNN NNNNNNNNNN NNNNNNNNNN NNNNNNNNNN NNNNNNNNNN
19451 NNNNNNNNNN NNNNNNNNNN NNNNNNNNNN NNNNNNNNNN NNNNNNNNNN
19501 NNNNNNNNNN NNNNNNNNNN NNNNNNNNNN NNNNNNNNNN NNNNNNNNNN
19551 NNNNNNNNNN NNNNNNNNNN NNNNNNNNNN NNNNNNNNNN NNNNNNNNNN
19601 NNNNNNNNNN NNNNNNNNNN NNNNNNNNNN NNNNNNNNNN NNNNNNNNNN
19651 NNNNNNNNNN NNNNNNNNNN NNNNNNNNNN NNNNNNNNNN NNNNNNNNNN
19701 NNNNNNNNNN NNNNNNNNNN NNNNNNNNNN NNNNNNNNNN NNNNNNNNNN
19751 NNNNNNNNNN NNNNNNNNNN NNNNNNCCTC CCAAAAAGGT AGGGTTTCAG
19801 GTTTGAGCCC CTCGCCACCC GTCCTGGTTT TTAATTTTTC TCAATTTTTT
19851 CCCCATTTTA AAATTTTCCA AGGGTTTTTT TTTTTTTTTT TTTTTTTTTT
19901 TTTTTTTTTG AGACAAAGTC TCTCTCGCTC TCTCGCTCTC TCACTCTCTC
19951 GCCCAGGCTG GAGTGCAGTG GCGCCATCTC GGCTCACTGC AAGCTCTGCC
20001 TCCCGGGTTC ACGCCATTCT CCTGCCTCAG CCTCCCGAGT AGCTGGGAGG
20051 GACTACAGGC GCCCCCCACC ATGCCCGGCT AATTTTTTGT ATTTTTATTA
20101 GAGATGGGGT TTCACCGTGT TAGCCAGGAT GGTCTCGATC TCCTGACCTC
20151 ATGATCCGCC CGCCTCGGCC TCCCAAAGTG CTGGGATTGC AGGCATGAGC
20201 CACCACGCCC GGCCTAAATT TTTCAGTTTT TATACTCATT TCCTTTTTGT
20251 TCGTTTTCTT TCTTTAATTT GTTAGTATTT GTTGTTTTTT GAGACAGCCT
20301 CACTTTATCA CCCAGGGTGG AGTGTGGTGG CACGATGTTG GCTCACTGCA
20351 ACTTCCACCT CCCAGGTTCA AGCAGTTCTC CTGCCTCTGC CTTCCCAGTA
20401 GCTGGGATTA TAGGCACTTG CCACCAAGTG ATTTTTGCAT TTTAGTAGAG
20451 ACGGGGTTTC TCCATGTTGG TCAGGCTGGT CTCCATGTTG GTCAGGCTGG
20501 TCTCGAACTC CTTACCTCAG GTGATCTGCC TGCCTTGGCC TCCCAAAGTG
20551 CTGGGATTAC AGGCATGAGC CACCGCCCCA GCCTGTTTTT TGGTCAGCTG
20601 TTTTGTTTTG ATTGCATTAT AAGATTAGTT CATCAGGTAG ACTTCCTTTG
20651 GTATATATTT AGTTGTGGTT TGGAAAATAA GTTTTTTATT AAAAATAAGT

FIGURE 3A-9

```
20701 CATTTATGTT TACATGTAAT GAGTTTACTC ATGTTCTGTT AAATGAATTG
20751 ATACATATTT AAATTTTTCC TCACTTGAAT TTCTAATATA GTAAATACTG
20801 ATAGATAAAA TTCATATAAA CAAAAGCTTC TGGGTGTTCA GTTATTTTTC
20851 AAAATGCAAA GAGTCCTGAA ACCAAAAACT GTAAGAATCA TGGTTGTAGA
20901 CAAAACTTGG TTTGGTTCTC CATGACTTTG GTTGATACAT TTTTTTTTTA
20951 TTTTTTTATT TTTTGAGACA AGTTCTCATT CTGTCACCCG GGTTAGAGTG
21001 GAATGGCATG ATCTCGGCTC ATTGCAGTCT CAACCTCCCA GGCTCAAGCA
21051 ATCCTCTCAT CTCAGCCTCC CAGAGTGCTG GGATTATAGA CATGAGCCAT
21101 TGTGCCTGGC TATATTATCA TCGTTATTAT TGTTTTGTTT TGTTTTTTGA
21151 GATGGAGTTT TGCTTTGTCA CCCAGGGTGG AGTGCAGTGG CACCATCTCA
21201 GCTCACTACA ACCTCTGCCT CCTGGGATCA AGCGATTCTT GTGCCTCAGC
21251 CTCCCAACTA GCTGGGATTA CAGGTGCACA GCACCACACT TGGCTCATTT
21301 TTGTATTTTT AGTAGAGACA GGGTTTTGCC ATGTTGGCTA GGCTCCTGGC
21351 TTCAATTGAT CTGCCTGCCT CGGCCTCCCA AAGTGCTAGG ATTACGGGCA
21401 TGAGCCACTG TGCCTGGCCC TGTAATATAA TTTTACATGA GTTAATAGTG
21451 TAACATTTTC TCAGTTGTAA TTTTTTTTTT TGAGACAGTG TCTCACTCTA
21501 TCACCCAGGC TGGAGTGCAA TGGCACGATC TCCACTCCCT GCAACCTCCC
21551 AGGTTCAAGT GATTCTCCTG CCTCAGCCTC TTGAGTAGCT GGGATTACAG
21601 GCATGCGCCA CCACACCCGG CTAATTTTTG TACTTTTAGT AGAGATAGGG
21651 TTTTCACCAT GTTGTTCAGG CTGGTCTCGA ACTCCTGACC TCGTGATCCA
21701 CCTGCCTCTG CCTCCTAAAG TGCTGGGATT ACAGGCCTGA GCCACTGTGC
21751 CTGGCCAGTT TTAATTTTAA TACAATAAAT ATCAGTAGCT ATCACCCACA
21801 TGAAGAAAGC CATTTGACGT CATCAGTAAG AGTAAAGGGA TTCCAGACAG
21851 TGTGAGAACT CTTTTGTAAA CAGAGATAGG ACTGATAATC CCTGTCCTCG
21901 ATTGGTTGAT TACTTGCTAT GACCTCATAA TGAGCCTCTG TTTTGCAATT
21951 TCTGGGGCCC TGGCTGGGCC TCAGGAAGGC ACTTGCTGTC TTGGTTTTCA
22001 GTTGTTCTAG CTGAGGAAGC TGGTTCTCAG TGACCTGATG GACCTTGGCC
22051 AAAGTTGGCT CATTTCCTCC TTTGAATACA TAGCATTACT TTATGTTTTT
22101 TTATTCCATT AAAAAGATCA TTTGGCTTAC TTGGATTTTA TTATGAGGTT
22151 TGTGTTTTAT TATGAGGTAG GTTTGTGTTT TTTTGTTTTT TTTTTAACTT
22201 ATATGTTGGC TATTGGTCAG TTCCAAATTT GAAAACTGCA ACGCTTACAC
22251 AGCTTCTATC CTTGAAGAAC CTTGGTGCCT ACAATAGCTG AGAGCTGGTA
22301 GGCTGCAGTC ACTAAGGCCA GACACTCAAT AGTCTATTCC CTGGGTGGCT
22351 TGAGACCTGA CATACTTTGT TTCTTTTTGT TTCTTTTCCT TTTGTACTTG
22401 ACTCTTTTTA ACCTGTTTAT TTCTTTTTTT TTTTTTTCCC CGAGAAGGGA
22451 GTCCTGCTCT GTCACGCAGG CTGGAGTGCA GTGGCACGAT CTCGGCCCAC
22501 GGCAACCCTC CGCCTCACAG GTTCAAGCAA TTCTCCTGCC TCAGCCTCCT
22551 GAGTAGCTGG GATTGCAGGT GCCCGCCAGT ATACCCGGTT AATTTTTGTA
22601 TTTTTAGTAG AGAAAGGGTT TCACCATGTT GGCCAGGCTG GTCTTGAATT
22651 CCTGACCTCG TGATCCACCC ACCTTGGCCT CCCAAAGTAC TAGGATTACA
22701 GGCACAAGCC CATGCCTGGG CTAACCCCTA TTTCTATCTT TCTTTTTTTT
22751 TTTCGAGACA GAGTCCCACT CTGTCGCCCA GGCTGGAGTG CGGTGGCCGG
22801 ATCTCAGCTC ACTGCAGCCT CCACCTCCCA GATTCAAGCA AATCTCCTGC
22851 CTCGGCCTCC CGAGTAGCTG GAACTACGGG TGCGTGCCAC CATGCCCGGC
22901 TTATTTTTGT ATTTTTAGTA GAGACAGGAT TTGCCATGA TGGCCAGGCT
22951 GGTCTTCAAC TCTTGACCTG GTGATCCACC TGCCGTGGCC TCCTAAAGTA
```

FIGURE 3A-10

```
23001 CTGGGATGAC AGTCATGAGC CACCACATCC GGCCTCTAAC CCTTGTTTCT
23051 TAATGAAACA TACCTGTAAA CCCCACTGTT ATGTAGGTAT ACTTTATTTT
23101 TCCTGTAAGA GGTAGGTTTA TTTGGAGTGT TTGTAGCAGT GTGTGAACTT
23151 TGTATTTCCT TGACAAGTCC TTAAGTGACA GGGAAAATTG TAGTAGTATA
23201 TAATCTGTAA ACTACCCTGT AATTCTCAAC TTTGTTCTTT TGCATATACT
23251 CATTCTCCAA TTTCCATAGC ACCTCTAACT TTTAACAGCT TCCCTAAGTC
23301 CTACAAATAA TAGACCTTGG GCCTCCTCTA ATAGTCACTT TGACCAACTT
23351 TAAGCAAATC TTTTAAAACT CATGTCGGCT GGGTGCAGTG GCTCACTCCT
23401 GTAATCCCAG CACTTTGGGA GGCTGAGGCG GGTGGATCAC GAGGTCAGGA
23451 GATCGAGACC ATCCTGGCCA ACATGGTGAA ACCCCGTCTC TACTAAAAAT
23501 ACAAAAATTA GCCGGGCGTG GTGGCGTGCG CCTGTAGTCC CAGCTACTTG
23551 GGAGGCTAAG GCAGGAGAAT TGCTTGAACC CAGGAGGGGG AGGCTACAGT
23601 GAGCCGAGAT CATGCCACTG CACTGTAGCC TGGGTGACAG AGACTCCCTC
23651 TCAAAAAAAA AAAAATAAAT AGAAATAAAA AAGCCAGGCA CAGTGGCCCA
23701 CATCTGTAAT CCCAGCACTT TGGGAGGCCA GGGCGGGTGG ATCACGAGGT
23751 CAGGAGTTCG AGACCAGCCT GGCCAATATG GTGAAACCCC GTCTCTACTT
23801 AAAATACAAA AAATTAGCTG GGTATGGTGG CGCGTGCCTA TAGTTCCAGC
23851 TCTTCAGGAG GCTGAGGCAG GAGAATCACT TGAACCCAGG AGGCGGTGGT
23901 TGCAGTGAGC ATAGATCACG CCACTGCACT CCAGCCTCGG TGACCGAGTG
23951 AGACTCCATC TCAATGAAAA AAAAAAACAA AAACAAAAAC TCATGTCATT
24001 TGCTCAGAAT CACATCTCAT TGGAATCATT TTTTTAAAAC TGTTTAATCA
24051 AGTGCTCAAC ATATCAATTC GTGTCTACAT AGAGGATCAT AGCTCCATTT
24101 CCCATCACTC AGCAAGTCCC ATAATCTGCT TTTTCCACAA AGCGTATTTC
24151 TTTTCAGATT TACATGTGGC ATGCATTTCA GTTCCAGAAT TGAACTTAAT
24201 GTGCTATTTT CTCTCTTCGG CTACTGGTCT GTGTGGAAGA TAAGGAACTT
24251 TAATTTCGGG TTGGGTGCAG TGGCTCACGC GGGTAATCCC AGCACTTAGG
24301 GAGGCTAAGG CGGGCGGATC ACGAGGTCAG GAGTTCAAGA CCAGCCTGGC
24351 CAAGATGGTG AAACCCCATC TCTACTAAAA ATACAAAAAA CGTAGCCAGG
24401 CGTGGTGGTG GGCGTCTGTA ATCCCAGCTA CTCTGGAGGC TGAGGCAGAG
24451 AATTGCTTGA CCCCGGGAGG TGGAGGTTGC AGTGAGCTGA GATCGCACCA
24501 CTGCACTCCT GCCTGGGCGA CAGAGCGAGA CTCCGTCTCA GAAAAAAAAA
24551 ACAAGAATTT TAATTTCAAA TATTTGTTTA CTGTATTAGT TAAGGCAACG
24601 GCTTAGTAAT GGCACCTCCT GGATGGCCCT GTAAGCGCAT TAATCTGGTC
24651 CAAGTCATTG GGAAACTCAG CCTTAAAGGG AATGGACTGA GTGGTTGAAG
24701 AGTAGGCAGG GTCTCCTCAT TTTTGCATGG TTTGCCTCTG AGGCTGTGTA
24751 TCTTTAGCTA CAGACAGAAT AGCTAACATT TATTGAGCCC TTACTCTGTC
24801 GCAAGCACTT GTTAGTTGT TTTACATTCA TTAACTCATT TACTCTTTTT
24851 TTTTTTTTTT TTTGAGACAG AGTCTCGCTC TTGTTGTCCA GGCTAGAGTG
24901 CAACGGCACA GACCTTGGCT CACTGCAACC TCCGCCTCCC GGGTTCAAGC
24951 AATTCTCCTG CCTCAGCCTC CCAAGTAGCT GGGATTATAA GTATCTGCCA
25001 CCATGCCTGG CTAATTTCTT TCTTTCTTTC TTTTTTTTTT TTTTTGAGAC
25051 GGTGTTTCGC TCTTGTTGCT CAGGCTAGAG TGCAGTGGCA CTGTCTTGGC
25101 TCACTGCAGT CTCCGCCTCC TGGGTTCAAG CAATTCTCCT GCCTCTGCCT
25151 CCCGAGTAGC TGGGATTGCA GGTATCCGCC ACCATGCCCG CTAATATTT
25201 TGTATTTCTA GTAGAGATGC GGTTTTACCG TGTTGGCCAG GCTGGTCTCA
25251 AACTCCGGAC ATCAGGTGAT CCACCCATCT CAGCTTCCCA AAGTGCTGGG
```

FIGURE 3A-11

```
25301 ATTACAGGCA TGAGCCACCA TGCCTGGCTT CATTTATTCT TTGTAAGTTA
25351 GTAGATCTCA CTGTTTTACA GGTGAGGAAA TAGAGGCCCA GAAATGTTGA
25401 ATAACTTGTT TAAGGCTACA AACCCAGGTG GTCCAGAGTA TGTCATTGTC
25451 AGAACCAGCT TTTCTTGGTT GTGAAGAATC CTTTGTCCCT GGCTTCAGTT
25501 GTGTCCAGGC AGTAGAAGAT AGTTTCCTTA GGATTAGCTC CCAGTCAGTG
25551 TGAGGCAGAT GTCTTGCAGC GGAATTTAGA GTCACAAATG GCCTCCTCTG
25601 CCTCCAGTTG TTTCTTTTGT CCTTGGTGGC CATTGGTAAA TGTGGCCGAA
25651 ATGGTGTGGA TGGAGTGGGA GCAGCTTTCT GGGCTCACCT CCCTACTATT
25701 GAGGGCTCTA CGCAAGAGCT ATGGGAGACC TTTTTAAGAA ACCCTCTTTA
25751 ACCCCAGCTT CTGATTCACA TCTTTATCTT TTCCCATCTT CCGGAATTTC
25801 AAGAACCCCT TTAGAAAAAC CAAAGCCCCG AGTCCTAAAA TTGATAACCA
25851 GCAATTAAGT ACCTTAAAGT GTAGGGCATG ATGGATTTCT AGGTTTGACT
25901 ATCCTGCTTT GTGGCACCCA TGAAATGTTG GGATTCTAGA ACTCTTTCTT
25951 TGTAAGCACC CCACTCCCCA CCAAAAAAAA CCCCACTAAA CATAAGAAGC
26001 TTTTGTCTGT GGATCTTAAC TGTGTATATT TTGTCTCTAG GAAGCAAACT
26051 CAGATTCTCT CTTACAACCG TCTGTGTGCC ACTTGCACAC ACACAGGCAC
26101 AGAGCTACTT GCTTGTAGCC TTGACTGCCA GCAGCCCTGA ACACCGTAGC
26151 TGGTGGTGCC AGGCCTTGTG TGTGTTTAGG ACTTGCCAGT TCAGTCCTGG
26201 GAGCTGAACT CTGGACATCC TGCTGTGTGT CTCTTTATCC CATCGCTGGT
26251 GTAATTTATG CCACTACTTC CTGTTTGCAT TTGCTCAGTC TCTCCTTTGG
26301 TTTGCTTCTC TCTGCTGAAG CCGGTCCCCA TAGCTGTGCA CATGGCTAGC
26351 TATGGGGACT AGGCATCTAG ATATTCTAGA CATCTGCAGT TGTTTCTTAG
26401 TGGGAATGGT TGCTTTATGT CTCTCTACAG AATTTTAGTT GAACTTGAGT
26451 GTATGATTTA ATTTACTTGC TTGTCTAACT TCGGCAAGGG TGCCTTTTAT
26501 TTTAAGATGC CAGCATGGGG TGAGAGTAAA GGGGTGAACT ATTGCCCTCC
26551 CCCACCCCCC CACCCCCCAC CCCCCACTT TTTTTTNNNN NNNNNNNNNN
26601 NNNNNNNNNN NNNNNNNNNN NNNNNNNNNN NNNNNNNNNN NNNNNNNNNN
26651 NNNNNNNNNN NNNNNNNNNN NNNNNNNNNN NNNNNNNNNN NNNNNNNNNN
26701 NNNNNNNNNN NNNNNNNNNN NNNNNNNNNN NNNNNNNNNN NNNNNNNNNN
26751 NNNNNNNNNN NNNNNNNNNN NNNNNNNNNN NNNNNNNNNN NNNNNNNNNN
26801 NNNNNNNNNN NNNNNNNNNN NNNNNNNNNN NNNNNNNNNN NNNNNNNNNN
26851 NNNNNNNNNN NNNNNNNNNN NNNNNNNNNN NNNNNNNNNN NNNNNNNNNN
26901 NNNNNNNNNN NNNNNNNNNN NNNNNNNNNN NNNNNNNNNN NNNNNNNNNN
26951 NNNNNNNNNN NNNNNNNNNN NNNNNNNNNN NNNNNNNNNN NNNNNNNNNN
27001 NNNNNNNNNN NNNNNNNNNN NNNNNNNNNN NNNNNNNNNN NNNNNNNNNN
27051 NNNNNNNNNN NNNNNNNNNN NNNNNNNNNN NNNNNNNNNN NNNNNNNNNN
27101 NNNNNNNNNN NNNNNNNNNN NNNNNNNNNN NNNNNNNNNN NNNNNNNNNN
27151 NNNNNNNNNN NNNNNNNNNN NNNNNNNNNN NNNNNNNNNN NNNNNNNNNN
27201 NNNNNNNNNN NNNNNNNNNN NNNNNNNNNN NNNNNNNNNN NNNNNNNNNN
27251 NNNNNNNNNN NNNNNNNNNN NNNNNNNNNN NNNNNNNNNN NNNNNNNNNN
27301 NNNNNNNNNN NNNNNNNNNN NNNNNNNNNN NNNNNNNNNN NNNNNNNNNN
27351 NNNNNNNNNN NNNNNNNNNN NNNNNNNNNN NNNNNNNNNN NNNNNNNNNN
27401 NNNNNNNNNN NNNNNNNNNN NNNNNNNNNN NNNNNNNNNN NNNNNNNNNN
27451 NNNNNNNNNN NNNNNNNNNN NNNNNNNNNN NNNNNNNNNN NNNNNNNNNN
27501 NNNNNNNNNN NNNNNNNNNN NNNNNNNNNN NNNNNNNNNN NNNNNNNNNN
27551 NNNNNNNNNN NNNNNNNNNN NNNNNNNNNN NNNNNNNNNN NNNNNNNNNN
```

FIGURE 3A-12

```
27601 NNNNNNNNNN NNNNNNNNNN NNNNNNNNNN NNNNNNNNNN NNNNNNNNNN
27651 NNNNNNNNNN NNNNNNNNNN NNNNNNNNNN NNNNNNNNNN NNNNNNNNNN
27701 NNNNNNNNNN NNNNNNNNNN NNNNNNNNNN NNNNNNNNNN NNNNNNNNNN
27751 NNNNNNNNNN NNNNNNNNNN NNNNNNNNNN NNNNNNNNNN NNNNNNNNNN
27801 NNNNNNNNNN NNNNNNNNNN NNNNNNNNNN NNNNNNNNNN NNNNNNNNNN
27851 NNNNNNNNNN NNNNNNNNNN NNNNNNNNNN NNNNNNNNNN NNNNNNNNNN
27901 NNNNNNNNNN NNNNNNNNNN NNNNNNNNNN NNNNNNNNNN NNNNNNNNNN
27951 NNNNNNNNNN NNNNNNNNNN NNNNNNNNNN NNNNNNNNNN NNNNNNNNNN
28001 NNNNNNNNNN NNNNNNNNNN NNNNNNNNNN NNNNNNNNNN NNNNNNNNNN
28051 NNNNNNNNNN NNNNNNNNNN NNNNNNNNNN NNNNNNNNNN NNNNNNNNNN
28101 NNNNNNNNNN NNNNNNNNTA TTAAATAAAT AAATAAGATT TACTTATCCA
28151 AAAGCACAAT TATGTGCCTT TTTTCTTTTC TTTTGAGACG AGAGTCTGAC
28201 TCTGTTGCCC AGGCTGCTGT AGTACAGTGA CGCAGTCTCG GCCTTGACCT
28251 CCCAGGCTCA AGCAATCCTC CCACCTCAGC CTCCCAAGTA GCTGGGACTA
28301 CAGGCATGTG CCACTATGCC TGGCTAATTT TTTGCACTTT TTGTAGAGAT
28351 GGGGTTTCGT CATGTTGCCC AGGCTGGCCT GGAACTCCTG GCGTCAAGCA
28401 ACCTACCTGC CTTCGCCTCC CAGAGTGCTG GGATTACAGG CAGTCGCCAT
28451 TGTATCCAGC CCAGTTATGT AGTTATGTGC CATTTCTAAA CTACTTTAGA
28501 ACCCATCTCT TTGGTGTTTG TTTGTTTGAG ACAGAGTCTC ACTCTGTCAC
28551 CTCAGCTGGA GTGCAGTGGT GTGATCTCAG CTCACTGCAG CCTCGGCCCC
28601 CAAGGTTCAA GCGACCCTCC CACCTCAGCC TCCCAAGTAG CTGGGACCAC
28651 AGGTGCTCTT TTTGTTAAGA GTGGAAAAGC CAAGGTCCAT GTACTTTTTT
28701 TGAGAAAGAC AGCCTGTTGG CTTTCTTCAG AGTGGTTCTG CCCCTTCCCG
28751 TACCCCATCT CCAACACATT TTTATCTCTC AACAGAGGTA GCTGCTATTC
28801 ACTCAGGTGT TCTTTAATGC TGTGGCCACG GCTTCCTTGG AGAGTGTGGC
28851 AGTGCTTTCC TTGCTAATGA AAAGGCTGTC ATAATGGGTT AGGTCCATAG
28901 GGGCTCTGCC CTTCTGTACT TGTATTCCCA GGGAGAAAAA TCTCTACCTT
28951 AATTACCGAC ATCTCATGCT GGCAGAGAGG TGTGGTTGCT AATTGATTAG
29001 ATGACAGTCC TTTTCATTGA TGTGGCACTG TTGGGGTGGT TTGTTGTGC
29051 TTTTTCAAGT AAACAGATAG ATTTGGGCCA GGTAAGTTGA TTTTGGAGAG
29101 ATGAAGTTCT GTGTAGGGAT TTCCCTTTAT TAAGCTCATG TCTTTAGTGC
29151 CACTTTTGTG TCCTGATTTT CTAACTTGAT AGTAAGAAGT ACTAAGTTGG
29201 CTTGTCTTGC TATTTTGGTG TGGGTGGTGA ATAATGTCTC TTCTACCCTG
29251 CTCTCTGGTG CGTTCCTGTT CTGTTTGGTA GCACCACATT CCTCTATTTC
29301 GTTTGGTTTT CATTCCCTCT TTCTCTCTTG TAATGGTTGG ACCCTATTCT
29351 GAAATATATA TTTTAAGATA GTGTTACTTT GGGTGGTCGA GGCGGGCAGA
29401 TCACCTGAGG CCAGGAGTTC GACACCAGCC TGGTCAACAT GATGAAACCC
29451 TGTCTCTACT AAAAATACCA AAATTAGCCA GGCGTGGTGG TGTGCATCTG
29501 TAATCCCAGC TACTCGGGAG ACTGAGGCAC GAGAATTGCT TGAACCCAGA
29551 AGGCAGAGGT TGCAGTGAGC AGAGATTGTG CCACTTTACT CCAGCCTGGG
29601 CAATAAAGCA AGACTCAGTC TCAAAAAAAA AAAAAAAAAA AGTAGTGTTT
29651 AAAAGCAAAC ACCCTGCCTT TTTTGAAACC ACAGAAACTG CTTGTGAAAC
29701 AGCCGATAGG GCAGGCTGCC AAATACAGAC TGTTAAAACC AATCTCTTAA
29751 TGACAAAATG TCAAACACTG ATGTTAAACC TTCATTATGA CTGTGGTGTG
29801 AGGATTTTTC TCAATAAGAA ATGTTTAGGT GCTGAACTCC CAGTTTCACA
29851 TTCAGAATGC TTCTATTATC AAATTCCTCT TGGTACATCA TTTCCGAGAG
```

FIGURE 3A-13

```
29901 GCTTGTGTAG CTAATCCACT ATCTACTGTA CAGGAAAGAT TTTAAATAAA
29951 CCTATTCCCA TTCATCCTCA TCTGTGTTTT TTTGTTTTTT GTTTTAATTT
30001 CAAGAAGTAA TTTTCTTTTG AGGTGATTTG GACCAACCGT CTCACTAGCT
30051 TTTCCCATTT AAGATAGGAG AACTAGATTC AGAATTGTGT CTTTTTCCTA
30101 ACAGAAGACT GGGGCCTTAA TCTTTACCCC CCAGGCTCTG ATTAACTGAC
30151 TTTTCTTTTT TTAGATGGCA TAGAATCTTC TGTCTGTCTA GAGAATTTTG
30201 TTTCTTGCCA GGCACTGTCA GGAATTAGTA TTCATTCCTC CCTGCTATCT
30251 TCCTGAAGAG CTGTGAACCT GCTGGTAGCC TGATGGATAA GGGTACAGTT
30301 GTTTGTTTAT TTATTGAGAC AGGGTCTCAT TCTCTCACCC AGGCTGGAGT
30351 GCAGTGGCAT GATCTTGGCT CACTGCAACC TCCGCCTCTC AGGCTCAAGC
30401 TATCCCCCAA CCTTAGCCTC CTGAGTAGCT GGGACCACAG TCATGTGCCA
30451 CAACACCCAG CAAATGTTTT GCGTTTTTTG TAGAGACAGG GTTTCCCCAT
30501 GTTGCCTTTG CTGGTCTTGA ACTCCTGGGC TCAAGTGATC CGCCTGCCTC
30551 AGCCTCCTGA AGTGCTGGGA TACCAGGTGT GAGCTACCAC AGTTGGCCAA
30601 GGTATAGTTT TATGAGCTGA GCTATAGAAC TGGTTGAATG GGAATTAGGG
30651 AAAACAGACA ACCAATAATT GGGAAGTAAA GGAAAAATAT ATAAGTGTGC
30701 CTCCTTGGTC ACAGCTAGCC TTGTGACATT GGGGTTTTGG ATATAGAACT
30751 TCAGGAATCC CTTCCACCTC CTTCCCAAGA GAATTTCTTC TGTTGGTGTT
30801 GTAAGGGGCT TTTTCCAACT TCATTTCCAT TACCAAGAGT CTTGAGTGGC
30851 TTTATTTTCA ACTTGGGTTT TTTAAGCGCT TCTCATGTCA CCTTTGTTTG
30901 TGTACTGGGC CTGTCTCAAG TTTCCAGAGG GAGATGAAAG ACAAGAAAAG
30951 CTAAATGACT GGTTCTTCAG TGAGTTTCCC AGAGTGGCTT CTTCTCATTC
31001 CAGCACTGCC TAACTCTCAC CATGGCTGAC GCCGTGGGCA GGCATCCGCA
31051 TTCATGGAAA GCCAGGTCCT AGCTGGAAGT GACACAGGGA TCTTCAGATC
31101 TCTCTTAGCC CACTGTTCCT CTGAAAAAAA AACAAAAGCC ATAGACAGTA
31151 AATTGGGGGA ATAGGCTGAC CATAACTTCA GTTCGTGGAT TTGGGTCCCA
31201 CACTGGATTG TGTGATTTGT GCTTATCTCC TACTAGATTG TTACCTTCTT
31251 TGAAGGCTGG ACTGTATCTT ATCCTTCTCT GTATCACTTC GGACACCCAG
31301 AAACTGTTGG AGTACTTGC ACATGGTCAC CTCTTAATGA ATTATTTGTG
31351 AAACAAAAAT TTTTTTAAAT TGTAACATGA GGCTGGGTGT GGTTGCTTAG
31401 GCCTGTAATC CCCGCACTTT GGGAGGTAGA AGTGGGCAGA TTGCTTGAGT
31451 CCAGGAGTTT GAGAACAGCC TGGGCAACAT AGCGAAACCC TGTCTCTATA
31501 AAAAATAGAA AAGTTAGCTG GGTGTGGTGG TGCGGGCCTG TAGTCCCAGC
31551 TCCTTGGGAG GCAGAGGTGG GAGGATTGCT TGAGACCTTG TCTCAAAAAA
31601 ATAAAAAAAA ATTACTTAAA AAAATCGTAA CATGGGTATT CTCCATTACA
31651 GTTACCCTTA GGGAAGTGTG TCCATATTGA TTTGTAAGTC TGATATCAGT
31701 CTATCTGATT CTTTGGCTGT GTAAGTCACA AGTCTTAACC AGTATCTTAA
31751 GTAGGTGTGG TAATGACTAC AGAGAAGTGC TTTTTCAGGA TGAGAAGATG
31801 AGGGAGAAAA TTTACACCAT TGCTGGATTG TGTTAAGAAC TCGGAGAGGA
31851 AACCACAGGG AGGATGCACT GCTGAGGAAA TCGTCTGGCT TCCTGGAGTG
31901 GGGACCAGAG CCAGAGAGCC AAGCCCTCCT GGCTTTGCTG AGTTCTGTCC
31951 TTGCCCCTGA CACCAACGTG TCTGCCTGCT TTGTTGCTCC TGGTTACAGT
32001 GGGCTCAGTC TTGCCTCTTT TTTGATGGGT GGGCAGAGGA ACACTAGTGT
32051 TGGGAATATT GTCCAGCGTT GGAGAGATCA TGTGGTCTGT CAGAAGGCTG
32101 GAGTTATTTA TAGTGGGAGA AAAGCCCAGG AGCATGGCAC GGGAAGAACT
32151 GATTTCACAC CAGCTCAGCG CCTGATGATG GTGAGGACCC AGATTTTCCT
```

FIGURE 3A-14

```
32201  TTGAGCATCT CAGAGCAGAT CAGTCGCTTT TCCTGATTGA CCCATGAACT
32251  GTGAGACTAG GGACCATGTT TTCCGAGGCC ACTGTGAGTG AGGGAAGAGT
32301  GAGAAGGATG ACCATTTTCT TCTTCCTTGA TTCTGGTCTT TGTGATGTGT
32351  GGTATGAAAG TGTCATCTGA CTTTTGAATC TCCTTTTATT GAACTGGTGA
32401  AGAAGGCACC AGCTGTGTGG GGTGGTGGAA ATAAGGACCT GTTAAACTGG
32451  TCTGCCTGTA TCTGCCTCCC TGCTCCCCCC TCACCCCACC CACCCCACC
32501  CTGGGCAGGG AGGCTGAAAC TGCTGCTTGC TAGGCTTTGC CAACTCAGTT
32551  TCTCTTCATG GATTACCTGC TCGCGGCAGG CAGGCAGGCA GCTCCCCACC
32601  TGGAAGCCTG CAGACTCGCC GAGCTGAGAG AATCATGCTG CAGGTGGGGG
32651  CAAGTGCTAG GAACTAGGTG TGCCACTTAC CTTAACAGGA GCTGTGCCTA
32701  GTCCGGGCTG CTCAAACTAA GGCTGCAGAG CCCTGGGGCC TGTTGGAAAT
32751  AGACTGTGCC TTTCCCTGCG CCTTGTGGCC ACATTTTTAT GGTATGTGGA
32801  GAGTCTGGGA GGGGCCGGGA GCTTGTAAAT TGTGAGTAAA TGAAGTCTAG
32851  GGAGGGAGAT GATCCTTCTT GAGGGCACCC TGAGTTCAGG GTTGTCATGT
32901  TTCTGAGGTG TGCTACTGCT TAGTACCCTG ATTTCTGGAG TTGTCTACCT
32951  AGGTTGCTTT TAATTTTTTC AGCCTTAGGT GGAAGAGATT TTCCATCTTG
33001  GTGTTTAGGC ATGTTAGGTG AGGTTTACTT CCGGAGCCAG ACTTTTAGGC
33051  AGGTTGTCTT GACATAAGTC AAGGTCAGGA AGCGATCTTC AGGACATGCA
33101  GACGATGCCC ACTTCCTGCT GTGGTCTTGA AGAGGGCTGG AAGGCTTGTG
33151  AGCACAGAGG CACTGAGGGC TGTCGCATCC ATACAGGAAG ACACTCAGGG
33201  CTCGTCTCCG GTGCCTCATT TTATAAGCAT GGAAACAAAA GTCCCAGGAG
33251  GGTGAATGAC TTGCCCAAGG TGACATAAAT TGTTTGCGCA GAGCTGGGTC
33301  TAGAATGGAT CTTATGCCCT TGGCAGCGTG CCCCCATTGC CATCACTTCA
33351  GAGGGGCTGG CTGCAGCCCT CAACGGCAGA AGGCAAGCTG GGAAAGGACA
33401  AGTGGAAGGG TAGCAGGCCC CAATTCTGCA CACTGGAGAG CACCTCTGAA
33451  ATCCTGCCGG AGACTATGCC CATAGAGGTG CCAGAGGCCC TAGGGAATGA
33501  TGATTTATTT TGTATTTTGT ATTTTTGTGG AGACAGGGTC TTACAATATT
33551  GCCCAGGCTG GTCTCAAATC CTAGGCTCAA GTGATCCTCC CACCTGGGTT
33601  CCCAGAGTGT TGGGATTGCA GACATGAGCC GTGGCGCCCG GCTGGGAATG
33651  ATTTAAAAGT CGGCACCAGC ATTCTAGCCC TGACCCAGGC TAAAAGGGGT
33701  CACATGGAGC AGAGCTGTGC AAAGAGCTTT TGGGTGAGGA GTCACTCCGA
33751  GAAAAGCGAG AAGACTCTGA CCCCGAGACT TCCCGTGGTG AGTTAGGAAA
33801  GCATTTCTGG AGAGCCTGTT AGGTGCCAGG CACTGTGGCT GGGCACTGAA
33851  GACACGAAGT GATTTAGTCT TGGAAATTCC CTTATGCTGC TCTCAGTCTG
33901  TGTAATAGTG AACAAGACAG CCAACAAGAG TTGTGAAGGA GGCCGTTCAG
33951  CAAGCAATGA AGTGCTAGTG CAGGAAGGCC CGAGCTGGGA AATGTCCGGA
34001  GAGACCCTGT GAAGTGATGC AGGGATCAGG AAAGCTTCCT GGTGGAAGCA
34051  ATGTCTGAGC TGAGGCTCAC CACAAAGAGG AATGGGAGTG ACTGCTAGAG
34101  GGAAAGTGTT CCAGGCAGTG GAAAGCTGTG GCCAAGACCT GGGGGGGTCT
34151  GAGAGGCCAT TGTACATTTG AAGACAGGTG GCTGGAACCC AGAGTGAGAC
34201  TCTAGGAAGG GAAGAGAGTT AGTCTGGAGC TGCAGGCAGG GAAGGGGAGA
34251  CAGCCAGCTC ATAATACAGT GTGGGCAAAA ATCCAGAAAC CATGTGGATC
34301  TAATTTGATA TCAATTTTAC ATGTATATGT GTATATACCT ACACACACAT
34351  ACATAAAATC AGTTATGTTT GTGTGTGTGT ATATGCATAT TTGTGTGTGT
34401  GTGTACGTGC GTGCATACAG AAAGTTGTTT TTTTAAGGCA TGCTTTAAAT
34451  ACGAAGCCAT CACTTCCTTT TCCCAGTCCT GGGTGCCTTT TGAGATGAGT
```

FIGURE 3A-15

```
34501 GTTGGTGCTC CCCCCACCGC CATGTGCCAT CTTCTGGAGT AAGAGGGAGT
34551 GCTTTCACTG TGTGCAGGTG TGGCTAAAGA GTATTCACTG TGTGCAGGTG
34601 TGGGTGAAGA GTATTCACCG TGTGCAGGTG TGGCTGAAGA GTATTCACCG
34651 TGTGCAGGTG TGGCTGAAGA GTATTCACTG TGTGCAGGTG TGGCTGAAGA
34701 GTATTCACTG TGTGCAGGTG TGGGTGAAGA GTATTCACTG TGTGCACGTG
34751 TGGCTGAAGA GTATTCACTG TGTGCAGGTG TGGGTGAAGA GTATTCACTG
34801 TGTGCAGGTG TGGGTGAAGA GTATTCACTG TGTGCAGGTG TGGGTGAAGA
34851 GTATTCACAG TGTGCAGGTG TGGGTGAAGA GTATTCACTG TGTGCAGGTG
34901 TGGGTGAAGA GTATTCACTG TGTGCAGGTG TGGGTGAAGA GTATTCACAG
34951 TGTGCAGGTG TGGGTGAAGA GTATTCACTG TGTGCAGGTG TGGGTGAAGA
35001 GTATTCACTG TGTGCAGGTG TGGGTGAAGA GTATTCACTG TGTGCAGGTG
35051 TGGGTGAAGA GTAGGCTGTC CAGGATTTCA ATCCTTGGCT TTTGCTCTGC
35101 AGCAAGGGCT GGCTGAGGGC ACTGTGAGGC TTCTTCAGGC CCAGGAGTCA
35151 GGCCCACTTT CCCTTTTCTC TTGAGGGAAT GACTCAGAGA ACACTCCTGC
35201 CACCGGAGGT TCTGCAGGCT TTTGAGAGGC AGCCAGTGGA GGCTGATGGT
35251 AGCAGTTGGT GAGAAAGAGG AAGTATGTAG TGGCCATTCC TCCGGCCACT
35301 CCTGACAAAT ATTTCTGTCA CTAAACAGCA CCTCTCTGTG GCAGCCTTGG
35351 GCTGTGTTCT GGAAAGGGAG GAGCTTTCCT CTCCCTGTGG GAGGGCCTGT
35401 CATCTGTGGC TTCTGCTTTG CCCTTGGCCA CAGACTAGAT TGCACAACAC
35451 AGCCAATGAG AGTCCCTCTT CCCTCACAAG TGCTTGGAGT GCAGACCTTA
35501 ACTTACAGGG TTGTAGAAGT GACCGTGTTC CACACTGCAG GGTCCAGGTC
35551 ACAGCCGGCA AAGCACATGA AAATTGACCT AAGGTTAGAA TGTGATTATC
35601 CTACTGGGAA AGGTTTACTG GGACAGCATT TCACTTCTGA CTCCATAGGC
35651 TGTCGTCTCC TGCCAGGGAG TGAGTTTTGT TTCCATGCTT GTCCAGTCTT
35701 TACTGCTTTC CCAGAGGCCA TAAACCTGCC TTTTCCCAGA GGCCATAAAC
35751 CTGCCCACCT CCTGCTATGT TCTAGTTCTG ATAGGAGTAC CATTCAGAGT
35801 TCTTGGCAGG GGACCAACCC GCTTCTACCG TGGTTGGTTT CCCCTCCTTT
35851 TCCCAGCTTG TTTGATGTGC ACGTTCTCCA AAATTCTTAT GCAGCTGGTT
35901 GGCTCTGTAG TGCCCAGAGA TTGGAGCTCC TGCAACGGGA ACCCCGCCGC
35951 TTCCCTCCCT GGTTTTAGGG GCAGGGCTTG AAAATAAAGA ATCATAATCT
36001 CCCTTCCTCC TCCTCCTCCT CTCCCCCACT TCTCCCTGCC CCCACCCCCA
36051 CCCCCACCCC CACCCTGCCA GGCAAACTGG AGTGACCAGC TCAGAGCGGG
36101 ACTCAGTCCA CCTCCCTGCT CTGCATGTCA GCAGTGATCT GGAGGAGATT
36151 CCGGGGCGCA TGAGTATGTG AACTCTGGAG CACGTTACTG TCCCGGGCTG
36201 GCACTCTGTG GCAGGTGTGT GCACTCATTC TGCTGTTACT GGAGACCAGT
36251 CTCCTTAGGG GTGATGGTGA CCCAGCTAGA TGTCTGCCAG GTCTGTCCAA
36301 GGCCACCCTG TTCTCTAATA GCTTGGGAAA TGGAAAGCAC TTCTAAATAC
36351 CCCTGCTCTT CAGAAGAGCT GGCTGGGTGG TTTGGGGAGT TTCTTCTTTG
36401 AATCTCTTAG AGTACAATAT CCCTTTTTTC CCGAAAGCCA GGTTCTTTAG
36451 TTCCTAAGCT CCATTCTCTT GTTGCTAACT TACTACCTTC AGTTTTCTTA
36501 GGTTGGGTGC ATCTTCCCTG GCCTCAACAA GACAGTGGCT GAAAGGTCAA
36551 GAGAGTGGTA GCTGCTCCTT TGAGAGAAAG GGGATGTTGG AGTGGGAGCA
36601 CAGGCTGCCA GCAGTTGTTT CACCTTCCCC CTTTGGCTGG CTAGGAAAGG
36651 GGCACCACTT TAGTCTTCTG CCAACCTCCA CAGCCAGCTG TGGGAAAACC
36701 CAAAAGGAAA CATCCTCTCG CTGCTAAGAC TTGAGAGCCT GAGGCAGAGA
36751 CCAGCCAGTA GCAGCCCGAC CCTGCTGAAT GGGGAGGATT GTTTATTTTA
```

FIGURE 3A-16

36801 TTTTATTTTT TTCTGAGACG GAGTCTTGCT CTGTTGCTCA TGCTGGAGTG
36851 CAGTGGCGCG ATCTCGGCTC GCTGCAACCT CCACACCCCA GATTAAAGCG
36901 ATTCTTCTGC CTCAGCCTCC CGAGTAGCTG AGACTGCAGG CATGCGCCAC
36951 CACGCCCAGC TAATTTTTGT ATTTTTAATA AGAGACAGAG CTTCACCATG
37001 TTGGCCAGGC TGGTCTTGAA CTCCCGAACT CAGGTGATCC GCCTGCCTCG
37051 GCCTCCCGAG GGACTGGGAT TACAGGCATG AGCTACTGTG CCCAGCCTGA
37101 AGATTGGTTA TTTAGGGGCT GTGACAAATG GTTTTGCAGA GGAGCACTGG
37151 AAAGCCTGTA ACTTCACAGA GCCAGGGGTC AGCTTTTGTG CCATAGCCTT
37201 ATAGCTTCTG TGGCCTGTAG TGCCTGAGGC CAGGGGATCA GGTGCTGACC
37251 ACCTTTCCCT CTTCCTTCCT GTGTCTTGCG GCCAGCGACT GTTATTGTCA
37301 GGTTGACCCT CTGGTTAGAG AGGATGACTT TGGCCTGGTG TCCAGACTCC
37351 CTGCTGCCTT ATCCCCTCTG CCCTGGAACT GCACCTAAAA ACAATTACTT
37401 TCCTCCTGAT TCCAACATAA GTGGTCACAG AAAGTTCTGT TTTGGCATTT
37451 TGATTTCTGA TTGGGAGTTT AGGCATCTGA GAATTGAATG CTTGCTTTAT
37501 ACAAATATAC CCTTAAGACA TCTCCTCTTT TTTCAGCCCT ACATGCTTTG
37551 CTTGGGTATT AATTGAACTT GGGGCTTTTT AGGGACCTTA TGTTGCCTAC
37601 CTTCCTAGTT TCCCCTCCAC TCCACCCCCA AAAAACCCAA AGAACATTGG
37651 AAAAATTGAG CAGTGCCTCA AGGTCACTTG ATCATAAGTG GTATTTGGCA
37701 TAGTTAACTG GTTTGGTGTT TGGTGAGAGA TTTCTGCTTT ATATTTGAGC
37751 AAAAAATTTC TTGGCGGGAG GCCTCTATGC TGTGTTGCCA ATGCTTGCCC
37801 TGTGCGCAGG GTTTGCCCCC TCCCCTCCCT TGACAGGTTG TTCTAATCCC
37851 CTTGTCTATA AACAAGTGCA GCAGAACTTG TCGGCCCAGC TCACATGACC
37901 TTGGTTATCT CTTTAACCAG CATCAGCGTT AGATACCACG GTCACTTGAC
37951 ATGGTAGAGC TGTCAGGGTA GAGTGGAGAT ACCAGCAGGA ATCCTGGTCC
38001 ACGAAGAAAG GTAAATGGGA GTGTGTGTGA GGCCTTAGGA CTGGGTGGGA
38051 AAAGTCTGTT CCCATGGGGT AGGGCTTTCA GCTGTGAGAA GAGGATAATT
38101 TCATTCCTTC TCCTTTTTTA AGAGACTGTC TCACTCTGTC GCCCAGGCTG
38151 GAGTGCAGTG GTCTAATCAA GGCTCACTGC AGCCTCAACT TCCTTAGCTC
38201 AAGCAATCCT CCTGCCTCAG CCTCCTGAGT AGCTGGGACC ACAGGTGCAT
38251 GCCACCATGC CCAGCTAATT TTTTTTTTTT TTTTTTTTTG AGGTAGAGTC
38301 TCACTCTGTC ACCCAGGCTT AAGTGCAGTG GTGCGATCTC GGCTCACTAC
38351 AGCCTCAGCC TCCCAGGTTC AAGCGATTCT CCTGCCTCAG CCTCTTGAGT
38401 ACCTGGGATT ACAAGTGTGT GCCACCATGC CCAGCTAATT TTTATATTTT
38451 TAGTAGAGAT GGGGTTACAC CATGTTGTTC AGGCTGGTCT GAAACTCCTG
38501 ACCTCGTGAT CCGCCCACCT CAGCCTCCCA AAGTTGTTGG GATTACAGGC
38551 GTGAGCCACC ACGCCCAGCT AATTTTTCTT TGTTGAGATG GGGAATCTCA
38601 TTATGTGGCC TAGGCTGGTC TCGAACTCCT TGCCTCAAAT GATCCGCCTA
38651 CCTCAGCCTC CCAAAGTGCT GGGATTACAG GTGTGAGACA CTGTGGCCAA
38701 CTTTCATTCC TTCTTTATCA CCCTAAAATT TCTAGTTCTG GCGTCTTGTT
38751 TATCTTTCTC AAATCCTGTC TGCAGGGGCC CAGGACATGC AGCTGTTTCA
38801 GGAAACCGCC CTTGAGATGG GGCAGATGTA TGCTAGTTCA TGGGCTATAA
38851 AACTCAACAC CAAAAATCCC ATCGTCCTAA ACAGTGACCT GTTATGTTGT
38901 GTGAAGGACA GTGGCGATGG GGGCCTGGCC GCCAGAGAGG CTGCTGGATT
38951 CTATGGCAGA CACACTCAGG AGCTGGAAGT GTGGCTAAGC TTTCAGCAGC
39001 ACCATCACTT CCCTCCCCAT ACACATGCAC ACAGGTTTCC TTTGTCTCAC
39051 AGCTGAAGAG GCAGCGCCCA GCTTCAGTAA GCACTGTGTA TGAGAATGGA

FIGURE 3A-17

```
39101 CTTACTCTGG CCACACTGTG CACACGCATG TGTGTGTAAA ACACTGATCA
39151 CATTTCCCAT AAAGACTGTT GATTTGCAGA GTTTCCAGGC CCATACATCT
39201 AGGGCGGGAT GTGTGTGTTT TCATCAGGGG AGAGTAGAGT GGCCTTTTGT
39251 GGAAGGGATA AAATGGTTGA GCTGCTGGAG ACTTTTCTAG CTCCATTTAT
39301 ACAGCAGCCT TTCTGCCTGG GTGCAGACTT GAACCCAAGT CCAAGTTCAA
39351 GCCATGTGTG TAGATGACCA GAACTTAGCC TTCAAACTTA GCCTTCAACT
39401 TCAGGACTCT CCTGGAGAAA ACATCCATCT CCTTTTGGAG ATACAGAGAA
39451 TTCGTGATGA GCTTTGAGTA CAGAAGTTCA AGTTATATTT TCTGGCAACC
39501 TACAGAATAA GTTGGGAAAG GATATGTAAT TATAGAAATA ACCAGCATGT
39551 CGCCAGGCAT TGTTGTCCGT GCTTTAGATG GTGTGGATAT TTTGTAATTT
39601 CTGATTCTTT ACCTACTGTT TTCAAGACTT GGTAGGGACC CCGTTATGGC
39651 TGTGGGGTTC TTTGTCCTTG GTAGTTAGCA TGAACTATGT AGAGCAACAG
39701 AATGGGTAGC CGTGGCCTCT GGCCACCCAG CTAAATTCTA CTGATGAGAG
39751 GTATCCTGGG TGGGTTTCTT CTTTGGGTCT TCGTTTATGC CGCCATTCCT
39801 ATTGCCAGTT AGAGCTGCCT TTTAGGATTT GTTGGGTAGG AGCTGTATTC
39851 CTCTTGGAGC CATCTTTTCT TCCCTGCCAT CTCTGAGTGA ATTCAGAGGT
39901 GGAGAGCTAC AGACTTGGCT GCTTGCCTCC TTCAAAACAC CCAGCATTCC
39951 CTTGTCCACA GTCTGTGTAG CAGCACATCT AACAATGCCC AAAAGCGGCC
40001 CCCTTCCTCC CAGCCACTTG TTAATGGGTG GTTCTGGTTC CTGAGGGCTT
40051 CGACCAGTGC ACGAGCTAAT CTCACTGAAG AGTGCCATTC CCAGGTTCAT
40101 ACCACAGAAG TTAGAAAGCT CAAAGCCCAG GTCTTCTGCA CCGAAGAGTG
40151 CCATTCCCAG GTTCATACCA CAGAGGTTAG AAAGCTCAAA GCCCAGGTCT
40201 TCTGCTGCCT TGGGCCATTC CCTTCTCTTA GAAACCAGTT CAATCAGACT
40251 CTTTTTTTTT TTTTTTTTTT TTTTTTTGA GACGGAGTCT TGCTCTGTCA
40301 ACGAGGCTGG AGTGCAGTGG CATGATTTCG GCTCACTGCA GCCTCGACCT
40351 CCCCAGGCAC AGGTGATCCT CCCACCTGGG CCTCCTGAGT ACCTGGGACT
40401 ACAGGTGCCC ACCACCACGC CTGGCTGATT TTTGTATTTT TAGTAGAGAT
40451 GGGGTTTCAT CATGTTGGCC AGTCTGGTCT CGAACGCCTG ACTTCAAGTG
40501 ATCCGCCCGC CTCAGCCTCC CAGAGTGCTG GGATTACAGG CGTGAGCCAC
40551 TGCACCCAGC CCAGACTCTT TTCATAGGAT GCTGAAAGGA TGAATTAAGT
40601 ATAAAAAGTG CCTTTTGGCC AGATGCAGTG GCTCATGCCT ATCACTTGAG
40651 AGGAGCTTGG GCAACATGGT GAAACCCCAT CTCTACAAAA AATACAAAAA
40701 TTAGTTGGGC ATGGTGGTGG GCACCTGTAG TCCCAGCTAC TCAGAAGGCT
40751 GAGGTGGGAG GATCACCTGA GCCTGGGGAG GTCGAGGCTG TAGTGAGCCA
40801 AGATCGCGCC ACTGCACTCC AGCATGGTGA CAGAGACCCT GTCTCAAAAA
40851 AAAAGTGCTT TTTAATAAGG TACACGTAAT GGAAAATGGC TGTCATCTGG
40901 TTTGCCATAC TCTGCTCCTA GGTAGAAAGT ACAAACAGCA AGGGCCCCTT
40951 GGAGCAAAAT TGTCATTGCC GCCAGTGAAT AAACAGCAGT GGTTGGCTTT
41001 GAGGGGCACC TTCAGCCTAA AGCCATAAGC TGACATATAC TCAGTCTCAC
41051 TGAGAAGCTC GGGCTTTCCA CTGTTCACCT AACTGCTGAC AAATGAATCC
41101 TCCATTGATC TGGCAAGCTG GCCAGGATAC CTGCCCAGGC CATGGCCACT
41151 TAGTAACAGG ATCCGGTTCT CAGTGCAGGG TTGAGACTGC AGCAGCAGTG
41201 GCAAGCCCAG TAAGGCAGGT ATGAAGCACA GCCCCCGCAT CGGTTGCCTA
41251 GTAGGGAAGA CAGTTGTAAA GAGCATTTGC CCCTGTTATG TCAGGGTACT
41301 GTTGCAGGTT GTCTTTTCTC CTCTAGCTGG AAGTTGTTCT ACCCAGTCTT
41351 CCTTAATTAG CTCTTCTTTT GTGTAAGGCA GCACCCATTT AAAATTCTTT
```

FIGURE 3A-18

```
41401 TCCTCCAGCC TCATTCCTCA TCTCCATTTG GGTTTATATC TCCTCAGAAC
41451 CTCTCTCCTA CCCAGCCTTA AGCTCTACCC CAAATGCTTT GAAGCTCTCT
41501 TGTTCAAGTC TTTTTTTTTT TTTTTTTTTT TTTTGAGAC AGAGTCTCTC
41551 TCGCTCTGTC GCCTAGGCTG GAGTCAGTGG CACGATCTCG GCTCACTGCA
41601 AGCTCCGCCT CCTGGGTTCA CGCCATTCTC CTGCCTCAGC CTCCCGAGTA
41651 GCTGAGACTA CAGGTGCCCA CCACCACGCC CGGCTAATTT TTTGTTTTTT
41701 TAGTAGAGAC AGGATTTCAC CGTGTTAGCC AGGATGGTCT CGATCTCCTG
41751 ACCTCGTGAT CCACCTGCCT CGGTCTCCCA AAGTGCTGGG ATTACAGGAG
41801 TGAGCCACCG CACCTGGCTC AAGTCTTCTT GATTCAAGCC CTCACCCAGA
41851 GCTTGAAGAC TAGGGAGCCC CCGTGTCTGC TGCCCATGGT GCTTGGAGAG
41901 CAAAGATCTG TTCCCGGGTC CTGAGTTGGA ACTCTGAATT CATTTCCTGT
41951 TCTGGGCTAT GGTTTAAGTC TTAAGTACAA TTCACGTACC CCTTGAAATA
42001 CTATGCTGGG ACCTCATGGG CTGGCCTGAG AACACAGCTA CCATTTGTAA
42051 CATGTTTCTA TGGAAAAAGA GTTCCTTCTT AGAACAGAAC TTTTGGTAAC
42101 TTGGGGATTT CTTGACTAAT ATGCTGCAAC AGATTTGCAT TTGCCTGTGG
42151 AAGTGTCTCT TTATTTTGTA TTCAGCTGGG CACGGTGACT CACGCCTGTA
42201 ATCCCAGCAC TTTGGGAGGC CGAGGCAGGC AGATCACTTG AGGACAGGAG
42251 TTTGAGACCA GCCTGGCCAA CATGGTAAAA CCCCATCTCT ACTAAAAATA
42301 CAAAAAAATA ATCTGGGCCT GGTGGTGAGC GCCTGTACTC CCAGCTACTC
42351 TGGAGGCTGA GGCAGGAGAA TCACTTGAAC CCAGGAGGTA GAGGTTGCAG
42401 TGAGCTGAGA TGACACCACT GCACTCCAGC CTGGGCGATA GAGTGAGACT
42451 CTGTCTCAAA AAAAAAACAT TTAAAAAATC ACATTTTGTG GTCATGGCAC
42501 TATCTATCAC ACAAGTAAGT TGTCCTCCTA TATGCCAAAT GACAGAAAAG
42551 AAGCACCCTC CTCTTCCCAC CCAGAAAGGT TGCTAGAGAG CTACCCTTGT
42601 CTTCTGTGAT TGCCTTGAGG GGCAGGTTTG TCTGGGTTCT CCATGTCAGC
42651 TGATTTGATC CATAGTCCAG TAGCACCTGA AACAGGATGC CCTCATTCCA
42701 CAACTTAGGT GCCCTCTCCT GCTTGGTTTT TTAATGATCT GCTACAGGAG
42751 AAAGATAGCA CCTCTCCCTT CAGCAGGAGC AGCCCAGTAA GGGCTTGCTT
42801 CTAGAAAGAT TGGCCAGTTG GATTTTTAGT GGTCACTTAA GTGGAGTAGC
42851 CACTTTGCAG CCTGGCCCAA CAGGGAGACA GTTCTGAGGT GAGGGTGGCA
42901 GTGACAGCCT TGGGGTGGTT TCTGATGTGC TCTGACCTCT GGCCATGGTG
42951 ACTTCTGGAG CAACAAACTT TGTCCCAGTA TTTTTTTCTG ACATTTCCTC
43001 CTCCTTATTC AACTCCCTCT TTGAAACTGG AGGAGTAGGG AGGCAGTATT
43051 TGTTCACTTC CAGAGAAAGA TGCAGCAGGA AGAGGCATAT GTCTTGTTCT
43101 GCACTTTCCA GCAGCAATGC TGGGACTAGG GGGTCTAGAA GGCCTGTTTC
43151 CCAGCTCCAG GCTGGATCTT ATCCTCAGCA TACAAGCAAG TTTTAAGGAA
43201 ACAACATTGG AAAGGGCAGA AACAAAGGGT TAAATCTGTA CCCAGGTAGA
43251 AAGACTGTTG CATAAATGCT GAGTTTTTTT TTTGTTTTTT TTTTTAAGAT
43301 CTCATGCTTC TTTTTTACTT TGTGTTGGCA AAAACCCCAG GAGAAGATGG
43351 GAGATTCTGG GAGGAGATGA TTATGCTGGG TGAGTCAACT GAGCTCCCCA
43401 GCTGCCGTTT TTAGTTCTTT TGCTTTTCTG TAACAGGAGG CAGTTTGGGG
43451 AGGGGTTGGG GGCAGGGTGG GAATGCTGAT TTTTGCAGCA GGACAGGAGG
43501 CAGGTGTGTA TGGGTGAAAT TATTTTGACA CCCTAGAGTT AACCGGGCCT
43551 TAGAGTCAGT ACATTGGTTC AAGTAACAAA TATCAAAGCA GAACTCTTAG
43601 TGTGGCAAAC AATAAATAAT TGTCTCCTAG ATTCTTATAC AAGTCACTGT
43651 CCGTCCCCAA TTGGTAGCTC TTAGAATGGC TCGAGTTGCA TTCATTGTCA
```

FIGURE 3A-19

```
43701 CAGCAAGACA CAATGGTTTT GATAGCAAAG CAGTAGAGAA ACTAAATGTA
43751 GAGAGGCAGA GAGAACTGTA TTAAGTCTGA GGACCTGGTG GTTGTCATGG
43801 GCAGCAGGAA GTGTGAAGGA GAGGGTTTTC CCTCCGATGA AAGGAAGGCT
43851 AGGGCTTGAT TCAGGGGAGC AAGTGGGATG GGCCCTGCTG GTCCCTGGCT
43901 GTGCCTATAT TCTGAGTCTG TCTCCAGCTC ACCTTGGTGA TCACTCACTT
43951 TTCATCCATC ACTGGGATAG GGATCTCGT GGCTCATTAC CCTCATGGGT
44001 ATTTTTTGCA GAGTACACTG AAGTGGGCTA TCAGTTATCA GTTGGTCCCA
44051 GAGACCGTCA TGAAGACATC GCAAATGTT TTCTTATGTA TTCATTTGTG
44101 CACATTTATT AATTCAGTAC TTTACTGAAT ACTGTGCTGG GCATTGTTCT
44151 GGGCCATGAA TAAGACAGAC CTGGCCTGGT GCAGTGGCTC ACGCCTGTAA
44201 TCCCAGCACT TTGGGAGGCC AAGGCAGGCA GATCACCTGA GGTCAGGAGT
44251 TCGAGACCAG CCTGGCCAAC ATGGTGAAAT CCCGTCTACT AAAAAAAAAA
44301 AACAAATTAG CCAGGCATGG TGGTGGGCAC CTGTAATCCC AGCTACTTGG
44351 GAGGCTGAGG CAGGAGAATC GCTTGAACTC GGGAGGCAGA GGTTGCAGTC
44401 AGCCGAGATC ACGCCACTGC ACTCCAGCCT GGATGGCCAG AGAGAAACTC
44451 TGTCTCAAAA AAAAATACCA AGGTCCCTCC TTTTGTAGTG TAGTCTAGCA
44501 GGAAGGACAG ATAGTAACCA ACCAACTTCA AGGGCAACGA ATGCCTCGAA
44551 AGAGGGGAAA TGGGGCTGGT AGCAAGAAAT TGTGATCTTC CTTCCTCTAC
44601 CCTTATCTCT TGGGGTCGAG AGTGGGGTCG AGAGTGGGCA ACTTTAAAGA
44651 TCAAAAGTT GTGCCTCTCT TGTTCCCTAA GTATTGTAAC ATGGGTCAGC
44701 TAGGTGTGGG CACTGTTGGG CACTGAGGGT ATATGAAGGT GAGGGAGATA
44751 CTGGCTCTCA TCTGTCAGAG CATGAGGGGG TTAAGGTATG GGACACAAA
44801 CAAGAAATCA ATGGGGCTGG GTGTGGTGGC TCACGCCTGT AATCCCAGCA
44851 CTTTGGGAGG CTGAGGCAGG AAGATTGCTT GAGCCTAGGA GTTTGAGGCC
44901 AGCCTGGGCA AGATGGCAAG ATGCCATCTC TACAAAAAAA ATGAAATAAA
44951 TAAAAAACTA GCCAGGCATA GTGGCACACA CCTGTAGTCC CAACTATTCG
45001 AGAGGCTGAA GCAGGAGAAT CCCTTGAACC CAGGAGTTTG AGGATGCAGT
45051 GAGCTGTGAT TGTGCCATTG CAGTCCAGCC TGGGCAAGAG AGCAAGACTT
45101 CATCTCACAA AAGAAGAAGA AATGAAGAGT ACAGATAGAG CGCTGAGAGT
45151 CTAGAGAAGT GAGTCTAGAG AAGTGAGTGA CCACTCCCCG CTAAGACGGT
45201 GTCTGGATTT GAGATAAACA ACGGATAAGA GGACTTACCT GGATCACAGG
45251 AAGGCGCATA GGATAGATGA CCACTTTCCT TTTAGTATGT GTAGATCTGG
45301 GTAGCTCTTT GTACCACAAT TCTGACCCAT TCTTTTTTCT TATTATTTTT
45351 ATTTATTTAT TCAAAATAAT AATTTTTTTT TTGAGACAGT CTTGCTCTGA
45401 GCCACCATGC CCAGCCTGAA ATAATAAAAG TTTTAATCTT TTAAAAAATA
45451 TGGGCCAGGC TTAGTGGCTC ACACCTGTAA TCCCAGCACT TTGGGAGGCC
45501 GAGCTGGGCG GATCACCTGA GATCAGGAGT TCGAGACTAG CCTGACCAAC
45551 GTGGAGAAAC CCTGTCTCTA CTAAAAATAC AAAATTAGCC GGGCATGGTG
45601 GCGCATACCT GTAATCCCAG TTACTTGGGA GGCTGAGGCA GGAGAATCAC
45651 TTGAACCCG GGAGGCGGAG GTTGCAGTGA GCCGAGATCA CGCCATTGCA
45701 TTCCAGCCTG GCAACAGGA GCGAAACTCT GTCTCAAAAA AAAAAGGAAT
45751 GCTTCACAAA TTTGTGTGTC ATCCTTGCAC AGGGGCCATG CTAATCTTCT
45801 CTTTATTGTT CCATTTTTTT GTATATGTGC ATGTACAGAG TAGTGGAGCT
45851 GGGTTATCAC TACAGTCTAA CTCCAGAATG ACACCCTTCA CTACTATACC
45901 ATATATGGTG CCCCAGTATA CAGCAGTGGA GCTAGGAAGA AAAGCCCAGT
45951 GTCTAGAGAG CCCAGAAAAT ATGCCAAGAA CATATATACT AGGCAAAGAA
```

FIGURE 3A-20

```
46001 AACGAGGTTA GGAGGAAGCC CAGCCACCTC AGCTGCACTG GTTAGGATCT
46051 GCTGCCTCCC CACAGTCCTC TGTAAAGTGA GCCAGACCTC TATGCTGCAG
46101 GCTTCCTTCT GCCTACCCCC ACCACCCCCA TCCCCCAGAG CCCTGGGCTA
46151 CTGGCAGGCT GGCTCTCCTG TGATATGGAG GAACTTGTTG GTCTCCATGG
46201 TTACGGTAAC CCACTGGTAT GGGAGGAACC GCATAAAGTG CGAGGCTGGC
46251 AGTGTGAGCT TCCCTCAGCC CTTGGCACCA TGTGGTACTG GTATGTCGGC
46301 TGTTTCATGG ACCTTTTCTG GGAGGAGGGA GTTAAGGAAC TGATGAAGAA
46351 GGGAAGAACC CTGGCAGGAC CACTGTCGTC ATCCTCTGGG CCACACAGAG
46401 GGCGAAGGCA TGGGCACCAT GTCATTCAGC TACTCCTCCT GCAGGATGGT
46451 TTTATGTTAG GAAAGAGGGT CCTCTTTGCC TGATTGCCCA GCCATGGCAG
46501 AATTTGACTT TTCCTTGTTA TAGAGGGAAT ACCAGGATGA CAGGAATCAA
46551 CTTAGCTATA CTGGTACTTA CAGTCAAATT TCTAGGTATT GTAGCTCTTC
46601 CCAGAGCCCA GAGAACCCTT GGAGAGGGGA AACAATGGTT CCTACCCAAA
46651 AATGAAGCTA GATAATAATA GAATACATCA TCAAGACATT ACTGAACACC
46701 ACGTTCTATG GTAAACACTG ACATGGATTT TCCTTTTTTT TTTCCTTTGA
46751 GACAGGGTCT TACTCTGTCA CCCAGGCTGG AGTGCAGCAG TGTGATCACG
46801 GCTCACTGCA GCCTCAGCCT ACCTCCCTGG GCTCAGGTGA TCCTTCCACC
46851 TCAGCCTCCC AAGTAGCTGG GATTGCAGGC ACTTGTCACC ACACCCCGGC
46901 TAATTTTTGT GTTTTTTTGT AGAGCCTGTG TTTTGCCATG TTGCCCAGGC
46951 TGGCCTCGAG TTCCTAGGCT CAAGGGATCT GCCTGTCTTG GCCTCCCAAA
47001 GTGCTGGAAT CAGAGGTGTA AGCCACCACG CCCGGCCAGA TTTTCTCATT
47051 TAATCTTCAC TCTAATTCTG TGAAATGGGT ACAGCTAGTA TCTTTATGTC
47101 CCAAATGAGG AAACAGATTT GGAGAAGTTA TGTCACTTTG CTCATGTTCA
47151 GTCAGCTGGT AAGCAACAGA GGTGGGCAGA GCGACTATAG TAAGTTTTCT
47201 GTATAGTTTA CCTCTTCTAA GTTTCTGGAA GGCAGGAGCC AGATCGCACT
47251 GAGCTTTGCA ACTGGAGCCA GGGCTCCAGA GTACTGCTCA ACAAAGGTTT
47301 GCTAGGGCAA CAGTAGCTGG GGATTTAGCG ACCAGACCCC AGCAAGCAGA
47351 TTCTCAGGGA TGAAAGTAGT CCTGGAAGCC TCTAAAGCCC TGGTTGCTCA
47401 GTAGAATCTA GTTTCAAGAG GAGCCCAGCA TTTCAAGTGG CTCTGAAGAC
47451 AGAGGAGATT TGGAGAGTGC TCTTTGCATT GTGGCTTCCA GGCCTGAAGG
47501 AGAGTGAGCT GGAGGTTGCT CTCTGTTCTC ACCTCTTATG CCATGTCAGG
47551 TTTTTCCCAG GCAGGCTTGA GTCCTGGGGG AGCCCCGCCT CATGGCCCAG
47601 GCTGCAGTGC TGATCTCCCT GCCTTGTGGT GAGGATTGCA GCTCAGAGAG
47651 CTAAAGGGCA GTAAACCACC TTGGTTTTGG CTTTGTGCTT AAGTTGCAGG
47701 CTCTTCTGGT TATCCTTTGT GAAGGAGGCT CTTACCCTGG CTGGAAAGAG
47751 GGAGCAGCCC CTGCCTCCCA TCTACAATGG GACAGTAAAG GAATATGGCT
47801 GTTTCTCAAG TGGAACAGTC ACAGTTAATT TTGGGGGTGG GAGCATCCAG
47851 GCTTTCCACT GGTGAGTGCC TGCCAGTTTT ACAAGCTCTC CTACACTGAA
47901 TGCTCCTCTG GTTTATTGAC TCTTGGCAGT TGATAGCGAT AGTTGCTCAT
47951 GGCAGTTGAT AGCGATAGTT GCTCAGAATC AAAGGATGAA AAGACAGTTT
48001 CTGGATACAG TGAGGGAGGA AGGGTTAAAA AACAAAGGAC TCCAACTCCC
48051 AGTTACGAGA TGTCCCATAT GGCCATGCGC AGTGGCTCAC TCCTGTGATC
48101 CCAGCACTTT AGGAGGCCGA GGTGAGAGGA TTGCTTGAGC CCAGGGAGTT
48151 CGAGACCAGC CTGGGCAACA TGGAGAAATC CTGTCTGTAC AAAAAATACA
48201 AAAATTAGCC GGGCTTGGTG GCCCATGCCT GTAGCCCCAG GTATTCAAGA
48251 GGAAGATCAC TTGAGCCCAG GAGGCGAAGA TTGCAGTGAG CCAAGATCGT
```

FIGURE 3A-21

48301 ACCACTGCAC TCCAGCCCGG GCAACAGAGC AAGACCCTGT TTAAAAATAA
48351 ATAAATAAAT AGGGACTTGC CACAGGCACA TGACCTTTCT TAAGAGACAA
48401 AGTCTTGTGC TGGGAATGGT AGCTCATGTC TATAATCCCA GCACTTTGGG
48451 AGGCCAAGGT GGGCAGTTCA CTTGAATTGT TGAGTTCAGT ACCAGCCTGG
48501 ACAAGCTTGC AAAACCCTAT CTCTACAAAA AATACAAAAA TTAGCCGGGC
48551 GTATTGCTGT GGGCCTATAG TTGCAGCTAT TCGGGAGGCT GAGGTGGGAG
48601 GATGGATTGA GCCCAGGAGG CAGAGGTTGT AGTGAGCCAA GATCGTGCTG
48651 CTGCACTCTA GCCTGGGTGA TAGAGTCATA CCTTGTCTTG AAAAAAAAAG
48701 AGAGGCTGGG CGTAGTGGCC CATGTCTGTA ATCCCAGCAC TTTGGGAGGC
48751 TGGGGCGGGT GGATTACTTG AGGCCAGGTG TTCAAGACTA GCCTGGCCAA
48801 GGTGGTGAAA CCCCATCTTA CTAAAAATAC AAAAATGATC TGGACGTGGT
48851 GGCACGCACC TGTAATCCCA GCTATTTGGG AGGCTCAGGC AGGAGAATCA
48901 CTGGAACACA GGAAGCGGAG GTTGCAGTGA GCCGAGATCG CACCACTGCA
48951 CTCCAGCCTG GGTGACAGAG CAAGACTCCA TCTCAAAAAA AAAAAGAGGC
49001 CGGGTGCAGT GGCTCAGACC TGTAATCCCA GCACTTTGGG AGGCCAAGGT
49051 GAGCAGATCA CAAGGCCAGG AGATCGAGAC CATCCTGGCC AACATGGTGA
49101 AACCTCGTCT CTACTAAAAA TATAAAAAAA TTAGCTGAGT GTGGTGGCGG
49151 GCGCCTGTAA TCCCAGCTAC TCGGGAGGCT GAGGCAGGAG AGTTACTTGA
49201 ACCCGGGAAG CAGAGGTTGC GGTGAGCCGA GATTGCGCCA CTGCACTCCA
49251 ACCTGGGCAA CAGAGTGAGA CTCTATCTCA AAAAAAAAAA AAAAGAGACG
49301 AGAGTCTAAT TCTGTCACCC AAGCTGGAGT GCAGTGGCAC GATCATAGCT
49351 CACTGTTACC TCCACCTCCT GGACTGAAAC GATTATCCTG CCTTAGCCTC
49401 CCGAGTAGCT GAGACTACAG ACCCATGGCA CCATGCCTGG CTAATTTTTG
49451 AATTTGGAGA GAGAGGGTCT CACTCTGTTG CCCAGGCTTG TCTCGAATTC
49501 CCAGGCGCAA GTCGTCTTCC CACCTTGGCC TCCCAAAGTG CTGGGATTAA
49551 GGCATGAGCA ACAGTGCTCA GCCCCGTGTG GCTTTTTTTT TTTGAGACAG
49601 AGTCTCACTC TGTTGCCCAG GCTGGAGTGC AGTGGTGCAA TCTCTGCTCA
49651 CTGCAACCTC CACCTCCCAG GCTCAAGCAG TTCTCATGCC TCAGCCTCCG
49701 AGTAGCTGGG ATTACAGGTG TACGCCACCA CGCTCAGCAA ATTTTTGTAT
49751 TTTTAGTGGA GATGGGGTTT CGCCATGTTG CTTAGGCTGG TCTCGAACTC
49801 CTGACCTCAA GTGATCCACC AGCCTCGGCC TCTCAAAGTG CTGGGATTAC
49851 ATGGTGGGGG CCACCATGCT TGGCCCCCAT GTGGCTTTTA ATCTAAATCC
49901 TACCCTATCT CTTCCCAGCT TTTCTGTTTG TAGTCAGTGC TTTGTATTTC
49951 CTCAGTTTAC AAAATCCCTT ACTGTCTCCC ACAAATAGGA TTGAGGAAAC
50001 AGTCCTTCTG TCACATTGCA AAGCCCTAGA AAAATGAAGG GACTAGAAAA
50051 ATGAAGCTGT TTGATCCTGC TCTGGTTCTC AGTCTACCAG TGAGTGAAGG
50101 GCCGGAGGGC CCGGGCAAGC TTGAGCCCAG GATCCAGTGG GCCCACTGAA
50151 GTCAGGGCCC ACTTTTGGGG GGCTGGGAAA AGGAAGGGTT GCTGTGGGAC
50201 CACTGGGATA GGCCTTTAAA CAGCACTTCA CCATTGGCCT GAATCAAACA
50251 TTGTCATTCC CAGTGTCCCG AGCACCTTCC CTGAGTCTTC ATACCTTCTG
50301 CCTCCTAGCT TATGGAGGAG GAGCCAGGGG CTTATCTTTT GGGGGAAATG
50351 AGAGCACGAT TAGGCATCAA GAAGGGTTGA TGAGAAACTG GTAAGGGGGA
50401 CTGTCAAGAA CAGCAGAGTG CTGAAATGGT GACAAAAGCT CTGGGCTCCG
50451 GCCCCAGCTC TGTACTGAGA AGCTGTGAGA TTTTGGGCAA GTCTCATAAC
50501 CTCTGAATGC CAATTTCTCA ATGGAAAACA GGGAGACTAC CTACCCTATA
50551 GGTCTGTGTT TGGAGAAAAC AAAGTGTAAG CGCTGGACAT ACAGTAGCAT

FIGURE 3A-22

50601 CAGAAATGCT GAATCCGTTG GCCAGGGCTC ATGTGTAAGG CAAACATTTC
50651 TTGGCCACTC CTGAGTAGCA TGGTCTTGCA GGAATATATG CTTAAGTGCT
50701 GTGAGAGCAC AGAGGAAGCT TTGCCCTTCC CTAGAGGGTT AATGGCTACC
50751 AACGTGAGAA GGTCACGGAG TTCCTTAATG AGAGGGAGCC TAGCCTAGAA
50801 TAGGGGATGA ATGAGAAATT GTTCTGAGAA CCAGAGGCAA GGCTGCAACC
50851 AGCACATAGA CAGGGGTCGT TGGTCTAGAA GGGGAGTCTT CTCCAGATGA
50901 GAGACAGCCA GCTTGCCCTG TGCTCACCAT GTGCCCAGAT AGTGGGGGCT
50951 TAGCAGGAGG AAGGTGTGAG GAATCCCAGG CCTTTGGAAT TCCTTGAGAA
51001 AGCAGTGTTG TTTTGAAGGT AAGGCAGGGG ATTGGTGACT GGAAACTTGG
51051 AGGTGAGTGA GAACCTAGGG ATGAACGTTC AGAAGCAGGG CTGGAAGGAA
51101 CTTAAAAGGG ACATTTGGAT TGTTTCTAGC TTTTGGGCAA AATCTAGGAT
51151 TAAATATGAT TTTTTCATTG ATAGAATGCT CTATCAGTGA TAAAGGCTCT
51201 TAATCTAGAA AACATACACC TCATAGGGGG CTTTACAGAG TCCCCAAACT
51251 CCCTGAAATT ATGCTCAAAA TATTTTGTGT CTAAGTGGAA TGTGCATGTT
51301 TCCAAGGTTA AGCACTGCTT TTTTAGGAAG TAGGAGGTCC GTCCGCCACT
51351 GTCAGCTTGC TGGTTTCTGC TTACCCTCCT CCCCACTTCG TTCTTGAGGG
51401 GGTGGTTTGC TGGTCTTTGG CAGGGCCGCC ACTCTGGGTC AGCACATCTG
51451 AGTCACACAT GTTCCTCCCC AGCCCTATTG GAGGCTTTGT TAAAGTCATC
51501 TGCCCCTACC CAGGTCCCAC CTGCCACAGG TGAGCTAGGG TTTTATGACA
51551 GCCGTGGCTG CAGTGAGTCT CCTCGACCTC TCGCCAGCTG TTACCCAGCA
51601 AAGCACCTTG GGGAGGGTGG GGCTGCCCAC TTCCGGGGAG GGAGGGAGGG
51651 GGAGGGGAGA AGGAAGTTGA TCTAAACCCG CCTCTTTCTC TGTCTCCCTT
51701 CCTGCCCTAT TCCCCTCCTG CCCCTTCCCT CCCACCTTGC TTCTGGTGTG
51751 CTGTCCTGGA ATTGCACGCG CTTCCTGACC ACCAGGCTCT GGCCCTTGAG
51801 AAGCCAGCGG GGCTTTGTCC CTGTTGCTCT CCTTGCCAAA CCCAGTCTCT
51851 CTGCTAGTGG TGGTTTCGGT TGCGACACCG TCCAGGTTCC CAGGCAGGAA
51901 CCGCTCGGCC TGGCTGCTTA GCTACTTTTC ACTGAGGAGG TGGTGGAAGG
51951 TGTCGCCTGC TCTGGCTGAG TAAGGGTGGC TGGCTGAGCC GGCAGCCCCC
52001 GCCCTAGGCC TGGCTCTTCC CGGCCTCTGT ACTTTGCCCT CGCTGCCTGA
52051 CAGGTTCTGC TGTGGGCTCT GCTGAATGGA AGTCGCTGGT AGTCCTTTTC
52101 CCTTTCTCCA GTCGGGTATG TTGTCCCCCT TTTTACTCTA GGATTGCCTC
52151 CTCCTCTTTC TTTCCTCTCA TCTCAAACAT AGGATCTTTA GAGAGTTGCT
52201 AAGGGGCGCC CTGCCTGAGT CCAGCATAGT AATATTCATG GAAGGGTGT
52251 CCAGATGTGG AAGAGGCATT GACTAGGAAA GGAAGAGGGG GCACATACCA
52301 GAAGGGTCTC CCCTGAGAAC AAGCAGCTTG ACAAGTGGGC GAGGAGGGGC
52351 TGGTGGGAGG CAGAGGCCTG AGGCCTCAGA GAGGATGCTC CCGTGCTACA
52401 GTGAGGGGGA GCCTAGGATC TGGGGCCATT GCCCAGGACT GGTGCCCAAG
52451 GGACACTTTT CTCCCCCAAC TCTATAGTGC CTGGCTTACT CTGCTTCTGG
52501 CCAGGGAATA TCACCCCTCC TGGTTTGGCT CCTTCTCAGC CCTCGGGAAG
52551 CCAAAGGACA CTTGAAGCCA GCCCTGAATG CAGAGCCCCA AAGCATGAGC
52601 TTCTCCATGG GACAACTGTT GGTAGGAGCC TCCAGCATTA GGGCAGGGGC
52651 CCTGCCTACC TGAGTCAGCG CCAGGCCTCT CGGGGTGGAG GCTGTCTTCC
52701 GGGCAAGCCT GACAACACAC CTAGGCCGAG TCTGAGATCC CAGGCGGAAG
52751 GGGCCTGACA GGCCCAGTGG ATGCAAAACT ATCTTTTTAT TTTCTCCTCC
52801 ATGTCCTGCC TTCTCTCTTC CTCTCAGTAG CAGACCCCAA AGCTGTTTCA
52851 GCCCTACTTC TGAATCAGGC CTGCTTAGTA ACTACTTGGT TTGCCTTTTG

FIGURE 3A-23

```
52901 GTTCCAAATA ACTGCCTTGC AGGGTGACCC CTTATTCTTT CTAAAGGCTA
52951 CTTGAGAGCC ATAGGGTCTA CTCTTGACAG ACCTCCTCCA TCCTTTAGGG
53001 CCTGTCTAGA GTATGATATA GGCCAGAGCT TTGGGAGTGC CTGGTGTGCC
53051 ACGTCTTACT ATAAGCAGGG AGGATGGTGG TAGAGGGGAG AGCGTGGCTT
53101 TTGCCAGGTC CTATTGAGTT GGCCCAGCAG GGCAGCTAAT CCTCAGCCTG
53151 CCATCCTGTT GGTGAGACCC AGGGCCAAGC TGAATGGTGC AGCCAGAACC
53201 AAAAAAGAGA AACTCTCTCT CCATATTAGC CACTGCATAC TCTTACCTCT
53251 TTATCCTTCA GGGAAGAAGC TAGGTGAGGA AGTTGCCTCA CTTGGGGCCT
53301 TGGCCCAAGA AGCATTTCTG TTGGAGACTC TCTCCTCTCT TTTCCCTTTT
53351 TCTTTTCTCT GCTTCCTTCC AGTGGCTTGC CTCCTTACCC TGGCTCACAT
53401 CCCTGCTGTG GGAAACATCT TACAGCATAG AAGAAGGGGT GCAGGGGTAA
53451 GTAAGGGAAG GATTGAGCAC TTGGAGTCCT CTGAGTTGGA TGGTTCAGTC
53501 CCGAAAAGGG GGTTGGTGAC TTTGGAGCAG GGGATCAAAG AGCAAGCACC
53551 AGTGCTTGTT GCTTCTCTGG CTCCTGAACA AGCAGAACCT CCTCTCTTTC
53601 CCTGTCCTGG ATACCCAGCG TGGGACCAGC CCTTCACAGC CACCCTGTCT
53651 TGAGTTCCTG ACTCTCCTCC TTCCCTCTTT TGAAGGCTAG AGGTGCTGGT
53701 GTCGGCTAGC AACAGGTTGA GGGAGTGTGG CATTTCACCA GGTCTGGAGG
53751 AGAGCGGGCA CTCAACCTGG CCCCTTCTGC GGAAAGGCCC GTAGCATCTC
53801 TTGTCAGCCT TCAGCTGAGC TGTAGCTGGC TTAGCGGGCT CAACTTCGAT
53851 TTGGAAGGTT GTTTTGACAG TGAGACTTCT GGATTGGCAG ACAGTAGTAT
53901 TTGGGGACAT AATGATTGCT CTTATTGAAC ATCGGATAAG GCATTTTACA
53951 TGTGCTCTTT CATCTACCTG TGTAAAGTAG GGAATGTTTA TTGCCACTTT
54001 ACAGATAAGG AAATTAAAGC TTGTACGTGG GGGAGCCAGG GCTTGAACCT
54051 GATTCTGTTG GACTGCAGAG TTCCTCGGGA TCCTCCCTGG CACAGATGTC
54101 TGGCAGTATT GGCCACTGGT CGTTTTTTGG GTAGTTCTCT TCCCCATTTG
54151 TAATAGTCTC ACCTCCTTCT TGACAATGTT GATGTTACAC TTGTTTTATT
54201 TTGGGGCTTT TTGTGTTTGT TTGTGTGTGT GTGTGTGTTT TCCTTTTTGT
54251 GAATGGGGGT CTCACTGTAT TGCCTTTTTA AATATATTCT TTTTTTTTTT
54301 TCCTTTTTGT GAACAGCAGG TCTTGAACTC TTGGGCTCAA GCTATCCTCC
54351 TGCCTCTGCC TCCCTAAGTG CTGCCTGTAA AGGCATGAGC CACTGTGCCT
54401 GGCTTGATGA TGTTGATGAT AATAATAAAG TTAATATGTG CTGAGTAGGT
54451 GACAGATTTA GGATTTGAAA CCTGGCAGCT TATCTCCGAC ATCTACAGTC
54501 TTAACCAGAA AGGAAGAGAA TGAATGGTAC AATCTTGCTT GTGGTTGTTA
54551 AGCTCCTTGA GGCCCACTTG TGCAGCAGGG CCAGGCAGGG AATGCTGACC
54601 TGCTGTGCCA CACAGACCAG CCCCTCGGTT CACCAAGAGG GATGGGCAGA
54651 GCAGAGCTCA GGATGGGCAT GGGATGCCCA GATTTGGTCT CAGTTGGCAA
54701 AAGGCCCAAG TCTGCAGGTA GATGCTAAAT CCCTGGTCTG GATTTTGAGA
54751 ACTTAGAGAC CGTCACACTT CCTGCTGCCT TGGGCTTATA TCCTCGGAGA
54801 AACAGGGAGT GACAACAAAC TTAGAAGGTG AACTAGAGGT TGCCAAGGAA
54851 ACTTTCCCAC CCATCTTCCT CTCGTAGGAG TTGGGGCAGA AGGAAGGTTT
54901 TTTCCTGTTC ATTGCCCGTT AGGCAGATGG GTAGGGTTGG AGGCAGTCTA
54951 GCAGCACTGA AAGGGAGGAT GGGGCTGAGA AAAAGGTAGC CTGAGGAGAC
55001 CAGGCTTTCA GTACCCTGCT GGACAGGGCT AGGGTACCCT TCAGGAGGCT
55051 GGCCCAATCA GGTGCCAGCA GGGCCTAGAA ATGCCCTTCT CTCCAAGGGG
55101 TGTGAACCCT AGAGTTCCTT TGGAAGGGAA AAAAGCAGGT ATTTAAAAAT
55151 CCACTTGTCT TGCAGACACT GTTTGAGGAC CAACCAGGCT TAGGTGAGCT
```

FIGURE 3A-24

```
55201 ACAGGGTGCG TGGAGAACAG AGCACCAGAG AGCTCTGTGG GCTGGAATGA
55251 GCAGACAATA AGAGCTGGGG GGCTTCATGG AGATGCAAAG GTTGATGAGG
55301 AAGAGAGAAG GAAGTTAAAA GGGCCTCTTC TGGGATGTGA GGAGCCTCCC
55351 CCTTCAAACA TCTACCAAAT GCATGGGATC TTCCTCCTCC AAGGTCCAAC
55401 CCCATGTGTT TCTGGGATCT GGTCAAACAG CTCACCAAAA GACAGCCTGC
55451 AGCTACCATG CAAAGGCCCT ACGTGGGCAC AGTGAAGAAG GGGAAATGTC
55501 AGAATCAGGA TACTGTACTT AACTTGCTGC TGTCGTTTCT GCCTGAAAAG
55551 CATCTGGTTG AGCTAGCAAG CTTCTTGTCT AGGAATGCTG GACAGTTCCT
55601 TGGGTAGTAG CAAGTCATTC TTTTTTTCTC TGTGGTTTTT GAGTGCTTCA
55651 CGTACAGCCA GCAGGGGCCA TGAAAGGAAG AACTTTCACT CACACTCCTC
55701 TGGTCACCCT GCTGCCCTCC AGACTGTTTC CTTGAAGTTT CCAAGGCAGC
55751 TCTGGATGGT TCTGGGATGA GGCTCTGGCC TCATATGCTT TGTTGCAGTA
55801 TGCTGGAGCG ATCGCTCCAG ATGTTCTTTG TGAGATGTAA ACCAGGGCGC
55851 TAATCAGGAG TTAGACCAGA CTCTGCATTT TTTTTTTTTT TTTTTTGAGA
55901 CAGGGTCTCG CTCTATCACC CAGGCTGGAG TACAATGGCA TGATCATGGC
55951 TCACTGCAGC CTCGAACTCC TCCTGGGTTC AAGCGATCCT CCCGCCTCAT
56001 CCTCCAGAGC AGCTGGGACT ATAGGTGCAT GCCACCACAC CCAGTTGATT
56051 TCTTAATTTT TTTTTTTTTT TTTTTTGAG ACGGAGTTTC ACTCTTGTTG
56101 CCCAGGCTGG AGTGCAGTGG TGCGATCTCA GCTCACTGTA ACCTCCTCCT
56151 CCTGGGTTCA AGCAATTCTC CTGCCTCAGC CTCCCTAGTA GCTGGGATTA
56201 CAGGCACCTG TAATCCACCA TGCCCAGCTA ATTTTTTGTA TTTTTAGTAG
56251 AGACAAGGTT TTACTATGTT GGCCAGGCTG GTCTCGAACT CCTGACCTCA
56301 AGCAATCCAC CTGCCTCAAC CTCCCAAGAT TTCTTAATTT CTTAATTTTT
56351 TGTAGAGACA GAGTCTCCCT GTGTTGCCCA GGCTCGTCTC AAGCTCCTGG
56401 CCTCAAGTGA TCCTCCTGCC TCAGCCTCCT AAAGTGCTGG GATTTAGGCA
56451 TGAGCTACCT TGCCTGGCCT AGACTCTGAA CAGTTTTAGT GAGATACCAT
56501 AAGTTTATCC AAGTTTCTTC TGTGTTGTAG CATATATTCT TTTTTACTGC
56551 CAACCAATAT TCCCCGGTAA GGATATGCTA CGTTTGTCTA TCCGTTCATC
56601 CAGCTGATGG GCATTTGAAT TGTTTCCACT TTTTGACTAT TATGGATTAT
56651 GGTGCTGTGA ACCTTGGTTA CAGGTTTTTT GTGGATTTCT GTTTTCATTT
56701 CTCTTTTGTA TATACTGAGG AGCGGAATTG CTGGCTCATA TAGTCTGTGT
56751 TTAGCACTTT GAGGAATGTA CACGTCTTCA CATAGATGTA TGTTTTTTGT
56801 CTAGACCATA CCCTTTTTGT ACAGGTTGAA CATCCGTAAT CCAAAAGCCA
56851 AAATGCTCCA AAATCTAAAC TTTTTGAGTG CCAGCATGAT GCCACAAGTG
56901 GAAAATTCTA CACGTAACCC CATATGACAG GTTATAAGCA AAATTCAATC
56951 ACTTTATTTC ATGCACAAAA TTATTTTAAA ATGTCATGAA ATTACCTTCA
57001 GGCCATGTAT ATAATGTACA CATGAAAAAT AAATGTTTAG ACTTGGGTCC
57051 CATCCCTGAG ATATCTGATT ATGTATATGC AAATATTCCA AAATCCAAAA
57101 CAATTTAAAA TCTGCCACGT TTCTGGTCCT AAGCATTTTG GATAAAGGAT
57151 ATTCAACCCG TATTATGTTT ATATGCCTCT TCAGTGCTGG TAGTTGTAGC
57201 TTCTGCTTCC TCATCCCCTC ATTTGAGCCG GGTGGCAGAG CAGGGCAGAC
57251 TGCTGCCTTG CTCAGACCTA ATCGTTCAGT TCTTTCATTG TACAAGTATT
57301 CATTGAGCAG CAAACATAAG CCAGTCTCTC TAAGTGCTGG GATGTATCAG
57351 TGAATAAAGA ATATATGCCT GCTTTCATGT GCTTCCATTT TTACTGGGGG
57401 AGATGGCAAA TAAATGTAAA GTGATAAATA ACAAAGGTTC AGTGGGGCAT
57451 TCGTAGTTCA GCGGCAGAAA TTTCGTCTCC TACGCGGGAG ACTCGGGTTC
```

FIGURE 3A-25

```
57501 GACTTCGGCC ATGCAGTCCT TCCATGCAGG AAGGGCTACT ACGTTTCTAC
57551 CCAACAAAGT TATTATGGCT GGACGCAGTG GCTCACGCCT GTAATTCCAG
57601 CACTTTGGGA GGCCAAGGCG GGCGGATCAC CTGAGATCAG GAGTTTGAGA
57651 CCAGCCTGAC CAACATGGAG AAACCCTATC TCTATTGAAA ATACAAAATT
57701 AGCCAGGCGT GGTGGCGCAT GACTGTAATC CCAGCTACTC GGGAGGCTGA
57751 GGTGGGAGAA TTGCTTGAAC CCGGGAGGTG GAGGTTGCGG TGAGCTGAGA
57801 TCGCACCATT GCACTCCAGC CTGGGCAACA AGAGTAAAGC TCTGTCTCAA
57851 AAAAATAAAT AAATAAAAAA TAAAGGTTCA TGTAAGTTTT GGGTGGCGAT
57901 GAGGGCGTTG AAGCAGTTAT GACCATGTAG CTACCATGAC TTTGAGATGC
57951 AGTCTTCTCG CAGTGTGCAC AGGCAGCATG GAGGGAGGCA GGGTACCGGC
58001 TCTCCCTCCT GAACCAGACG AGCTGTTGTG TTGCCAATGG AGGTTCAGGG
58051 AGCCAGTGAT GGGACAGCTC TGCTCCTGAG CTTTGCCACC CACAGGACCT
58101 GGGCACTGGA CCTTATGATG TGCTTCTCTG GAGTGAAGAC TGGCTGTCAC
58151 CTCAGCCCCC TCTCCTTTCT TCTGCTGCCA TATCATTCTT CACATGCCTA
58201 CCAGCCCCCT GGAATCTGCC CCTGCACCCT CATCCCTTAT ATATTTTGCA
58251 GAGAGCGTTT AGAGGACTGG AAGTGTGGCA TGTAATGGTA TCTCTGTTTC
58301 CACCCCGCAG CCCACCTTGG GACACCTTGA CTCCAAGCCC AGCAGTAAGT
58351 CCAACATGAT TCGGGGCCGC AACTCAGCCA CCTCTGCTGA TGAGCAGCCC
58401 CACATTGGAA ACTACCGGCT CCTCAAGACC ATTGGCAAGG GTAATTTTGC
58451 CAAGGTGAAG TTGGCCCGAC ACATCCTGAC TGGGAAAGAG GTGAGCACTG
58501 GGACTGGGGA CATGGCAGCA CCTCCCAGCC CTGTTGACAC TCCAGCAGGT
58551 GGTGATGGGA CTACTACTGC AGCCAACCTC TTGTTTATCC GGCAGAAATG
58601 AGATCTGAGA TATAGGGGTG CAAAAAGCTG TGGGATGAAA AGGAGTAAGA
58651 AATATAAAGG AGGAAGTAGA TTGGAATCCT GGGTTTCGCT GGTCAGAGAA
58701 GTGATTTGGG GCCTTTTTGT CTCATCCTCA GGTAGCTGTG AAGATCATTG
58751 ACAAGACTCA ACTGAACTCC TCCAGCCTCC AGAAAGTAAG CACATGGCAC
58801 CTCCTGTCCC TTTTTTTTTT TTTTTTTTTT TTTTTTTGAG TCAGAGCCTC
58851 ACTCTTGTCG CCCAGGCTGG AGTGCAATGG TGTGATCTCG GCTCACTGCA
58901 ACCTCCGCCT TTTGGTTTCA AGCGATTCTC CCGCCTCAGC CTCCCGAGTA
58951 GCTGGGATTA TAGGCACCCG CCACCACACC TGGCTAAGTT TTGTATTTTT
59001 AGTAGAGATG GGGTTTCACC ATGGTAGCCA GGCTGGTCTC GAACTCCTGA
59051 CCTCAAGTGA TCCGCTCGCC TCGGCCTCCC AAAGTGCTAG GATTATAGGC
59101 GTGAACCACT GCCCCAGCC CACCTGTCCC TTTCTAAATC TCTCTTCTGG
59151 GGTCAATGAT CTACTGACCC CATTTAGACC TTCTCTTGAA TTCCTAGTTT
59201 AAATTTTCTG GCCATTTCGC TCACCGTCCC CCAACCATTC CCTCCCATGG
59251 CTCTGCTACC TTCGGGGCTT TGGTTGGATC ATCTGTGGTG ACTCCTCCTG
59301 AGTGGGCTTC CTGGCCATAG GCACTGGCTC TTGTGAAGTC TTTCTGTTCA
59351 TTCCCAGCCA CTTGGCCTAC CTGTCTGACC TACTTCCTGC ATCTTGTTAT
59401 CTTCTGGCTT GTGGCCAGCC CTATGCAAAA ACACATGTTT GTAGCCACTA
59451 CTAGAAACAC GTGCAGCTAC TTCAAGATCT GGAATGATAC AGGGGAGTGG
59501 CTTTAGAAAT ACAAGAATAA GAGGAAGCAG GGAACCTGCC GGTGGGTTCT
59551 GTGCCAGCTA CCTTTTAGAG AATGAGCTCC AGCTCAAATT TTCTGAACAA
59601 AACCTAGTTC TGTTCATCTT GTGGCAAATC AGATATTTTC TCCATAAGCA
59651 TATTGTGGCA GTTGAGTTAG GAGAAGGCAT GATTCGTGCT AACAGAGTCA
59701 GATAGTGATA CTGGGAACCT TAGGAGTAAG GGCTGAGGAT TGTTGTTGAG
59751 GGCGATGCTC ATGGAATTAG AGTGGATGAG TTGTTCTCCG GACATGCAAA
```

FIGURE 3A-26

59801 TAGCCAGAAC CAAGGTGTTT CCTATTTATT GTTACCCCTG GGATCCCTTC
59851 AAGGGTTCTT CAGTTCAGTA GAAACATTGT TGTCATCATC AGGGTGTCTC
59901 TGCTTGAAGC TTTCCAGGAG GAAGGGAAAA AGGGCTGCTT ATGACATCCT
59951 GGCTCCAGCC CCACAGAAGA AGTCAGCGTG GGGTAGGCCA TTTGGCCTTG
60001 GGAGCAGTCT AGCCTGCCAT CGTAATAATC GCCAGTCCAC CAAGCCATCT
60051 TATTCCTGAC CTTGTTTTTC TCCCTAATTC TTCTTGGTTT TCTCCCTAAT
60101 TCTTCCTGAC TCTCTGGAAG GCACCAACAC CAGACAAATA GAGCCATTTT
60151 CAAAACCTTT TGAGACTCTT TGTTACTAAA GCCAGTCTGA TTCTGGCCAA
60201 AAATGTGATC TCAGCAATGA TCCCTGAAAA ATGAACATTG AAGAAGCTAG
60251 CCCCCCTCAGG GGTCTAGACA AGCCCAGAAA ACCCCAAGTT CTCCCAGAAG
60301 AATGTCACTT CCATGCCAGG TGAGCAGCCT CAGGGGAAGA AGCCCTGGCA
60351 GCTGCCTCTG GCCCTATTTC AGAGCTGCTC CCCATTACTG CCCCAGAGGG
60401 TGGTATCCAG GCTTTTTGCC TCTCCATCCA AAATATCTGT TGGACCAGGG
60451 AAAAAAGTAA GAAAAACCTA GGCCCTAATA AAGGGTAAGG TCAGCATTGG
60501 GTTCCTGAGG ATTGGAAAGC CTTTTTCTTC TTTTCCTTTC TAGCTTAGGA
60551 AAGCTCTGGG GCATCATTAA AGGGGAAACA AATGTATTCA CTTTATTCCA
60601 TAAACCATAT CTTGAATTAG GGCTTCCCCT ACCCCCAACA AAAACAACAA
60651 CAAAAACTAG TTCTGTTCTT TGTGCAAGTG ATGAGGCCTG AAATTACAAA
60701 AAGCCCCACC TCCAGTTCTC TGGCCCCCGC AGAGGGGAAG GAGTTCATTT
60751 CTGTCATCTT TCTTTATGGA AATACATGGT TTGGAGCCCC TGGTTTTGTT
60801 TCACAAAGAG AGCGTGAGTG TGTGGAGGTG GATTTGATTA AAATTGGCAT
60851 CAGCTATATA TAGGAGTGGC TTCTTCTGTC ACCACCCTAG AGGCCCAGGA
60901 AGGAAAGGCC TATCCCCTAG AACAGAGCCC TCTGACTACT GTAAATCAGA
60951 AAATGATGGG GTCCCCCTCT GGTGCTCTAC CACCCCTTTA CACAGACCAA
61001 GCTGGGGTGT GTACTGTCAC TGAACCAAGG CAGCAGCTCG GATTCTGAAT
61051 ATTCACGCAC ACGGGCTCAC ACTCCCTCCA GTAGAGGCAC CCAGCCAAAA
61101 CCTGCCTGCT GTTTTGGGGC TGGATTTGGT AGACGCAGCA GAGGGCATGG
61151 CTGGCTCATC CTGATGCCAT CCCGGGTAGC ACGTCCCCAC AGCCAGCCCT
61201 CCTCCAGCTT CCCCAACTTC CCAGCCACAG GGAAGGCCGT GCATGAGCTA
61251 GACAACCACC CTATTTTCTT TTCCCTGCCC GGTTTTGGTT TTTTGGGAAA
61301 AACAAATCCT GGCAGGGACT GTTTGGAGAG ACCTGATGGG AGCAAGTTGG
61351 GCAGGCATGA CCCCTGGTAT TTTATCTTCC AGCTATTCCG CGAAGTAAGA
61401 ATAATGAAGG TTTTGAATCA TCCCAACATA GGTGAGCACA AGTTGTTATT
61451 TCTTTCTTCT TCCCCAACAG CAAGGCACTG CTTTCCAGCA TGTCATCTTC
61501 TCCCCGAGGT GCACTGCCTT CTGGAGTCTG CAGTCTTCAA GGATACCCCT
61551 GGGGAAGCTC AGCTCAAAAT CCATCTCCCC TTCTGGCACA CTGGGCTGTC
61601 TTTAGCAGTT TGGCTGGCAT GAGAGGAACT TGTTCTTGGG AGTGGGGGAT
61651 CATGAAAGGA GGGGAGACTT TCGTTCCTAG GATGCTCCTG GACATGTTGG
61701 AGAGCAGTAT GTGGCCCCTG TTGCTTCTTG ACTTAAGGCT TGGCCTTTTC
61751 TCTTGTAGTT AAATTATTTG AAGTGATTGA GACTGAGAAA ACGCTCTACC
61801 TTGTCATGGA GTACGCTAGT GGCGGTAGGT GTGGAACTGC CTCTTCCTGT
61851 TGTGCCCCCA CTTCTTCCAC CTCCAGCCAG CTCTGACTGA GATCCCTGCC
61901 TGGTCTCTTA CAGGAGAGGT ATTTGATTAC CTAGTGGCTC ATGGCAGGAT
61951 GAAAGAAAAA GAGGCTCGAG CCAAATTCCG CCAGGTAGGT GTGACTCCCT
62001 CCATAGGAGC TAGGCCTGAC CTCTGCTTTT GGGGTTTGAC ATGTAAGGAT
62051 AAGCTGCCTG TCTGTAAGTG GCCCTTGGAG GGTACTTTGG GCTCTGCTTA

FIGURE 3A-27

```
62101 TCCGTGTGGC AGGTTAGCAC TAAGTCACAG GGTCACTGCT CTGTCAGCCC
62151 CTGTGGCCCA CCCTCAGGCA CCCCTGGGTT AACCCTTCTT CCTTCCTTTC
62201 AGATAGTGTC TGCTGTGCAG TACTGTCACC AGAAGTTTAT TGTCCATAGA
62251 GACTTAAAGG TAAGGCATGC ACTTCTCCTT GTGCCTTTGA GTGGGAGCCA
62301 GGTTGTTGCC TCTTGGTTCT CCATGATAAA ACCATCAATA ACCATCAGGC
62351 CCTGAGTGTT CCAGGAAACT CCAGCCTTTC TTTTTTTCTT TCTTTCTTTC
62401 TTTTTTTTTT TTTGAGATGA CCAGAAAGCC CCTAGGGCTG CCTCTGATAG
62451 AGGCCTTGTG GCTGGACCTC GGGTTCCATT CTAGCCCTTG AGCAGGGGCC
62501 CTCTGCCATT TCACCTCTTG GCACATCACC TTTTAGTGCT GCCAAGCAAG
62551 GCAGGCACAC TCCAGGCTTT CTCAGTCTTT CAGGCAACCT GGTAGCTGAC
62601 CCAGGGAAGA GTGCTGAAAG TTCCACAGCT GTATCCCAGC TGCTTTGCAG
62651 GCAGGCACAC ACATACCATC TCCATCACCA AGATACTCAA GTTTGAGGAC
62701 ACCTGTGGGT CTCTTGGCTG CTGAGTCCTC ACAGACATGA TTTGATTAAC
62751 CTGGGCCTGA TGCTGAAGCT TTGCACAGCT CACAGGGTCT CTGGGCCTTC
62801 AGATCCCATC TCTCCCATGG CTGCCCACGT GAGGAGTGGC CTGCATTGCC
62851 TTCCTCCTGC CCAGCCTATT CACGCTGATT GAAGCCCTGC CCTGAAATTG
62901 GTGGAGAAAG TTCTGAGACT GAAGATGACT TTCCGTTTGT TCTCCCATTC
62951 CCCTCAGCTC CTTCCTGCCC AGGGCCTTAG TCTGGTCCAC TTGGTTCCCT
63001 GATGTTTTCC ATCTTACCTC CCAGGCAGAA AACCTGCTCT TGGATGCTGA
63051 TATGAACATC AAGATTGCAG ACTTTGGCTT CAGCAATGAA TTCACCTTTG
63101 GGAACAAGCT GGACACCTTC TGTGGCAGTC CCCCTTATGC TGCCCCAGAA
63151 CTCTTCCAGG GCAAAAAATA TGATGGACCC GAGGTGGATG TGTGGAGCCT
63201 AGGAGTTATC CTCTATACAC TGGTCAGCGG ATCCCTGCCT TTTGATGGAC
63251 AGAACCTCAA GGTGGAGTGA AGTGCAAGCT TTTTATTGCT TCTCATTTCC
63301 TCTCGGCCTC TGGTCTTAGC CCTGACCTCC TGCCTTTGCC ACCTGTCTAC
63351 ATTTGTCCCA AGCCAAAGCT TCAGAGAAGG GCTTGCTGAG GTAGCAGCAG
63401 TCAAAGGCCT TCTGCACCTG GGAATGAATA ACCTCAGTTC CTTTCTCGAA
63451 AGATGGGATA AACTGTGTGT GTGTTCATCC CCCAAGGCAC TCCGGATTGC
63501 AGGCCTCGGA CTGGTCAAGT TAGAGGGTAC GAGGGTATTT GACTTCACTT
63551 GCCTCTCTGG TGAGGTGTCT TGTCCCCAGG CTGTCTGCCT TCTTCCATAT
63601 TTCATTTATG TCTGCTTTGC CAGGCTTAAG CTCTCAGGAT CTTGGATATT
63651 AGGTTTCTTC CTTTGGCCTT GGGGTGATTT CAATTTTCTA ACCCTGGATC
63701 CTCCTGCAGG AGCTGCGGGA ACGGGTACTG AGGGGAAAAT ACCGTATTCC
63751 ATTCTACATG TCCACGGACT GTGAAAACCT GCTTAAGAAA TTTCTCATTC
63801 TTAATCCCAG CAAGAGAGGC ACTTTAGAGG TGAGCAGTGG AGCCCAACTG
63851 GCGGAAGGGC CTGGGGTCCC CACAGAAACT TTCCAGCTGA GTTTCTTCCC
63901 CCTGCCCTTT TCCTTCTCTG TGCTCCCCAG CAAATCATGA AAGATCGATG
63951 GATGAATGTG GGTCACGAAG ATGATGAACT AAAGCCTTAC GTGGAGCCAC
64001 TCCCTGACTA CAAGGACCCC CGGCGGACAG TGAGGCTGT GCCGGGCTGT
64051 GAGGTTAAGC TTGCCTAGGA GTTGAGGCCA GTCTTAACTG TATGTCCCCC
64101 TGTGCAGAGC TGATGGTGTC CATGGGTTAT ACACGGGAAG AGATCCAGGA
64151 CTCGCTGGTG GGCCAGAGAT ACAACGAGGT GATGGCCACC TATCTGCTCC
64201 TGGGCTACAA GAGCTCCGAG GTGTGTGCTC CCCGCTCCAT TCTCTGACCT
64251 GGCCAGCCTC ACTGTCTGTA GCACCTATGC TTCTAACACC TGTTGAGGGC
64301 AGAAGCTCAT CTCTGAGTAG GTGTGCTCTC TGCTCACCAA TTTTAAGCCT
64351 CAGCTTTGGT GTCTAAGGTC CTCTGGCCCA TTCACTGATC TCCATGAGTG
```

FIGURE 3A-28

```
64401 AATTAATAGA AAGCTGGTAG GGTCGGTGTG GGACTGGGTC AGAGTTTCAA
64451 TACGGGTGAG TTGATCTAGG TTAGTCTGCA TTGATTAGAT GTGTCTAGGT
64501 CATCGGCTAG CACTACTACA TTGATCTAGA TATCTTTGTG TCTCTTTTTG
64551 TATCTGGAAG TGTACATTTC TGGGTGTGTG TGTGTGTCTC TGTGTGTGTC
64601 TGATCGGAAG TTTGAGTCTG TTGCTTTTTT TTTTTTTTTT TTTTTTTTTT
64651 GAGACGGAAT TCGCTCTTG TTGCCCAGGC TGGAGTGCAA TGGCAGGATC
64701 TTGGCTCACT GCAACCTCCG CCTCCCGGGT TCAAGCGATT CTCCTGCCTC
64751 AGCCTCCCAA GTAGCTGGGA TTACAGGCAT GTGCCACCAT ACCCGGCTAT
64801 TGAGTCTGTT GCTTCTGTCT AGTGCTTTAT GTTGGGTGT GTGTATCTGT
64851 GTGTGTGTGT GTGTGTGTGT GTGTGTGTAT GTGTCCGTCT TCCCGTCTGT
64901 GGATCTGGAG ACTTTGTGAT TGTTCTTCTG CCCATTTGGG TTTTGTTCAT
64951 CATCTGAGTA TCCCCACATG AACTCCCAGC CTCCCTGCCC TGCTCTCCCT
65001 CTGGTGGTGG GATCCTTAAG AGGCACCTGG TGACACTTGG TATAGGCCCA
65051 TATTGCTCTG TGTTGAGGGG AGTGGACTTG AGTCTGGACA TGTGTTCTTG
65101 CGGATGTTTG TGTCTCTGGG TGTGTGGGCT TATGTATTCC TTTCTGAGAC
65151 TGTGTTTGTC AGTGTCTGTG TCAGAGCATG TGTGTCTCCA GGGTCTCCTC
65201 CAGGGGGGAT GTATTGGTCT TACAAGTGGA TGTCCGGTAT GATCCTGGGG
65251 TGTTTGAGTG TTGGGAGAGG GCGGTATGTG TAAATGTGTC CATCCATAGG
65301 GATCTCCACA TGACTTCTGC CCTCCCTTGA AGCTGTTTTC TGTTTCTTTC
65351 AGCTGGAAGG CGACACCATC ACCCTGAAAC CCCGGCCTTC AGCTGATCTG
65401 ACCAATAGCA GCGCCCCATC CCCATCCCAC AAGGTACAGC GCAGCGTGTC
65451 GGCCAATCCC AAGCAGCGGC GCTTCAGCGA CCAGGGTAAA TGCTTTTGGG
65501 AGTTGTAGGT GGGGACTCAC CCCTCTCCAG AGAGGTTACA GGTTCTGTGG
65551 GGACTTGGGT AACACAACTA AGTTTCAGTC CTGGTTCAGC CACTTATTAG
65601 TAGTGTGGCT ATGGGCAAGC CACTTCCCTT CCCTCGCCTC TGTGGAATGG
65651 GGGCTTGCTG GGTTGTTGGC CAGCCCTGTA GGAAATGAGC ATGCGTGGGG
65701 CTGGCACTCA GTGGACCCCT TGGCCTTACC CATTCCCATC CTCCCTCTGG
65751 CCCAGCAGCT GGTCCTGCCA TTCCCACCTC TAATTCTTAC TCTAAGAAGA
65801 CTCAGAGTAA CAACGCAGAA AATAAGCGGC CTGAGGAGGA CCGGGAGTCA
65851 GGGCGGAAAG CCAGCAGCAC AGCCAAGGTG CCTGCCAGCC CCTGCCCGG
65901 TCTGGAGAGG AAGAAGACCA CCCCAACCCC CTCCACGGTG AGCCGCACCC
65951 CCCGCTCTCT CCTTCCTTCC TGCGGTGGGG CCTGCCCTCT CCAGGCAGCT
66001 CTTCTCTTAA TTCAGACTCT GTTCCCTTTG GCTACTACTT CTGCTTATAG
66051 CAGGAAGCCT CGCTCCCAGC AGTAAATGCA GAATCCTTTC CTTAACCTAC
66101 CACTGTCTGC TTCAGGTGGA AGGGACAGGA AGCCTGTTCC ATGAACCTGG
66151 GGGAGAACC TGGCTGTAGA CCACTTTGGC TTTCTGATAG AACGCTTGCC
66201 CTTTATTCCC CACAGAACAG CGTCCTCTCC ACCAGCACAA ATCGAAGCAG
66251 GAATTCCCCA CTTTTGGAGC GGGCCAGCCT CGGCCAGGCC TCCATCCAGA
66301 ATGGCAAAGA CAGGTGAGAG ACCCGGGCCC TGCCTGCCTC ACTCCCTAGG
66351 AGCCATGTCT CACAGGGTGA TGTCTGTCAG CAGCACCGTC TCCTGTCCCT
66401 GCCAGCGCAT TGCTCCCTGC TCCCTGGAGT TCCATCCTGG CTGTGTCCAG
66451 TCCAGCTTTC CCCTCCCCTA TTCCACGCCA TTGCCTCCTC CCCATCTTCC
66501 TCTGACTGCT ACTTGCAGTT TGCCAAGTGT GGGGCTGACC GTGGCCATCT
66551 CAGCTACATG CTCGCTTCTT GACCACGGCC AGGGCATGGC AGCTGCCCTC
66601 CTCTAGACAT GAGCAGCTAA GGCCTTGTGT TGGGGTCCC AGCTCAGGGC
66651 AGAACCAAGA GATGCCCACC TTGAGGGGTG TACACATAGA GGGCGACTCC
```

FIGURE 3A-29

```
66701 AGCCATCCCC ATGAGACCAG AGCTCCCCAG CCTTCACCGG CCGCATTTCT
66751 TGGTGTTGCA TTCCTGGCTC TATCTCTTCT GAGTTTATGA AAGTTTCCCC
66801 TCAGCAACAC CCCACTCTTT CTGTAGAAGA AACTCTCCTG TTCTTAAAAT
66851 TCTTAGGAGG CCAGTGCAGC CTGGAGGCAG CGGCCCCTTG TCTGCTCTCC
66901 TTCATTTCTG ATTCCTCTTC CCAGGCACTG ACCCACCTCG CTGCTTCCCG
66951 ACCTCACTCA CCTCCACTTC TCAGCCCCGC ATTCCTCAGT TCTGACTTGC
67001 ATCCCGCTGC TGCCCAGGCC TGACTTCTAC CCTGCCAGAG CTCCCCAGCT
67051 CTGGCCCTTC CCCTGCCCTT GCTTCCTAAT CCAGGCCTCC CGCCCTCACT
67101 CACCCCTAAC ACGGGCCTCT CCGCTGCTTT TGTTTCCTAG CCTAACCATG
67151 CCAGGGTCCC GGGCCTCCAC GGCTTCTGCT TCTGCCGCAG TCTCTGCGGC
67201 CCGGCCCCGC CAGCACCAGA AATCCATGTC GGCCTCCGTG CACCCCAACA
67251 AGGCCTCTGG GCTGCCCCCC ACGGAGAGTA ACTGTGAGGT GCCGCGGCCC
67301 AGGCAAGTGT GCTGGGGCAG CTGGTGCACC TGCTGCCCTC AGCCCACCCT
67351 ACCCCCTTGC CCCAACAATT TCTTCTTCCC ACTTGGGGGT CCTGCTGTGT
67401 TCTTGTCATC TTAGCCACAA GAAATGGGTC TGTCCCCTGC GGCCAGGAAG
67451 TGGAGGGAAC AAAAAAGAGC ATTAATGCCC CTCTTTTCCA GTTCTCCCTC
67501 TCAGAACAGG TATGCAGGAA GCTGTCCTAA GGCTCCAAAG GGAAACCTTT
67551 TTGTTCTGAA CCTTCCAGGG TTTCCTTAGG GACCCCGGGG ATAGTCGGCA
67601 TCACAGGGAC TCAATCCTCA AGGGTTGGTC CCCATTGCCG CCTTGAGGGT
67651 CCAGTCTGCC CGGCTCCCAG GGAGCCCGCT GTCTCCAGCC TAAACCACAC
67701 TCCACACAGG GGTCCTTCCT TGCCTCCCTC CCTCCCTTCC CAAACCATCT
67751 CCTTCCACTT CCACGAGACT TCCTTCTCAC CACTGTCCTC AGTAGTCACA
67801 CCCTTCCTTC TGTGTCCTCG TGATGGCTGC CTCTGCCCTA GCATCCCCCT
67851 CCCTGTCCCC ACCACAGGGT GTCCAGGTGC CCAGTGATGG CTGTCCTGTA
67901 CCCTAATTCG TCCCCCTCAA CCCCACTTCT CTTCCCACAG CACAGCCCCC
67951 CAGCGTGTCC CTGTTGCCTC CCCATCCGCC ACAACATCA GCAGCAGTGG
68001 TGGAGCCCCA GACCGAACTA ACTTCCCCCG GGGTGTGTCC AGCCGAAGCA
68051 CCTTCCATGC TGGGCAGCTC CGACAGGTGC GGGACCAGCA GAATTTGCCC
68101 TACGGTGTGA CCCCAGCCTC TCCCTCTGGC CACAGCCAGG GCCGGCGGGG
68151 GGCCTCTGGG AGCATCTTCA GCAAGTTCAC CTCCAAGTTT GTACGCAGGT
68201 AAGCAAGGAG CTTTGGGTGG CAGAGAGGCT CAGGCCAGGC CTTCCTGCTT
68251 TACTCGGGGT GGGTTGGGGG TTGGGGGTTG GGGTTTGGGA CACTCTGTAC
68301 CGGTATTGGG TCCTGGGGTT AGAAGAGGCT TCAGGAAGCA CAAGAAATTA
68351 GGTCTTTGTC AACACCTTAT GTGCCCAGGC CCACCCCTCT TAGGCCTCTC
68401 CCCAACTCCT CACAGGCACC CCTCATTCTC TGGCCCCAAG CAGATGGCCG
68451 ATGCCGCCTC CTCTCTAGGA GAGTGTGAAC TCAGATGCTA AAATAAAAGC
68501 CCCCCCTTCT CTCCTGGGTT CCCATGGAAA CTTATATTTG GTGACGCAGC
68551 TGCAAAGTCA TGAGGCATGA GCCAGGCTGG GGCCAGCAAG GAAAATTTTG
68601 TCCTGGTCTC TTGCCCCTTT GACTGCCTCT CCCACTAGTT GGTTCTGTTT
68651 CTGGCTGCAG GCGCAGCCAT GCCCTTCTGC CCGGGGGTTT TAGGGTGAAA
68701 CCTATAAATG AAATCACTGG CGAGGGCCTA CAGTGGCCTC TTCCCTAACC
68751 TAACTCCGAT GTGCCAAAGG TTTCCTGTGT TGGACCCAGG GTGGGGATCT
68801 CTTCACGGGG TTTCTCACAC CTGAGCCCCC AGCCACCACA GAGGTGCAGC
68851 TTGAAGTGCA TCCAGCCAAC TGGCTGGCCT CCTGGGATGC TCCGCATCCC
68901 CATCCTGCCA TTCCTCTCCC TGCCTTGGAG TAGCAGCTCA GGAAGCAGCA
68951 GGGGCTTTGA GAGAACAGGC TCGCCTGCCC TTCCTCTACG TTTCACTCCA
```

FIGURE 3A-30

```
69001 CTCTGCTGGA GGAGCCAAAG CCACTGCCCC ATCCGAGCCC CAGAATGCAA
69051 GTGTGAGGCC TGCAGAGAGT GTGGGCAGGT CTGAAAGCCT GGGACTCTAG
69101 TCTCGCTGAG CGGCTCTTCC GAAAATGGGA TGACCCTTGA ACCTGTAAAG
69151 CCACCTCCCC CACCTGCTTA TCCACATACC GTCTTGTTGG TTTTTTTTTT
69201 ATTTCTTTTT TTATTTTGTC TTTTTTTTGT TTGTTTTTTT AGAAATCTGT
69251 CTTTCAGGTT TGCCAGAAGG TAGGCGTTGA GCCCGCTGTG TGTGTGTGTG
69301 TGTGTGTGTG TGTCTGTGTC CTGTGTCCTG CCTCCATCAC TAACTCCCCT
69351 TTTCTGGCTC TTACTCTCCT CCATCTGCTT AACCAAGTCT GTGTGGCCCT
69401 CCTCTCTCTG CCATCTTAAA GGGATGAAGA CTGCCTCTGA TTGGGCATCA
69451 GCACAAGGCC TGCCCTCCGT GCCCCCAGTA CAAACAGGCA GGGCTAAGAG
69501 GCCACATTGG CCCACTCAGG GCAAATGGCT TTAAAAATGA GGGCCTTCCT
69551 TGGGCCCACA GTTAACGCCT GTCCTCAAGT AAGGGGAGAC TGTCTCAGGG
69601 AAGCCTCCCT TTAAGATTGT CTCCTCTCAC CCACCCCACC CCACCCCCAC
69651 TCCCTCTCAC CCCAGGTTTT GGTCACAAGT GTTGGGATCC TTTCCTGCCC
69701 TTTCCCTTGT CATGTGCATG CGCTATGAGG AAGCTCCAGG GTTACAAGTG
69751 CATCTGGGAT GGTATCTTGT TTGTTGTCTC CTGGGTTTCC TGAACTTCAG
69801 AGCTATGTGA CCTCTTCCCC GTGGCCTATG GGATCGCAGG ACTTTGGAGA
69851 CACTACGGGG ACCCTGGGGC CCCAAGGTTT CAGTCTGGCT CCCCCAGACC
69901 TTAGGAGCTT TTGTCTCACA AATGGAGCAC AGCACCCCCT CCTGGCAGCT
69951 CCTGCAGAAC TAGCCCCACC CACCCGCACC CCTGCCCCAG CACCCCTGCC
70001 ACCAGCAGCA TCTGGATAAA TCAAGCCTCT TCTCCTCTAG GCTGTTTTCT
70051 CCAGATATGG CCTGTCTCTT CCAAAGTGCG GGGAGCTGGG ACATTCTAGG
70101 GCAACGGCCA TTCTACCCCA AGCCGTAGCA AAACAACAGG AGATCTCTGC
70151 ACCCTTACTC AGGGGTCTCC CTTCACAGTC CCCTTCCTGG CTCTTTCACC
70201 CCTGGCCTTA TGCTCATCCT CTCTGCAGGC CTCGGGGACC AAATACCAAG
70251 CTGAAGACCA AGGGCCAGGT TAAGAGTGCT TGTTCCCCAA GGCTGTCTGC
70301 TCAGGCCCTG CATTGGGACT GGGATGCCTG GCAGGCACAT TGGTGCCACA
70351 GCTGATGGAG GAACGTCCAG ACAGGGTCTT CAGGCTTTCC CTATCCCCTC
70401 CTCCTCCCAC CCAGCTGTTG ACTGCATGAC TGGCTGCTGC CTCAAGGGGC
70451 CCCAGCAGGG GGCTGCCCCA CAGGGGGTCT GGAGAGAGCA GGGAGGGTGC
70501 CTTCCTCGCA CAGCCGGGCT CCCTGCTCGC AGTGCGCTTG TGTGCACCCC
70551 TGTGTTGGTT GTGTCTTCCT GTTTATTTCT ATGTGCTGCT GCTCTTCCTC
70601 CTTCCTCTCA CATCCTTCCT CCTCTGCAAT CCCCAGTTTC CTAGCTCCAG
70651 ACACCCATCT TCCAGCCAGG AGCTGGAGAA GCCGCTCAGC GGGGCCAGAC
70701 CTCTTCCCCA CCCACCCAAC CAAGGTGTCT GCCCTGCCCT GCCCCACCCC
70751 ACCCTCATCC TCCCTGCGTA TGAGCAGATG GCCTGGCAGG CCAGCAGGTA
70801 GGGGAGTTGG GAAAGGTCGG AGGAGGCCGC CTTTTCCACT CAGCAGCAGG
70851 AAGCCATCCC CAGGTGCCTA CCATGCAGAC CCAGGCCTTG GCACTTTGAG
70901 TCTCCTGACA GGCCCTTGCG TAGCCACGGC CCCTCCTCCT ACAGAGATTC
70951 AAAGCATTGC AGCCCCTTTC CTCCAAAAGG ACTGCAGTCC TGAGACCCTA
71001 GCGTGTGGCT CCAAAAACGC ACTCACACCT GCAACCCCCA GAACAGCGCG
71051 TGAGCCCTGG CTGTGGGGGA GCAGCCTCGT GCCGGGCCGT GTGCTCAGTG
71101 TGCTCAGTGA AGTGCGTGCA CAGCCACTCC CCCTCCTCCC CCAGAGCAGA
71151 GGCTCCTTCT CCCCGGCACA GATCTGGGAA TGTGGGGAGG ACAAGCCCC
71201 ATGTGCTGGG CTCCCTGCTG GAAAGGAATG GTTGAGCCGC CAGTGTGAGG
71251 TGCTGCAGAG CCCTGTTGGC TTGCCAGGTG ATGGGCAGAG GGCCCTGGGC
```

FIGURE 3A-31

```
71301 TTGGGTCCTG CCCACCCACT GGTGGCACCT CCCCAGACCC ACTCTCATCT
71351 GGGTCTGTGG CGGCGGAAGG AGCGAGAGAT CCCAGCACTA AACTCTCCCT
71401 CGCTCTGTTT TTTGAGGAAC CTGAATGAAC CTGAAAGCAA AGACCGAGTG
71451 GAGACGCTCA GGTGAGAGGG CTGGAGCCAG CACTGGCCCT GCCCGGGCCA
71501 CCGGGCTTGC CACAGCCTCC TGCTCCTCTC TTCCTTCTGC CACTTGGCTC
71551 TTCCTCCCGT GGTTCTGCCC TGTCCCTACC CTCTGGGGCC TCCCTTTCCT
71601 CAGAGAGTTT CCCCTTCCCA AACCCAATTG CAGGAGTTAC GGGCCCTTCT
71651 CCTCAGGTCT GGTATATTCT GGAAGTCGGA GTTCTGGGTC GGGTGGTTGG
71701 GGCTACAGAT TCCTACCCCT GGACTATCCC ACCTCCCTGT GCTCGGAGGC
71751 TGCTTTCTGG AGAGAGAGTC TGTGCTCGTG CTGTTGAGGG CACTGGTGTC
71801 TTCCCTGACC CCACCCCGCC TACCCCAAGG CTGGCTTCTC CTCCCCTTCG
71851 CTGTCCTGAG AGATGGGGGT TGGAGGACTG CCACCCTCCG CCCCCGCAGG
71901 CCAGGGGCCA CGCCTGGCTG CTCCTGCTCC CTCCCGCTCT CCTCTCTGGG
71951 CTCAGGGGCT GTCTGCCAGG GTGGCTCTCC TGGGGTGGGG TGCCTCAGCC
72001 CCCCCGTGAC GCCCGCCTCT GCCCTCTCCA CAGACCTCAC GTGGTGGGCA
72051 GTGGCGGCAA CGACAAAGAA AAGGAAGAAT TCGGGAGGC CAAGCCCCGC
72101 TCCCTCCGCT TCACGTGGAG TATGAAGACC ACGAGCTCCA TGGAGCCCAA
72151 CGAGATGATG CGGGAGATCC GCAAGGTGCT GGACGCGAAC AGCTGCCAGA
72201 GCGAGCTGCA TGAGAAGTAC ATGCTGCTGT GCATGCACGG CACGCCGGGC
72251 CACGAGGACT TCGTGCAGTG GGAGATGGAG GTGTGCAAAC TGCCGCGGCT
72301 CTCTCTCAAC GGGGTTCGAT TTAAGCGGAT ATCGGGCACC TCCATGGCCT
72351 TCAAAAACAT TGCCTCCAAA ATAGCCAACG AGCTGAAGCT TTAACAGGCT
72401 GCCAGGAGCG GGGGCGGCGG GGGCGGGCCA GCTGGACGGG CTGCCGGCCG
72451 CTGCGCCGCC CCACCTGGGC GAGACTGCAG CGATGGATTG GTGTGTCTCC
72501 CCTGCTGGCA CTTCTCCCCT CCCTGGCCCT TCTCAGTTTT CTCTTACATG
72551 TTTGTGGGGG GTGGGAGATT GTTCTCCAGC ACCCCACATT CACCCCTGCC
72601 CAGAGATTCC CCCTTCTCCT CTCCCCTACT GGAGGCAAAG GAAGGGGAGG
72651 GTGGATGGGG GGGCAGGGCT CCCCCTCGGT ACTGCGGTTG CACAGAGTAT
72701 TTCGCCTAAA CCAAGAAATT TTTTATTACC AAAAAGAAAA AAGAAAAAAA
72751 AAATCCCAGC GGCCACCTTT CCTCCCTGCC CCATTGGGAC AGTCGAGACT
72801 GGATCTGTGG GGTTTCCCGG GAGGGTGGCT CAGGGCTGGA ACACTCTCAG
72851 GCAAGAGTGG TGGAGCTCCC GTCAGGCCCT CCGCCAGGCC CACTGTGGGC
72901 TTCTCCCCTC TCCTCCCTCC TTCCCCTCCA AGCAAACCAC CAGAGGTGGC
72951 CTTCCCCTGA CCTCAGGCCC CTGGGCTGGA GGCCTGGGCG GTGGGGCAGG
73001 GGGCGGGGGT GCTGCGCAGC CCTGCAGTGG GTGGGGCTGG GGGCTGCTCC
73051 GGGGCTGCTG AGGCTGGAGG GCCGGCACAA GGCTCCGCCT CCCTCCACAC
73101 TGTACCCTCT GCCCCTCCTC CCCAGAGCTG GGCATTTCCT TCCACAAGCT
73151 GCTGTGGGGA CGTGTGTTCC CTCAAAGTCT GTGCCATCTT CTCCCACCCC
73201 TCCCGGGTAG AAGGAGGGGC TGACCCCAGG GCTGGGAGAG GGGAGGGGAC
73251 TGGAGGGCAG ACTGGCTTCT CGGTCCCCAG GGGGCCGCTT GGGCTGTTGG
73301 TCTCCAGAGC AGGGCCACTG GCACTCTGT GATGGGGGAG CCTTTGTCTG
73351 AAAGCACAGC CCCCTCGCCC TTCCTCTCCC CATGGCTTCC CCTTCATTGG
73401 CATTAATCTG GCACCAGCT CTCTCCATAG CAGTGACTTC CCTCACCACT
73451 CTCATCTCTC AGCCTTGCCT TTTCTTCCTG ACACTGTCGC CCCCTCCTCT
73501 CAGGAGACAC TGCCGAGGGC CACCTGGCAG AAGGCTGAGT TAGGCAGCAG
73551 GGCCGGGAGC GTCTGCCCTC CACAGGGTGG GGGACAGATA GGCTAAGCGA
```

FIGURE 3A-32

```
73601 CTCCCAGCTT GCTACCCTCA GTGGCCAGTG TGGGCGTGGG CGGTTTGGGG
73651 CGCTTGGCTG GTGGTGGCCA CTGCATCCCT TAATTTATTT CTCTGCTGTT
73701 TCTGTTCTTG AGAAATTGGG GGTGGGAGTC CTACACAGAG GCTGCCCCTA
73751 CCCTCACCTG AGTTGTACAT TTTTTTGTGA TGGGTTTTAT TTTTTATTAT
73801 TTTATTTTAT TTTTTTTTTT TTTTGATTTA TGATGACTCC ACCCCTCTTC
73851 ATCACCCCCG CTCCCAGGCC AGGCTCAGCG ATTAAGCCGA GCCCTTGCGT
73901 CCTAGGAAGG GGCCTTGCCA ACCTCAGCCC TCCTGCCCCA CACTCCTACT
73951 GCGGCTCAGA CCAAGGGCTC CCCCTCCCTC CCTTCCCCCC TCCTGCCCTA
74001 TGGAACAGCC CGGGTGCTCT GAGGGGGCTG GGAGGGCATG GCTTGGCTCC
74051 CAAAGGGGGT AGGGGCCCGG GGCACCCAGG CAAGGTGGCC CCTCCCCGTC
74101 TAGCCCCCTC CTCCCCAACC CTGCACTTAG TTTCTCCTCT GGATCAAACA
74151 CGTAATAAAG AGAATGTTTG AATCTGAGC TGCCTCCTCC TGTCTCTTCT
74201 CCCAGCCAGG CAGGGACCCA GTCTCCTGTG GGCAAGATGT GGCCTAGCCC
74251 ACCTGCCTTG CAGGAGAGAC TTGATTCCTG TCTGGGCCA GTGCTGGGTG
74301 GGCCCAGCTC CCCACTTACC CACAGGGCAC AGACAGGAAG CAAAGCCCAG
74351 GGCCCTTGCA CCAAAAGGGA AAGAAAACTC AGTAAGCTTA GATTTTATTT
74401 TTTTTAATTT TTAAAAAATG TTGAAAAATA AATCCATGTC TGCATAAGTT
74451 CCCAACCCCC ATTTCTCCAA GTTTCTGGAA GGTGGGCTTG GTGGGCACCC
74501 TCAGCTCCTT AGCATTTCCC AGCTGGCCCC TGAAGACAGA GCTTCTCTTC
74551 CAGCCTCTGC TGCTGTAAGG CCCCTCTGCC CACCTCCCCC CCTGCAGCCT
74601 CCCTCCCCAC CTCACCCCAG ACTTATTGCT AAAAGAAGGG AAAGAGGAAT
74651 GAGAACAGCC AGCACACCCA ACTGCCCTCT CCCCACTCCA CGCTAAGGTC
74701 ACTACCCCGG ACACACAAAG GGCAGGACCC AGAGGCCAAG CCCCAGCAGA
74751 CTAGGACACA GCCATTCCAG TACCGGCCAG GAAGCGAAAG TGCCCTCAGG
74801 CCAGCTCAAA GGCCCCTGAG CCCGGCCATG GCCCCAGGAG ACAGGCCCAG
74851 CTGCCAGGAA CACATGCAGA ACCCAAAGGG CGGGGCTGGG CTGTCCGAAA
74901 CTCTGGTCTT ACAAAGACCC CGCCAGAGCC CTAGTCCCTT CTGTCCTCAG
74951 TGACACCAGA GATGCCTGGG GATGGCCAGC AAAGGGGTCC TGGAGCCCGT
75001 GGTTGGTGGA GGACGTCAGG GCTCAGAGTG AGGGTGCTGG GGGCTCCAGA
75051 GGGGTTCCAA TCAGGGTGGG TGGGGCTGA GGGCCAGGGC GGGCGCTGTG
75101 GCGGGGGGCA GCCAGAGCGG GGCGGATGAG AGGCGGTGGG GGCTGGTTGG
75151 GGGCCAGCCG GGGCTGGAGG AAGCGGCCCT GCTGCAGTGG GGGTGGCTGT
75201 CGGAGCAGAG TGGGAGCCGT GGGCAAAGGT GGCCTCAGCA GCGGGGGTGG
75251 CTGGGACAGC GAGGTGGGAG GTGGAGGGGG TGGTGGCGCA GGGGGCACTG
75301 ATCGGGGCAC GGACGTGGAG ACCGATGTAA TCTGGACCTG AGGGGAGAGG
75351 AAAGAGTGAG AAGCCAGGCT CTTCCCGCCC TCAGCCCAGT CTAAG  (SEQ ID NO:3)
```

FEATURES:
Genewise results:
Start: 2396
Exon: 2396-2449
Exon: 58311-58490
Exon: 58732-58785

FIGURE 3A-33

```
Exon:    61383-61431
Exon:    61759-61824
Exon:    61914-61988
Exon:    62207-62259
Exon:    63025-63261
Exon:    63710-63829
Exon:    63931-64030
Exon:    64108-64220
Exon:    65353-65485
Exon:    65759-65937
Exon:    66216-66313
Exon:    67941-68198
Exon:    71417-71461
Exon:    72034-72391
Stop:    72392
```

Sim4 results:
```
Exon:    2396-2449, (Transcript Position: 1-54)
Exon:    58311-58490, (Transcript Position: 55-234)
Exon:    58732-58785, (Transcript Position: 235-288)
Exon:    61383-61431, (Transcript Position: 289-337)
Exon:    61759-61824, (Transcript Position: 338-403)
Exon:    61914-61988, (Transcript Position: 404-478)
Exon:    62207-62259, (Transcript Position: 479-531)
Exon:    63025-63261, (Transcript Position: 532-768)
Exon:    63710-63829, (Transcript Position: 769-888)
Exon:    63931-64030, (Transcript Position: 889-988)
Exon:    64108-64220, (Transcript Position: 989-1101)
Exon:    65353-65485, (Transcript Position: 1102-1234)
Exon:    65759-65937, (Transcript Position: 1235-1413)
Exon:    66216-66313, (Transcript Position: 1414-1511)
Exon:    67941-68198, (Transcript Position: 1512-1769)
Exon:    71417-71461, (Transcript Position: 1770-1814)
Exon:    72034-72394, (Transcript Position: 1815-2175)
```

CHROMOSOME MAP POSITION:
chromosome 11

ALLELIC VARIANTS (SNPs):

| DNA Position | Major | Minor | Domain |
|---|---|---|---|
| 6469 | A | G | Intron |
| 10970 | T | C | Intron |
| 10977 | T | C | Intron |

FIGURE 3A-34

| | | | | |
|---|---|---|---|---|
| 11044 | T | A | G C | Intron |
| 11470 | G | A | | Intron |
| 13050 | T | G | | Intron |
| 13231 | T | G | | Intron |
| 13813 | C | G | | Intron |
| 28240 | G | C | | Intron |
| 28472 | G | T | | Intron |
| 36051 | C | A | | Intron |
| 37118 | A | G | | Intron |
| 46715 | A | T | | Intron |
| 47190 | G | A | | Intron |
| 50801 | T | C | | Intron |
| 50877 | - | A | | Intron |
| 53173 | G | A | | Intron |
| 53756 | G | A | | Intron |
| 55878 | - | T | | Intron |
| 57192 | A | C | | Intron |
| 57500 | C | T | | Intron |
| 58984 | C | A | | Intron |
| 59775 | G | A | | Intron |
| 59869 | T | G | | Intron |
| 59985 | A | G | | Intron |
| 65094 | G | A | | Intron |
| 73617 | T | C | | Intron |
| 75055 | T | A | G C | Intron |

Context:

DNA
Position
6469    TGGAGAAAGGTCCAGCTTCCAGAGTTCACCTGCTAGAGTTTTCCATAACACCTGGGGGAG
AGGCTACTCCATCTGGGACCTGCCCCACCTCTGGGCCTCAGAAACTATGAGAGAGGGATT
GAGAGAAAACTTGCCCCACTTCTGCTGCAGTGGGAAGGGAGGGGGCTGCTGTCAGGCTTC
TAGGCAGTGAGCGGCATTGTTTATTCTCTCAGTTCTAGGAAGGGGAGTTTAGAAGTACTG
GTGAAGAAAACAAAGTTACAAGATCCTATAAGGAACAGCTGAACTACTCCAAACACTCTC
[A,G]
CTGGACCCCCATTGTTGATTCTGGATAAAAATATATATATATATAAAACTCTTTTTTTTTT
TTGACACAGAGTCTTGCTCTGTCGCCCAGGCTGGAGTGTAGCGATGCGATCTCGGCTCAC
TGCAACCTCCGCCTCCCGGGTCAAGCGATTCTCCTGCCTCAGCCTCCTGGGAGTAGCTGG
GACTACAGGCGCCCACCACCATGCTGGCTAATTTTTTGTATTTTTAGTAGAGACGGGGTTT
TGCCATATTGGCCAAGCTGGTCTCGATCTCCTGACCTCAGGTGATCTGCTGGATAAATAT 10970   GACTCCCTTCCCAATTCACAACTTGGTGAAAGACCCTCAGCCTAGCCAGGAGGAAGGGAC
TGGGTCTGCCTTTGGCTCCTCATTTATGGGTCTGGGAGGGGATCAGGACTCCTTACTGCT
ATGATCTGGCTGCTAAATTCAGTGACATCCCAGGCCTTTTTTCGTCCACGCAATGGGACT
GTCTGTCCAGGCCTGCTGGGAAAGAAAAGAGAGAAAAAATAGTTTTTTGCTCTTTGGCAGC

FIGURE 3A-35

```
           TTACAGGGACTTCAGCCATAGGAAACAACCTGTAGGAAAGGTGGGAGCTTCCGGTCACCA
           [T,C]
           GTGTGCTGACACTTCCTGCAATAGCACTAGGGAGTCTTTCTCAGGGAGCAAGGCCAGCCA
           GGTAGGATTATTTCCCAGTCTCCCAGCTAAGCAGGAAATGCCAAAATATGAACGTTTAGT
           AATTAGTGAGTGTAACTACCTGCTGACAGAGCTCCAGCCTAGACCTTGTCCTTGGGGCT
           GGTTGCCCCTGTTGATACTACAGTGAGCTACTCATTGCTTCTGATTACCATTTCAGTATG
           AGTTTTGCTTTGGTTTCTGATATCCCATGTGCGGCTGCCTTTTTTCTCCACCTTCTTTTT

10977    TTCCCAATTCACAACTTGGTGAAAGACCCTCAGCCTAGCCAGGAGGAAGGGACTGGGTCT
           GCCTTTGGCTCCTCATTTATGGGTCTGGGAGGGGATCAGGACTCCTTACTGCTATGATCT
           GGCTGCTAAATTCAGTGACATCCCAGGCCTTTTTTCGTCCACGCAATGGGACTGTCTGTC
           CAGGCCTGCTGGGAAAGAAAAGAGAGAAAAAATAGTTTTTGCTCTTTGGCAGCTTACAGG
           GACTTCAGCCATAGGAAACAACCTGTAGGAAAGGTGGGAGCTTCCGGTCACCATGTGTGC
           [T,C]
           GACACTTCCTGCAATAGCACTAGGGAGTCTTTCTCAGGGAGCAAGGCCAGCCAGGTAGGA
           TTATTTCCCAGTCTCCCAGCTAAGCAGGAAATGCCAAAATATGAACGTTTAGTAATTAGT
           GAGTGTAACTACCTGCTGACAGAGCTCCAGCCTAGACCTTGTCCTTGGGGCTGGTTGCC
           CCTGTTGATACTACAGTGAGCTACTCATTGCTTCTGATTACCATTTCAGTATGAGTTTTG
           CTTTGGTTTCTGATATCCCATGTGCGGCTGCCTTTTTTCTCCACCTTCTTTTTGTTGTGT

11044    GCTCCTCATTTATGGGTCTGGGAGGGGATCAGGACTCCTTACTGCTATGATCTGGCTGCT
           AAATTCAGTGACATCCCAGGCCTTTTTTCGTCCACGCAATGGGACTGTCTGTCCAGGCCT
           GCTGGGAAAGAAAAGAGAGAAAAAATAGTTTTTGCTCTTTGGCAGCTTACAGGGACTTCA
           GCCATAGGAAACAACCTGTAGGAAAGGTGGGAGCTTCCGGTCACCATGTGTGCTGACACT
           TCCTGCAATAGCACTAGGGAGTCTTTCTCAGGGAGCAAGGCCAGCCAGGTAGGATTATTT
           [T,A,G,C]
           CCAGTCTCCCAGCTAAGCAGGAAATGCCAAAATATGAACGTTTAGTAATTAGTGAGTGTA
           ACTACCTGCTGACAGAGCTCCAGCCTAGACCTTGTCCTTGGGGCTGGTTGCCCCTGTTG
           ATACTACAGTGAGCTACTCATTGCTTCTGATTACCATTTCAGTATGAGTTTTGCTTTGGT
           TTCTGATATCCCATGTGCGGCTGCCTTTTTTCTCCACCTTCTTTTTGTTGTGTCTTTTTG
           TTTTTTTGAGACGGAGTCTTGCTCTGTTGCCCAGGCTGGAGTACAGTGGCACAATCTCAG

11470    ACAGTGAGCTACTCATTGCTTCTGATTACCATTTCAGTATGAGTTTTGCTTTGGTTTCTG
           ATATCCCATGTGCGGCTGCCTTTTTTCTCCACCTTCTTTTTGTTGTGTCTTTTTGTTTTT
           TTGAGACGGAGTCTTGCTCTGTTGCCCAGGCTGGAGTACAGTGGCACAATCTCAGCTCAC
           TGCAACCTCCGCTTCCCAGGTTCAAGCAATTCTGCCTTAGCCTCCCAAGTAGCTGGTACT
           ACAGGCATGTGCCAGCACACCCGGCTAATTTTTTTTTTTTTTTTTTTGAGACAGGGTCTC
           [G,A]
           CTCTGTCGCCCAGGCTGGAGTGCAGTGGCGCGATCTCAGCTCACTGCAAGCTCTGCCTCC
           CGGGTTCACACCATTCTCCTGCCTCAGCCTCCCGAGTAGCTGGGACTTCAGGCGCCCACC
           ACCATGCCCAGCTAATTTTTTGTACTTTTTTTTTTTTAAAGTAGAGATGAGGTTTCACC
           ATGTTAGCCAGGATGGTCTCAATCTCCTGACCTCATGATCCACCCACCTCGGCCTCCCAA
           AGTGCTGGGATTACAGGCGTGAGCCACCGTGCCCGGCTGTAACACCTGGCTAATTTTTGT

13050    ATGGGAGAAGAATAGTACCCATCTTATAGGTATAGCTGTTATGAGTATTAAAAGAGTTAA
           TGAATAGAAAGCATTTAGAATAGCGCCTGGCACAGCAGAATGATCATTGTCATTATTGTT
```

FIGURE 3A-36

CCAGTTGAACAACACAGTGAATTTTATCTGAGCACCACACAACTCTAGGTCAGTATAAGG
GGTGATGTTTGGGATTTCTCTGTAATCAGTTGAAAAAATCTTGTTCTGGCATCTTCAAGC
CACTGGGGTCCTATAGGTGCTTTTTTCTAACATTTCTGTTTTTTTGTTTGTTTGTTTGTTT
[T,G]
TTTGAGATGGAGTCTTGCTCTTGTTACCCAGGCTGGAGTGCAGTAGCACCATCTTGGCTC
ACTGTGACCTCCACCTCCCAGGTTCAAGCGATTCTCCTGCCTCAGCCTCCCAAGTAGCTG
GGATTACAGGCACCTGCCACCATACCTGGCTAATTTTTTTTTTTTTTTTTTTTTTTTTG
TATTTTTAGTAGAGATGGGGTTTCACCATGTTGACCAGGCTGGTCTTGAACTCCTGACCT
CATGATCTGCCCACCTCGGCCTCCCAAAGTGCTGGGATTACAGGCGTGAGCCACTGCACC

13231   GTGATGTTTGGGATTTCTCTGTAATCAGTTGAAAAAATCTTGTTCTGGCATCTTCAAGCC
        ACTGGGGTCCTATAGGTGCTTTTTTCTAACATTTCTGTTTTTTTGTTTGTTTGTTTGTTTT
        TTTGAGATGGAGTCTTGCTCTTGTTACCCAGGCTGGAGTGCAGTAGCACCATCTTGGCTC
        ACTGTGACCTCCACCTCCCAGGTTCAAGCGATTCTCCTGCCTCAGCCTCCCAAGTAGCTG
        GGATTACAGGCACCTGCCACCATACCTGGCTAATTTTTTTTTTTTTTTTTTTTTTTTTTG
        [T,G]
        ATTTTTAGTAGAGATGGGGTTTCACCATGTTGACCAGGCTGGTCTTGAACTCCTGACCTC
        ATGATCTGCCCACCTCGGCCTCCCAAAGTGCTGGGATTACAGGCGTGAGCCACTGCACCC
        GCCCTAGTTTGCTTTTTTTACCAATCACCTATCTGAAAAAAAATGGAATGCTACTGGAGAG
        ATTCATGTACTTCTGAGAACACTTTTAGCTCATTTTTTATAAGGCATCAATATTAGATAG
        TTTTCTTGATTAAAGAAAAAAAAACACCACCCACTGCCTGCCTATATTTCTGGGTTGCAA

13813   CTATATTTCTGGGTTGCAAATGATGGCGGTGGATGTGCAGCCTCATCCGTGGCTAGAAGG
        CCAAATCCAAAGTCACCAGAGCTTGAGTTTTTTGAGAGTTGAGATCTGTGTGTCAAAGGG
        GAAGCCCTAGGGTGGTTCTCTGCAGCACCAAGAGCAGGGATTCATACCATCATGTTCCTT
        TCTTTTTTCTTTTCTCGTCTTTTCTTTCTTCCTTTCTTTTTGTTCTCATGAGTTCTCACT
        GTGTTGCCCAGGCTGGTCTTGAATATTTGGCCTCAAGTGATCCTCCCGCATTGGCCTCCC
        [C,G]
        AAGTGCTGGGATTACACACTCAGCCATGTTCCTTTCTTCAAGTACGGTATTGACCCTTTG
        GCCACAGGAGAACGTGCCCAGTTTTTCTTAAAGACCACGTGGGAACTCAGCAGCCCATGA
        TTGTAGGTTCCTTTTTTCCCTCATAGAGTGGCCTTCAAGGGCAGGTTCTTGTTATCTGCGT
        TTCAGAGACCCAAAGGGACACAGGCATTTCTGCTCCTGGGAATTTGCGGACTTTGAATCT
        TGAGCTCAGATTTTGGTCTCTGTTGGTTGCTTGTTTATCTTCATCTCTTGTCATTTCTGG

28240   TATTAAATAAATAAATAAGATTTACTTATCCAAAAGCACAATTATGTGCCTTTTTTCTTT
        TCTTTTTGAGACGAGAGTCTGACTCTGTTGCCCAGGCTGCTGTAGTACAGTGACGCAGTCT
        C
        [G,C]
        GCCTTGACCTCCCAGGCTCAAGCAATCCTCCCACCTCAGCCTCCCAAGTAGCTGGGACTA
        CAGGCATGTGCCACTATGCCTGGCTAATTTTTTGCACTTTTTGTAGAGATGGGGTTTCGT
        C

28472   TTTCTTTTCTTTTGAGACGAGAGTCTGACTCTGTTGCCCAGGCTGCTGTAGTACAGTGAC
        GCAGTCTCGGCCTTGACCTCCCAGGCTCAAGCAATCCTCCCACCTCAGCCTCCCAAGTAG
        CTGGGACTACAGGCATGTGCCACTATGCCTGGCTAATTTTTTGCACTTTTTGTAGAGATG
        GGGTTTCGTCATGTTGCCCAGGCTGGCCTGGAACTCCTGGCGTCAAGCAACCTACCTGCC

FIGURE 3A-37

TTCGCCTCCCAGAGTGCTGGGATTACAGGCAGTCGCCATTGTATCCAGCCCAGTTATGTA
[G,T]
TTATGTGCCATTTCTAAACTACTTTAGAACCCATCTCTTTGGTGTTTGTTTGTTTGAGAC
AGAGTCTCACTCTGTCACCTCAGCTGGAGTGCAGTGGTGTGATCTCAGCTCACTGCAGCC
TCGGCCCCCAAGGTTCAAGCGACCCTCCCACCTCAGCCTCCCAAGTAGCTGGGACCACAG
GTGCTCTTTTTGTTAAGAGTGGAAAAGCCAAGGTCCATGTACTTTTTTTGAGAAAGACAG
CCTGTTGGCTTTCTTCAGAGTGGTTCTGCCCCTTCCCGTACCCCATCTCCAACACATTTT

36051   CTGCCCACCTCCTGCTATGTTCTAGTTCTGATAGGAGTACCATTCAGAGTTCTTGGCAGG
GGACCAACCCGCTTCTACCGTGGTTGGTTTCCCCTCCTTTTCCCAGCTTGTTTGATGTGC
ACGTTCTCCAAAATTCTTATGCAGCTGGTTGGCTCTGTAGTGCCCAGAGATTGGAGCTCC
TGCAACGGGAACCCCGCCGCTTCCCTCCCTGGTTTTAGGGGCAGGGCTTGAAAATAAAGA
ATCATAATCTCCCTTCCTCCTCCTCCTCTCCCCCACTTCTCCCTGCCCCCACCCCCA
[C,A]
CCCCACCCCCACCCTGCCAGGCAAACTGGAGTGACCAGCTCAGAGCGGGACTCAGTCCAC
CTCCCTGCTCTGCATGTCAGCAGTGATCTGGAGGAGATTCCGGGGCGCATGAGTATGTGA
ACTCTGGAGCACGTTACTGTCCCGGGCTGGCACTCTGTGGCAGGTGTGTGCACTCATTCT
GCTGTTACTGGAGACCAGTCTCCTTAGGGGTGATGGTGACCCAGCTAGATGTCTGCCAGG
TCTGTCCAAGGCCACCCTGTTCTCTAATAGCTTGGGAAATGGAAAGCACTTCTAAATACC

37118   ACGGAGTCTTGCTCTGTTGCTCATGCTGGAGTGCAGTGGCGCGATCTCGGCTCGCTGCAA
CCTCCACACCCCAGATTAAAGCGATTCTTCTGCCTCAGCCTCCCGAGTAGCTGAGACTGC
AGGCATGCGCCACCACGCCCAGCTAATTTTTTGTATTTTTAATAAGAGACAGAGCTTCACC
ATGTTGGCCAGGCTGGTCTTGAACTCCCGAACTCAGGTGATCCGCCTGCCTCGGCCTCCC
GAGGGACTGGGATTACAGGCATGAGCTACTGTGCCCAGCCTGAAGATTGGTTATTTAGGG
[A,G]
CTGTGACAAATGGTTTTGCAGAGGAGCACTGGAAAGCCTGTAACTTCACAGAGCCAGGGG
TCAGCTTTTGTGCCATAGCCTTATAGCTTCTGTGGCCTGTAGTGCCTGAGGCCAGGGGAT
CAGGTGCTGACCACCTTTCCCTCTTCCTTCCTGTGTCTTGCGGCCAGCGACTGTTATTGT
CAGGTTGACCCTCTGGTTAGAGAGGATGACTTTGGCCTGGTGTCCAGACTCCCTGCTGCC
TTATCCCCTCTGCCCTGGAACTGCACCTAAAAACAATTACTTTCCTCCTGATTCCAACAT

46715   CACCATGTCATTCAGCTACTCCTCCTGCAGGATGGTTTTATGTTAGGAAAGAGGGTCCTC
TTTGCCTGATTGCCCAGCCATGGCAGAATTTGACTTTTCCTTGTTATAGAGGGAATACCA
GGATGACAGGAATCAACTTAGCTATACTGGTACTTACAGTCAAATTTCTAGGTATTGTAG
CTCTTCCCAGAGCCCAGAGAACCCTTGGAGAGGGGAAACAATGGTTCCTACCCAAAAATG
AAGCTAGATAATAATAGAATACATCATCAAGACATTACTGAACACCACGTTCTATGGTAA
[A,T]
CACTGACATGGATTTTCCTTTTTTTTTTCCTTTGAGACAGGGTCTTACTCTGTCACCCAG
GCTGGAGTGCAGCAGTGTGATCACGGCTCACTGCAGCCTCAGCCTACCTCCCTGGGCTCA
GGTGATCCTTCCACCTCAGCCTCCCAAGTAGCTGGATTGCAGGCACTTGTCACCACACC
CCGGCTAATTTTTGTGTTTTTTTGTAGAGCCTGTGTTTTGCCATGTTGCCCAGGCTGGCC
TCGAGTTCCTAGGCTCAAGGGATCTGCCTGTCTTGGCCTCCCAAAGTGCTGGAATCAGAG

47190   CACACCCCGGCTAATTTTTGTGTTTTTTTGTAGAGCCTGTGTTTTGCCATGTTGCCCAGG
CTGGCCTCGAGTTCCTAGGCTCAAGGGATCTGCCTGTCTTGGCCTCCCAAAGTGCTGGAA

FIGURE 3A-38

```
        TCAGAGGTGTAAGCCACCACGCCCGGCCAGATTTTCTCATTTAATCTTCACTCTAATTCT
        GTGAAATGGGTACAGCTAGTATCTTTATGTCCCAAATGAGGAAACAGATTTGGAGAAGTT
        ATGTCACTTTGCTCATGTTCAGTCAGCTGGTAAGCAACAGAGGTGGGCAGAGCGACTATA
        [G,A]
        TAAGTTTTCTGTATAGTTTACCTCTTCTAAGTTTCTGGAAGGCAGGAGCCAGATCGCACT
        GAGCTTTGCAACTGGAGCCAGGGCTCCAGAGTACTGCTCAACAAAGGTTTGCTAGGGCAA
        CAGTAGCTGGGGATTTAGCGACCAGACCCCAGCAAGCAGATTCTCAGGGATGAAAGTAGT
        CCTGGAAGCCTCTAAAGCCCTGGTTGCTCAGTAGAATCTAGTTTCAAGAGGAGCCCAGCA
        TTTCAAGTGGCTCTGAAGACAGAGGAGATTTGGAGAGTGCTCTTTGCATTGTGGCTTCCA

50801   CTCTGAATGCCAATTTCTCAATGGAAAACAGGGAGACTACCTACCCTATAGGTCTGTGTT
        TGGAGAAAACAAAGTGTAAGCGCTGGACATACAGTAGCATCAGAAATGCTGAATCCGTTG
        GCCAGGGCTCATGTGTAAGGCAAACATTTCTTGGCCACTCCTGAGTAGCATGGTCTTGCA
        GGAATATATGCTTAAGTGCTGTGAGAGCACAGAGGAAGCTTTGCCCTTCCCTAGAGGGTT
        AATGGCTACCAACGTGAGAAGGTCACGGAGTTCCTTAATGAGAGGGAGCCTAGCCTAGAA
        [T,C]
        AGGGGATGAATGAGAAATTGTTCTGAGAACCAGAGGCAAGGCTGCAACCAGCACATAGAC
        AGGGGTCGTTGGTCTAGAAGGGGAGTCTTCTCCAGATGAGAGACAGCCAGCTTGCCCTGT
        GCTCACCATGTGCCCAGATAGTGGGGGCTTAGCAGGAGGAAGGTGTGAGGAATCCCAGGC
        CTTTGGAATTCCTTGAGAAAGCAGTGTTGTTTTGAAGGTAAGGCAGGGGATTGGTGACTG
        GAAACTTGGAGGTGAGTGAGAACCTAGGGATGAACGTTCAGAAGCAGGGCTGGAAGGAAC

50877   TAAGCGCTGGACATACAGTAGCATCAGAAATGCTGAATCCGTTGGCCAGGGCTCATGTGT
        AAGGCAAACATTTCTTGGCCACTCCTGAGTAGCATGGTCTTGCAGGAATATATGCTTAAG
        TGCTGTGAGAGCACAGAGGAAGCTTTGCCCTTCCCTAGAGGGTTAATGGCTACCAACGTG
        AGAAGGTCACGGAGTTCCTTAATGAGAGGGAGCCTAGCCTAGAATAGGGGATGAATGAGA
        AATTGTTCTGAGAACCAGAGGCAAGGCTGCAACCAGCACATAGACAGGGGTCGTTGGTCT
        [-,A]
        GAAGGGGAGTCTTCTCCAGATGAGAGACAGCCAGCTTGCCCTGTGCTCACCATGTGCCCA
        GATAGTGGGGGCTTAGCAGGAGGAAGGTGTGAGGAATCCCAGGCCTTTGGAATTCCTTGA
        GAAAGCAGTGTTGTTTTGAAGGTAAGGCAGGGGATTGGTGACTGGAAACTTGGAGGTGAG
        TGAGAACCTAGGGATGAACGTTCAGAAGCAGGGCTGGAAGGAACTTAAAAGGGACATTTG
        GATTGTTTCTAGCTTTTGGGCAAAATCTAGGATTAAATATGATTTTTTCATTGATAGAAT

53173   GCTTAGTAACTACTTGGTTTGCCTTTTGGTTCCAAATAACTGCCTTGCAGGGTGACCCCT
        TATTCTTTCTAAAGGCTACTTGAGAGCCATAGGGTCTACTCTTGACAGACCTCCTCCATC
        CTTTAGGGCCTGTCTAGAGTATGATATAGGCCAGAGCTTTGGGAGTGCCTGGTGTGCCAC
        GTCTTACTATAAGCAGGGAGGATGGTGGTAGAGGGGAGAGCGTGGCTTTTGCCAGGTCCT
        ATTGAGTTGGCCCAGCAGGGCAGCTAATCCTCAGCCTGCCATCCTGTTGGTGAGACCCAG
        [G,A]
        GCCAAGCTGAATGGTGCAGCCAGAACCAAAAAAGAGAAACTCTCTCTCCATATTAGCCAC
        TGCATACTCTTACCTCTTTATCCTTCAGGGAAGAAGCTAGGTGAGGAAGTTGCCTCACTT
        GGGGCCTTGGCCCAAGAAGCATTTCTGTTGGAGACTCTCTCCTCTCTTTTCCCTTTTTCT
        TTTCTCTGCTTCCTTCCAGTGGCTTGCCTCCTTACCCTGGCTCACATCCCTGCTGTGGGA
        AACATCTTACAGCATAGAAGAAGGGGTGCAGGGGTAAGTAAGGGAAGGATTGAGCACTTG
```

FIGURE 3A-39

53756     GGAAGGATTGAGCACTTGGAGTCCTCTGAGTTGGATGGTTCAGTCCCGAAAAGGGGGTTG
GTGACTTTGGAGCAGGGGATCAAAGAGCAAGCACCAGTGCTTGTTGCTTCTCTGGCTCCT
GAACAAGCAGAACCTCCTCTCTTTCCCTGTCCTGGATACCCAGCGTGGGACCAGCCCTTC
ACAGCCACCCTGTCTTGAGTTCCTGACTCTCCTCCTTCCCTCTTTTGAAGGCTAGAGGTG
CTGGTGTCGGCTAGCAACAGGTTGAGGGAGTGTGGCATTTCACCAGGTCTGGAGGAGAGC
[G,A]
GGCACTCAACCTGGCCCCTTCTGCGGAAAGGCCCGTAGCATCTCTTGTCAGCCTTCAGCT
GAGCTGTAGCTGGCTTAGCGGGCTCAACTTCGATTTGGAAGGTTGTTTTGACAGTGAGAC
TTCTGGATTGGCAGACAGTAGTATTTGGGGACATAATGATTGCTCTTATTGAACATCGGA
TAAGGCATTTTACATGTGCTCTTTCATCTACCTGTGTAAAGTAGGGAATGTTTATTGCCA
CTTTACAGATAAGGAAATTAAAGCTTGTACGTGGGGGAGCCAGGGCTTGAACCTGATTCT

55878     TCTAGGAATGCTGGACAGTTCCTTGGGTAGTAGCAAGTCATTCTTTTTTTCTCTGTGGTT
TTTGAGTGCTTCACGTACAGCCAGCAGGGGCCATGAAAGGAAGAACTTTCACTCACACTC
CTCTGGTCACCCTGCTGCCCTCCAGACTGTTTCCTTGAAGTTTCCAAGGCAGCTCTGGAT
GGTTCTGGGATGAGGCTCTGGCCTCATATGCTTTGTTGCAGTATGCTGGAGCGATCGCTC
CAGATGTTCTTTGTGAGATGTAAACCAGGGCGCTAATCAGGAGTTAGACCAGACTCTGCA
[-,T]
TTTTTTTTTTTTTTTTTTGAGACAGGGTCTCGCTCTATCACCCAGGCTGGAGTACAATGG
CATGATCATGGCTCACTGCAGCCTCGAACTCCTCCTGGGTTCAAGCGATCCTCCCGCCTC
ATCCTCCAGAGCAGCTGGGACTATAGGTGCATGCCACCACACCCAGTTGATTTCTTAATT
TTTTTTTTTTTTTTTTTTGAGACGGAGTTTCACTCTTGTTGCCCAGGCTGGAGTGCAGT
GGTGCGATCTCAGCTCACTGTAACCTCCTCCTCCTGGGTTCAAGCAATTCTCCTGCCTCA

57192     CCACAAGTGGAAAATTCTACACGTAACCCCATATGACAGGTTATAAGCAAAATTCAATCA
CTTTATTTCATGCACAAAATTATTTTAAAATGTCATGAAATTACCTTCAGGCCATGTATA
TAATGTACACATGAAAAATAAATGTTTAGACTTGGGTCCCATCCCTGAGATATCTGATTA
TGTATATGCAAATATTCCAAAATCCAAAACAATTTAAAATCTGCCACGTTTCTGGTCCTA
AGCATTTTGGATAAAGGATATTCAACCCGTATTATGTTTATATGCCTCTTCAGTGCTGGT
[A,C]
GTTGTAGCTTCTGCTTCCTCATCCCCTCATTTGAGCCGGGTGGCAGAGCAGGGCAGACTG
CTGCCTTGCTCAGACCTAATCGTTCAGTTCTTTCATTGTACAAGTATTCATTGAGCAGCA
AACATAAGCCAGTCTCTCTAAGTGCTGGGATGTATCAGTGAATAAAGAATATATGCCTGC
TTTCATGTGCTTCCATTTTTACTGGGGGAGATGGCAAATAAATGTAAAGTGATAAATAAC
AAAGGTTCAGTGGGGCATTCGTAGTTCAGCGGCAGAAATTTCGTCTCCTACGCGGGAGAC

57500     CTTCTGCTTCCTCATCCCCTCATTTGAGCCGGGTGGCAGAGCAGGGCAGACTGCTGCCTT
GCTCAGACCTAATCGTTCAGTTCTTTCATTGTACAAGTATTCATTGAGCAGCAAACATAA
GCCAGTCTCTCTAAGTGCTGGGATGTATCAGTGAATAAAGAATATATGCCTGCTTTCATG
TGCTTCCATTTTTACTGGGGGAGATGGCAAATAAATGTAAAGTGATAAATAACAAAGGTT
CAGTGGGGCATTCGTAGTTCAGCGGCAGAAATTTCGTCTCCTACGCGGGAGACTCGGGTT
[C,T]
GACTTCGGCCATGCAGTCCTTCCATGCAGGAAGGGCTACTACGTTTCTACCCAACAAAGT
TATTATGGCTGGACGCAGTGGCTCACGCCTGTAATTCCAGCACTTTGGGAGGCCAAGGCG
GGCGGATCACCTGAGATCAGGAGTTTGAGACCAGCCTGACCAACATGGAGAAACCCTATC
TCTATTGAAAATACAAAATTAGCCAGGCGTGGTGGCGCATGACTGTAATCCCAGCTACTC

FIGURE 3A-40

GGGAGGCTGAGGTGGGAGAATTGCTTGAACCCGGGAGGTGGAGGTTGCGGTGAGCTGAGA

58984　TTTCGCTGGTCAGAGAAGTGATTTGGGGCCTTTTTGTCTCATCCTCAGGTAGCTGTGAAG
ATCATTGACAAGACTCAACTGAACTCCTCCAGCCTCCAGAAAGTAAGCACATGGCACCTC
CTGTCCCTTTTTTTTTTTTTTTTTTTTTTTTTTTTGAGTCAGAGCCTCACTCTTGTCGCCC
AGGCTGGAGTGCAATGGTGTGATCTCGGCTCACTGCAACCTCCGCCTTTTGGTTTCAAGC
GATTCTCCCGCCTCAGCCTCCCGAGTAGCTGGGATTATAGGCACCCGCCACCACACCTGG
[C,A]
TAAGTTTTGTATTTTTAGTAGAGATGGGGTTTCACCATGGTAGCCAGGCTGGTCTCGAAC
TCCTGACCTCAAGTGATCCGCTCGCCTCGGCCTCCCAAAGTGCTAGGATTATAGGCGTGA
ACCACTGCCCCAGCCCACCTGTCCCTTTCTAAATCTCTCTTCTGGGGTCAATGATCTAC
TGACCCCATTTAGACCTTCTCTTGAATTCCTAGTTTAAATTTTCTGGCCATTTCGCTCAC
CGTCCCCCAACCATTCCCTCCCATGGCTCTGCTACCTTCGGGGCTTTGGTTGGATCATCT

59775　AGATCTGGAATGATACAGGGGAGTGGCTTTAGAAATACAAGAATAAGAGGAAGCAGGGAA
CCTGCCGGTGGGTTCTGTGCCAGCTACCTTTTAGAGAATGAGCTCCAGCTCAAATTTTCT
GAACAAAACCTAGTTCTGTTCATCTTGTGGCAAATCAGATATTTTCTCCATAAGCATATT
GTGGCAGTTGAGTTAGGAGAAGGCATGATTCGTGCTAACAGAGTCAGATAGTGATACTGG
GAACCTTAGGAGTAAGGGCTGAGGATTGTTGTTGAGGGCGATGCTCATGGAATTAGAGTG
[G,A]
ATGAGTTGTTCTCCGGACATGCAAATAGCCAGAACCAAGGTGTTTCCTATTTATTGTTAC
CCCTGGGATCCCTTCAAGGGTTCTTCAGTTCAGTAGAAACATTGTTGTCATCATCAGGGT
GTCTCTGCTTGAAGCTTTCCAGGAGGAAGGGAAAAAGGGCTGCTTATGACATCCTGGCTC
CAGCCCCACAGAAGAAGTCAGCGTGGGGTAGGCCATTTGGCCTTGGGAGCAGTCTAGCCT
GCCATCGTAATAATCGCCAGTCCACCAAGCCATCTTATTCCTGACCTTGTTTTTCTCCCT

59869　AGAATGAGCTCCAGCTCAAATTTTCTGAACAAAACCTAGTTCTGTTCATCTTGTGGCAAA
TCAGATATTTTCTCCATAAGCATATTGTGGCAGTTGAGTTAGGAGAAGGCATGATTCGTG
CTAACAGAGTCAGATAGTGATACTGGGAACCTTAGGAGTAAGGGCTGAGGATTGTTGTTG
AGGGCGATGCTCATGGAATTAGAGTGGATGAGTTGTTCTCCGGACATGCAAATAGCCAGA
ACCAAGGTGTTTCCTATTTATTGTTACCCCTGGGATCCCTTCAAGGGTTCTTCAGTTCAG
[T,G]
AGAAACATTGTTGTCATCATCAGGGTGTCTCTGCTTGAAGCTTTCCAGGAGGAAGGGAAA
AAGGGCTGCTTATGACATCCTGGCTCCAGCCCCACAGAAGAAGTCAGCGTGGGGTAGGCC
ATTTGGCCTTGGGAGCAGTCTAGCCTGCCATCGTAATAATCGCCAGTCCACCAAGCCATC
TTATTCCTGACCTTGTTTTTCTCCCTAATTCTTCTTGGTTTTCTCCCTAATTCTTCCTGA
CTCTCTGGAAGGCACCAACACCAGACAAATAGAGCCATTTTCAAAACCTTTTGAGACTCT

59985　CGTGCTAACAGAGTCAGATAGTGATACTGGGAACCTTAGGAGTAAGGGCTGAGGATTGTT
GTTGAGGGCGATGCTCATGGAATTAGAGTGGATGAGTTGTTCTCCGGACATGCAAATAGC
CAGAACCAAGGTGTTTCCTATTTATTGTTACCCCTGGGATCCCTTCAAGGGTTCTTCAGT
TCAGTAGAAACATTGTTGTCATCATCAGGGTGTCTCTGCTTGAAGCTTTCCAGGAGGAAG
GGAAAAAGGGCTGCTTATGACATCCTGGCTCCAGCCCCACAGAAGAAGTCAGCGTGGGGT
[A,G]
GGCCATTTGGCCTTGGGAGCAGTCTAGCCTGCCATCGTAATAATCGCCAGTCCACCAAGC
CATCTTATTCCTGACCTTGTTTTTCTCCCTAATTCTTCTTGGTTTTCTCCCTAATTCTTC

FIGURE 3A-41

```
          CTGACTCTCTGGAAGGCACCAACACCAGACAAATAGAGCCATTTTTCAAAACCTTTTGAGA
          CTCTTTGTTACTAAAGCCAGTCTGATTCTGGCCAAAAATGTGATCTCAGCAATGATCCCT
          GAAAAATGAACATTGAAGAAGCTAGCCCCCTCAGGGGTCTAGACAAGCCCAGAAAACCCC

65094     CGGCTATTGAGTCTGTTGCTTCTGTCTAGTGCTTTATGTTTGGGTGTGTGTATCTGTGTG
          TGTGTGTGTGTGTGTGTGTGTGTATGTGTCCGTCTTCCCGTCTGTGGATCTGGAGACT
          TTGTGATTGTTCTTCTGCCCATTTGGGTTTTGTTCATCATCTGAGTATCCCCACATGAAC
          TCCCAGCCTCCCTGCCCTGCTCTCCCTCTGGTGGTGGGATCCTTAAGAGGCACCTGGTGA
          CACTTGGTATAGGCCCATATTGCTCTGTGTTGAGGGGAGTGGACTTGAGTCTGGACATGT
          [G,A]
          TTCTTGCGGATGTTTGTGTCTCTGGGTGTGTGGGCTTATGTATTCCTTTCTGAGACTGTG
          TTTGTCAGTGTCTGTGTCAGAGCATGTGTGTCTCCAGGGTCTCCTCCAGGGGGGATGTAT
          TGGTCTTACAAGTGGATGTCCGGTATGATCCTGGGGTGTTTGAGTGTTGGGAGAGGGCGG
          TATGTGTAAATGTGTCCATCCATAGGGATCTCCACATGACTTCTGCCCTCCCTTGAAGCT
          GTTTTCTGTTTCTTTCAGCTGGAAGGCGACACCATCACCCTGAAACCCCGGCCTTCAGCT

73617     ACTGGGCACTCTGTGATGGGGGAGCCTTTGTCTGAAAGCACAGCCCCCTCGCCCTTCCTC
          TCCCCATGGCTTCCCCTTCATTGGCATTAATCTGGGCACCAGCTCTCTCCATAGCAGTGA
          CTTCCCTCACCACTCTCATCTCTCAGCCTTGCCTTTTCTTCCTGACACTGTCGCCCCCTC
          CTCTCAGGAGACACTGCCGAGGGCCACCTGGCAGAAGGCTGAGTTAGGCAGCAGGGCCGG
          GAGCGTCTGCCCTCCACAGGGTGGGGGACAGATAGGCTAAGCGACTCCCAGCTTGCTACC
          [T,C]
          TCAGTGGCCAGTGTGGGCGTGGGCGGTTTGGGGCGCTTGGCTGGTGGTGGCCACTGCATC
          CCTTAATTTATTTCTCTGCTGTTTCTGTTCTTGAGAAATTGGGGGTGGGAGTCCTACACA
          GAGGCTGCCCCTACCCTCACCTGAGTTGTACATTTTTTTGTGATGGGTTTTATTTTTTAT
          TATTTTATTTTATTTTTTTTTTTTTTTGATTTATGATGACTCCACCCCTCTTCATCACCC
          CCGCTCCCAGGCCAGGCTCAGCGATTAAGCCGAGCCCTTGCGTCCTAGGAAGGGGCCTTG

75055     GACACAGCCATTCCAGTACCGGCCAGGAAGCGAAAGTGCCCTCAGGCCAGCTCAAAGGCC
          CCTGAGCCCGGCCATGGCCCCAGGAGACAGGCCCAGCTGCCAGGAACACATGCAGAACCC
          AAAGGGCGGGGCTGGGCTGTCCGAAACTCTGGTCTTACAAAGACCCCGCCAGAGCCCTAG
          TCCCTTCTGTCCTCAGTGACACCAGAGATGCCTGGGGATGGCCAGCAAAGGGGTCCTGGA
          GCCCGTGGTTGGTGGAGGACGTCAGGGCTCAGAGTGAGGGTGCTGGGGGCTCCAGAGGGG
          [T,A,G,C]
          TCCAATCAGGGTGGGTGGGGGCTGAGGGCCAGGGCGGGCGCTGTGGCGGGGGGCAGCCAG
          AGCGGGGCGGATGAGAGGCGGTGGGGGCTGGTTGGGGGCCAGCCGGGGCTGGAGGAAGCG
          GCCCTGCTGCAGTGGGGGTGGCTGTCGGAGCAGAGTGGGAGCCGTGGGCAAAGGTGGCCT
          CAGCAGCGGGGGTGGCTGGGACAGCGAGGTGGGAGGTGGAGGGGGTGGTGGCGCAGGGGG
          CACTGATCGGGGCACGGACGTGGAGACCGATGTAATCTGGACCTGAGGGGAGAGGAAAGA
```

FIGURE 3A-42

ISOLATED HUMAN KINASE PROTEINS

RELATED APPLICATIONS

The present application is a divisional of U.S. application Ser. No. 09/984,890, filed on Oct. 31, 2001 and issued on Dec. 10, 2002 as U.S. Pat. No. 6,492,156.

FIELD OF THE INVENTION

The present invention is in the field of kinase proteins that are related to the serine/threonine kinase subfamily, recombinant DNA molecules, and protein production. The present invention specifically provides novel peptides and proteins that effect protein phosphorylation and nucleic acid molecules encoding such peptide and protein molecules, all of which are useful in the development of human therapeutics and diagnostic compositions and methods.

BACKGROUND OF THE INVENTION

Protein Kinases

Kinases regulate many different cell proliferation, differentiation, and signaling processes by adding phosphate groups to proteins. Uncontrolled signaling has been implicated in a variety of disease conditions including inflammation, cancer, arteriosclerosis, and psoriasis. Reversible protein phosphorylation is the main strategy for controlling activities of eukaryotic cells. It is estimated that more than 1000 of the 10,000 proteins active in a typical mammalian cell are phosphorylated. The high energy phosphate, which drives activation, is generally transferred from adenosine triphosphate molecules (ATP) to a particular protein by protein kinases and removed from that protein by protein phosphatases. Phosphorylation occurs in response to extracellular signals (hormones, neurotransmitters, growth and differentiation factors, etc), cell cycle checkpoints, and environmental or nutritional stresses and is roughly analogous to turning on a molecular switch. When the switch goes on, the appropriate protein kinase activates a metabolic enzyme, regulatory protein, receptor, cytoskeletal protein, ion channel or pump, or transcription factor.

The kinases comprise the largest known protein group, a superfamily of enzymes with widely varied functions and specificities. They are usually named after their substrate, their regulatory molecules, or some aspect of a mutant phenotype. With regard to substrates, the protein kinases may be roughly divided into two groups; those that phosphorylate tyrosine residues (protein tyrosine kinases, PTK) and those that phosphorylate serine or threonine residues (serine/threonine kinases, STK). A few protein kinases have dual specificity and phosphorylate threonine and tyrosine residues. Almost all kinases contain a similar 250–300 amino acid catalytic domain. The N-terminal domain, which contains subdomains I–IV, generally folds into a two-lobed structure, which binds and orients the ATP (or GTP) donor molecule. The larger C terminal lobe, which contains subdomains VI A–XI, binds the protein substrate and carries out the transfer of the gamma phosphate from ATP to the hydroxyl group of a serine, threonine, or tyrosine residue. Subdomain V spans the two lobes.

The kinases may be categorized into families by the different amino acid sequences (generally between 5 and 100 residues) located on either side of, or inserted into loops of, the kinase domain. These added amino acid sequences allow the regulation of each kinase as it recognizes and interacts with its target protein. The primary structure of the kinase domains is conserved and can be further subdivided into 11 subdomains. Each of the 11 subdomains contains specific residues and motifs or patterns of amino acids that are characteristic of that subdomain and are highly conserved (Hardie, G. and Hanks, S. (1995) *The Protein Kinase Facts Books*, Vol I:7–20 Academic Press, San Diego, Calif.).

The second messenger dependent protein kinases primarily mediate the effects of second messengers such as cyclic AMP (cAMP), cyclic GMP, inositol triphosphate, phosphatidylinositol, 3,4,5-triphosphate, cyclic-ADPribose, arachidonic acid, diacylglycerol and calcium-calmodulin. The cyclic-AMP dependent protein kinases (PKA) are important members of the STK family. Cyclic-AMP is an intracellular mediator of hormone action in all prokaryotic and animal cells that have been studied. Such hormone-induced cellular responses include thyroid hormone secretion, cortisol secretion, progesterone secretion, glycogen breakdown, bone resorption, and regulation of heart rate and force of heart muscle contraction. PKA is found in all animal cells and is thought to account for the effects of cyclic-AMP in most of these cells. Altered PKA expression is implicated in a variety of disorders and diseases including cancer, thyroid disorders, diabetes, atherosclerosis, and cardiovascular disease (Isselbacher, K. J. et al. (1994) *Harrison's Principles of Internal Medicine*, McGraw-Hill, New York, N.Y., pp. 416–431, 1887).

Calcium-calmodulin (CaM) dependent protein kinases are also members of STK family. Calmodulin is a calcium receptor that mediates many calcium regulated processes by binding to target proteins in response to the binding of calcium. The principle target protein in these processes is CaM dependent protein kinases. CaM-kinases are involved in regulation of smooth muscle contraction (MLC kinase), glycogen breakdown (phosphorylase kinase), and neurotransmission (CaM kinase I and CaM kinase II). CaM kinase I phosphorylates a variety of substrates including the neurotransmitter related proteins synapsin I and II, the gene transcription regulator, CREB, and the cystic fibrosis conductance regulator protein, CFTR (Haribabu, B. et al. (1995) *EMBO Journal* 14:3679–86). CaM II kinase also phosphorylates synapsin at different sites, and controls the synthesis of catecholamines in the brain through phosphorylation and activation of tyrosine hydroxylase. Many of the CaM kinases are activated by phosphorylation in addition to binding to CaM. The kinase may autophosphorylate itself, or be phosphorylated by another kinase as part of a "kinase cascade".

Another ligand-activated protein kinase is 5'-AMP-activated protein kinase (AMPK) (Gao, G. et al. (1996) *J. Biol Chem.* 15:8675–81). Mammalian AMPK is a regulator of fatty acid and sterol synthesis through phosphorylation of the enzymes acetyl-CoA carboxylase and hydroxymethylglutaryl-CoA reductase and mediates responses of these pathways to cellular stresses such as heat shock and depletion of glucose and ATP. AMPK is a heterotrimeric complex comprised of a catalytic alpha subunit and two non-catalytic beta and gamma subunits that are believed to regulate the activity of the alpha subunit. Subunits of AMPK have a much wider distribution in non-lipogenic tissues such as brain, heart, spleen, and lung than expected. This distribution suggests that its role may extend beyond regulation of lipid metabolism alone.

The mitogen-activated protein kinases (MAP) are also members of the STK family. MAP kinases also regulate intracellular signaling pathways. They mediate signal transduction from the cell surface to the nucleus via phosphorylation cascades. Several subgroups have been identified, and each manifests different substrate specificities and responds to distinct extracellular stimuli (Egan, S. E. and Weinberg, R. A. (1993) *Nature* 365:781–783). MAP kinase signaling pathways are present in mammalian cells as well as in yeast. The extracellular stimuli that activate mammalian pathways include epidermal growth factor (EGF), ultraviolet light, hyperosmolar medium, heat shock, endotoxic lipopolysaccharide (LPS), and pro-inflammatory cytokines such as tumor necrosis factor (TNF) and interleukin-1 (IL-1).

PRK (proliferation-related kinase) is a serum/cytokine inducible STK that is involved in regulation of the cell cycle and cell proliferation in human megakaroytic cells (Li, B. et al. (1996) *J. Biol. Chem.* 271:19402–8). PRK is related to the polo (derived from humans polo gene) family of STKs implicated in cell division. PRK is downregulated in lung tumor tissue and may be a proto-oncogene whose deregulated expression in normal tissue leads to oncogenic transformation. Altered MAP kinase expression is implicated in a variety of disease conditions including cancer, inflammation, immune disorders, and disorders affecting growth and development.

The cyclin-dependent protein kinases (CDKs) are another group of STKs that control the progression of cells through the cell cycle. Cyclins are small regulatory proteins that act by binding to and activating CDKs that then trigger various phases of the cell cycle by phosphorylating and activating selected proteins involved in the mitotic process. CDKs are unique in that they require multiple inputs to become activated. In addition to the binding of cyclin, CDK activation requires the phosphorylation of a specific threonine residue and the dephosphorylation of a specific tyrosine residue.

Protein tyrosine kinases, PTKs, specifically phosphorylate tyrosine residues on their target proteins and may be divided into transmembrane, receptor PTKs and nontransmembrane, non-receptor PTKs. Transmembrane protein-tyrosine kinases are receptors for most growth factors. Binding of growth factor to the receptor activates the transfer of a phosphate group from ATP to selected tyrosine side chains of the receptor and other specific proteins. Growth factors (GF) associated with receptor PTKs include; epidermal GF, platelet-derived GF, fibroblast GF, hepatocyte GF, insulin and insulin-like GFs, nerve GF, vascular endothelial GF, and macrophage colony stimulating factor.

Non-receptor PTKs lack transmembrane regions and, instead, form complexes with the intracellular regions of cell surface receptors. Such receptors that function through non-receptor PTKs include those for cytokines, hormones (growth hormone and prolactin) and antigen-specific receptors on T and B lymphocytes.

Many of these PTKs were first identified as the products of mutant oncogenes in cancer cells where their activation was no longer subject to normal cellular controls. In fact, about one third of the known oncogenes encode PTKs, and it is well known that cellular transformation (oncogenesis) is often accompanied by increased tyrosine phosphorylation activity (Carbonneau H and Tonks N K (1992) *Annu. Rev. Cell. Biol.* 8:463–93). Regulation of PTK activity may therefore be an important strategy in controlling some types of cancer.

Serine/threonine Kinases

The novel human protein, and encoding gene, provided by the present invention is related to the serine/threonine kinase subfamily and shows a particularly high degree of similarity to MAP/microtubule affinity regulating kinases (MARK). MARK plays important roles in controlling cytoskeletal dynamics. Due to their important role of MARK proteins in cytoskeletal dynamics, and the finding that the protein of the present invention is expressed in numerous cancerous tissues (see FIG. 1), the protein/gene of the present invention represents an important therapeutic/diagnostic target for a wide variety of cancers.

Microtubules facilitate molecular transport and are particularly important in the regulation of cellular shape and polarity. Microtubule-associated proteins (MAPs) play a critical role in regulating the inter-conversion between stable and dynamic microtubules. MARK phosphorylates the microtubule-associated-proteins MAP4, MAP2c, and tau at their microtubule-binding domain, thereby triggering their detachment from the microtubules and leading to an increased dynamic instability of the microtubules. MARK2 over-expression has been shown to cause microtubule-disruption, detachment of cells from the substratum, and cell death, as well as disruption of the vimentin network. (Ebneth et al., *Cell Motil Cytoskeleton* 1999 Nov;44(3):209–24). Also see Drewes et al., *Cell* 1997 Apr 18;89(2):297–308).

Kinase proteins, particularly members of the serine/threonine kinase subfamily, are a major target for drug action and development. Accordingly, it is valuable to the field of pharmaceutical development to identify and characterize previously unknown members of this subfamily of kinase proteins. The present invention advances the state of the art by providing previously unidentified human kinase proteins that have homology to members of the serine/threonine kinase subfamily.

SUMMARY OF THE INVENTION

The present invention is based in part on the identification of amino acid sequences of human kinase peptides and proteins that are related to the serine/threonine kinase subfamily, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate kinase activity in cells and tissues that express the kinase. Experimental data as provided in FIG. 1 indicates expression in brain (neuroblastoma), lung (small cell carcinoma), muscle (rhabdomyosarcoma), lymph (Burkitt lymphoma), ovary tumor, placenta (normal and choriocarcinoma), colon (normal, adenocarcinoma, and colon tumor), kidney (renal cell adenocarcinoma), breast, cervix (carcinoma), uterus tumor, pancreas (pancreatic islet), a pooled colon/kidney/stomach sample, and a pooled pancreas/spleen sample.

DESCRIPTION OF THE FIGURE SHEETS

FIGS. 1A–1C provides the nucleotide sequence of a cDNA molecule or transcript sequence that encodes the kinase protein of the present invention. (SEQ ID NO: 1) In addition, structure and functional information is provided, such as ATG start, stop and tissue distribution, where available, that allows one to readily determine specific uses of inventions based on this molecular sequence. Experimental data as provided in FIG. 1 indicates expression in brain (neuroblastoma), lung (small cell carcinoma), muscle (rhabdomyosarcoma), lymph (Burkitt lymphoma), ovary tumor, placenta (normal and choriocarcinoma), colon (normal, adenocarcinoma, and colon tumor), kidney (renal cell adenocarcinoma), breast, cervix (carcinoma), uterus tumor, pancreas (pancreatic islet), a pooled colon/kidney/stomach sample, and a pooled pancreas/spleen sample.

FIGS. 2A–2E provide the predicted amino acid sequence of the kinase of the present invention. (SEQ ID NO:2) In addition structure and functional information such as protein family, function, and modification sites is provided where available, allowing one to readily determine specific uses of inventions based on this molecular sequence.

FIGS. 3A-1 to 3A-42 provide genomic sequences that span the gene encoding the kinase protein of the present invention. (SEQ ID NO:3) In addition structure and functional information, such as intron/exon structure, promoter location, etc., is provided where available, allowing one to readily determine specific uses of inventions based on this molecular sequence. As illustrated in FIG. 3, SNPs were identified at 28 different nucleotide positions.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a kinase protein or part of a kinase protein and are related to the serine/threonine kinase subfamily. Utilizing these sequences, additional genomic sequences were assembled and transcript and/or cDNA sequences were isolated and characterized. Based on this analysis, the present invention provides amino acid sequences of human kinase peptides and proteins that are related to the serine/threonine kinase subfamily, nucleic acid sequences in the form of transcript sequences, cDNA sequences and/or genomic sequences that encode these kinase peptides and proteins, nucleic acid variation (allelic information), tissue distribution of expression, and information about the closest art known protein/peptide/domain that has structural or sequence homology to the kinase of the present invention.

In addition to being previously unknown, the peptides that are provided in the present invention are selected based on their ability to be used for the development of commercially important products and services. Specifically, the present peptides are selected based on homology and/or structural relatedness to known kinase proteins of the serine/threonine kinase subfamily and the expression pattern observed. Experimental data as provided in FIG. 1 indicates expression in brain (neuroblastoma), lung (small cell carcinoma), muscle (rhabdomyosarcoma), lymph (Burkitt lymphoma), ovary tumor, placenta (normal and choriocarcinoma), colon (normal, adenocarcinoma, and colon tumor), kidney (renal cell adenocarcinoma), breast, cervix (carcinoma), uterus tumor, pancreas (pancreatic islet), a pooled colon/kidney/stomach sample, and a pooled pancreas/spleen sample. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known serine/threonine kinase family or subfamily of kinase proteins.

Specific Embodiments
Peptide Molecules

The present invention provides nucleic acid sequences that encode protein molecules that have been identified as being members of the kinase family of proteins and are related to the serine/threonine kinase subfamily (protein sequences are provided in FIG. 2, transcript/cDNA sequences are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the kinase peptides of the present invention, kinase peptides, or peptides/proteins of the present invention.

The present invention provides isolated peptide and protein molecules that consist of, consist essentially of, or comprise the amino acid sequences of the kinase peptides disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the kinase peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated kinase peptide can be purified from cells that naturally express it, purified from cells that have been altered to express it (recombinant), or synthesized using known protein synthesis methods. Experimental data as provided in FIG. 1 indicates expression in brain (neuroblastoma), lung (small cell carcinoma), muscle (rhabdomyosarcoma), lymph (Burkitt lymphoma), ovary tumor, placenta (normal and choriocarcinoma), colon (normal, adenocarcinoma, and colon tumor), kidney (renal cell adenocarcinoma), breast, cervix (carcinoma), uterus tumor, pancreas (pancreatic islet), a pooled colon/kidney/stomach sample, and a pooled pancreas/spleen sample. For example, a nucleic acid molecule encoding the kinase peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/ cDNA nucleic acid sequences shown in FIG. 1 (SEQ ID NO:1) and the genomic sequences provided in FIG. 3 (SEQ ID NO:3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO:2), for example, proteins encoded by the transcript/ cDNA nucleic acid sequences shown in FIG. 1 (SEQ ID NO:1) and the genomic sequences provided in FIG. 3 (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the kinase peptides of the present invention are the naturally occurring mature proteins. A brief description of how various types of these proteins can be made/isolated is provided below.

The kinase peptides of the present invention can be attached to heterologous sequences to form chimeric or fusion proteins. Such chimeric and fusion proteins comprise a kinase peptide operatively linked to a heterologous protein having an amino acid sequence not substantially homologous to the kinase peptide. "Operatively linked" indicates that the kinase peptide and the heterologous protein are fused in-frame. The heterologous protein can be fused to the N-terminus or C-terminus of the kinase peptide.

In some uses, the fusion protein does not affect the activity of the kinase peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant kinase peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., *Current Protocols in Molecular Biology*, 1992). Moreover, many expression vectors are commercially available that already encode a fusion moiety (e.g., a GST protein). A kinase peptide-encoding nucleic acid can be cloned into such an expression vector such that the fusion moiety is linked in-frame to the kinase peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the kinase peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part 1*, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)) (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11–17 (1989)) which has been incorporated into the ALIGN program (version 2.0), using a PAM 120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol. Biol.* 215:403–10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the kinase peptides of the present invention as well as being encoded by the same genetic locus as the kinase peptide provided herein. As indicated by the data presented in FIG. 3, the map position was determined to be on human chromosome 11.

Allelic variants of a kinase peptide can readily be identified as being a human protein having a high degree (significant) of sequence homology/identity to at least a portion of the kinase peptide as well as being encoded by the same genetic locus as the kinase peptide provided herein. Genetic locus can readily be determined based on the genomic information provided in FIG. 3, such as the genomic sequence mapped to the reference human. As indicated by the data presented in FIG. 3, the map position was determined to be on human chromosome 11. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a kinase peptide encoding nucleic acid molecule under stringent conditions as more fully described below.

FIG. 3 provides information on SNPs that have been identified at 28 different nucleotide positions in the gene encoding the kinase protein of the present invention.

Paralogs of a kinase peptide can readily be identified as having some degree of significant sequence homology/identity to at least a portion of the kinase peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a kinase peptide encoding nucleic acid molecule under moderate to stringent conditions as more fully described below.

Orthologs of a kinase peptide can readily be identified as having some degree of significant sequence homology/identity to at least a portion of the kinase peptide as well as being encoded by a gene from another organism. Preferred orthologs will be isolated from mammals, preferably primates, for the development of human therapeutic targets and agents. Such orthologs will be encoded by a nucleic acid sequence that will hybridize to a kinase peptide encoding nucleic acid molecule under moderate to stringent conditions, as more fully described below, depending on the degree of relatedness of the two organisms yielding the proteins.

Non-naturally occurring variants of the kinase peptides of the present invention can readily be generated using recombinant techniques. Such variants include, but are not limited to deletions, additions and substitutions in the amino acid sequence of the kinase peptide. For example, one class of substitutions are conserved amino acid substitution. Such substitutions are those that substitute a given amino acid in a kinase peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306–1310 (1990).

Variant kinase peptides can be fully functional or can lack function in one or more activities, e.g. ability to bind substrate, ability to phosphorylate substrate, ability to mediate signaling, etc. Fully functional variants typically contain only conservative variation or variation in non-critical residues or in non-critical regions. FIG. 2 provides the result of protein analysis and can be used to identify critical domains/regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)), particularly using the results provided in FIG. 2. The latter procedure introduces single alanine mutations at every residue in the molecule. The resulting mutant molecules are then tested for biological activity such as kinase activity or in assays such as an in vitro proliferative activity. Sites that are critical for binding partner/substrate binding can also be determined by structural analysis such as crystallization, nuclear magnetic resonance or photoaffinity labeling (Smith et al., *J. Mol. Biol.* 224:899–904 (1992); de Vos et al. *Science* 255:306–312 (1992)).

The present invention further provides fragments of the kinase peptides, in addition to proteins and peptides that comprise and consist of such fragments, particularly those comprising the residues identified in FIG. 2. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a kinase peptide. Such fragments can be chosen based on the ability to retain one or more of the biological activities of the kinase peptide or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the kinase peptide, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in kinase peptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties*, 2nd Ed., T. E. Creighton, W. H. Freeman and Company, New York (1993). Many detailed reviews are available on this subject, such as by Wold, F., *Posttranslational Covalent Modification of Proteins*, B. C. Johnson, Ed., Academic Press, New York 1–12 (1983); Seifter et al. (*Meth. Enzymol*. 182: 626–646 (1990)) and Rattan et al. (*Ann. N.Y Acad. Sci*. 663:48–62 (1992)).

Accordingly, the kinase peptides of the present invention also encompass derivatives or analogs in which a substituted amino acid residue is not one encoded by the genetic code, in which a substituent group is included, in which the mature kinase peptide is fused with another compound, such as a compound to increase the half-life of the kinase peptide (for example, polyethylene glycol), or in which the additional amino acids are fused to the mature kinase peptide, such as a leader or secretory sequence or a sequence for purification of the mature kinase peptide or a pro-protein sequence.

Protein/Peptide Uses

The proteins of the present invention can be used in substantial and specific assays related to the functional information provided in the Figures; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed (either constitutively or at a particular stage of tissue differentiation or development or in a disease state). Where the protein binds or potentially binds to another protein or ligand (such as, for example, in a kinase-effector protein interaction or kinase-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, kinases isolated from humans and their human/mammalian orthologs serve as targets for identifying agents for use in mammalian therapeutic applications, e.g. a human drug, particularly in modulating a biological or pathological response in a cell or tissue that expresses the kinase. Experimental data as provided in FIG. 1 indicates that kinase proteins of the present invention are expressed in brain (neuroblastoma), lung (small cell carcinoma), muscle (rhabdomyosarcoma), lymph (Burkitt lymphoma), ovary tumor, placenta (normal and choriocarcinoma), colon (normal, adenocarcinoma, and colon tumor), kidney (renal cell adenocarcinoma), breast, cervix (carcinoma), uterus tumor, pancreas (pancreatic islet), a pooled colon/kidney/stomach sample, and a pooled pancreas/spleen sample, as indicated by virtual northern blot analysis. A large percentage of pharmaceutical agents are being developed that modulate the activity of kinase proteins, particularly members of the serine/threonine kinase subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates expression in brain (neuroblastoma), lung (small cell carcinoma), muscle (rhabdomyosarcoma), lymph (Burkitt lymphoma), ovary tumor, placenta (normal and choriocarcinoma), colon (normal, adenocarcinoma, and colon tumor), kidney (renal cell adenocarcinoma), breast, cervix (carcinoma), uterus tumor, pancreas (pancreatic islet), a pooled colon/kidney/stomach sample, and a pooled pancreas/spleen sample. Such uses can readily be determined using the information provided herein, that which is known in the art, and routine experimentation.

The proteins of the present invention (including variants and fragments that may have been disclosed prior to the present invention) are useful for biological assays related to kinases that are related to members of the serine/threonine kinase subfamily. Such assays involve any of the known kinase functions or activities or properties useful for diagnosis and treatment of kinase-related conditions that are specific for the subfamily of kinases that the one of the present invention belongs to, particularly in cells and tissues that express the kinase. Experimental data as provided in FIG. 1 indicates that kinase proteins of the present invention are expressed in brain (neuroblastoma), lung (small cell carcinoma), muscle (rhabdomyosarcoma), lymph (Burkitt lymphoma), ovary tumor, placenta (normal and choriocarcinoma), colon (normal, adenocarcinoma, and colon tumor), kidney (renal cell adenocarcinoma), breast, cervix (carcinoma), uterus tumor, pancreas (pancreatic islet), a pooled colon/kidney/stomach sample, and a pooled pancreas/spleen sample, as indicated by virtual northern blot analysis.

The proteins of the present invention are also useful in drug screening assays, in cell-based or cell-free systems. Cell-based systems can be native, i.e., cells that normally express the kinase, as a biopsy or expanded in cell culture. Experimental data as provided in FIG. 1 indicates expression in brain (neuroblastoma), lung (small cell carcinoma), muscle (rhabdomyosarcoma), lymph (Burkitt lymphoma), ovary tumor, placenta (normal and choriocarcinoma), colon (normal, adenocarcinoma, and colon tumor), kidney (renal cell adenocarcinoma), breast, cervix (carcinoma), uterus tumor, pancreas (pancreatic islet), a pooled colon/kidney/stomach sample, and a pooled pancreas/spleen sample. In an alternate embodiment, cell-based assays involve recombinant host cells expressing the kinase protein.

The polypeptides can be used to identify compounds that modulate kinase activity of the protein in its natural state or an altered form that causes a specific disease or pathology associated with the kinase. Both the kinases of the present invention and appropriate variants and fragments can be used in high-throughput screens to assay candidate compounds for the ability to bind to the kinase. These compounds can be further screened against a functional kinase to determine the effect of the compound on the kinase activity. Further, these compounds can be tested in animal or invertebrate systems to determine activity/effectiveness. Compounds can be identified that activate (agonist) or inactivate (antagonist) the kinase to a desired degree.

Further, the proteins of the present invention can be used to screen a compound for the ability to stimulate or inhibit interaction between the kinase protein and a molecule that normally interacts with the kinase protein, e.g. a substrate or a component of the signal pathway that the kinase protein normally interacts (for example, another kinase). Such assays typically include the steps of combining the kinase protein with a candidate compound under conditions that allow the kinase protein, or fragment, to interact with the target molecule, and to detect the formation of a complex between the protein and the target or to detect the biochemical consequence of the interaction with the kinase protein and the target, such as any of the associated effects of signal transduction such as protein phosphorylation, cAMP turnover, and adenylate cyclase activation, etc.

Candidate compounds include, for example, 1) peptides such as soluble peptides, including Ig-tailed fusion peptides and members of random peptide libraries (see, e.g., Lam et al., *Nature* 354:82–84 (1991); Houghten et al., *Nature* 354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., *Cell* 72:767–778 (1993)); 3) antibodies (e.g., polyclonal, monoclonal, humanized, anti-idiotypic, chimeric, and single chain antibodies as well as Fab, F(ab')$_2$, Fab expression library fragments, and epit6pe-binding fragments of antibodies); and 4) small organic and inorganic molecules (e.g., molecules obtained from combinatorial and natural product libraries).

One candidate compound is a soluble fragment of the receptor that competes for substrate binding. Other candidate compounds include mutant kinases or appropriate fragments containing mutations that affect kinase function and thus compete for substrate. Accordingly, a fragment that competes for substrate, for example with a higher affinity, or a fragment that binds substrate but does not allow release, is encompassed by the invention.

The invention further includes other end point assays to identify compounds that modulate (stimulate or inhibit) kinase activity. The assays typically involve an assay of events in the signal transduction pathway that indicate kinase activity. Thus, the phosphorylation of a substrate, activation of a protein, a change in the expression of genes that are up- or down-regulated in response to the kinase protein dependent signal cascade can be assayed.

Any of the biological or biochemical functions mediated by the kinase can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in the Figures, particularly FIG. 2. Specifically, a biological function of a cell or tissues that expresses the kinase can be assayed. Experimental data as provided in FIG. 1 indicates that kinase proteins of the present invention are expressed in brain (neuroblastoma), lung (small cell carcinoma), muscle (rhabdomyosarcoma), lymph (Burkitt lymphoma), ovary tumor, placenta (normal and choriocarcinoma), colon (normal, adenocarcinoma, and colon tumor), kidney (renal cell adenocarcinoma), breast, cervix (carcinoma), uterus tumor, pancreas (pancreatic islet), a pooled colon/kidney/stomach sample, and a pooled pancreas/spleen sample, as indicated by virtual northern blot analysis.

Binding and/or activating compounds can also be screened by using chimeric kinase proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a substrate-binding region can be used that interacts with a different substrate then that which is recognized by the native kinase. Accordingly, a different set of signal transduction components is available as an endpoint assay for activation. This allows for assays to be performed in other than the specific host cell from which the kinase is derived.

The proteins of the present invention are also useful in competition binding assays in methods designed to discover compounds that interact with the kinase (e.g. binding partners and/or ligands). Thus, a compound is exposed to a kinase polypeptide under conditions that allow the compound to bind or to otherwise interact with the polypeptide. Soluble kinase polypeptide is also added to the mixture. If the test compound interacts with the soluble kinase polypeptide, it decreases the amount of complex formed or activity from the kinase target. This type of assay is particularly useful in cases in which compounds are sought that interact with specific regions of the kinase. Thus, the soluble polypeptide that competes with the target kinase region is designed to contain peptide sequences corresponding to the region of interest.

To perform cell free drug screening assays, it is sometimes desirable to immobilize either the kinase protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of kinase-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a kinase-binding protein and a candidate compound are incubated in the kinase protein-presenting wells and the amount of complex trapped in the well can be quantitated. Methods for detecting such complexes, in addition to those described above for the GST-immobilized complexes, include immunodetection of complexes using antibodies reactive with the kinase protein target molecule, or which are reactive with kinase protein and compete with the target molecule, as well as enzyme-linked assays which rely on detecting an enzymatic activity associated with the target molecule.

Agents that modulate one of the kinases of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of kinase protein activity identified according to these drug screening assays can be used to treat a subject with a disorder mediated by the kinase pathway, by treating cells or tissues that express the kinase. Experimental data as provided in FIG. 1 indicates expression in brain (neuroblastoma), lung (small cell carcinoma), muscle (rhabdomyosarcoma), lymph (Burkitt lymphoma), ovary tumor, placenta (normal and choriocarcinoma), colon (normal, adenocarcinoma, and colon tumor), kidney (renal cell adenocarcinoma), breast, cervix (carcinoma), uterus tumor, pancreas (pancreatic islet), a pooled colon/kidney/stomach sample, and a pooled pancreas/spleen sample.

These methods of treatment include the steps of administering a modulator of kinase activity in a pharmaceutical composition to a subject in need of such treatment, the modulator being identified as described herein.

In yet another aspect of the invention, the kinase proteins can be used as "bait proteins" in a two-hybrid assay or three-hybrid assay (see, e.g., U.S. Pat. No. 5,283,317; Zervos et al. (1993) Cell 72:223–232; Madura et al. (1993) J. Biol. Chem. 268:12046–12054; Bartel et al. (1993) Biotechniques 14:920–924; Iwabuchi et al. (1993) Oncogene 8:1693–1696; and Brent WO94/10300), to identify other proteins, which bind to or interact with the kinase and are involved in kinase activity. Such kinase-binding proteins are also likely to be involved in the propagation of signals by the kinase proteins or kinase targets as, for example, downstream elements of a kinase-mediated signaling pathway. Alternatively, such kinase-binding proteins are likely to be kinase inhibitors.

The two-hybrid system is based on the modular nature of most transcription factors, which consist of separable DNA-binding and activation domains. Briefly, the assay utilizes two different DNA constructs. In one construct, the gene that codes for a kinase protein is fused to a gene encoding the DNA binding domain of a known transcription factor (e.g., GAL-4). In the other construct, a DNA sequence, from a library of DNA sequences, that encodes an unidentified protein. ("prey" or "sample") is fused to a gene that codes for the activation domain of the known transcription factor. If the "bait" and the "prey" proteins are able to interact, in vivo, forming a kinase-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the kinase protein.

This invention further pertains to novel agents identified by the above-described screening assays. Accordingly, it is within the scope of this invention to further use an agent identified as described herein in an appropriate animal model. For example, an agent identified as described herein (e.g., a kinase-modulating agent, an antisense kinase nucleic acid molecule, a kinase-specific antibody, or a kinase-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The kinase proteins of the present invention are also useful to provide a target for diagnosing a disease or predisposition to disease mediated by the peptide. Accordingly, the invention provides methods for detecting the presence, or levels of, the protein (or encoding mRNA) in a cell, tissue, or organism. Experimental data as provided in FIG. 1 indicates expression in brain (neuroblastoma), lung (small cell carcinoma), muscle (rhabdomyosarcoma), lymph (Burkitt lymphoma), ovary tumor, placenta (normal and choriocarcinoma), colon (normal, adenocarcinoma, and colon tumor), kidney (renal cell adenocarcinoma), breast, cervix (carcinoma), uterus tumor, pancreas (pancreatic islet), a pooled colon/kidney/stomach sample, and a pooled pancreas/spleen sample. The method involves contacting a biological sample with a compound capable of interacting with the kinase protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered kinase activity in cell-based or cell-free assay, alteration in substrate or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (Clin. Exp. Pharmacol. Physiol. 23(10–11):983–985 (1996)), and Linder, M. W. (Clin. Chem. 43(2):254–266 (1997). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the kinase protein in which one or more of the kinase functions in one population is different from those in another population. The peptides thus allow a target to ascertain a genetic predisposition that can affect treatment modality. Thus, in a ligand-based treatment, polymorphism may give rise to amino terminal extracellular domains and/or other substrate-binding regions that are more or less active in substrate binding, and kinase activation. Accordingly, substrate dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in brain (neuroblastoma), lung (small cell carcinoma), muscle (rhabdomyosarcoma), lymph (Burkitt lymphoma), ovary tumor, placenta (normal and choriocarcinoma), colon (normal, adenocarcinoma, and colon tumor), kidney (renal cell adenocarcinoma), breast, cervix (carcinoma), uterus tumor, pancreas (pancreatic islet), a pooled colon/kidney/stomach sample, and a pooled pancreas/spleen sample. Accordingly, methods for treatment include the use of the kinase protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or F(ab')$_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The fill-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the kinase proteins. Antibodies can be prepared from any region of the peptide as described herein. However, preferred regions will include those involved in function/activity and/or kinase/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that kinase proteins of the present invention are expressed in brain (neuroblastoma), lung (small cell carcinoma), muscle (rhabdomyosarcoma), lymph (Burkitt lymphoma), ovary tumor, placenta (normal and choriocarcinoma), colon (normal, adenocarcinoma, and colon tumor), kidney (renal cell adenocarcinoma), breast, cervix (carcinoma), uterus tumor, pancreas (pancreatic islet), a pooled colon/kidney/stomach sample, and a pooled pancreas/spleen sample, as indicated by virtual northern blot analysis. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in brain (neuroblastoma), lung (small cell carcinoma), muscle (rhabdomyosarcoma), lymph (Burkitt lymphoma), ovary tumor, placenta (normal and choriocarcinoma), colon (normal, adenocarcinoma, and colon tumor), kidney (renal cell adenocarcinoma), breast, cervix (carcinoma), uterus tumor, pancreas (pancreatic islet), a pooled colon/kidney/stomach sample, and a pooled pancreas/spleen sample. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in brain (neuroblastoma), lung (small cell carcinoma), muscle (rhabdomyosarcoma), lymph (Burkitt lymphoma), ovary tumor, placenta (normal and choriocarcinoma), colon (normal, adenocarcinoma, and colon tumor), kidney (renal cell adenocarcinoma), breast, cervix (carcinoma), uterus tumor, pancreas (pancreatic islet), a pooled colon/kidney/stomach sample, and a pooled pancreas/spleen sample. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression in brain (neuroblastoma), lung (small cell carcinoma), muscle (rhabdomyosarcoma), lymph (Burkitt lymphoma), ovary tumor, placenta (normal and choriocarcinoma), colon (normal, adenocarcinoma, and colon tumor), kidney (renal cell adenocarcinoma), breast, cervix (carcinoma), uterus tumor, pancreas (pancreatic islet), a pooled colon/kidney/ stomach sample, and a pooled pancreas/spleen sample. Thus, where a specific protein has been correlated with expression in a specific tissue, antibodies that are specific for this protein can be used to identify a tissue type.

The antibodies are also useful for inhibiting protein function, for example, blocking the binding of the kinase peptide to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nuleic acid arrays and similar methods have been developed for antibody arrays.

Nucleic Acid Molecules

The present invention further provides isolated nucleic acid molecules that encode a kinase peptide or protein of the present invention (cDNA, transcript and genomic sequence). Such nucleic acid molecules will consist of, consist essentially of, or comprise a nucleotide sequence that encodes one of the kinase peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5KB, 4KB, 3KB, 2KB, or 1KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the kinase peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (antisense strand).

The invention further provides nucleic acid molecules that encode fragments of the peptides of the present invention as well as nucleic acid molecules that encode obvious variants of the kinase proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in FIGS. 1 and 3. Preferred non-coding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genomic sequence provided in FIG. 3.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene. As indicated by the data presented in FIG. 3, the map position was determined to be on human chromosome 11.

FIG. 3 provides information on SNPs that have been identified at 28 different nucleotide positions in the gene encoding the kinase protein of the present invention.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in Current Protocols in Molecular Biology, John Wiley & Sons, N.Y. (1989), 6.3.1–6.3.6. One example of stringent hybridization conditions are hybridization in 6× sodium chloride/sodium citrate (SSC) at about 45C, followed by one or more washes in 0.2×SSC, 0.1% SDS at 50–65C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2. As illustrated in FIG. 3, SNPs were identified at 28 different nucleotide positions.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. As indicated by the data presented in FIG. 3, the map position was determined to be on human chromosome 11.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of nucleic acid expression. Experimental data as provided in FIG. 1 indicates that kinase proteins of the present invention are expressed in brain (neuroblastoma), lung (small cell carcinoma), muscle (rhabdomyosarcoma), lymph (Burkitt lymphoma), ovary tumor, placenta (normal and choriocarcinoma), colon (normal, adenocarcinoma, and colon tumor), kidney (renal cell adenocarcinoma), breast, cervix (carcinoma), uterus tumor, pancreas (pancreatic islet), a pooled colon/kidney/stomach sample, and a pooled pancreas/spleen sample, as indicated by virtual northern blot analysis. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in kinase protein expression relative to normal results.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express a kinase protein, such as by measuring a level of a kinase-encoding nucleic acid in a sample of cells from a subject e.g., mRNA or genomic DNA, or determining if a kinase gene has been mutated. Experimental data as provided in FIG. 1 indicates that kinase proteins of the present invention are expressed in brain (neuroblastoma), lung (small cell carcinoma), muscle (rhabdomyosarcoma), lymph (Burkitt lymphoma), ovary tumor, placenta (normal and choriocarcinoma), colon (normal, adenocarcinoma, and colon tumor), kidney (renal cell adenocarcinoma), breast, cervix (carcinoma), uterus tumor, pancreas (pancreatic islet), a pooled colon/kidney/stomach sample, and a pooled pancreas/spleen sample, as indicated by virtual northern blot analysis.

Nucleic acid expression assays are useful for drug screening to identify compounds that modulate kinase nucleic acid expression.

The invention thus provides a method for identifying a compound that can be used to treat a disorder associated with nucleic acid expression of the kinase gene, particularly biological and pathological processes that are mediated by the kinase in cells and tissues that express it. Experimental data as provided in FIG. 1 indicates expression in brain (neuroblastoma), lung (small cell carcinoma), muscle (rhabdomyosarcoma), lymph (Burkitt lymphoma), ovary tumor, placenta (normal and choriocarcinoma), colon (normal, adenocarcinoma, and colon tumor), kidney (renal cell adenocarcinoma), breast, cervix (carcinoma), uterus tumor, pancreas (pancreatic islet), a pooled colon/kidney/stomach sample, and a pooled pancreas/spleen sample. The method typically includes assaying the ability of the compound to modulate the expression of the kinase nucleic acid and thus identifying a compound that can be used to treat a disorder characterized by undesired kinase nucleic acid expression. The assays can be performed in cell-based and cell-free systems. Cell-based assays include cells naturally expressing the kinase nucleic acid or recombinant cells genetically engineered to express specific nucleic acid sequences.

The assay for kinase nucleic acid expression can involve direct assay of nucleic acid levels, such as mRNA levels, or on collateral compounds involved in the signal pathway. Further, the expression of genes that are up- or down-regulated in response to the kinase protein signal pathway can also be assayed. In this embodiment the regulatory regions of these genes can be operably linked to a reporter gene such as luciferase.

Thus, modulators of kinase gene expression can be identified in a method wherein a cell is contacted with a candidate compound and the expression of mRNA determined. The level of expression of kinase mRNA in the presence of the candidate compound is compared to the level of expression of kinase mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate kinase nucleic acid expression in cells and tissues that express the kinase. Experimental data as provided in FIG. 1 indicates that kinase proteins of the present invention are expressed in brain (neuroblastoma), lung (small cell carcinoma), muscle (rhabdomyosarcoma), lymph (Burkitt lymphoma), ovary tumor, placenta (normal and choriocarcinoma), colon (normal, adenocarcinoma, and colon tumor), kidney (renal cell adenocarcinoma), breast, cervix (carcinoma), uterus tumor, pancreas (pancreatic islet), a pooled colon/kidney/stomach sample, and a pooled pancreas/spleen sample, as indicated by virtual northern blot analysis. Modulation includes both up-regulation (i.e. activation or agonization) or down-regulation (suppression or antagonization) or nucleic acid expression.

Alternatively, a modulator for kinase nucleic acid expression can be a small molecule or drug identified using the screening assays described herein as long as the drug or small molecule inhibits the kinase nucleic acid expression in the cells and tissues that express the protein. Experimental data as provided in FIG. 1 indicates expression in brain (neuroblastoma), lung (small cell carcinoma), muscle (rhabdomyosarcoma), lymph (Burkitt lymphoma), ovary tumor, placenta (normal and choriocarcinoma), colon (normal, adenocarcinoma, and colon tumor), kidney (renal cell adenocarcinoma), breast, cervix (carcinoma), uterus tumor, pancreas (pancreatic islet), a pooled colon/kidney/stomach sample, and a pooled pancreas/spleen sample.

The nucleic acid molecules are also useful for monitoring the effectiveness of modulating compounds on the expression or activity of the kinase gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in kinase nucleic acid expression, and particularly in qualitative changes that lead to pathology. The nucleic acid molecules can be used to detect mutations in kinase genes and gene expression products such as mRNA. The nucleic acid molecules can be used as hybridization probes to detect naturally occurring genetic mutations in the kinase gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the kinase gene associated with a dysfunction provides a diagnostic tool for an active disease or susceptibility to disease when the disease results from overexpression, underexpression, or altered expression of a kinase protein.

Individuals carrying mutations in the kinase gene can be detected at the nucleic acid level by a variety of techniques. FIG. 3 provides information on SNPs that have been identified at 28 different nucleotide positions in the gene encoding the kinase protein of the present invention. As indicated by the data presented in FIG. 3, the map position was determined to be on human chromosome 11. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077–1080 (1988); and Nakazawa et al., *PNAS* 91:360–364 (1994)), the latter of which can be particularly useful for detecting point mutations in the gene (see Abravaya et al., *Nucleic Acids Res.* 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a kinase gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant kinase gene and a wild-type gene can be determined by direct DNA sequencing. A variety of automated sequencing procedures can be utilized when performing the diagnostic assays (Naeve, C. W., (1995) *Biotechniques* 19:448), including sequencing by mass spectrometry (see, e.g., PCT International Publication No. WO 94/16101; Cohen et al., *Adv. Chromatogr.* 36:127–162 (1996); and Griffin et al., *Appl. Biochem. Biotechnol.* 38:147–159 (1993)).

Other methods for detecting mutations in the gene include methods in which protection from cleavage agents is used to detect mismatched bases in RNA/RNA or RNA/DNA duplexes (Myers et al., *Science* 230:1242 (1985)); Cotton et al., PNAS 85:4397 (1988); Saleeba et al., *Meth. Enzymol.* 217:286–295 (1992)), electrophoretic mobility of mutant and wild type nucleic acid is compared (Orita et al., *PNAS* 86:2766 (1989); Cotton et al., *Mutat. Res.* 285:125–144 (1993); and Hayashi et al., *Genet. Anal. Tech. Appl.* 9:73–79 (1992)), and movement of mutant or wild-type fragments in polyacrylamide gels containing a gradient of denaturant is assayed using denaturing gradient gel electrophoresis (Myers et al., *Nature* 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the kinase gene in an individual in order to select an appropriate compound or dosage regimen for treatment. FIG. 3 provides information on SNPs that have been identified at 28 different nucleotide positions in the gene encoding the kinase protein of the present invention.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control kinase gene expression in cells, tissues, and organisms. A DNA antisense nucleic acid molecule is designed to be complementary to a region of the gene involved in transcription, preventing transcription and hence production of kinase protein. An antisense RNA or DNA nucleic acid molecule would hybridize to the mRNA and thus block translation of mRNA into kinase protein.

Alternatively, a class of antisense molecules can be used to inactivate mRNA in order to decrease expression of kinase nucleic acid. Accordingly, these molecules can treat a disorder characterized by abnormal or undesired kinase nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the kinase protein, such as substrate binding.

The nucleic acid molecules also provide vectors for gene therapy in patients containing cells that are aberrant in kinase gene expression. Thus, recombinant cells, which include the patient's cells that have been engineered ex vivo and returned to the patient, are introduced into an individual where the cells produce the desired kinase protein to treat the individual.

The invention also encompasses kits for detecting the presence of a kinase nucleic acid in a biological sample. Experimental data as provided in FIG. 1 indicates that kinase proteins of the present invention are expressed in brain (neuroblastoma), lung (small cell carcinoma), muscle (rhabdomyosarcoma), lymph (Burkitt lymphoma), ovary tumor, placenta (normal and choriocarcinoma), colon (normal, adenocarcinoma, and colon tumor), kidney (renal cell adenocarcinoma), breast, cervix (carcinoma), uterus tumor, pancreas (pancreatic islet), a pooled colon/kidney/stomach sample, and a pooled pancreas/spleen sample, as indicated by virtual northern blot analysis. For example, the kit can comprise reagents such as a labeled or labelable nucleic acid or agent capable of detecting kinase nucleic acid in a biological sample; means for determining the amount of kinase nucleic acid in the sample; and means for comparing the amount of kinase nucleic acid in the sample with a standard. The compound or agent can be packaged in a suitable container. The kit can further comprise instructions for using the kit to detect kinase protein mRNA or DNA.

Nucleic Acid Arrays

The present invention further provides nucleic acid detection kits, such as arrays or microarrays of nucleic acid molecules that are based on the sequence information provided in FIGS. 1 and 3 (SEQ ID NOS:1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference. In other embodiments, such arrays are produced by the methods described by Brown et al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides which cover the full length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of the kinase proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the kinase gene of the present invention. FIG. 3 provides information on SNPs that have been identified at 28 different nucleotide positions in the gene encoding the kinase protein of the present invention.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein. Examples of such assays can be found in Chard, T, *An Introduction to Radioimmunoassay and Related Techniques*, Elsevier Science Publishers, Amsterdam, The Netherlands (1986); Bullock, G. R. et al., *Techniques in Immunocytochemistry*, Academic Press, Orlando, Fla. Vol. 1 (1982), Vol. 2 (1983), Vol. 3 (1985); Tijssen, P., *Practice and Theory of Enzyme Immunoassays: Laboratory Techniques in Biochemistry and Molecular Biology*, Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the Human genome disclosed herein; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified kinase gene of the present invention can be routinely identified using the sequence information disclosed herein can be readily incorporated into one of the established kit formats which are well known in the art, particularly expression arrays.

Vectors/host cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extra-chromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in prokaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual.* 2nd. ed., Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual.* 2nd. ed., Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli*, Streptomyces, and *Salmonella typhimurium*. Eukaryotic cells include, but are not limited to, yeast, insect cells such as Drosophila, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enterokinase. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11d (Studier et al., *Gene Expression Technology: Methods in Enzymology* 185:60–89 (1990)).

Recombinant protein expression can be maximized in host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990)119–128). Alternatively, the sequence of the nucleic acid molecule of interest can be altered to provide preferential codon usage for a specific host cell, for example *E. coli*. (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J* 6:229–234 (1987)), pMFa (Kujari et al., *Cell* 30:933–943(1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf 9 cells) include the pAc series (Smith et al., *Mol. Cell Biol.* 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufman et al., *EMBO J.* 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual.* 2nd, ed., Cold Spring Harbor Laboratory, Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as kinases, appropriate secretion signals are incorporated into the vector. The signal sequence can be endogenous to the peptides or heterologous to these peptides.

Where the peptide is not secreted into the medium, which is typically the case with kinases, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a kinase protein or peptide that can be further purified to produce desired amounts of kinase protein or fragments. Thus, host cells containing expression vectors are useful for peptide production.

Host cells are also useful for conducting cell-based assays involving the kinase protein or kinase protein fragments, such as those described above as well as other formats known in the art. Thus, a recombinant host cell expressing a native kinase protein is useful for assaying compounds that stimulate or inhibit kinase protein function.

Host cells are also useful for identifying kinase protein mutants in which these functions are affected. If the mutants naturally occur and give rise to a pathology, host cells containing the mutations are useful to assay compounds that have a desired effect on the mutant kinase protein (for example, stimulating or inhibiting function) which may not be indicated by their effect on the native kinase protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a kinase protein and identifying and evaluating modulators of kinase protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the kinase protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence (s) can be operably linked to the transgene to direct expression of the kinase protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_0$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect substrate binding, kinase protein activation, and signal transduction, may not be evident from in vitro cell-free or cell-based assays. Accordingly, it is useful to provide non-human transgenic animals to assay in vivo kinase protein function, including substrate interaction, the effect of specific mutant kinase proteins on kinase protein function and substrate interaction, and the effect of chimeric kinase proteins. It is also possible to assess the effect of null mutations, that is, mutations that substantially or completely eliminate one or more kinase protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

That which is claimed is:

1. An isolated polypeptide having an amino acid sequence consisting of SEQ ID NO:2.

2. An isolated polypeptide having an amino acid sequence comprising SEQ ID NO:2.

3. A composition comprising the polypeptide of claim 1 and a carrier.

4. A composition comprising the polypeptide of claim 2 and a carrier.

* * * * *

SEQUENCE LISTING

<160> NUMBER OF SEQ ID NOS: 4

<210> SEQ ID NO 1
<211> LENGTH: 2175
<212> TYPE: DNA
<213> ORGANISM: Homo sapiens

<400> SEQUENCE: 1

```
atgtccagcg ctcggacccc cctacccacg ctgaacgaga gggacacgga gcagcccacc      60
ttgggacacc ttgactccaa gcccagcagt aagtccaaca tgattcgggg ccgcaactca     120
gccacctctg ctgatgagca gccccacatt ggaaactacc ggctcctcaa gaccattggc     180
aagggtaatt ttgccaaggt gaagttggcc cgacacatcc tgactgggaa agaggtagct     240
gtgaagatca ttgacaagac tcaactgaac tcctccagcc tccagaaact attccgcgaa     300
gtaagaataa tgaaggtttt gaatcatccc aacatagtta aattatttga agtgattgag     360
actgagaaaa cgctctacct tgtcatggag tacgctagtg gcggagaggt atttgattac     420
ctagtggctc atggcaggat gaaagaaaaa gaggctcgag ccaaattccg ccaggtagtg     480
tctgctgtgc agtactgtca ccagaagttt attgtccata gagacttaaa ggcagaaaac     540
ctgctcttgg atgctgatat gaacatcaag attgcagact ttggcttcag caatgaattc     600
acctttggga caagctgga caccttctgt ggcagtcccc cttatgctgc cccagaactc     660
ttccagggca aaaatatga tggacccgag gtggatgtgt ggagcctagg agttatcctc     720
tatacactgg tcagcggatc cctgcctttt gatggacaga acctcaagga gctgcgggaa     780
cgggtactga ggggaaaata ccgtattcca ttctacatgt ccacggactg tgaaaacctg     840
cttaagaaat ttctcattct taatcccagc aagagaggca ctttagagca aatcatgaaa     900
gatcgatgga tgaatgtggg tcacgaagat gatgaactaa agccttacgt ggagccactc     960
cctgactaca aggaccccg gcggacagag ctgatggtgt ccatgggtta tacggggaa    1020 gagatccagg actcgctggt gggccagaga tacaacgagg tgatggccac ctatctgctc    1080
ctgggctaca gagctccga gctggaaggc gacaccatca ccctgaaacc ccggccttca    1140
gctgatctga ccaatagcag cgccccatcc ccatcccaca ggtacagcg cagcgtgtcg    1200 gccaatccca gcagcggcg cttcagcgac caggctggtc ctgccattcc cacctctaat    1260
tcttactcta agaagactca gagtaacaac gcagaaaata gcggcctga ggaggaccgg    1320 gagtcagggc ggaaagccag cagcacagcc aaggtgcctg ccagcccct gcccggtctg    1380 gagaggaaga agaccacccc aacccctcc acgaacagcg tcctctccac cagcacaaat    1440
cgaagcagga attccccact tttggagcgg gccagcctcg gccaggcctc catccagaat    1500
ggcaaagaca gcacagcccc ccagcgtgtc cctgttgcct ccccatccgc ccacaacatc    1560
agcagcagtg gtggagcccc agaccgaact aacttccccc ggggtgtgtc cagccgaagc    1620
accttccatg ctgggcagct ccgacaggtg cgggaccagc agaatttgcc ctacggtgtg    1680
accccagcct ctccctctgg ccacagccag ggccggcggg gggcctctgg gagcatcttc    1740
agcaagttca cctccaagtt tgtacgcagg aacctgaatg aacctgaaag caaagaccga    1800
gtggagacgc tcagacctca cgtggtgggc agtggcggca cgacaaaga aaaggaagaa    1860 tttcgggagg ccaagcccg ctccctccgc ttcacgtgga gtatgaagac cacgagctcc    1920
atggagccca cgagatgat gcgggagatc cgcaaggtgc tggacgcgaa cagctgccag    1980
agcgagctgc atgagaagta catgctgctg tgcatgcacg gcacgccggg ccacgaggac    2040
```

-continued

```
ttcgtgcagt gggagatgga ggtgtgcaaa ctgccgcggc tctctctcaa cggggttcga    2100
tttaagcgga tatcgggcac ctccatggcc ttcaaaaaca ttgcctccaa aatagccaac    2160
gagctgaagc tttaa                                                      2175
```

<210> SEQ ID NO 2
<211> LENGTH: 724
<212> TYPE: PRT
<213> ORGANISM: Homo sapiens

<400> SEQUENCE: 2

```
Met Ser Ser Ala Arg Thr Pro Leu Pro Thr Leu Asn Glu Arg Asp Thr
1               5                   10                  15

Glu Gln Pro Thr Leu Gly His Leu Asp Ser Lys Pro Ser Ser Lys Ser
            20                  25                  30

Asn Met Ile Arg Gly Arg Asn Ser Ala Thr Ser Ala Asp Glu Gln Pro
        35                  40                  45

His Ile Gly Asn Tyr Arg Leu Leu Lys Thr Ile Gly Lys Gly Asn Phe
    50                  55                  60

Ala Lys Val Lys Leu Ala Arg His Ile Leu Thr Gly Lys Glu Val Ala
65                  70                  75                  80

Val Lys Ile Ile Asp Lys Thr Gln Leu Asn Ser Ser Ser Leu Gln Lys
                85                  90                  95

Leu Phe Arg Glu Val Arg Ile Met Lys Val Leu Asn His Pro Asn Ile
            100                 105                 110

Val Lys Leu Phe Glu Val Ile Glu Thr Glu Lys Thr Leu Tyr Leu Val
        115                 120                 125

Met Glu Tyr Ala Ser Gly Gly Glu Val Phe Asp Tyr Leu Val Ala His
    130                 135                 140

Gly Arg Met Lys Glu Lys Glu Ala Arg Ala Lys Phe Arg Gln Val Val
145                 150                 155                 160

Ser Ala Val Gln Tyr Cys His Gln Lys Phe Ile Val His Arg Asp Leu
                165                 170                 175

Lys Ala Glu Asn Leu Leu Leu Asp Ala Asp Met Asn Ile Lys Ile Ala
            180                 185                 190

Asp Phe Gly Phe Ser Asn Glu Phe Thr Phe Gly Asn Lys Leu Asp Thr
        195                 200                 205

Phe Cys Gly Ser Pro Pro Tyr Ala Ala Pro Glu Leu Phe Gln Gly Lys
    210                 215                 220

Lys Tyr Asp Gly Pro Glu Val Asp Val Trp Ser Leu Gly Val Ile Leu
225                 230                 235                 240

Tyr Thr Leu Val Ser Gly Ser Leu Pro Phe Asp Gly Gln Asn Leu Lys
                245                 250                 255

Glu Leu Arg Glu Arg Val Leu Arg Gly Lys Tyr Arg Ile Pro Phe Tyr
            260                 265                 270

Met Ser Thr Asp Cys Glu Asn Leu Leu Lys Lys Phe Leu Ile Leu Asn
        275                 280                 285

Pro Ser Lys Arg Gly Thr Leu Glu Gln Ile Met Lys Asp Arg Trp Met
    290                 295                 300

Asn Val Gly His Glu Asp Asp Glu Leu Lys Pro Tyr Val Glu Pro Leu
305                 310                 315                 320

Pro Asp Tyr Lys Asp Pro Arg Arg Thr Glu Leu Met Val Ser Met Gly
                325                 330                 335

Tyr Thr Arg Glu Glu Ile Gln Asp Ser Leu Val Gly Gln Arg Tyr Asn
            340                 345                 350
```

-continued

```
Glu Val Met Ala Thr Tyr Leu Leu Leu Gly Tyr Lys Ser Ser Glu Leu
            355                 360                 365

Glu Gly Asp Thr Ile Thr Leu Lys Pro Arg Pro Ser Ala Asp Leu Thr
        370                 375                 380

Asn Ser Ser Ala Pro Ser Pro Ser His Lys Val Gln Arg Ser Val Ser
385                 390                 395                 400

Ala Asn Pro Lys Gln Arg Arg Phe Ser Asp Gln Ala Gly Pro Ala Ile
                405                 410                 415

Pro Thr Ser Asn Ser Tyr Ser Lys Lys Thr Gln Ser Asn Asn Ala Glu
                420                 425                 430

Asn Lys Arg Pro Glu Glu Asp Arg Glu Ser Gly Arg Lys Ala Ser Ser
            435                 440                 445

Thr Ala Lys Val Pro Ala Ser Pro Leu Pro Gly Leu Glu Arg Lys Lys
        450                 455                 460

Thr Thr Pro Thr Pro Ser Thr Asn Ser Val Leu Ser Thr Ser Thr Asn
465                 470                 475                 480

Arg Ser Arg Asn Ser Pro Leu Leu Glu Arg Ala Ser Leu Gly Gln Ala
                485                 490                 495

Ser Ile Gln Asn Gly Lys Asp Ser Thr Ala Pro Gln Arg Val Pro Val
                500                 505                 510

Ala Ser Pro Ser Ala His Asn Ile Ser Ser Ser Gly Gly Ala Pro Asp
            515                 520                 525

Arg Thr Asn Phe Pro Arg Gly Val Ser Ser Arg Ser Thr Phe His Ala
        530                 535                 540

Gly Gln Leu Arg Gln Val Arg Asp Gln Gln Asn Leu Pro Tyr Gly Val
545                 550                 555                 560

Thr Pro Ala Ser Pro Ser Gly His Ser Gln Gly Arg Arg Gly Ala Ser
                565                 570                 575

Gly Ser Ile Phe Ser Lys Phe Thr Ser Lys Phe Val Arg Arg Asn Leu
                580                 585                 590

Asn Glu Pro Glu Ser Lys Asp Arg Val Glu Thr Leu Arg Pro His Val
            595                 600                 605

Val Gly Ser Gly Gly Asn Asp Lys Glu Lys Glu Glu Phe Arg Glu Ala
        610                 615                 620

Lys Pro Arg Ser Leu Arg Phe Thr Trp Ser Met Lys Thr Thr Ser Ser
625                 630                 635                 640

Met Glu Pro Asn Glu Met Met Arg Glu Ile Arg Lys Val Leu Asp Ala
                645                 650                 655

Asn Ser Cys Gln Ser Glu Leu His Glu Lys Tyr Met Leu Leu Cys Met
                660                 665                 670

His Gly Thr Pro Gly His Glu Asp Phe Val Gln Trp Glu Met Glu Val
            675                 680                 685

Cys Lys Leu Pro Arg Leu Ser Leu Asn Gly Val Arg Phe Lys Arg Ile
        690                 695                 700

Ser Gly Thr Ser Met Ala Phe Lys Asn Ile Ala Ser Lys Ile Ala Asn
705                 710                 715                 720

Glu Leu Lys Leu
```

<210> SEQ ID NO 3
<211> LENGTH: 75395
<212> TYPE: DNA
<213> ORGANISM: Homo sapiens

```
<220> FEATURE:
<221> NAME/KEY: misc_feature
<222> LOCATION: (1)...(75395)
<223> OTHER INFORMATION: n = A,T,C or G

<400> SEQUENCE: 3
tctaggcggg gagacaagct cagcagcctt gtgcaaagct agcaaggaag agaaaggata      60
ggtagggtag gggttgggga tgaaggtcaa agggcagggg tgaggcaggg gttagagcta     120
gagtgagaag cttggagaag atggagtcta tttagacgag agtgtggacc agggagagac     180
tgctggaaca ccaaccacca actgcttcct ctctcttttc cctgctttcc agaccctggc     240
attagaggtg ataccaggca caggaatcag caacgtgtct ccctttggcc accagagggc     300
agatgattct caaggatcga atttggggttg gggagtgagg tgttctctgt cctcctcttc    360
tctctttccc tcaccttcat gggtgtgcct tcaccttctt cctcaacggt tgggtgcctg     420
aatagagctg gtatgggca tggggagcag tgctgaagtc ccaggattta ctaagagtgt      480
agtgatacct gttgccttag gaagtacttt catacctgg taattacatc tgctcagatg      540
cctatttctc tgattgatgg gatgaaggct ggctcaagat gctgtagctg ggagttggag     600
gtcaagtagc agggtccaa tcagcagttt tcccaataac tcctggagcc tctctgctcc     660
tgtacctttg ggaacctgtt gcctgagtct ggtttctgac tcctgcgggg cctctgcctc     720
ctgcccacct taagccactg atgggagggt gtggttccaa cgtgttccag gtactatggg     780
tgaggacagc ttggcgctgg ggaaatcagc ccaggatact ccctgtcctt ggtaacgcag     840
tgtaagggga agtgaggaat ggactgcagt tgccatacag acttcctgtt agtcaagggc     900
tctccaaagc tgagaaggac ctccgagttc atgaatccaa tggcttcact ttactgatgg     960
ggaaaatgag gcccagagga ggaaagaaaa gaaactttaa atgccttatc ttgcagaggc    1020
attttaaaag gtaactggaa ttcagaaatg tcattttgaa tgtcaacgca ggagcaaagg    1080
caaaggaaag aggagcctaa actcagtgat gttatgtgat ttttccaaga tcacgcagca    1140
ttggcacttg gcagagctgg ggctgaaatg cagggccctg gacgctcccg catccggtgc    1200
agaggacgct gccctgggcc tgcctgggc cttgccgagc cctgcggact agatgcggga     1260
atgcacggat gaatccacag aagccaagat agacggtggc agacaggcaa tagactgatg    1320
ctgcatttga caggtatatt gataggctag atgataaaaa gaagatgaat tttatgagct    1380
gaccgacaga tggacagaaa tgcagacagg aagctgctat agaaccagag gatgccaatc    1440
acagggacgg ctaacaatct tgttttgtat ttagtcaaat cacaagcaca gacaggtgac    1500
ccacgcttcc tgttcaaggt ttgaaaatgc ccgaaaactg acggaaagac acgaagcgaa    1560
tcagactccg agagccaccc ggggaaacga ccgggtgctc ggagggcctc gggtgttgcc    1620
ggaaatggcc gacgaccgcc ctcggcaggg ctgtgggagg gggcgtggcc ggctcagcac    1680
gcggagcagc ttcgggtatt tccggaaact gccgaaagcc cccttgaagt gggcggggaa    1740
aggccggtgg gcgtggctgg atggccgtgg acggggcgg ggggtaggca cccggggtcg     1800
cttcgtggat ttccgtaaac agagccgaag cttcgtcttc ggaatcgagg aggagagcgc    1860
gtccccgggg tttaccttct tcggctgttt ccggaattca cccgtagtct gtggccggga    1920
ggagaaggcg cgcccacct cccgtttcta gccgcttcgg atgtttccgg ctgctgccgg     1980
cgaaaagagc cgagggccgg cggtggtggc ggccatgttg ggagcagcag gtccggcggc    2040
ggctgcctgt gtgccgggcg cggagcagtg ccgctgaggg caggggagga gcgaggcagg    2100
cggccggctg cggcggcaga gagtaggcgg agcggcgcgg cccggccgaa aggcggcaca    2160
```

-continued

```
gcccagccgg gggtcggggg ggtgcggtcc ggagccgctc ggagccggcg cggcctagcc    2220
cgagcggcgc atccccgggc tggcgtgagc ggctgcccgg cctccccgca ccccggccg     2280 gggcccatgc ggcgggtgct cctgctgtga agcccccgc ccggccgggc tccgcgcctt    2340
cccttccctc ccttcctcca agcttctcgg ttccctcccc cgagataccg cgccatgtc    2400 cagcgctcgg accccctac ccacgctgaa cgagagggac acggagcagg taaggagccc    2460
cgagggctcc ccgaattctc tggctgggcc ctttgcacct tgcggagcct cctccctctt   2520
ctgctctcct cgtgccctg ctgccatcct gcaagcctcg gctgccctgt catccggctc    2580
ctggctccgg ctccgcacat cccgcttccg agtcctgacc tgggacccac ctcgtcctga   2640
ctccaagctg cacacttgtc tttctgccaa ccccgtctc ccctcaccgc cctcctgcgc    2700
tcttccgtgt cacctcccca gcttcccttt ctcttccctt tttctctcag gggccttcct   2760
ggtcttcctc cacccacgct taaagcagcc ccctcccgc tcctcgaata gcagcacccc    2820
gcgatttgcc acagatcgtt gtccacctct cccttcgtct ctcctgcctc gcttcccctc   2880
cgcccgcacc ggttctgcca gtctctgggt tatcaccctc agggtccttg ccctggactg   2940
cgctctcgat ccctggcccc ttgcagttcc cccagctttt tctaccctgc ttcttcgttt   3000
tccaaattgt gctctccctc ttgcttgcaa cccaccagct ccaccctcat caccttttcca   3060 aatccttcgc ctactctttg ctcatcactt tccctttcttt gctccaggag ctccctggat   3120
cctggcgctg gcatttgtcg cttccgtgtt tccccacagc tgtcatgcgc atagttttcc    3180
cacaggttgc gtttggggtt ccaatcatca ctcccttcag agtctttgga tccctctgtg   3240
tctcttcccc tcgggtttgg ctttaaggtc cctgggcctc ttgtttctct ctgtgagtgt    3300
tctaccagcc ttctactggg ctcttcctcc caacccaaag acacttggcc ccaccgtatt    3360
aacacaacct gttgctcagt ccttttccag acctcgctgc atcacagttt ttgccttct    3420 gtcttcgtac gctggaacac aaaccatgat gactttctgt gtcttcactc ccgtgcctgg    3480
cacttagagt atttttctttc ttgcttgttg ccttcctgtt tctccaccct cacccccatct   3540 tccttactgt gccttttaat cagcgttgcc tttcatctcc gcattagtct cctgccttct    3600
tcatgtcctg tgtatcccca caccgtgctt ggatccattc tgttcctatt ggctaagtct    3660
ctgtaatgcc caggaagtcc aggtgttttg catgctagtt tcttgagcta cacctcagcc    3720
tcacgactct acacggtccc cctcatcctg gcagtcactg ctatgttttt cacccaagtc    3780
ttagcctttc tgtgtcatct cacttttgat cccagagacg tccactttcc acacctcccc    3840
tttatttcac catctctagc gtcctttgct gactgctctg tgcagagtcc cctgcctgtc    3900 ataccttttct tggtggagaa ctttactagg ccaaaaaaac ttgacttgaa aaagaagtgc   3960
ttctgccccg gggctgctgt gcttttttgcc ttctttcccc tccttccatc ctttatgttt   4020
ccctcttact ccccttcttttc tttgtagccc ggtagagcag ttgttgtatt ctcttgcatg   4080
tgaacattct tctttgaaaa atcttacctc ctttctttta ctgtgttttt ctattttgtt    4140 acccctggc cctctgtcac ctgggcagtt aggaactaaa gagaagttct aggcagagtt    4200
tttctctgca gggttgaccc tttatttact tgtggattat ttgcttctgg gggtgaaata    4260 gggggttgaga ggagggatg gttgattttcc atttcatcac tgggtttggc agctggttct   4320
gcatgggaca ggggtctttg gagacagagg agcatgttct gtgtctcgca gtctttctct   4380
cccttgccta ccggctgttt ctctctccttt actgggaatt gctttctctg ggccctcttg    4440
aggttgctta ttccacccat tttcctctca caacctttgt tttagcaggt aaaccctgct    4500
taaccagaga actttcccag actgttgatc gtgagctggt aggaggaggc caagtgactg     4560
```

-continued

```
actggcaccc tcaggcattt ggggagtggc gatggagtgc ctactctcag tgaggctggt      4620 gggggcatt gtgttcagca gagcagagta acagactgcc tcagtgtggt ttctttgtgc       4680
tgcttactac atgtaaatgt attattgcca tggtatttt cctgtgatgt gtgtgttgat      4740 ttccttctt ccttacatgc ctagcatact gctgagcata tagtaggaat tccaccgtag       4800
tgtgcatcca ctgattccat gatagcagca atcagtgacc atttgggaat gtaagtaagc     4860
tctttgctct tgataactt tgcccagagc agtagctgca tacattgtca tcctgttagg      4920
attattaatt acccatccta tttctactct ttatggactt agattctcct tagccccttc     4980
ataccttcta ctgttgttct cagggtagcc agtcactgta tcgatttaat attaagtctc    5040
attccagtaa aagcagggac tttggaaaac cttggatgca cctattccag acagattcct    5100
gtattctttt ttttttttt ttttgagata gagtctcgtt ctgtcgccag gctggagtgc      5160
agtggcacaa tcttggctca ctgcaatctc cgcctcctgg gttcaagcga ttccctgcc     5220 tcagcctcct gagtagctgg gactacaggc acacaccgcc acgcccggct aattttttgg    5280
attttagtag agacagcgtt tcaccatgtt gtccaggatg gtctcagtct cctgtcctcg     5340
tgatccggcc tcccaaagtg ctgggattac aggtgtgagc cactgcgccg ggcctgattc    5400
ctgtattctt taaaacggga aaaagacaa gcagcagctc ctcaggtcac aaggccaggt      5460
atatcaaaca ctggcctccg agaatagatc atgccaccaa gtgaaagaaa cctcttcttg    5520
gtcctgttgt gattttagat aaagtagtca tggaagcttg gtcattacta tagtcttaat    5580 gttattttt ttaaaaggg gatttagttg ggctgatttc ctcccctaaa ggtcctctgt      5640
caccttattt aaatttaaaa ctggttttac cagaaaatag gtaaacaaac accactggtt    5700
gtctccagtc tcttttcttg ctcttcctct ccctcttctt taaaaatgtg gctgatgaga    5760
acctgtttcc aggagcccctt taatcactct gaaacacaca gacactgaaa atgttgaagc   5820
ataaaaataa accttgcgtt acagggagat tgcctgtgtg ctgtccactt cgcttataac    5880
agtgaaagta ggagattaaa aaaaaaaaaa agttaagccc tgtctttaag atggtttttg   5940
tgacacctga ttccagatgt gcttttcac agccatagac ttcctgcttt tgcagaagga   6000
gggttctaat ctggggctcg tagcttgggg gattcttagt ttgtgagctg agcttttgt     6060 tcacttcttt tccaaatgac tctgctggcc tgaagcttgg cagttgtgaa agcaatcagc   6120
aagatgactg tttgtcttcc agccagcagc agcagtcaca ggcaagcctg gagaaaggtc   6180
cagcttccag agttcacctg ctagagtttt ccataacacc tgggggagag gctactccat    6240
ctgggacctg ccccacctct gggcctcaga aactatgaga gagggattga gagaaaactt   6300
gccccacttc tgctgcagtg ggaagggagg gggctgctgt caggcttcta ggcagtgagc   6360
ggcattgttt attctctcag ttctaggaag gggagtttag aagtactggt gaagaaaaca   6420
aagttacaag atcctataag gaacagctga actactccaa acactctcac tggacccca   6480 ttgttgattc tggataaaaa tatatatata tataaaactc ttttttttt tgacacagag     6540 tcttgctctg tcgcccaggc tggagtgtag cgatgcgatc tcggctcact gcaacctccg    6600
cctcccgggt caagcgattc tcctgcctca gcctcctggg agtagctggg actacaggcg   6660
cccaccacca tgctggctaa ttttttgtatt tttagtagag acggggtttt gccatattgg   6720
ccaagctggt ctcgatctcc tgacctcagg tgatctgctg gataaatatt ttttttttgc    6780
ttttggtgta acttaggtag attggatcgg ctagctagca tctcagtcca cactctgagc    6840
tgtgcagcag tgtgccctgg tgctaattct cactctgtcc tttgattctg gccagggggt    6900
ccttggtggt gctgccttct ggtcaggaat gtgggtgaat gtcagaccaa atagtgtcac    6960
```

-continued

```
tttcggcttg gccctagaga tcaggaagga agtgttgtta gagcaagggc tttgggagtc   7020
cttggagttc gtaacctttg aatctgaaaa gtaactgtac ctagtaaatt agaataattt   7080
ctctctggtc aggcaccatg gctcatgcct gtagtcctag cactttggga agccaaggca   7140
ggaggattgc ttgaggccag gagttcaaga ccagcctgat caataaagtg agactccatc   7200
tctacaaaaa aatttttta aatttagctg ggcatggtgg cacatgcctg tggttgcagc   7260
tacacagaag gctgaggcag gaggatggct tgagctgggg aggtcgagac tgcattgagc   7320
tgtgtttgtg ccactgcact tcagcctggg tgacagagca agacactatc tcagaaaaaa   7380
aaaattactt ttctccaatt tatggacttc ggaaagtagc taaacagatg gatataagac   7440
agttgttgaa actcggcctg ctgcagatta aataaagtt tgcacaagga taacttaatc   7500
tttcagacca accaaagttt gggctggaga ttttctcag cataaatgtc ctaagcagag   7560
ttggtgccta tgaggtagga aaagattgag actttgcttg cctaagaggt ttgcagggtt   7620
cgagcttttg ggagtcagaa cttctcagac tagattgttt cccctttgga cagaacaacc   7680
caattctcag tgggcatttg atcaggacta acccaggcct tcatgaactc tttcccattg   7740
agcacttagc cacctggctg gcatttctct tctcccagga gcttccatga ggttcctact   7800
tatgtattat gtcgacttga atgaatattt tatgtctaga gtgcagccaa gcctcagact   7860
ttgtggccca ttatcgacaa atggggtagg gggtgggcgc cacctttggc cccgtgatag   7920
cttctctgct aaatgactc cccccagcag cactttgaag cccattaatg gattggaatg   7980
aagtaacctc agcagatgga aagggtgagg agggtggtca tcttccttcc ctgagactgc   8040
ctgatgaggc tttcctacag taaccaggac aagcccctat tccctctgct tggttaagct   8100
gtggactgga gctactaggc ctctgctttg agaggaagta tagaaaggat ttgattctct   8160
tttagccatg gtggggccgc cagtttcccc actttcccat caaagcaaaa attgagaagg   8220
atgtggaaag ggtgggtgga gtttaaagct ggccttcct ccttcagtgg aagttcagca   8280
aaatgacaaa ccagataggt ggctaaattt ccttctcttg atgggagatt ccagtatttg   8340
tacgttttgt gcttgtagct tggattctcc aggcctcctc ccagctttca tcaaacatga   8400
gtgagtcact gaagtgttgt ctatgcattt tctcccttct gtctctgcaa agggaagagt   8460
aagcctttac aaacctgtgg gggaggaagt caccctcttc ccactgctgg agagccaggc   8520
tatccccagg ttaaccctga aagtgctaac tcctgagcag aatgttactg ccacccgccc   8580
ccttcctttt tgttataggc cattgaaggt cattgctcgt ctttttttt gagacagtct   8640 tgctctggtc acccaggctg gagtgcagtg gcaggatctc agctcactgc aacctccacc   8700
tactgggttc aagcgattct catgcctcag tcttccaaat aaccaggatt acaggtgcgc   8760
acctccatgc ctggccactt tttgtatttt tagtagagat agggtttcac catgttggcc   8820
aggctggtct tgaactcctg gactcaagtg atccgcctgc cgtggcctct caaagtactg   8880
ggattacagg agtgagccac cgcgcccggc atcattgctt atcttttaga ctgagatagt   8940
acagctgatt ctaaacagca cccagagaga atctggcctc ttgatttcca gttgtgtctc   9000
agaggaggag gcatcccagt tcctcctctt gccctctaga catctcctcc tctgataagt   9060
ataaataggc tagatccctt tatcttcata tctgtttttg tctggaatgt ttcaagtttc   9120
tcaagctagg tgtggtggct catatctgta atcccagcac ttcgggaggc cacggcagga   9180
ggatcacttg agcccaggag ttcaagacca gcctgagcaa catagtgaga cctcatttct   9240
acaaaaaaaa aatttttttt ttgagacagt cttgctctgg tcacccaggc tggagtgcag   9300
tggcaggatc tcagctcact gcaacctcca cctactgggt tcaagcgatt ctcatgcctc   9360
```

-continued

| | | | | |
|---|---|---|---|---|
| agtctcccaa | atagctgaga | ttacaggtgt | acgccactat | gcctggctaa ttttttgtatt | 9420 |
| tttagtagag | atggggtttc | accatgttgg | tcaggctggc | cttgaactca tgacctcgtg | 9480 |
| atctgcctca | gcctcccaaa | gtgctaggat | tataggcatg | agtcaccccg cctggccaaa | 9540 |
| aaaaattttt | tttttttttt | tgagacgttg | tcttgccctg | tcgcccaggc tggagtgcag | 9600 |
| tggcacgatc | tcggctcact | gcaaggtccg | cctcccggat | tcacgccatt ctcctgcctc | 9660 |
| agcctcccga | gtagctggga | ctacaggtgc | ccgccaccac acccggctaa | ttttttttgta | 9720 |
| ttttcagtag | agacggggtt | tcaccttgtt | agccaggatg | gtctcgatct tctgacctcg | 9780 |
| tgatccaccc | acctcggcct | cccaaagtgc | tgggattaca | ggcgggagcc accgcgccca | 9840 |
| gcccaaaaaa | attttaaaa | agttacctgg | gtgtggtagc | acatgcgtgt atcccaccta | 9900 |
| ctcagaaggc | tgagatgtga | ggatcacttg | agcctgggaa | gttgaggctg cagtgagctg | 9960 |
| tgatcatgcc | actgcattcc | agcctgggca | acagagtgag | accccatctc aagataaata | 10020 |
| aggtttgtca | gtccctgtgg | tggttctttc | cgcagatgtc | tgtctttggg ttggcactta | 10080 |
| tttcccccta | cttgcagtta | ttccttacat | ttctcattag | aaaatggcaa aaagggcaaa | 10140 |
| agtaaattca | tttccttttt | acaccaaatc | attaatttta | ggcttataaa actaaatgaa | 10200 |
| cagaagattt | ggtaggagag | gaggggagag | ggacactgat | actggtggct aggtgatcct | 10260 |
| gagggacaac | tggtgcctgg | cagaaagaga | ggagggctgt | gttcagtgac tggctcccag | 10320 |
| ccaccttttt | ggccttttc | ttttttaacat | gaggaaggcg | gagcagacca ggggcttctc | 10380 |
| tgtagaacca | gtcaagctgg | ttttgggcag | ccttggccta | ttttcttgtg tgctctttgg | 10440 |
| gaagttggca | atacaaaggt | ctgcctcctt | tggggctgtg | ttcgttgagg cgaaagtttg | 10500 |
| gaagacaact | atctgtcaac | aaccccttc | tccccaaaca | ctgaatgggt ctctgagctg | 10560 |
| gtccttcact | ccagggagga | ggctttctct | ccaccctatg | ctgaacctga aggcagcttt | 10620 |
| gctttataca | ccttttcactg | aaagctctaa | gacattaact | cctttttttgg actcccttcc | 10680 |
| caattcacaa | cttggtgaaa | gaccctcagc | ctagccagga | ggaagggact gggtctgcct | 10740 |
| ttggctcctc | atttatgggt | ctgggagggg | atcaggactc | cttactgcta tgatctggct | 10800 |
| gctaaattca | gtgacatccc | aggcctttt | tcgtccacgc | aatgggactg tctgtccagg | 10860 |
| cctgctggga | agaaaagag | agaaaaata | gttttgctc | tttggcagct tacagggact | 10920 |
| tcagccatag | gaaacaacct | gtaggaaagg | tgggagcttc | cggtcaccat gtgtgctgac | 10980 |
| acttcctgca | atagcactag | ggagtctttc | tcagggagca | aggccagcca ggtaggatta | 11040 |
| tttcccagtc | tcccagctaa | gcaggaaatg | ccaaaatatg | aacgtttagt aattagtgag | 11100 |
| tgtaactacc | tgctgacaga | gctccagcct | agaccttgtc | cttgggggct ggttgccct | 11160 |
| gttgatacta | cagtgagcta | ctcattgctt | ctgattacca | tttcagtatg agttttgctt | 11220 |
| tggtttctga | tatcccatgt | gcggctgcct | ttttctcca | ccttctttt gttgtgtctt | 11280 |
| tttgtttttt | tgagacggag | tcttgctctg | ttgcccaggc | tggagtacag tggcacaatc | 11340 |
| tcagctcact | gcaacctccg | cttcccaggt | tcaagcaatt | ctgccttagc ctcccaagta | 11400 |
| gctggtacta | caggcatgtg | ccagcacacc | cggctaattt | tttttttttt tttttgaga | 11460 |
| cagggtctcg | ctctgtcgcc | caggctggag | tgcagtggcg | cgatctcagc tcactgcaag | 11520 |
| ctctgcctcc | cgggttcaca | ccattctcct | gcctcagcct | cccgagtagc tgggacttca | 11580 |
| ggcgcccacc | accatgccca | gctaattttt | tgtactttt | tttttttaa agtagagatg | 11640 |
| aggtttcacc | atgttagcca | ggatggtctc | aatctcctga | cctcatgatc cacccacctc | 11700 |
| ggcctcccaa | agtgctggga | ttacaggcgt | gagccaccgt | gcccggctgt aacacctggc | 11760 |

-continued

```
taattttttgt attttttagta gagatgggat ttcaccatgt tggccaggat ggtctcgatc   11820
tcctgacctc gtgatccgcc cgcctcggct tcccaaagtg ctgagattgc aggcgtgagc   11880
caccgcgcct gaccttgttg gtgtttttaa gagacagggt ctcaccctgt cacccaggct   11940
agtatgcagt ggtgtgatca tagcccactg cggcctcaaa tagctcctag gctcaagtga   12000
ttctcccacc ttagcttcca gagtactggg actacaggtc acacctggcc ccctcaacct   12060
tctggacttt tcactcaccc catcactccc tacttctccg ccacagaaga ctgtcattgg   12120
ctatctttgc aagtagtatt gaagccactc ggagattgtt gctttgtctt tttgctcatg   12180
aaagtttgaa ttactggttc tccagtcaca ggaagtgggg ctccttaggc cagctccatc   12240
tcacgtagtg tactgattat gttgagctta tggcacagct gagaggagag tccaaacttt   12300
ttgaacactt tttgacttcc aataagtggt tccactatgg ttaagagcag gtttggtggg   12360
ccgggcgcgg tggctcatgc ctgtaatccc agcactttgg gaggccaagg caggcggatc   12420
acctgaggtc aggagttcga ccagcctg accaacatgg taaaaccta tctcaactgg   12480 aaatacaaaa attagcccgg tgtggtgttg tacacctata gtcccagcta ctcggaaggc   12540
tgaggcacaa gaatcacttg aatctgggag gtggaggttg cagtgaacag agatcatgcc   12600
actgcactcc agcctgggca acaaagcaag actttgtctc aaacaaacaa taagagcagg   12660
ttttgcggct agatttcctg tattggaatc ctggatcatc ctctcctgtg atcttaggtt   12720
ccctctgtgt ctgtttgctc atctgtaaaa tgggagaaga atagtaccca tcttataggt   12780
atagctgtta tgagtattaa aagagttaat gaatagaaag catttagaat agcgcctggc   12840
acagcagaat gatcattgtc attattgttc cagttgaaca acacagtgaa ttttatctga   12900
gcaccacaca actctaggtc agtataaggg gtgatgtttg ggatttctct gtaatcagtt   12960
gaaaaaatct tgttctggca tcttcaagcc actggggtcc tataggtgct ttttctaaca   13020
tttctgtttt tttgtttgtt tgtttgtttt tttgagatgg agtcttgctc ttgttaccca   13080
ggctggagtg cagtagcacc atcttggctc actgtgacct ccacctccca ggttcaagcg   13140
attctcctgc ctcagcctcc caagtagctg ggattacagg cacctgccac catacctggc   13200
taattttttt ttttttttt ttttttttg tattttttagt agagatgggg tttcaccatg   13260
ttgaccaggc tggtcttgaa ctcctgacct catgatctgc ccacctcggc ctcccaaagt   13320
gctgggatta caggcgtgag ccactgcacc cgccctagtt tgctttttta ccaatcacct   13380
atctgaaaaa aaatggaatg ctactggaga gattcatgta cttctgagaa cacttttagc   13440
tcatttttta taaggcatca atattagata gttttcttga ttaaagaaaa aaaaacacca   13500
cccactgcct gcctatattt ctgggttgca aatgatggcg gtggatgtgc agcctcatcc   13560
gtggctagaa ggccaaatcc aaagtcacca gagcttgagt tttttgagag ttgagatctg   13620
tgtgtcaaag gggaagccct aggtggttc tctgcagcac caagagcagg gattcatacc   13680
atcatgttcc tttctttttt cttttctcgt cttttctttc ttcctttctt tttgttctca   13740
tgagttctca ctgtgttgcc caggctggtc ttgaatattt ggcctcaagt gatcctcccg   13800
cattggcctc cccaagtgct gggattacac actcagccat gttcctttct tcaagtacgg   13860
tattgaccct ttggccacag gagaacgtgc ccagttttc ttaaagacca cgtgggaact   13920
cagcagccca tgattgtagg ttccttttc cctcatagag tggccttcaa gggcaggttc   13980
ttgttatctg cgtttcagag acccaaaggg acacaggcat ttctgctcct gggaatttgc   14040
ggactttgaa tcttgagctc agattttggt ctctgttggt tgcttgttta tcttcatctc   14100
ttgtcatttc tggagcctgc atgccttctc agagcagcag gtaagttgct tagttttttc   14160
```

```
acattgaagc tgtggctggg ggaaggtaac agtgtcccct cagaactcat ggagatgcca    14220
ggcatagtgg aggctgaggc aggagggtca cttgaggctg gaggattgct tgaggccagc    14280
ctgggcaaca tggtgagagc tcatctctaa aaaatttttt taaaaataac tcatcagggg    14340
ctatttcttt cattgtattt tcctcttcct tttgaacccc tctgctgact tgtttcactt    14400 tcttttttc tgtttggttt ctttgaactc cctttcttca ttatcatgtc tcattcccg      14460 tccatcttag gtttttcatt tccttgttcc actctcccta acctgtttct gtgccctgtt    14520
tatggcatgc tcaggatat gaattttgat ctccgtctga gatctccttc aggtatagaa     14580
tcccagacca cctggtcctt tgttctctc attcctctga tttctgtaca tttaaggatt     14640
cactgcttta gaaaacttt tttttttttc ttgtttctgg agccacctct ctcagtaaag     14700
ccaggcttgg caacttatta gggacagcat tctggttttcc ctggtgacag ggtttaagct   14760
gattctaggc tgttgcctct aacccatcag gaatgccata agtatagacc ctgtcttggg    14820
agagatctgg agagatactt gagaattttg gacactgtaa tattgaattt ggttctaatt    14880
gtgatctaga gaccctcaga ctctttcagg tgatgcacga agtcaaaatt ctgttcatag    14940
taacgttaac acagtgttgc tttttcactc tcattccctc accagtatac agtggcattt    15000
tccagaggct aaatgatgtg tggtaacatc acattcttct ggctaatgaa atgtgtaatt    15060
ctgtattctt gtgttttcta aattttaa ggtagtactt taaggtaaaa atatggaagt      15120
tttcattgat ggactcagtt tgttcttagt acttctgtgc tcttactagg tttcttcagt    15180
tataactgct atcatctttt tgtacacttc attactgtct aataaatcct tattttgaaa    15240
tcccagcatt ttcctggaac ctttgagaaa atataagaag taagtactac ttgtaaaact    15300
tgcttgtaaa aacttttggg aaaactccta attttaaaaa ttttattgac aacttatttt    15360
agcactttat tctaaaatag aaaaaaattt atattatttc tcttatatgt aagggtggat    15420
tgttggctta aaaagggag attagaagac ttgcttttc aacccatagc tgcaacttgt      15480
atgttaaaaa tactgaagtg gacataccaa caagtataaa ggaggacttt aaagaatctg    15540
ggcagaactg taaataagaa ctaaaaaaa aaaaaagaa agaaatgaa agtgtaatga       15600 aagctacctt ctcagtttca taaatgttca taatgtacct tactgcgtct tatgcgacag    15660
aacattttca tgtagtatta tggtaccagt taagttgtgg cattctttca agatcattta    15720
gagtttaaag aaaaaggaat tgcatatttt atgcgtacgt actatgagct ctttaaaagc    15780
caaaatttct tccagttttt aaactagaaa taaaaagtc actgaagcct ctatctaaca     15840
ggataagttg ccacattgct ttggctggaa aagcccacac agaaactgag agacgaatga    15900
agtcttgaac agctgacatt cctgaatgcc cactggatga aaagtcagta aaattcaagg    15960
cagtgccgct ttaaatgtta ccaggattca ttaaattaaa gatttagcca ggcgcggtgg    16020
ctcatgcctg taatcccagc agtttgggag accgaggcag gtggatcacc tgaggtcagg    16080
agtttgagac cagcctggcc aacatggtga aactccttct ctactaaaaa tacaaaaatt    16140
agccaggcgt ggtggcgcat gcctgtaatc ccagctactc gggaggctga ggcaggagaa    16200
tcgtttgaac ccaagagatg gaggttgcag tgagccgaga tcgtgccatt gcactccagc    16260
ctgggcgaca gagcgaaac taaaaaaaaa aaaagatg tagctgcaca catgaagacc       16320
aagttaatat cttatttaca gaattttact ttcaccttac aaatgagcaa atctatagat    16380
gtggctcgac ttgctgtatc agcaccaact gctcatcaaa gaataattta ttttatgtga    16440
atgctcagca gcagatacaa atggtgataa atattcaaag ggttgaataa cttcctgaat    16500
ctcatgactt atcctggaac aactttattt ccatttgcac ccttggtgca gaagcagtgg    16560
```

-continued

```
tggagaaaac tgctgacgcc gtaacatgga tcaaggaagt ggcactaagc tctactagtg    16620
gtcattgtca tggtcttctt tcccaccaca aacttgtggt tgaaaaataa aagccattt     16680 tacttgagaa tgtcttgaat gaaggattaa agactatcat ttttttatt tacttattta    16740 tttatttatt tattttaatt tttatctatt tattttttg aaacagagtc tcactctgtc     16800
tcctaggctg aagtgcaatg gcgtgatctg tgctcactgc cacctctgcc tcctgggttc    16860
aagtgattct cctgcctcag cctcccaagt tgctgggatt acaggcacct gccaccacgc    16920
ctggctaatt tttgtatttt tagtagagac agggtttcgc cacgttggcc gggctggtct    16980
ggaattcctg acctcaggtg atccacctgc ctcggcctcc caaagtgctg ggattacagg    17040
catgagccac catgcctggc caagactatt aattctgtgt gtgtgtgtgt gtgtgtgtgt    17100
gtgtgtgtgt gtgaggtctc actgtgtcac ttaggctgga gtgcattggt gcaacctccg    17160
cccactgcaa cctctgcctc ccgggttcaa gtgttttctc acctcagcat ccccagtagc    17220
tggtactaca gtgggatac tccaccccag gagtgaagca tataacccag ttccnnnnnn    17280
nnnnnnnnnn nnnnnnnnnn nnnnnnnnnn nnnnnnnnnn nnnnnnnnnn nnnnnnnnnn    17340
nnnnnnnnnn nnnnnnnnnn nnnnnnnnnn nnnnnnnnnn nnnnnnnnnn nnnnnnnnnn    17400
nnnnnnnnnn nnnnnnnnnn nnnnnnnnnn nnnnnnnnnn nnnnnnnnnn nnnnnnnnnn    17460
nnnnnnnnnn nnnnnnnnnn nnnnnnnnnn nnnnnnnnnn nnnnnnnnnn nnnnnnnnnn    17520
nnnnnnnnnn nnnnnnnnnn nnnnnnnnnn nnnnnnnnnn nnnnnnnnnn nnnnnnnnnn    17580
nnnnnnnnnn nnnnnnnnnn nnnnnnnnnn nnnnnnnnnn nnnnnnnnnn nnnnnnnnnn    17640
nnnnnnnnnn nnnnnnnnnn nnnnnnnnnn nnnnnnnnnn nnnnnnnnnn nnnnnnnnnn    17700
nnnnnnnnnn nnnnnnnnnn nnnnnnnnnn nnnnnnnnnn nnnnnnnnnn nnnnnnnnnn    17760
nnnnnnnnnn nnnnnnnnnn nnnnnnnnnn nnnnnnnnnn nnnnnnnnnn nnnnnnnnnn    17820
nnnnnnnnnn nnnnnnnnnn nnnnnnnnnn nnnnnnnnnn nnnnnnnnnn nnnnnnnnnn    17880
nnnnnnnnnn nnnnnnnnnn nnnnnnnnnn nnnnnnnnnn nnnnnnnnnn nnnnnnnnnn    17940
nnnnnnnnnn nnnnnnnnnn nnnnnnnnnn nnnnnnnnnn nnnnnnnnnn nnnnnnnnnn    18000
nnnnnnnnnn nnnnnnnnnn nnnnnnnnnn nnnnnnnnnn nnnnnnnnnn nnnnnnnnnn    18060
nnnnnnnnnn nnnnnnnnnn nnnnnnnnnn nnnnnnnnnn nnnnnnnnnn nnnnnnnnnn    18120
nnnnnnnnnn nnnnnnnnnn nnnnnnnnnn nnnnnnnnnn nnnnnnnnnn nnnnnnnnnn    18180
nnnnnnnnnn nnnnnnnnnn nnnnnnnnnn nnnnnnnnnn nnnnnnnnnn nnnnnnnnnn    18240
nnnnnnnnnn nnnnnnnnnn nnnnnnnnnn nnnnnnnnnn nnnnnnnnnn nnnnnnnnnn    18300
nnnnnnnnnn nnnnnnnnnn nnnnnnnnnn nnnnnnnnnn nnnnnnnnnn nnnnnnnnnn    18360
nnnnnnnnnn nnnnnnnnnn nnnnnnnnnn nnnnnnnnnn nnnnnnnnnn nnnnnnnnnn    18420
nnnnnnnnnn nnnnnnnnnn nnnnnnnnnn nnnnnnnnnn nnnnnnnnnn nnnnnnnnnn    18480
nnnnnnnnnn nnnnnnnnnn nnnnnnnnnn nnnnnnnnnn nnnnnnnnnn nnnnnnnnnn    18540
nnnnnnnnnn nnnnnnnnnn nnnnnnnnnn nnnnnnnnnn nnnnnnnnnn nnnnnnnnnn    18600
nnnnnnnnnn nnnnnnnnnn nnnnnnnnnn nnnnnnnnnn nnnnnnnnnn nnnnnnnnnn    18660
nnnnnnnnnn nnnnnnnnnn nnnnnnnnnn nnnnnnnnnn nnnnnnnnnn nnnnnnnnnn    18720
nnnnnnnnnn nnnnnnnnnn nnnnnnnnnn nnnnnnnnnn nnnnnnnnnn nnnnnnnnnn    18780
nnnnnnnnnn nnnnnnnnnn nnnnnnnnnn nnnnnnnnnn nnnnnnnnnn nnnnnnnnnn    18840
nnnnnnnnnn nnnnnnnnnn nnnnnnnnnn nnnnnnnnnn nnnnnnnnnn nnnnnnnnnn    18900
nnnnnnnnnn nnnnnnnnnn nnnnnnnnnn nnnnnnnnnn nnnnnnnnnn nnnnnnnnnn    18960
```

-continued

| | | | | | |
|---|---|---|---|---|---|
| nnnnnnnnnn | nnnnnnnnnn | nnnnnnnnnn | nnnnnnnnnn | nnnnnnnnnn | nnnnnnnnnn 19020 |
| nnnnnnnnnn | nnnnnnnnnn | nnnnnnnnnn | nnnnnnnnnn | nnnnnnnnnn | nnnnnnnnnn 19080 |
| nnnnnnnnnn | nnnnnnnnnn | nnnnnnnnnn | nnnnnnnnnn | nnnnnnnnnn | nnnnnnnnnn 19140 |
| nnnnnnnnnn | nnnnnnnnnn | nnnnnnnnnn | nnnnnnnnnn | nnnnnnnnnn | nnnnnnnnnn 19200 |
| nnnnnnnnnn | nnnnnnnnnn | nnnnnnnnnn | nnnnnnnnnn | nnnnnnnnnn | nnnnnnnnnn 19260 |
| nnnnnnnnnn | nnnnnnnnnn | nnnnnnnnnn | nnnnnnnnnn | nnnnnnnnnn | nnnnnnnnnn 19320 |
| nnnnnnnnnn | nnnnnnnnnn | nnnnnnnnnn | nnnnnnnnnn | nnnnnnnnnn | nnnnnnnnnn 19380 |
| nnnnnnnnnn | nnnnnnnnnn | nnnnnnnnnn | nnnnnnnnnn | nnnnnnnnnn | nnnnnnnnnn 19440 |
| nnnnnnnnnn | nnnnnnnnnn | nnnnnnnnnn | nnnnnnnnnn | nnnnnnnnnn | nnnnnnnnnn 19500 |
| nnnnnnnnnn | nnnnnnnnnn | nnnnnnnnnn | nnnnnnnnnn | nnnnnnnnnn | nnnnnnnnnn 19560 |
| nnnnnnnnnn | nnnnnnnnnn | nnnnnnnnnn | nnnnnnnnnn | nnnnnnnnnn | nnnnnnnnnn 19620 |
| nnnnnnnnnn | nnnnnnnnnn | nnnnnnnnnn | nnnnnnnnnn | nnnnnnnnnn | nnnnnnnnnn 19680 |
| nnnnnnnnnn | nnnnnnnnnn | nnnnnnnnnn | nnnnnnnnnn | nnnnnnnnnn | nnnnnnnnnn 19740 |
| nnnnnnnnnn | nnnnnnnnnn | nnnnnnnnnn | nnnnnncctc | ccaaaaaggt | agggtttcag 19800 |
| gtttgagccc | ctcgccaccc | gtcctggttt | ttaatttttc | tcattttttt | ccccatttta 19860 |
| aaattttcca | agggttttt | ttttttttt | ttttttttt | tttttttttg | agacaaagtc 19920 |
| tctctcgctc | tctcgctctc | tcactctctc | gcccaggctg | gagtgcagtg | gcgccatctc 19980 |
| ggctcactgc | aagctctgcc | tcccgggttc | acgccattct | cctgcctcag | cctcccgagt 20040 |
| agctgggagg | gactacaggc | gccccccacc | atgcccggct | aatttttgt | attttatta 20100 |
| gagatggggt | ttcaccgtgt | tagccaggat | ggtctcgatc | tcctgacctc | atgatccgcc 20160 |
| cgcctcggcc | tcccaaagtg | ctgggattgc | aggcatgagc | caccacgccc | ggcctaaatt 20220 |
| tttcagtttt | tatactcatt | tccttttgt | tcgtttctt | tctttaattt | gttagtattt 20280 |
| gttgttttt | gagacagcct | cactttatca | cccagggtgg | agtgtggtgg | cacgatgttg 20340 |
| gctcactgca | acttccacct | cccaggttca | agcagttctc | ctgcctctgc | cttcccagta 20400 |
| gctgggatta | taggcacttg | ccaccaagtg | attttttgcat | tttagtagag | acggggtttc 20460 |
| tccatgttgg | tcaggctggt | ctccatgttg | gtcaggctgg | tctcgaactc | cttacctcag 20520 |
| gtgatctgcc | tgccttggcc | tcccaaagtg | ctgggattac | aggcatgagc | caccgcccca 20580 |
| gcctgttttt | tggtcagctg | ttttgttttg | attgcattat | aagattagtt | catcaggtag 20640 |
| acttcctttg | gtatatattt | agttgtggtt | tggaaaataa | gttttttatt | aaaataagt 20700 |
| catttatgtt | tacatgtaat | gagtttactc | atgttctgtt | aaatgaattg | atacatattt 20760 |
| aaattttttcc | tcacttgaat | ttctaatata | gtaaatactg | atagataaaa | ttcatataaa 20820 |
| caaaagcttc | tgggtgttca | gttattttc | aaaatgcaaa | gagtcctgaa | accaaaaact 20880 |
| gtaagaatca | tggttgtaga | caaaacttgg | tttggttctc | catgactttg | gttgatacat 20940 |
| tttttttta | ttttttatt | ttttgagaca | agttctcatt | ctgtcacccg | ggttagagtg 21000 |
| gaatggcatg | atctcggctc | attgcagtct | caacctccca | ggctcaagca | atcctctcat 21060 |
| ctcagcctcc | cagagtgctg | ggattataga | catgagccat | tgtgcctggc | tatattatca 21120 |
| tcgttattat | tgttttgttt | tgttttttga | gatggagttt | tgctttgtca | cccagggtgg 21180 |
| agtgcagtgg | caccatctca | gctcactaca | acctctgcct | cctgggatca | agcgattctt 21240 |
| gtgcctcagc | ctcccaacta | gctgggatta | caggtgcaca | gcaccacact | tggctcattt 21300 |
| ttgtattttt | agtagagaca | gggttttgcc | atgttggcta | ggctcctggc | ttcaattgat 21360 |

```
ctgcctgcct cggcctccca aagtgctagg attacgggca tgagccactg tgcctggccc    21420
tgtaatataa ttttacatga gttaatagtg taacattttc tcagttgtaa tttttttttt    21480
tgagacagtg tctcactcta tcacccaggc tggagtgcaa tggcacgatc tccactccct    21540
gcaacctccc aggttcaagt gattctcctg cctcagcctc ttgagtagct gggattacag    21600
gcatgcgcca ccacccggg ctaattttg tactttagt agagataggg ttttcaccat    21660
gttgttcagg ctggtctcga actcctgacc tcgtgatcca cctgcctctg cctcctaaag    21720
tgctgggatt acaggcctga gccactgtgc ctggccagtt ttaattttaa tacaataaat    21780
atcagtagct atcacccaca tgaagaaagc catttgacgt catcagtaag agtaaaggga    21840
ttccagacag tgtgagaact cttttgtaaa cagagatagg actgataatc cctgtcctcg    21900
attggttgat tacttgctat gacctcataa tgagcctctg ttttgcaatt tctggggccc    21960
tggctgggcc tcaggaaggc acttgctgtc ttggttttca gttgttctag ctgaggaagc    22020
tggttctcag tgacctgatg gaccttggcc aaagttggct catttcctcc tttgaataca    22080
tagcattact ttatgttttt ttattccatt aaaaagatca tttggcttac ttggatttta    22140
ttatgaggtt tgtgttttat tatgaggtag gtttgtgttt ttttgttttt tttttaactt    22200
atatgttggc tattggtcag ttccaaattt gaaaactgca acgcttacac agcttctatc    22260
cttgaagaac cttggtgcct acaatagctg agagctggta ggctgcagtc actaaggcca    22320
gacactcaat agtctattcc ctgggtggct tgagacctga catactttgt ttcttttgt     22380
ttcttttcct tttgtacttg actctttta acctgtttat ttctttttt tttttttccc     22440
cgagaaggga gtcctgctct gtcacgcagg ctggagtgca gtggcacgat ctcggcccac    22500
ggcaaccctc cgcctcacag gttcaagcaa ttctcctgcc tcagcctcct gagtagctgg    22560
gattgcaggt gccgccagt atcccggtt aattttgta ttttagtag agaaagggtt        22620
tcaccatgtt ggcaggctg gtcttgaatt cctgacctcg tgatccaccc accttggcct    22680
cccaaagtac taggattaca ggcacaagcc catgcctggg ctaaccccta tttctatctt    22740
tcttttttt tttcgagaca gagtcccact ctgtcgccca ggctggagtg cggtggccgg    22800
atctcagctc actgcagcct ccacctccca gattcaagca aatctcctgc ctcggcctcc    22860
cgagtagctg gaactacggg tgcgtgccac catgcccggc ttattttgt atttttagta    22920
gagacaggat tttgccatga tggccaggct ggtcttcaac tcttgacctg gtgatccacc    22980
tgccgtggcc tcctaaagta ctgggatgac agtcatgagc caccacatcc ggcctctaac    23040
ccttgtttct taatgaaaca tacctgtaaa ccccactgtt atgtaggtat actttatttt    23100
tcctgtaaga ggtaggttta tttggagtgt ttgtagcagt gtgtgaactt tgtatttcct    23160
tgacaagtcc ttaagtgaca gggaaaattg tagtagtata taatctgtaa actaccctgt    23220
aattctcaac tttgttcttt tgcatatact cattctccaa tttccatagc acctctaact    23280
tttaacagct tccctaagtc ctacaaataa tagaccttgg gcctcctcta atagtcactt    23340
tgaccaactt taagcaaatc ttttaaaact catgtcggct gggtgcagtg gctcactcct    23400
gtaatcccag cactttggga ggctgaggcg ggtggatcac gaggtcagga gatcgagacc    23460
atcctggcca acatggtgaa accccgtctc tactaaaaat acaaaaatta gccgggcgtg    23520
gtggcgtgcg cctgtagtcc cagctacttg ggaggctaag gcaggagaat tgcttgaacc    23580
caggaggggg aggctacagt gagccgagat catgccactg cactgtagcc tgggtgacag    23640
agactccctc tcaaaaaaaa aaaataaat agaaataaaa aagccaggca cagtgggcca    23700
catctgtaat cccagcactt tgggaggcca gggcgggtgg atcacgaggt caggagttcg    23760
```

```
agaccagcct ggccaatatg gtgaaacccc gtctctactt aaaatacaaa aaattagctg   23820
ggtatggtgg cgcgtgccta tagttccagc tcttcaggag gctgaggcag gagaatcact   23880
tgaacccagg aggcggtggt tgcagtgagc atagatcacg ccactgcact ccagcctcgg   23940
tgaccgagtg agactccatc tcaatgaaaa aaaaaaacaa aaacaaaaac tcatgtcatt   24000
tgctcagaat cacatctcat tggaatcatt tttttaaaac tgtttaatca agtgctcaac   24060
atatcaattc gtgtctacat agaggatcat agctccattt cccatcactc agcaagtccc   24120
ataatctgct ttttccacaa agcgtatttc ttttcagatt tacatgtggc atgcatttca   24180
gttccagaat tgaacttaat gtgctatttt ctctcttcgg ctactggtct gtgtggaaga   24240
taaggaactt taatttcggg ttgggtgcag tggctcacgc gggtaatccc agcacttagg   24300
gaggctaagg cgggcggatc acgaggtcag gagttcaaga ccagcctggc caagatggtg   24360
aaaccccatc tctactaaaa atacaaaaaa cgtagccagg cgtggtggtg ggcgtctgta   24420
atcccagcta ctctggaggc tgaggcagag aattgcttga ccccgggagg tggaggttgc   24480
agtgagctga gatcgcacca ctgcactcct gcctgggcga cagagcgaga ctccgtctca   24540
gaaaaaaaaa acaagaattt taatttcaaa tatttgttta ctgtattagt taaggcaacg   24600
gcttagtaat ggcacctcct ggatggccct gtaagcgcat taatctggtc caagtcattg   24660
ggaaactcag ccttaaaggg aatggactga gtggttgaag agtaggcagg gtctcctcat   24720
ttttgcatgg tttgcctctg aggctgtgta tctttagcta cagacagaat agctaacatt   24780
tattgagccc ttactctgtc gcaagcactt gtttagttgt tttacattca ttaactcatt   24840 tactctttt tttttttttt tttgagacag agtctcgctc ttgttgtcca ggctagagtg   24900
caacggcaca gaccttggct cactgcaacc tccgcctccc gggttcaagc aattctcctg   24960
cctcagcctc ccaagtagct gggattataa gtatctgcca ccatgcctgg ctaatttctt   25020
tctttctttc tttttttttt ttttttgagac ggtgtttcgc tcttgttgct caggctagag   25080
tgcagtggca ctgtcttggc tcactgcagt ctccgcctcc tgggttcaag caattctcct   25140
gcctctgcct cccgagtagc tgggattgca ggtatccgcc accatgcccg ctaatatttt   25200
tgtatttcta gtagagatgc ggttttaccg tgttggccag gctggtctca aactccggac   25260
atcaggtgat ccaccatctc agcttccca aagtgctggg attacaggca tgagccacca   25320
tgcctggctt catttattct ttgtaagtta gtagatctca ctgttttaca ggtgaggaaa   25380
tagaggccca gaaatgttga ataacttgtt taaggctaca aacccaggtg gtccagagta   25440
tgtcattgtc agaaccagct tttcttggtt gtgaagaatc cttttgtccct ggcttcagtt   25500 gtgtccaggc agtagaagat agtttcctta ggattagctc ccagtcagtg tgaggcagat   25560
gtcttgcagc ggaatttaga gtcacaaatg gcctcctctg cctccagttg tttcttttgt   25620
ccttggtggc cattggtaaa tgtggccgaa atggtgtgga tggagtggga gcagcttttct   25680 gggctcacct ccctactatt gagggctcta cgcaagagct atgggagacc tttttaagaa   25740
accctcttta accccagctt ctgattcaca tctttatctt ttcccatctt ccggaatttc   25800 aagaaccct ttagaaaaac caaagccccg agtcctaaaa ttgataacca gcaattaagt   25860
accttaaagt gtagggcatg atggatttct aggtttgact atcctgcttt gtggcaccca   25920
tgaaatgttg ggattctaga actctttctt tgtaagcacc ccactcccca ccaaaaaaaa   25980
ccccactaaa cataagaagc ttttgtctgt ggatcttaac tgtgtatatt ttgtctctag   26040
gaagcaaact cagattctct cttacaaccg tctgtgtgcc acttgcacac acacaggcac   26100
agagctactt gcttgtagcc ttgactgcca gcagccctga acaccgtagc tggtggtgcc   26160
```

-continued

```
aggccttgtg tgtgtttagg acttgccagt tcagtcctgg gagctgaact ctggacatcc    26220
tgctgtgtgt ctctttatcc catcgctggt gtaatttatg ccactacttc ctgtttgcat    26280
ttgctcagtc tctcctttgg tttgcttctc tctgctgaag ccggtcccca tagctgtgca    26340
catggctagc tatggggact aggcatctag atattctaga catctgcagt tgtttcttag    26400
tgggaatggt tgctttatgt ctctctacag aattttagtt gaacttgagt gtatgattta    26460
atttacttgc ttgtctaact tcggcaaggg tgcctttat tttaagatgc cagcatgggg     26520
tgagagtaaa ggggtgaact attgccctcc cccaccccc cacccccac cccccactt       26580 tttttnnnn nnnnnnnnnn nnnnnnnnnn nnnnnnnnnn nnnnnnnnnn nnnnnnnnnn    26640
nnnnnnnnnn nnnnnnnnnn nnnnnnnnnn nnnnnnnnnn nnnnnnnnnn nnnnnnnnnn    26700
nnnnnnnnnn nnnnnnnnnn nnnnnnnnnn nnnnnnnnnn nnnnnnnnnn nnnnnnnnnn    26760
nnnnnnnnnn nnnnnnnnnn nnnnnnnnnn nnnnnnnnnn nnnnnnnnnn nnnnnnnnnn    26820
nnnnnnnnnn nnnnnnnnnn nnnnnnnnnn nnnnnnnnnn nnnnnnnnnn nnnnnnnnnn    26880
nnnnnnnnnn nnnnnnnnnn nnnnnnnnnn nnnnnnnnnn nnnnnnnnnn nnnnnnnnnn    26940
nnnnnnnnnn nnnnnnnnnn nnnnnnnnnn nnnnnnnnnn nnnnnnnnnn nnnnnnnnnn    27000
nnnnnnnnnn nnnnnnnnnn nnnnnnnnnn nnnnnnnnnn nnnnnnnnnn nnnnnnnnnn    27060
nnnnnnnnnn nnnnnnnnnn nnnnnnnnnn nnnnnnnnnn nnnnnnnnnn nnnnnnnnnn    27120
nnnnnnnnnn nnnnnnnnnn nnnnnnnnnn nnnnnnnnnn nnnnnnnnnn nnnnnnnnnn    27180
nnnnnnnnnn nnnnnnnnnn nnnnnnnnnn nnnnnnnnnn nnnnnnnnnn nnnnnnnnnn    27240
nnnnnnnnnn nnnnnnnnnn nnnnnnnnnn nnnnnnnnnn nnnnnnnnnn nnnnnnnnnn    27300
nnnnnnnnnn nnnnnnnnnn nnnnnnnnnn nnnnnnnnnn nnnnnnnnnn nnnnnnnnnn    27360
nnnnnnnnnn nnnnnnnnnn nnnnnnnnnn nnnnnnnnnn nnnnnnnnnn nnnnnnnnnn    27420
nnnnnnnnnn nnnnnnnnnn nnnnnnnnnn nnnnnnnnnn nnnnnnnnnn nnnnnnnnnn    27480
nnnnnnnnnn nnnnnnnnnn nnnnnnnnnn nnnnnnnnnn nnnnnnnnnn nnnnnnnnnn    27540
nnnnnnnnnn nnnnnnnnnn nnnnnnnnnn nnnnnnnnnn nnnnnnnnnn nnnnnnnnnn    27600
nnnnnnnnnn nnnnnnnnnn nnnnnnnnnn nnnnnnnnnn nnnnnnnnnn nnnnnnnnnn    27660
nnnnnnnnnn nnnnnnnnnn nnnnnnnnnn nnnnnnnnnn nnnnnnnnnn nnnnnnnnnn    27720
nnnnnnnnnn nnnnnnnnnn nnnnnnnnnn nnnnnnnnnn nnnnnnnnnn nnnnnnnnnn    27780
nnnnnnnnnn nnnnnnnnnn nnnnnnnnnn nnnnnnnnnn nnnnnnnnnn nnnnnnnnnn    27840
nnnnnnnnnn nnnnnnnnnn nnnnnnnnnn nnnnnnnnnn nnnnnnnnnn nnnnnnnnnn    27900
nnnnnnnnnn nnnnnnnnnn nnnnnnnnnn nnnnnnnnnn nnnnnnnnnn nnnnnnnnnn    27960
nnnnnnnnnn nnnnnnnnnn nnnnnnnnnn nnnnnnnnnn nnnnnnnnnn nnnnnnnnnn    28020
nnnnnnnnnn nnnnnnnnnn nnnnnnnnnn nnnnnnnnnn nnnnnnnnnn nnnnnnnnnn    28080
nnnnnnnnnn nnnnnnnnnn nnnnnnnnnn nnnnnnnnnn nnnnnnnnta ttaaataaat aaataagatt    28140
tacttatcca aaagcacaat tatgtgcctt ttttcttttc ttttgagacg agagtctgac    28200
tctgttgccc aggctgctgt agtacagtga cgcagtctcg gccttgacct cccaggctca    28260
agcaatcctc ccacctcagc ctcccaagta gctgggacta caggcatgtg ccactatgcc    28320
tggctaattt tttgcacttt ttgtagagat ggggtttcgt catgttgccc aggctggcct    28380
ggaactcctg gcgtcaagca acctacctgc cttcgcctcc cagagtgctg ggattacagg    28440
cagtcgccat tgtatccagc ccagttatgt agttatgtgc catttctaaa ctactttaga    28500
acccatctct ttggtgtttg tttgtttgag acagagtctc actctgtcac ctcagctgga    28560
```

-continued

```
gtgcagtggt gtgatctcag ctcactgcag cctcggcccc caaggttcaa gcgaccctcc    28620
cacctcagcc tcccaagtag ctgggaccac aggtgctctt tttgttaaga gtggaaaagc    28680
caaggtccat gtactttttt tgagaaagac agcctgttgg cttcttcag agtggttctg     28740 cccttcccg tacccatct ccaacacatt tttatctctc aacagaggta gctgctattc     28800
actcaggtgt tctttaatgc tgtggccacg gcttccttgg agagtgtggc agtgctttcc    28860
ttgctaatga aaaggctgtc ataatggggt aggtccatag gggctctgcc cttctgtact    28920
tgtattccca gggagaaaaa tctctacctt aattaccgac atctcatgct ggcagagagg    28980
tgtggttgct aattgattag atgacagtcc ttttcattga tgtggcactg ttggggtggt    29040
tttgttgtgc tttttcaagt aaacagatag atttgggcca ggtaagttga ttttggagag    29100
atgaagttct gtgtagggat ttcccttat taagctcatg tctttagtgc cacttttgtg    29160
tcctgatttt ctaacttgat agtaagaagt actaagttgg cttgtcttgc tattttggtg    29220
tgggtggtga ataatgtctc ttctaccctg ctctctggtg cgttcctgtt ctgtttggta    29280
gcaccacatt cctctatttc gtttggtttt cattccctct ttctctcttg taatggttgg    29340
accctattct gaaatatata ttttaagata gtgttacttt gggtggtcga ggcgggcaga    29400
tcacctgagg ccaggagttc gacaccagcc tggtcaacat gatgaaaccc tgtctctact    29460
aaaaatacca aaattagcca ggcgtggtgg tgtgcatctg taatcccagc tactcgggag    29520
actgaggcac gagaattgct tgaacccaga aggcagaggt tgcagtgagc agagattgtg    29580
ccactttact ccagcctggg caataaagca agactcagtc tcaaaaaaaa aaaaaaaaa    29640 agtagtgttt aaaagcaaac accctgcctt ttttgaaacc acagaaactg cttgtgaaac    29700
agccgatagg gcaggctgcc aaatacagac tgttaaaacc aatctcttaa tgacaaaatg    29760
tcaaacactg atgttaaacc ttcattatga ctgtggtgtg aggatttttc tcaataagaa    29820
atgtttaggt gctgaactcc cagtttcaca ttcagaatgc ttctattatc aaattcctct    29880
tggtacatca tttccgagag gcttgtgtag ctaatccact atctactgta caggaaagat    29940
tttaaataaa cctattccca ttcatcctca tctgtgtttt tttgttttt gttttaattt     30000 caagaagtaa ttttcttttg aggtgatttg gaccaaccgt ctcactagct tttcccattt    30060
aagataggag aactagattc agaattgtgt cttttttccta acagaagact ggggccttaa    30120 tcttttacccc ccaggctctg attaactgac ttttctttt ttagatggca tagaatcttc    30180
tgtctgtcta gagaattttg tttcttgcca ggcactgtca ggaattagta ttcattcctc    30240
cctgctatct tcctgaagag ctgtgaacct gctggtagcc tgatggataa gggtacagtt    30300
gtttgtttat ttattgagac agggtctcat ctctcaccc aggctggagt gcagtggcat     30360
gatcttggct cactgcaacc tccgcctctc aggctcaagc tatcccccaa ccttagcctc    30420
ctgagtagct gggaccacag tcatgtgcca caacacccag caaatgtttt gcgttttttg    30480
tagagacagg gtttccccat gttgccttg ctggtcttga actcctgggc tcaagtgatc     30540
cgcctgcctc agcctcctga agtgctggga taccaggtgt gagctaccac agttggccaa    30600
ggtatagttt tatgagctga gctatagaac tggttgaatg ggaattaggg aaaacagaca    30660
accaataatt gggaagtaaa ggaaaaatat ataagtgtgc ctccttggtc acagctagcc    30720
ttgtgacatt ggggttttgg atatagaact tcaggaatcc cttccacctc cttcccaaga    30780
gaatttcttc tgttggtgtt gtaagggggct ttttccaact tcatttccat taccaagagt   30840
cttgagtggc tttattttca acttgggttt tttaagcgct tctcatgtca cctttgtttg    30900
tgtactgggc ctgtctcaag tttccagagg gagatgaaag acaagaaaag ctaaatgact    30960
```

```
ggttcttcag tgagtttccc agagtggctt cttctcattc cagcactgcc taactctcac    31020
catggctgac gccgtgggca ggcatccgca ttcatggaaa gccaggtcct agctggaagt    31080
gacacaggga tcttcagatc tctcttagcc cactgttcct ctgaaaaaaa aacaaaagcc    31140
atagacagta aattggggga ataggctgac cataacttca gttcgtggat ttgggtccca    31200
cactggattg tgtgatttgt gcttatctcc tactagattt ttaccttctt tgaaggctgg    31260
actgtatctt atccttctct gtatcacttc ggacacccag aaactgttgg agtactttgc    31320
acatggtcac ctcttaatga attatttgtg aaacaaaaat ttttttaaat tgtaacatga    31380
ggctgggtgt ggttgcttag gcctgtaatc cccgcacttt gggaggtaga agtgggcaga    31440
ttgcttgagt ccaggagttt gagaacagcc tgggcaacat agcgaaaccc tgtctctata    31500
aaaaatagaa aagttagctg ggtgtggtgg tgcgggcctg tagtcccagc tccttgggag    31560
gcagaggtgg gaggattgct tgagaccttg tctcaaaaaa ataaaaaaaa attacttaaa    31620
aaaatcgtaa catgggtatt tccattaca gttaccctta gggaagtgtg tccatattga    31680
tttgtaagtc tgatatcagt ctatctgatt ctttggctgt gtaagtcaca agtcttaacc    31740
agtatcttaa gtaggtgtgg taatgactac agagaagtgc ttttcagga tgagaagatg    31800
agggagaaaa tttacaccat tgctggattg tgttaagaac tcggagagga aaccacaggg    31860
aggatgcact gctgaggaaa tcgtctggct tcctggagtg gggaccagag ccagagagcc    31920
aagccctcct ggctttgctg agttctgtcc ttgcccctga caccaacgtg tctgcctgct    31980
ttgttgctcc tggttacagt gggctcagtc ttgcctcttt tttgatgggt gggcagagga    32040
acactagtgt tgggaatatt gtccagcgtt ggagagatca tgtggtctgt cagaaggctg    32100
gagttatttta tagtgggaga aaagcccagg agcatggcac gggaagaact gatttcacac    32160
cagctcagcg cctgatgatg gtgaggaccc agattttcct ttgagcatct cagagcagat    32220
cagtcgcttt tcctgattga cccatgaact gtgagactag gaccatgtt ttccgaggcc    32280
actgtgagtg agggaagagt gagaaggatg accatttttct tcttccttga ttctggtctt    32340
tgtgatgtgt ggtatgaaag tgtcatctga cttttgaatc tccttttatt gaactggtga    32400
agaaggcacc agctgtgtgg ggtggtggaa ataaggacct gttaaactgg tctgcctgta    32460
tctgcctccc tgctccccc tcaccccacc caccccacc ctgggcaggg aggctgaaac    32520
tgctgcttgc taggctttgc caactcagtt tctcttcatg gattacctgc tcgcggcagg    32580
caggcaggca gctcccccacc tggaagcctg cagactcgcc gagctgagag aatcatgctg    32640
caggtggggg caagtgctag gaactaggtg tgccacttac cttaacagga gctgtgccta    32700
gtccgggctg ctcaaaactaa ggctgcagag ccctggggcc tgttggaaat agactgtgcc    32760
tttccctgcg ccttgtggcc acatttttat ggtatgtgga gagtctggga ggggccggga    32820
gcttgtaaat tgtgagtaaa tgaagtctag ggagggagat gatccttctt gagggcaccc    32880
tgagttcagg gttgtcatgt ttctgaggtg tgctactgct tagtaccctg atttctggag    32940
ttgtctacct aggttgcttt taatttttttc agccttaggt ggaagagatt ttccatcttg    33000
gtgtttaggc atgttaggtg aggtttactt ccggagccag acttttaggc aggttgtctt    33060
gacataagtc aaggtcagga agcgatcttc aggacatgca gacgatgccc acttcctgct    33120
gtggtcttga agagggctgg aaggcttgtg agcacagagg cactgagggc tgtcgcatcc    33180
atacaggaag acactcaggg ctcgtctccg gtgcctcatt ttataagcat ggaaacaaaa    33240
gtcccaggag ggtgaatgac ttgcccaagg tgacataaat tgtttgcgca gagctgggtc    33300
tagaatggat cttatgccct tggcagcgtg cccccattgc catcacttca gaggggctgg    33360
```

```
ctgcagccct caacggcaga aggcaagctg ggaaaggaca agtggaaggg tagcaggccc    33420
caattctgca cactggagag cacctctgaa atcctgccgg agactatgcc catagaggtg    33480
ccagaggccc tagggaatga tgatttattt tgtattttgt attttttgtgg agacagggtc   33540 ttacaatatt gcccaggctg gtctcaaatc ctaggctcaa gtgatcctcc cacctgggtt    33600
cccagagtgt tgggattgca gacatgagcc gtggcgcccg gctgggaatg atttaaaagt    33660
cggcaccagc attctagccc tgacccaggc taaaaggggt cacatggagc agagctgtgc    33720
aaagagcttt tgggtgagga gtcactccga gaaaagcgag aagactctga ccccgagact    33780
tcccgtggtg agttaggaaa gcatttctgg agagcctgtt aggtgccagg cactgtggct    33840
gggcactgaa gacacgaagt gatttagtct tggaaattcc cttatgctgc tctcagtctg    33900
tgtaatagtg aacaagacag ccaacaagag ttgtgaagga ggccgttcag caagcaatga    33960
agtgctagtg caggaaggcc cgagctggga aatgtccgga gagaccctgt gaagtgatgc    34020
agggatcagg aaagcttcct ggtggaagca atgtctgagc tgaggctcac cacaaagagg    34080
aatgggagtg actgctagag ggaaagtgtt ccaggcagtg gaaagctgtg gccaagacct    34140 ggggggggtct gagaggccat tgtacatttg aagacaggtg gctggaaccc agagtgagac    34200
tctaggaagg gaagagagtt agtctggagc tgcaggcagg gaaggggaga cagccagctc    34260
ataatacagt gtgggcaaaa atccagaaac catgtggatc taatttgata tcaattttac    34320
atgtatatgt gtataacct acacacacat acataaaatc agttatgttt gtgtgtgtgt    34380
atatgcatat ttgtgtgtgt gtgtacgtgc gtgcatacag aaagttgttt ttttaaggca    34440
tgctttaaat acgaagccat cacttccttt tcccagtcct gggtgccttt tgagatgagt    34500
gttggtgctc cccccaccgc catgtgccat cttctggagt aagagggagt gctttcactg    34560
tgtgcaggtg tggctaaaga gtattcactg tgtgcaggtg tgggtgaaga gtattcaccg    34620
tgtgcaggtg tggctgaaga gtattcaccg tgtgcaggtg tggctgaaga gtattcactg    34680
tgtgcaggtg tggctgaaga gtattcactg tgtgcaggtg tgggtgaaga gtattcactg    34740
tgtgcacgtg tggctgaaga gtattcactg tgtgcaggtg tgggtgaaga gtattcactg    34800
tgtgcaggtg tgggtgaaga gtattcactg tgtgcaggtg tgggtgaaga gtattcacag    34860
tgtgcaggtg tgggtgaaga gtattcactg tgtgcaggtg tgggtgaaga gtattcactg    34920
tgtgcaggtg tgggtgaaga gtattcacag tgtgcaggtg tgggtgaaga gtattcactg    34980
tgtgcaggtg tgggtgaaga gtattcactg tgtgcaggtg tgggtgaaga gtattcactg    35040
tgtgcaggtg tgggtgaaga gtaggctgtc caggatttca atccttggct tttgctctgc    35100
agcaagggct ggctgagggc actgtgaggc ttcttcaggc ccaggagtca ggcccacttt    35160 ccctttctc ttgagggaat gactcagaga acactcctgc caccggaggt tctgcaggct    35220
tttgagaggc agccagtgga ggctgatggt agcagttggt gagaaagagg aagtatgtag    35280
tggccattcc tccggccact cctgacaaat atttctgtca ctaaacagca cctctctgtg    35340
gcagccttgg gctgtgttct ggaaagggag gagctttcct ctccctgtgg gagggcctgt    35400
catctgtggc ttctgctttg cccttggcca cagactagat tgcacaacac agccaatgag    35460
agtccctctt ccctcacaag tgcttggagt gcagacctta acttacaggg ttgtagaagt    35520
gaccgtgttc cacactgcag ggtccaggtc acagccggca aagcacatga aaattgacct    35580
aaggttagaa tgtgattatc ctactgggaa aggtttactg ggacagcatt tcacttctga    35640
ctccataggc tgtcgtctcc tgccagggag tgagttttgt ttccatgctt gtccagtctt    35700
tactgctttc ccagaggcca taaacctgcc ttttcccaga ggccataaac ctgcccacct    35760
```

-continued

```
cctgctatgt tctagttctg ataggagtac cattcagagt tcttggcagg ggaccaaccc      35820
gcttctaccg tggttggttt ccctcctttt tcccagcttg tttgatgtgc acgttctcca      35880
aaattcttat gcagctggtt ggctctgtag tgcccagaga ttggagctcc tgcaacggga      35940 acccgccgc ttccctccct ggttttaggg gcagggcttg aaaataaaga atcataatct       36000 ccttcctcc tcctcctcct ctcccccact tctccctgcc cccaccccca ccccaccccc       36060
caccctgcca ggcaaactgg agtgaccagc tcagagcggg actcagtcca cctccctgct     36120
ctgcatgtca gcagtgatct ggaggagatt ccggggcgca tgagtatgtg aactctggag     36180
cacgttactg tcccgggctg gcactctgtg gcaggtgtgt gcactcattc tgctgttact     36240
ggagaccagt ctccttaggg gtgatggtga cccagctaga tgtctgccag gtctgtccaa     36300
ggccaccctg ttctctaata gcttgggaaa tggaaagcac ttctaaatac ccctgctctt    36360
cagaagagct ggctggggtgg tttgggggagt ttcttctttg aatctcttag agtacaatat   36420
cccttttttc ccgaaagcca ggttctttag ttcctaagct ccattctctt gttgctaact     36480
tactaccttc agttttctta ggttgggtgc atcttccctg gcctcaacaa gacagtggct     36540
gaaaggtcaa gagagtggta gctgctcctt tgagagaaag gggatgttgg agtgggagca    36600
caggctgcca gcagttgttt caccttcccc ctttggctgg ctaggaaagg ggcaccactt     36660
tagtcttctg ccaacctcca cagccagctg tgggaaaacc caaaaggaaa catcctctcg    36720
ctgctaagac ttgagagcct gaggcagaga ccagccagta gcagcccgac cctgctgaat    36780
ggggaggatt gtttatttta ttttattttt tctgagacg gagtcttgct ctgttgctca     36840
tgctggagtg cagtggcgcg atctcggctc gctgcaacct ccacacccca gattaaagcg    36900
attcttctgc ctcagcctcc cgagtagctg agactgcagg catgcgccac cacgcccagc    36960
taatttttgt attttaata agagacagag cttcaccatg ttggccaggc tggtcttgaa      37020
ctcccgaact caggtgatcc gcctgcctcg gcctcccgag ggactgggat tacaggcatg    37080
agctactgtg cccagcctga agattggtta tttagggct gtgacaaatg gttttgcaga     37140
ggagcactgg aaagcctgta acttcacaga gccaggggtc agcttttgtg ccatagcctt    37200
atagcttctg tggcctgtag tgcctgaggc caggggatca ggtgctgacc acctttccct    37260
cttccttcct gtgtcttgcg gccagcgact gttattgtca ggttgaccct ctggttagag    37320
aggatgactt tggcctggtg tccagactcc ctgctgcctt atccctctg ccctggaact     37380 gcacctaaaa acaattactt tcctcctgat tccaacataa gtggtcacag aaagttctgt    37440
tttggcattt tgatttctga ttgggagttt aggcatctga gaattgaatg cttgctttat    37500
acaaatatac ccttaagaca tctcctcttt tttcagccct acatgctttg cttgggtatt    37560
aattgaactt ggggcttttt agggaccta tgttgcctac cttcctagtt tcccctccac     37620
tccaccccca aaaacccaa agaacattgg aaaaattgag cagtgcctca aggtcacttg     37680
atcataagtg gtatttggca tagttaactg gtttggtgtt tggtgagaga tttctgcttt    37740
atatttgagc aaaaaatttc ttggcgggag gcctctatgc tgtgttgcca atgcttgccc   37800
tgtgcgcagg gtttgccccc tcccctccct tgacaggttg ttctaatccc cttgtctata   37860
aacaagtgca gcagaacttg tcggcccagc tcacatgacc ttggttatct ctttaaccag   37920
catcagcgtt agataccacg gtcacttgac atggtagagc tgtcagggta gagtggagat   37980
accagcagga atcctggtcc acgaagaaag gtaaatggga gtgtgtgtga ggccttagga   38040
ctgggtggga aaagtctgtt cccatggggt agggctttca gctgtgagaa gaggataatt    38100
tcattccttc tcctttttta agagactgtc tcactctgtc gcccaggctg gagtgcagtg   38160
```

-continued

```
gtctaatcaa ggctcactgc agcctcaact tccttagctc aagcaatcct cctgcctcag    38220
cctcctgagt agctgggacc acaggtgcat gccaccatgc ccagctaatt tttttttttt    38280 ttttttttg aggtagagtc tcactctgtc acccaggctt aagtgcagtg gtgcgatctc    38340
ggctcactac agcctcagcc tcccaggttc aagcgattct cctgcctcag cctcttgagt    38400
acctgggatt acaagtgtgt gccaccatgc ccagctaatt tttatatttt tagtagagat    38460
ggggttacac catgttgttc aggctggtct gaaactcctg acctcgtgat ccgcccacct    38520
cagcctccca aagttgttgg gattacaggc gtgagccacc acgcccagct aattttcctt    38580
tgttgagatg gggaatctca ttatgtggcc taggctggtc tcgaactcct tgcctcaaat    38640
gatccgccta cctcagcctc ccaaagtgct gggattacag gtgtgagaca ctgtggccaa    38700 cttcattcc ttctttatca ccctaaaatt tctagttctg gcgtcttgtt tatctttctc    38760
aaatcctgtc tgcaggggcc caggacatgc agctgtttca ggaaaccgcc cttgagatgg    38820
ggcagatgta tgctagttca tgggctataa aactcaacac caaaaatccc atcgtcctaa    38880
acagtgacct gttatgttgt gtgaaggaca gtggcgatgg gggcctggcc gccagagagg    38940
ctgctggatt ctatggcaga cacactcagg agctggaagt gtggctaagc tttcagcagc    39000
accatcactt ccctcccat acacatgcac acaggtttcc tttgtctcac agctgaagag    39060
gcagcgccca gcttcagtaa gcactgtgta tgagaatgga cttactctgg ccacactgtg    39120
cacacgcatg tgtgtgtaaa acactgatca catttcccat aaagactgtt gatttgcaga    39180
gtttccaggc ccatacatct agggcgggat gtgtgtgttt tcatcagggg agagtagagt    39240
ggccttttgt ggaagggata aaatggttga gctgctggag acttttctag ctccatttat    39300
acagcagcct ttctgcctgg gtgcagactt gaacccaagt ccaagttcaa gccatgtgtg    39360
tagatgacca gaacttagcc ttcaaactta gccttcaact tcaggactct cctggagaaa    39420
acatccatct cctttttggag atacagagaa ttcgtgatga gctttgagta cagaagttca    39480
agttatattt tctggcaacc tacagaataa gttgggaaag gatatgtaat tatagaaata    39540
accagcatgt cgccaggcat tgttgtccgt gctttagatg gtgtggatat tttgtaattt    39600
ctgattcttt acctactgtt ttcaagactt ggtagggacc ccgttatggc tgtggggttc    39660
tttgtccttg gtagttagca tgaactatgt agagcaacag aatgggtagc cgtggcctct    39720
ggccacccag ctaaattcta ctgatgagag gtatcctggg tgggtttctt ctttgggtct    39780
tcgtttatgc cgccattcct attgccagtt agagctgcct tttaggattt gttgggtagg    39840
agctgtattc ctcttggagc catcttttct tccctgccat ctctgagtga attcagaggt    39900
ggagagctac agacttggct gcttgcctcc ttcaaaacac ccagcattcc cttgtccaca    39960
gtctgtgtag cagcacatct aacaatgccc aaaagcggcc cccttcctcc cagccacttg    40020
ttaatgggtg gttctggttc ctgagggctt cgaccagtgc acgagctaat ctcactgaag    40080
agtgccattc ccaggttcat accacagaag ttagaaagct caaagcccag tcttctgca    40140 ccgaagagtg ccattcccag gttcatacca cagaggttag aaagctcaaa gcccaggtct    40200
tctgctgcct tgggccattc ccttctctta gaaaccagtt caatcagact cttttttttt    40260
tttttttttt tttttttga gacggagtct tgctctgtca acgaggctgg agtgcagtgg    40320
catgatttcg gctcactgca gcctcgacct ccccaggcac aggtgatcct cccacctggg    40380
cctcctgagt acctgggact acaggtgccc accaccacgc ctggctgatt tttgtatttt    40440
tagtagagat ggggtttcat catgttgcc agtctggtct cgaacgcctg acttcaagtg    40500
atccgcccgc ctcagcctcc cagagtgctg ggattacagg cgtgagccac tgcacccagc    40560
```

```
ccagactctt tcataggat gctgaaagga tgaattaagt ataaaagtg ccttttggcc    40620 agatgcagtg gctcatgcct atcacttgag aggagcttgg gcaacatggt gaaacccat    40680 ctctacaaaa aatacaaaaa ttagttgggc atggtggtgg gcacctgtag tcccagctac    40740
tcagaaggct gaggtgggag gatcacctga gcctgggag gtcgaggctg tagtgagcca     40800
agatcgcgcc actgcactcc agcatggtga cagagaccct gtctcaaaaa aaagtgctt    40860 tttaataagg tacacgtaat ggaaaatggc tgtcatctgg tttgccatac tctgctccta    40920
ggtagaaagt acaaacagca agggcccctt ggagcaaaat tgtcattgcc gccagtgaat    40980
aaacagcagt ggttggcttt gaggggcacc ttcagcctaa agccataagc tgacatatac    41040
tcagtctcac tgagaagctc gggctttcca ctgttcacct aactgctgac aaatgaatcc    41100
tccattgatc tggcaagctg ccaggatac ctgcccaggc catggccact tagtaacagg     41160
atccggttct cagtgcaggg ttgagactgc agcagcagtg gcaagcccag taaggcaggt    41220
atgaagcaca gcccccgcat cggttgccta gtagggaaga cagttgtaaa gagcatttgc    41280
ccctgttatg tcagggtact gttgcaggtt gtcttttctc ctctagctgg aagttgttct    41340
acccagtctt ccttaattag ctcttctttt gtgtaaggca gcacccattt aaaattcttt    41400
tcctccagcc tcattcctca tctccatttg ggtttatatc tcctcagaac ctctctccta    41460
cccagcctta agctctaccc caaatgcttt gaagctctct tgttcaagtc ttttttttt     41520 tttttttttt tttttgagac agagtctctc tcgctctgtc gcctaggctg gagtcagtgg    41580
cacgatctcg gctcactgca agctccgcct cctgggttca cgccattctc ctgcctcagc    41640
ctcccgagta gctgagacta caggtgccca ccaccacgcc cggctaattt tttgtttttt    41700
tagtagagac aggatttcac cgtgttagcc aggatggtct cgatctcctg acctcgtgat    41760
ccacctgcct cggtctccca aagtgctggg attacaggag tgagccaccg cacctggctc    41820
aagtcttctt gattcaagcc ctcacccaga gcttgaagac tagggagccc ccgtgtctgc    41880
tgcccatggt gcttggagag caaagatctg ttcccgggtc ctgagttgga actctgaatt    41940
catttcctgt tctgggctat ggtttaagtc ttaagtacaa ttcacgtacc ccttgaaata    42000
ctatgctggg acctcatggg ctggcctgag aacacagcta ccatttgtaa catgtttcta    42060
tggaaaaaga gttccttctt agaacagaac ttttggtaac ttggggatt cttgactaat     42120 atgctgcaac agatttgcat ttgcctgtgg aagtgtctct ttattttgta ttcagctggg    42180
cacggtgact cacgcctgta atcccagcac tttgggaggc cgaggcaggc agatcacttg    42240
aggacaggag tttgagacca gcctggccaa catggtaaaa ccccatctct actaaaaata    42300
caaaaaaata atctgggcct ggtggtgagc gcctgtactc ccagctactc tggaggctga    42360
ggcaggagaa tcacttgaac ccaggaggta gaggttgcag tgagctgaga tgacaccact    42420
gcactccagc ctgggcgata gagtgagact ctgtctcaaa aaaaaacat ttaaaaaatc     42480 acattttgtg gtcatggcac tatctatcac acaagtaagt tgtcctccta tatgccaaat    42540
gacagaaaag aagcaccctc ctcttcccac ccagaaaggt tgctagagag ctacccttgt    42600
cttctgtgat tgccttgagg ggcaggtttg tctgggttct ccatgtcagc tgatttgatc    42660
catagtccag tagcacctga aacaggatgc cctcattcca caactaggt gccctctcct     42720 gcttggtttt ttaatgatct gctacaggag aaagatagca cctctcccttt cagcaggagc    42780 agcccagtaa gggcttgctt ctagaaagat tggccagttg gattttagt ggtcacttaa     42840 gtggagtagc cactttgcag cctggcccaa caggagaca gttctgaggt gagggtggca    42900
gtgacagcct tggggtggtt tctgatgtgc tctgacctct ggccatggtg acttctggag    42960
```

```
caacaaactt tgtcccagta ttttttttctg acatttcctc ctccttattc aactccctct    43020
ttgaaactgg aggagtaggg aggcagtatt tgttcacttc cagagaaaga tgcagcagga    43080
agaggcatat gtcttgttct gcactttcca gcagcaatgc tgggactagg gggtctagaa    43140
ggcctgtttc ccagctccag gctggatctt atcctcagca tacaagcaag ttttaaggaa    43200
acaacattgg aaagggcaga acaaaggggt taaatctgta cccaggtaga aagactgttg    43260
cataaatgct gagttttttt tttgttttttt ttttttaagat ctcatgcttc ttttttactt    43320
tgtgttggca aaaccccag gagaagatgg gagattctgg gaggagatga ttatgctggg    43380
tgagtcaact gagctcccca gctgccgttt ttagttcttt tgcttttctg taacaggagg    43440
cagtttgggg aggggttggg ggcagggtgg gaatgctgat ttttgcagca ggacaggagg    43500
caggtgtgta tgggtgaaat tattttgaca ccctagagtt aaccgggcct tagagtcagt    43560
acattggttc aagtaacaaa tatcaaagca gaactcttag tgtggcaaac aataaataat    43620
tgtctcctag attcttatac aagtcactgt ccgtccccaa ttggtagctc ttagaatggc    43680
tcgagttgca ttcattgtca cagcaagaca caatggtttt gatagcaaag cagtagagaa    43740
actaaatgta gagaggcaga gagaactgta ttaagtctga ggacctggtg gttgtcatgg    43800
gcagcaggaa gtgtgaagga gagggttttc cctccgatga aaggaaggct agggcttgat    43860 tcagggagc aagtgggatg ggccctgctg gtccctggct gtgcctatat tctgagtctg    43920
tctccagctc accttggtga tcactcactt ttcatccatc actgggatag gggatctcgt    43980
ggctcattac cctcatgggt attttttgca gagtacactg aagtgggcta tcagttatca    44040
gttggtccca gagaccgtca tgaagacatc gcaaaatgtt ttcttatgta ttcatttgtg    44100
cacatttatt aattcagtac tttactgaat actgtgctgg gcattgttct gggccatgaa    44160
taagacagac ctggcctggt gcagtggctc acgcctgtaa tcccagcact ttgggaggcc    44220
aaggcaggca gatcacctga ggtcaggagt tcgagaccag cctggccaac atggtgaaat    44280
cccgtctact aaaaaaaaaa aacaaattag ccaggcatgg tggtgggcac ctgtaatccc    44340
agctacttgg gaggctgagg caggagaatc gcttgaactc gggaggcaga ggttgcagtc    44400
agccgagatc acgccactgc actccagcct ggatggccag agagaaactc tgtctcaaaa    44460
aaaaatacca aggtccctcc ttttgtagtg tagtctagca ggaaggacag atagtaacca    44520
accaacttca agggcaacga atgcctcgaa agaggggaaa tggggctggt agcaagaaat    44580
tgtgatcttc cttcctctac ccttatctct tggggtcgag agtgggtcg agagtgggca    44640 actttaaaga tcaaaaagtt gtgcctctct tgttccctaa gtattgtaac atgggtcagc    44700
taggtgtggg cactgttggg cactgagggt atatgaaggt gagggagata ctggctctca    44760
tctgtcagag catgaggggg ttaaggtatg gggacacaaa caagaaatca atggggctgg    44820
gtgtggtggc tcacgcctgt aatcccagca ctttgggagg ctgaggcagg aagattgctt    44880
gagcctagga gtttgaggcc agcctgggca agatggcaag atgccatctc tacaaaaaaa    44940
atgaaataaa taaaaaacta gccaggcata gtggcacaca cctgtagtcc caactattcg    45000
agaggctgaa gcaggagaat cccttgaacc caggagtttg aggatgcagt gagctgtgat    45060
tgtgccattg cagtccagcc tgggcaagag agcaagactt catctcacaa agaagaaga    45120 aatgaagagt acagatagag cgctgagagt ctagagaagt gagtctagag aagtgagtga    45180
ccactccccg ctaagacggt gtctggattt gagataaaca acggataaga ggacttacct    45240
ggatcacagg aaggcgcata ggatagatga ccactttcct tttagtatgt gtagatctgg    45300
gtagctcttt gtaccacaat tctgacccat tcttttttct tattatttttt atttattttat    45360
```

-continued

```
tcaaaataat aatttttttt ttgagacagt cttgctctga gccaccatgc ccagcctgaa    45420
ataataaaag ttttaatctt ttaaaaaata tgggccaggc ttagtggctc acacctgtaa    45480
tcccagcact tgggaggcc gagctgggcg gatcacctga gatcaggagt tcgagactag    45540
cctgaccaac gtggagaaac cctgtctcta ctaaaaatac aaaattagcc gggcatggtg    45600
gcgcatacct gtaatcccag ttacttggga ggctgaggca ggagaatcac ttgaaacccg    45660
ggaggcggag gttgcagtga gccgagatca cgccattgca ttccagcctg gcaacagga    45720 gcgaaactct gtctcaaaaa aaaaaggaat gcttcacaaa tttgtgtgtc atccttgcac    45780
aggggccatg ctaatcttct ctttattgtt ccattttttt gtatatgtgc atgtacagag    45840
tagtggagct gggttatcac tacagtctaa ctccagaatg acaccttca ctactatacc    45900 atatatggtg ccccagtata cagcagtgga gctaggaaga aaagcccagt gtctagagag    45960
cccagaaaat atgccaagaa catatatact aggcaaagaa aacgaggtta ggaggaagcc    46020
cagccacctc agctgcactg gttaggatct gctgcctccc cacagtcctc tgtaaagtga    46080
gccagacctc tatgctgcag gcttccttct gcctaccccc accaccccca tcccccagag    46140
ccctgggcta ctgcaggct ggctctcctg tgatatggag gaacttgttg gtctccatgg    46200
ttacggtaac ccactggtat gggaggaacc gcataaagtg cgaggctggc agtgtgagct    46260
tccctcagcc cttggcacca tgtggtactg gtatgtcggc tgtttcatgg accttttctg    46320
ggaggaggga gttaaggaac tgatgaagaa gggaagaacc ctggcaggac cactgtcgtc    46380
atcctctggg ccacacagag ggcgaaggca tgggcaccat gtcattcagc tactcctcct    46440
gcaggatggt tttatgttag gaaagagggt cctcttttgcc tgattgccca gccatggcag    46500
aatttgactt ttccttgtta tagagggaat accaggatga caggaatcaa cttagctata    46560
ctggtactta cagtcaaatt tctaggtatt gtagctcttc ccagagccca gagaaccctt    46620
ggagagggga acaatggtt cctacccaaa aatgaagcta ataataata gaatacatca    46680 tcaagacatt actgaacacc acgttctatg gtaaacactg acatggattt ccttttttt    46740 tttcctttga gacagggtct tactctgtca cccaggctgg agtgcagcag tgtgatcacg    46800
gctcactgca gcctcagcct acctccctgg gctcaggtga tccttccacc tcagcctccc    46860
aagtagctgg gattgcaggc acttgtcacc acacccccgc taatttttgt gtttttttgt    46920
agagcctgtg ttttgccatg ttgcccaggc tggcctcgag ttcctaggct caagggatct    46980
gcctgtcttg gcctcccaaa gtgctggaat cagaggtgta agccaccacg cccggccaga    47040
ttttctcatt taatcttcac tctaattctg tgaaatgggt acagctagta tctttatgtc    47100
ccaaatgagg aaacagattt ggagaagtta tgtcactttg ctcatgttca gtcagctggt    47160
aagcaacaga ggtgggcaga gcgactatag taagttttct gtatagttta cctcttctaa    47220
gtttctggaa ggcaggagcc agatcgcact gagctttgca actggagcca gggctccaga    47280
gtactgctca acaaaggttt gctagggcaa cagtagctgg ggatttagcg accagacccc    47340
agcaagcaga ttctcaggga tgaaagtagt cctggaagcc tctaaagccc tggttgctca    47400
gtagaatcta gtttcaagag gagcccagca tttcaagtgg ctctgaagac agaggagatt    47460
tggagagtgc tctttgcatt gtggcttcca ggcctgaagg agagtgagct ggaggttgct    47520
ctctgttctc acctcttatg ccatgtcagg ttttcccag gcaggcttga gtcctggggg    47580
agccccgcct catggcccag gctgcagtgc tgatctccct gccttgtggt gaggattgca    47640
gctcagagag ctaaagggca gtaaaccacc ttggttttgg ctttgtgctt aagttgcagg    47700
ctcttctggt tatcctttgt gaaggaggct cttaccctgg ctggaaagag ggagcagccc    47760
```

```
ctgcctccca tctacaatgg gacagtaaag gaatatggct gtttctcaag tggaacagtc   47820
acagttaatt ttgggggtgg gagcatccag gctttccact ggtgagtgcc tgccagtttt   47880
acaagctctc ctacactgaa tgctcctctg gtttattgac tcttggcagt tgatagcgat   47940
agttgctcat ggcagttgat agcgatagtt gctcagaatc aaaggatgaa agacagtttt   48000
ctggatacag tgagggagga agggttaaaa aacaaaggac tccaactccc agttacgaga   48060
tgtcccatat ggccatgcgc agtggctcac tcctgtgatc ccagcacttt aggaggccga   48120
ggtgagagga ttgcttgagc ccagggagtt cgagaccagc ctgggcaaca tggagaaatc   48180
ctgtctgtac aaaaaataca aaaattagcc gggcttggtg gcccatgcct gtagccccag   48240
gtattcaaga ggaagatcac ttgagcccag gaggcgaaga ttgcagtgag ccaagatcgt   48300
accactgcac tccagcccgg gcaacagagc aagaccctgt ttaaaaataa ataaataaat   48360
agggacttgc cacaggcaca tgacctttct taagagacaa agtcttgtgc tgggaatggt   48420
agctcatgtc tataatccca gcactttggg aggccaaggt gggcagttca cttgaattgt   48480
tgagttcagt accagcctgg acaagcttgc aaaaccctat ctctacaaaa aatacaaaaa   48540
ttagccgggc gtattgctgt gggcctatag ttgcagctat tcgggaggct gaggtgggag   48600
gatggattga gcccaggagg cagaggttgt agtgagccaa gatcgtgctg ctgcactcta   48660
gcctgggtga tagagtcata ccttgtcttg aaaaaaaaag agaggctggg cgtagtggcc   48720
catgtctgta atcccagcac tttgggaggc tggggcgggt ggattacttg aggccaggtg   48780
ttcaagacta gcctggccaa ggtggtgaaa ccccatctta ctaaaaatac aaaaatgatc   48840
tggacgtggt ggcacgcacc tgtaatccca gctatttggg aggctcaggc aggagaatca   48900
ctggaacaca ggaagcggag gttgcagtga gccgagatcg caccactgca ctccagcctg   48960
ggtgacagag caagactcca tctcaaaaaa aaaagaggc cgggtgcagt ggctcagacc   49020
tgtaatccca gcactttggg aggccaaggt gagcagatca caaggccagg agatcgagac   49080
catcctggcc aacatggtga aacctcgtct ctactaaaaa tataaaaaaa ttagctgagt   49140
gtggtggcgg gcgcctgtaa tcccagctac tcgggaggct gaggcaggag agttacttga   49200
acccgggaag cagaggttgc ggtgagccga gattgcgcca ctgcactcca acctgggcaa   49260
cagagtgaga ctctatctca aaaaaaaaa aaagagacg agagtctaat tctgtcaccc   49320
aagctggagt gcagtggcac gatcatagct cactgttacc tccacctcct ggactgaaac   49380
gattatcctg cctagcctc ccgagtagct gagactacag acccatggca ccatgcctgg   49440 ctaattttttg aatttggaga gagagggtct cactctgttg cccaggcttg tctcgaattc   49500
ccaggcgcaa gtcgtcttcc caccttggcc tccaaagtg ctgggattaa ggcatgagca   49560
acagtgctca gccccgtgtg gcttttttttt tttgagacag agtctcactc tgttgcccag   49620
gctggagtgc agtggtgcaa tctctgctca ctgcaacctc cacctcccag gctcaagcag   49680
ttctcatgcc tcagcctccg agtagctggg attacaggtg tacgccacca cgctcagcaa   49740 attttttgtat ttttagtgga gatggggttt cgccatgttg cttaggctgg tctcgaactc   49800
ctgacctcaa gtgatccacc agcctcggcc tctcaaagtg ctgggattac atggtgggg   49860 ccaccatgct tggccccccat gtggcttta atctaaatcc tacctatct cttcccagct   49920 tttctgtttg tagtcagtgc tttgtatttc ctcagtttac aaaatccctt actgtctccc   49980
acaaatagga ttgaggaaac agtccttctg tcacattgca aagccctaga aaatgaagg   50040 gactagaaaa atgaagctgt tgatcctgc tctggttctc agtctaccag tgagtgaagg   50100
gccggagggc ccgggcaagc ttgagcccag gatccagtgg gcccactgaa gtcagggccc   50160
```

```
acttttgggg ggctgggaaa aggaagggtt gctgtgggac cactgggata ggcctttaaa   50220
cagcacttca ccattggcct gaatcaaaca ttgtcattcc cagtgtcccg agcaccttcc   50280
ctgagtcttc ataccttctg cctcctagct tatggaggag gagccagggg cttatctttt   50340
gggggaaatg agagcacgat taggcatcaa gaagggttga tgagaaactg gtaaggggga   50400
ctgtcaagaa cagcagagtg ctgaaatggt gacaaaagct ctgggctccg gccccagctc   50460
tgtactgaga agctgtgaga ttttgggcaa gtctcataac ctctgaatgc caatttctca   50520
atggaaaaca gggagactac ctaccctata ggtctgtgtt tggagaaaac aaagtgtaag   50580
cgctggacat acagtagcat cagaaatgct gaatccgttg gccagggctc atgtgtaagg   50640
caaacatttc ttggccactc ctgagtagca tggtcttgca ggaatatatg cttaagtgct   50700
gtgagagcac agaggaagct ttgcccttcc ctagagggtt aatggctacc aacgtgagaa   50760
ggtcacggag ttccttaatg agagggagcc tagcctagaa tagggatgaa atgagaaatt   50820
gttctgagaa ccagaggcaa ggctgcaacc agcacataga caggggtcgt tggtctagaa   50880
ggggagtctt ctccagatga gagacagcca gcttgccctg tgctcaccat gtgcccagat   50940
agtgggggct tagcaggagg aaggtgtgag gaatcccagg cctttggaat tccttgagaa   51000
agcagtgttg ttttgaaggt aaggcagggg attggtgact ggaaacttgg aggtgagtga   51060
gaacctaggg atgaacgttc agaagcaggg ctggaaggaa cttaaaaggg acatttggat   51120
tgtttctagc ttttgggcaa aatctaggat taaatatgat ttttttcattg atagaatgct   51180 ctatcagtga taaaggctct taatctagaa aacatacacc tcataggggg ctttacagag   51240
tccccaaact ccctgaaatt atgctcaaaa tattttgtgt ctaagtggaa tgtgcatgtt   51300
tccaaggtta agcactgctt ttttaggaag taggaggtcc gtccgccact gtcagcttgc   51360
tggtttctgc ttaccctcct ccccacttcg ttcttgaggg ggtggtttgc tggtctttgg   51420
cagggccgcc actctgggtc agcacatctg agtcacacat gttcctcccc agccctattg   51480
gaggctttgt taaagtcatc tgcccctacc caggtcccac ctgccacagg tgagctaggg   51540
ttttatgaca gccgtggctg cagtgagtct cctcgacctc tcgccagctg ttacccagca   51600
aagcaccttg ggagggtgg ggctgcccac ttccggggag ggagggaggg ggaggggaga   51660
aggaagttga tctaaacccg cctctttctc tgtctccctt cctgccctat tcccctcctg   51720
ccccttccct cccaccttgc ttctggtgtg ctgtcctgga attgcacgcg cttcctgacc   51780
accaggctct ggcccttgag aagccagcgg ggctttgtcc ctgttgctct ccttgccaaa   51840
cccagtctct ctgctagtgg tggtttcggt tgcgacaccg tccaggttcc caggcaggaa   51900
ccgctcggcc tggctgctta gctactttttc actgaggagg tggtggaagg tgtcgcctgc   51960
tctggctgag taagggtggc tggctgagcc ggcagccccc gccctaggcc tggctcttcc   52020
cggcctctgt actttgccct cgctgcctga caggttctgc tgtgggctct gctgaatgga   52080
agtcgctggt agtccttttc cctttctcca gtcgggtatg ttgtcccct ttttactcta    52140 ggattgcctc ctcctctttc tttcctctca tctcaaacat aggatcttta gagagttgct   52200 aagggcgcc ctgcctgagt ccagcatagt aatattcatg ggaagggtgt ccagatgtgg   52260
aagaggcatt gactaggaaa ggaagagggg gcacatacca gaagggtctc ccctgagaac   52320
aagcagcttg acaagtgggc gaggagggc tggtgggagg cagaggcctg aggcctcaga   52380
gaggatgctc ccgtgctaca gtgaggggga gcctaggatc tggggccatt gcccaggact   52440
ggtgcccaag ggacactttt ctcccccaac tctatagtgc ctggcttact ctgcttctgg   52500
ccagggaata tcacccctcc tggtttggct ccttctcagc cctcgggaag ccaaaggaca   52560
```

-continued

```
cttgaagcca gccctgaatg cagagcccca aagcatgagc ttctccatgg gacaactgtt      52620
ggtaggagcc tccagcatta gggcaggggc cctgcctacc tgagtcagcg ccaggcctct      52680
cggggtggag gctgtcttcc gggcaagcct gacaacacac ctaggccgag tctgagatcc      52740
caggcggaag gggcctgaca ggcccagtgg atgcaaaact atcttttat tttctcctcc       52800 atgtcctgcc ttctctcttc ctctcagtag cagaccccaa agctgtttca gccctacttc      52860
tgaatcaggc ctgcttagta actacttggt ttgccttttg gttccaaata actgccttgc      52920
agggtgaccc cttattcttt ctaaaggcta cttgagagcc atagggtcta ctcttgacag      52980
acctcctcca tcctttaggg cctgtctaga gtatgatata ggccagagct ttgggagtgc      53040
ctggtgtgcc acgtcttact ataagcaggg aggatggtgg tagaggggag agcgtggctt      53100
ttgccaggtc ctattgagtt ggcccagcag ggcagctaat cctcagcctg ccatcctgtt      53160
ggtgagaccc agggccaagc tgaatggtgc agccagaacc aaaaaagaga aactctctct      53220
ccatattagc cactgcatac tcttacctct ttatccttca gggaagaagc taggtgagga      53280
agttgcctca cttggggcct tggcccaaga agcatttctg ttggagactc tctcctctct      53340
tttccctttt tcttttctct gcttccttcc agtggcttgc ctccttaccc tggctcacat      53400
ccctgctgtg ggaaacatct tacagcatag aagaagggggt gcaggggtaa gtaagggaag     53460
gattgagcac ttggagtcct ctgagttgga tggttcagtc ccgaaaaggg ggttggtgac      53520
tttggagcag gggatcaaag agcaagcacc agtgcttgtt gcttctctgg ctcctgaaca     53580
agcagaacct cctctctttc cctgtcctgg atacccagcg tgggaccagc ccttcacagc     53640
caccctgtct tgagttcctg actctcctcc ttccctcttt tgaaggctag aggtgctggt      53700
gtcggctagc aacaggttga gggagtgtgg catttcacca ggtctggagg agagcgggca     53760
ctcaacctgg cccccttctgc ggaaaggccc gtagcatctc ttgtcagcct tcagctgagc     53820
tgtagctggc ttagcgggct caacttcgat ttggaaggtt gttttgacag tgagacttct     53880
ggattggcag acagtagtat ttggggacat aatgattgct cttattgaac atcggataag      53940
gcattttaca tgtgctcttt catctacctg tgtaaagtag ggaatgttta ttgccacttt      54000
acagataagg aaattaaagc ttgtacgtgg gggagccagg gcttgaacct gattctgttg      54060
gactgcagag ttcctcggga tcctccctgg cacagatgtc tggcagtatt ggccactggt     54120
cgttttttgg gtagttctct tccccatttg taatagtctc acctccttct tgacaatgtt     54180
gatgttacac ttgttttatt ttggggcttt ttgtgtttgt ttgtgtgtgt gtgtgtgttt     54240 tccttttttgt gaatgggggt ctcactgtat tgccttttta aatatattct ttttttttttt   54300 tccttttttgt gaacagcagg tcttgaactc ttgggctcaa gctatcctcc tgcctctgcc     54360
tccctaagtg ctgcctgtaa aggcatgagc cactgtgcct ggcttgatga tgttgatgat     54420
aataataaag ttaatatgtg ctgagtaggt gacagattta ggatttgaaa cctggcagct     54480
tatctccgac atctacagtc ttaaccagaa aggaagagaa tgaatggtac aatcttgctt     54540
gtggttgtta agctccttga ggcccacttg tgcagcaggg ccaggcaggg aatgctgacc      54600
tgctgtgcca cacagaccag cccctcggtt caccaagagg gatgggcaga gcagagctca     54660
ggatgggcat gggatgccca gatttggtct cagttggcaa aaggcccaag tctgcaggta     54720
gatgctaaat ccctggtctg gattttgaga acttagagac cgtcacactt cctgctgcct     54780
tgggcttata tcctcggaga aacagggagt gacaacaaac ttagaaggtg aactagaggt     54840
tgccaaggaa actttcccac ccatcttcct ctcgtaggag ttggggcaga ggaaggtttt     54900
tttcctgttc attgcccgtt aggcagatgg gtagggttgg aggcagtcta gcagcactga     54960
```

```
aagggaggat ggggctgaga aaaaggtagc ctgaggagac caggctttca gtaccctgct   55020
ggacagggct agggtaccct tcaggaggct ggcccaatca ggtgccagca gggcctagaa   55080
atgcccttct ctccaagggg tgtgaaccct agagttcctt tggaagggaa aaaagcaggt   55140
atttaaaaat ccacttgtct tgcagacact gtttgaggac caaccaggct taggtgagct   55200
acagggtgcg tggagaacag agcaccagag agctctgtgg gctggaatga gcagacaata   55260
agagctgggg ggcttcatgg agatgcaaag gttgatgagg aagagagaag gaagttaaaa   55320
gggcctcttc tgggatgtga ggagcctccc ccttcaaaca tctaccaaat gcatgggatc   55380
ttcctcctcc aaggtccaac cccatgtgtt tctgggatct ggtcaaacag ctcaccaaaa   55440
gacagcctgc agctaccatg caaaggcccc acgtgggcac agtgaagaag gggaaatgtc   55500
agaatcagga tactgtactt aacttgctgc tgtcgtttct gcctgaaaag catctggttg   55560
agctagcaag cttcttgtct aggaatgctg gacagttcct tgggtagtag caagtcattc   55620
tttttttctc tgtggttttt gagtgcttca cgtacagcca gcaggggcca tgaaaggaag   55680
aactttcact cacactcctc tggtcaccct gctgccctcc agactgtttc cttgaagttt   55740
ccaaggcagc tctggatggt tctgggatga ggctctggcc tcatatgctt tgttgcagta   55800
tgctggagcg atcgctccag atgttctttg tgagatgtaa accagggcgc taatcaggag   55860
ttagaccaga ctctgcattt tttttttttt tttttttgaga caggggtctcg ctctatcacc   55920 caggctggag tacaatggca tgatcatggc tcactgcagc ctcgaactcc tcctgggttc   55980
aagcgatcct cccgcctcat cctccagagc agctgggact ataggtgcat gccaccacac   56040
ccagttgatt tcttaatttt tttttttttt tttttttgag acggagtttc actcttgttg   56100
cccaggctgg agtgcagtgg tgcgatctca gctcactgta acctcctcct cctgggttca   56160
agcaattctc ctgcctcagc ctccctagta gctgggatta caggcacctg taatccacca   56220
tgcccagcta attttttgta tttttagtag agacaaggtt ttactatgtt ggccaggctg   56280
gtctcgaact cctgacctca agcaatccac ctgcctcaac ctcccaagat ttcttaattt   56340
cttaattttt tgtagagaca gagtctccct gtgttgccca ggctcgtctc aagctcctgg   56400
cctcaagtga tcctcctgcc tcagcctcct aaagtgctgg gatttaggca tgagctacct   56460
tgcctggcct agactctgaa cagttttagt gagataccat aagtttatcc aagtttcttc   56520
tgtgttgtag catatattct tttttactgc caaccaatat tccccggtaa ggatatgcta   56580
cgtttgtcta tccgttcatc cagctgatgg gcatttgaat tgtttccact ttttgactat   56640
tatggattat ggtgctgtga accttggtta caggtttttt gtggatttct gttttcattt   56700
ctcttttgta tatactgagg agcggaattg ctggctcata tagtctgtgt ttagcacttt   56760
gaggaatgta cacgtcttca catagatgta tgttttttgt ctagaccata cccttttttgt   56820 acaggttgaa catccgtaat ccaaaagcca aaatgctcca aaatctaaac ttttttgagtg   56880 ccagcatgat gccacaagtg gaaaattcta cacgtaaccc catatgacag gttataagca   56940
aaattcaatc actttatttc atgcacaaaa ttattttaaa atgtcatgaa attaccttca   57000
ggccatgtat ataatgtaca catgaaaaat aaatgtttag acttgggtcc catccctgag   57060
atatctgatt atgtatatgc aaatattcca aaatccaaaa caatttaaaa tctgccacgt   57120
ttctggtcct aagcattttg gataaaggat attcaacccg tattatgttt atatgcctct   57180
tcagtgctgg tagttgtagc ttctgcttcc tcatcccctc atttgagccg ggtggcagag   57240
cagggcagac tgctgccttg ctcagaccta atcgttcagt tctttcattg tacaagtatt   57300
cattgagcag caaacataag ccagtctctc taagtgctgg gatgtatcag tgaataaaga   57360
```

```
atatatgcct gctttcatgt gcttccattt ttactgggggg agatggcaaa taaatgtaaa    57420
gtgataaata acaaaggttc agtggggcat tcgtagttca gcggcagaaa tttcgtctcc    57480
tacgcgggag actcgggttc gacttcggcc atgcagtcct tccatgcagg aagggctact    57540
acgtttctac ccaacaaagt tattatggct ggacgcagtg gctcacgcct gtaattccag    57600
cactttggga ggccaaggcg gcggatcac  ctgagatcag gagtttgaga ccagcctgac    57660
caacatggag aaaccctatc tctattgaaa atacaaaatt agccaggcgt ggtggcgcat    57720
gactgtaatc ccagctactc gggaggctga ggtgggagaa ttgcttgaac ccgggaggtg    57780
gaggttgcgg tgagctgaga tcgcaccatt gcactccagc ctgggcaaca agagtaaagc    57840
tctgtctcaa aaaataaat  aaataaaaaa taaaggttca tgtaagtttt gggtggcgat    57900
gagggcgttg aagcagttat gaccatgtag ctaccatgac tttgagatgc agtcttctcg    57960
cagtgtgcac aggcagcatg gagggaggca gggtaccggc tctccctcct gaaccagacg    58020
agctgttgtg ttgccaatgg aggttcaggg agccagtgat gggacagctc tgctcctgag    58080
ctttgccacc cacaggacct gggcactgga ccttatgatg tgcttctctg gagtgaagac    58140
tggctgtcac ctcagccccc tctcctttct tctgctgcca tatcattctt cacatgccta    58200
ccagccccct ggaatctgcc cctgcaccct catcccttat atattttgca gagagcgttt    58260
agaggactgg aagtgtggca tgtaatggta tctctgtttc caccccgcag cccaccttgg    58320
gacaccttga ctccaagccc agcagtaagt ccaacatgat tcggggccgc aactcagcca    58380
cctctgctga tgagcagccc acattggaa  actaccggct cctcaagacc attggcaagg    58440
gtaattttgc caaggtgaag ttggcccgac acatcctgac tgggaaagag gtgagcactg    58500
ggactgggga catggcagca cctcccagcc ctgttgacac tccagcaggt ggtgatggga    58560
ctactactgc agccaacctc ttgtttatcc ggcagaaatg agatctgaga tatagggggtg   58620 caaaaagctg tgggatgaaa aggagtaaga aatataaagg aggaagtaga ttggaatcct    58680
gggtttcgct ggtcagagaa gtgatttggg gccttttttgt ctcatcctca ggtagctgtg    58740
aagatcattg acaagactca actgaactcc tccagcctcc agaaagtaag cacatggcac    58800
ctcctgtccc ttttttttt  ttttttttt  tttttttgag tcagagcctc actcttgtcg    58860
cccaggctgg agtgcaatgg tgtgatctcg gctcactgca acctccgcct tttggttttca    58920 agcgattctc ccgcctcagc ctcccgagta gctgggatta taggcacccg ccaccacacc    58980
tggctaagtt ttgtattttt agtagagatg gggtttcacc atggtagcca ggctggtctc    59040
gaactcctga cctcaagtga tccgctcgcc tcggcctccc aaagtgctag gattataggc    59100
gtgaaccact gccccccagcc cacctgtccc tttctaaatc tctcttctgg ggtcaatgat    59160
ctactgaccc catttagacc ttctcttgaa ttcctagttt aaattttctg gccatttcgc    59220
tcaccgtccc ccaaccattc cctcccatgg ctctgctacc ttcggggctt tggttggatc    59280
atctgtggtg actcctcctg agtgggcttc ctggccatag gcactggctc ttgtgaagtc    59340
tttctgttca ttcccagcca cttggcctac ctgtctgacc tacttcctgc atcttgttat    59400
cttctggctt gtgccagcc  ctatgcaaaa acacatgttt gtagccacta ctagaaacac    59460
gtgcagctac ttcaagatct ggaatgatac aggggagtgg ctttagaaat acaagaataa    59520
gaggaagcag ggaacctgcc ggtgggttct gtgccagcta cctttt agag aatgagctcc    59580 agctcaaatt ttctgaacaa aacctagttc tgttcatctt gtggcaaatc agatattttc    59640
tccataagca tattgtggca gttgagttag gagaaggcat gattcgtgct aacagagtca    59700
gatagtgata ctgggaacct taggagtaag ggctgaggat tgttgttgag ggcgatgctc    59760
```

```
atggaattag agtggatgag ttgttctccg gacatgcaaa tagccagaac caaggtgttt   59820
cctatttatt gttacccctg ggatcccttc aagggttctt cagttcagta gaaacattgt   59880
tgtcatcatc agggtgtctc tgcttgaagc tttccaggag gaagggaaaa agggctgctt   59940
atgacatcct ggctccagcc ccacagaaga agtcagcgtg gggtaggcca tttggccttg   60000
ggagcagtct agcctgccat cgtaataatc gccagtccac caagccatct tattcctgac   60060
cttgtttttc tccctaattc ttcttggttt tctccctaat tcttcctgac tctctggaag   60120
gcaccaacac cagacaaata gagccatttt caaaacccttt tgagactctt tgttactaaa   60180
gccagtctga ttctggccaa aaatgtgatc tcagcaatga tccctgaaaa atgaacattg   60240
aagaagctag ccccctcagg ggtctagaca agcccagaaa accccaagtt ctcccagaag   60300
aatgtcactt ccatgccagg tgagcagcct caggggaaga agccctggca gctgcctctg   60360
gccctatttc agagctgctc cccattactg ccccagaggg tggtatccag gctttttgcc   60420
tctccatcca aaatatctgt tggaccaggg aaaaaagtaa gaaaaaccta ggccctaata   60480
aagggtaagg tcagcattgg gttcctgagg attggaaagc cttttttcttc ttttcctttc   60540
tagcttagga aagctctggg gcatcattaa agggaaaca aatgtattca ctttattcca   60600
taaaccatat cttgaattag ggcttcccct accccaaca aaaacaacaa caaaaactag   60660
ttctgttctt tgtgcaagtg atgaggcctg aaattacaaa aagccccacc tccagttctc   60720
tggcccccgc agaggggaag gagttcattt ctgtcatctt tctttatgga aatacatggt   60780
ttggagcccc tggttttgtt tcacaaagag agcgtgagtg tgtggaggtg gatttgatta   60840
aaattggcat cagctatata taggagtggc ttcttctgtc accaccctag aggcccagga   60900
aggaaaggcc tatcccctag aacagagccc tctgactact gtaaatcaga aaatgatggg   60960
gtcccccctct ggtgctctac cacccttta cacagaccaa gctggggtgt gtactgtcac   61020
tgaaccaagg cagcagctcg gattctgaat attcacgcac acgggctcac actccctcca   61080
gtagaggcac ccagccaaaa cctgcctgct gttttgggc tggatttggt agacgcagca   61140
gagggcatgg ctggctcatc ctgatgccat cccgggtagc acgtcccac agccagccct   61200
cctccagctt ccccaacttc ccagccacag ggaaggccgt gcatgagcta gacaaccacc   61260
ctattttctt ttccctgccc ggttttggtt ttttgggaaa aacaaatcct ggcagggact   61320
gtttggagag acctgatggg agcaagttgg gcaggcatga cccctggtat tttatcttcc   61380
agctattccg cgaagtaaga ataatgaagg ttttgaatca tcccaacata ggtgagcaca   61440
agttgttatt tctttcttct tccccaacag caaggcactg ctttccagca tgtcatcttc   61500
tccccgaggt gcactgcctt ctggagtctg cagtcttcaa ggatacccct ggggaagctc   61560
agctcaaaat ccatctcccc ttctggcaca ctgggctgtc tttagcagtt tggctggcat   61620
gagaggaact tgttcttggg agtgggggat catgaaagga gggagactt tcgttcctag   61680
gatgctcctg gacatgttgg agagcagtat gtggcccctg ttgcttcttg acttaaggct   61740
tggccttttc tcttgtagtt aaattatttg aagtgattga gactgagaaa acgctctacc   61800
ttgtcatgga gtacgctagt ggcggtaggt gtggaactgc ctcttcctgt tgtgccccca   61860
cttcttccac ctccagccag ctctgactga gatccctgcc tggtctctta caggagaggt   61920
atttgattac ctagtggctc atggcaggat gaaagaaaaa gaggctcgag ccaaattccg   61980
ccaggtaggt gtgactccct ccataggagc taggcctgac ctctgctttt ggggtttgac   62040
atgtaaggat aagctgcctg tctgtaagtg gcccttggag ggtactttgg gctctgctta   62100
tccgtgtggc aggttagcac taagtcacag ggtcactgct ctgtcagccc ctgtggccca   62160
```

```
ccctcaggca ccccctgggtt aacccttctt ccttccttc agatagtgtc tgctgtgcag   62220
tactgtcacc agaagtttat tgtccataga gacttaaagg taaggcatgc acttctcctt   62280
gtgcctttga gtgggagcca ggttgttgcc tcttggttct ccatgataaa accatcaata   62340
accatcaggc cctgagtgtt ccaggaaact ccagcctttc ttttttcctt tctttctttc   62400
tttttttttt tttgagatga ccagaaagcc cctaggctg cctctgatag aggccttgtg   62460
gctggacctc gggttccatt ctagcccttg agcaggggcc ctctgccatt tcacctcttg   62520
gcacatcacc ttttagtgct gccaagcaag gcaggcacac tccaggcttt ctcagtcttt   62580
caggcaacct ggtagctgac ccagggaaga gtgctgaaag ttccacagct gtatcccagc   62640
tgctttgcag gcaggcacac acataccatc tccatcacca agatactcaa gtttgaggac   62700
acctgtgggt ctcttggctg ctgagtcctc acagacatga tttgattaac ctgggcctga   62760
tgctgaagct ttgcacagct cacagggtct ctgggccttc agatcccatc tctcccatgg   62820
ctgcccacgt gaggagtggc ctgcattgcc ttcctcctgc ccagcctatt cacgctgatt   62880
gaagccctgc cctgaaattg gtggagaaag ttctgagact gaagatgact ttccgttttgt   62940 tctcccattc ccctcagctc cttcctgccc agggcttag tctggtccac ttggttccct   63000
gatgttttcc atcttacctc ccaggcagaa aacctgctct tggatgctga tatgaacatc   63060
aagattgcag actttggctt cagcaatgaa ttcacctttg gaacaagct ggacaccttc   63120 tgtggcagtc cccttatgc tgccccagaa ctcttccagg gcaaaaaata tgatggaccc   63180
gaggtggatg tgtggagcct aggagttatc ctctatacac tggtcagcgg atccctgcct   63240
tttgatggac agaacctcaa ggtggagtga agtgcaagct ttttattgct tctcatttcc   63300
tctcggcctc tggtcttagc cctgacctcc tgcctttgcc acctgtctac atttgtccca   63360
agccaaagct tcagagaagg gcttgctgag gtagcagcag tcaaaggcct tctgcacctg   63420
ggaatgaata acctcagttc ctttctcgaa agatgggata aactgtgtgt gtgttcatcc   63480
cccaaggcac tccggattgc aggcctcgga ctggtcaagt tagagggtac gagggtattt   63540
gacttcactt gcctctctgg tgaggtgtct tgtcccagg ctgtctgcct tcttccatat   63600
ttcatttatg tctgctttgc caggcttaag ctctcaggat cttggatatt aggtttcttc   63660
ctttggcctt ggggtgattt caattttcta accctggatc ctcctgcagg agctgcggga   63720
acgggtactg aggggaaaat accgtattcc attctacatg tccacggact gtgaaaacct   63780
gcttaagaaa tttctcattc ttaatcccag caagagaggc actttagagg tgagcagtgg   63840
agcccaactg gcggaagggc ctggggtccc cacagaaact ttccagctga gtttcttccc   63900
cctgcccttt tccttctctg tgctccccag caaatcatga aagatcgatg gatgaatgtg   63960
ggtcacgaag atgatgaact aaagccttac gtggagccac tccctgacta caaggacccc   64020
cggcggacag tgaggctgt gccgggctgt gaggttaagc ttgcctagga gttgaggcca   64080
gtcttaactg tatgtccccc tgtgcagagc tgatggtgtc catgggttat acacgggaag   64140
agatccagga ctcgctggtg ggccagagat acaacgaggt gatggccacc tatctgctcc   64200
tgggctacaa gagctccgag gtgtgtgctc cccgctccat tctctgacct ggccagcctc   64260
actgtctgta gcacctatgc ttctaacacc tgttgagggc agaagctcat ctctgagtag   64320
gtgtgctctc tgctcaccaa ttttaagcct cagctttggt gtctaaggtc ctctggccca   64380
ttcactgatc tccatgagtg aattaataga aagctggtag gtcggtgtg ggactgggtc   64440 agagtttcaa tacgggtgag ttgatctagg ttagtctgca ttgattagat gtgtctaggt   64500
catcggctag cactactaca ttgatctaga tatctttgtg tctcttttgt tatctggaag   64560
```

-continued

```
tgtacatttc tgggtgtgtg tgtgtgtctc tgtgtgtgtc tgatcggaag tttgagtctg  64620 ttgcttttttt ttttttttttt ttttttttttt gagacggaat tcgctcttg ttgcccaggc  64680 tggagtgcaa tggcaggatc ttggctcact gcaacctccg cctcccgggt tcaagcgatt  64740
ctcctgcctc agcctcccaa gtagctggga ttacaggcat gtgccaccat acccggctat  64800
tgagtctgtt gcttctgtct agtgctttat gtttgggtgt gtgtatctgt gtgtgtgtgt  64860
gtgtgtgtgt gtgtgtgtat gtgtccgtct tcccgtctgt ggatctggag actttgtgat  64920
tgttcttctg cccatttggg ttttgttcat catctgagta tccccacatg aactcccagc  64980
ctccctgccc tgctctccct ctggtggtgg gatccttaag aggcacctgg tgacacttgg  65040
tataggccca tattgctctg tgttgagggg agtggacttg agtctggaca tgtgttcttg  65100
cggatgtttg tgtctctggg tgtgtgggct tatgtattcc tttctgagac tgtgtttgtc  65160
agtgtctgtg tcagagcatg tgtgtctcca gggtctcctc caggggggat gtattggtct  65220
tacaagtgga tgtccggtat gatcctgggg tgtttgagtg ttgggagagg gcggtatgtg  65280
taaatgtgtc catccatagg gatctcccaca tgacttctgc cctcccttga agctgttttc  65340
tgtttctttc agctggaagg cgacaccatc accctgaaac cccggccttc agctgatctg  65400
accaatagca gcgccccatc cccatcccac aaggtacagc gcagcgtgtc ggccaatccc  65460
aagcagcggc gcttcagcga ccagggtaaa tgcttttggg agttgtaggt ggggactcac  65520
ccctctccag agaggttaca ggttctgtgg ggacttgggt aacacaacta agtttcagtc  65580
ctggttcagc cacttattag tagtgtggct atgggcaagc cacttccctt ccctcgcctc  65640
tgtggaatgg gggcttgctg ggttgttggc cagccctgta ggaaatgagc atgcgtgggg  65700
ctggcactca gtggaccct tggccttacc cattcccatc ctccctctgg cccagcagct  65760
ggtcctgcca ttcccaccctc taattcttac tctaagaaga ctcagagtaa caacgcagaa  65820
aataagcggc ctgaggagga ccgggagtca gggcggaaag ccagcagcac agccaaggtg  65880
cctgccagcc ccctgcccgg tctggagagg aagaagacca cccccaacccc ctccacggtg  65940 agccgcaccc cccgctctct ccttccttcc tgcggtgggg cctgccctct ccaggcagct  66000
cttctcttaa ttcagactct gttcccttg gctactactt ctgcttatag caggaagcct  66060
cgctcccagc agtaaatgca gaatccttc cttaacctac cactgtctgc ttcaggtgga  66120
agggacagga agcctgttcc atgaacctgg ggggagaacc tggctgtaga ccactttggc  66180 tttctgataag aacgcttgcc ctttattccc cacagaacag cgtcctctcc accagcacaa  66240
atcgaagcag gaattcccca ctttttggagc gggccagcct cggccaggcc tccatccaga  66300
atggcaaaga caggtgagag acccgggccc tgcctgcctc actccctagg agccatgtct  66360
cacagggtga tgtctgtcag cagcaccgtc tcctgtccct gccagcgcat tgctccctgc  66420
tccctggagt tccatcctgg ctgtgtccag tccagctttc ccctccccta ttccacgcca  66480
ttgcctcctc cccatcttcc tctgactgct acttgcagtt tgccaagtgt ggggctgacc  66540
gtggccatct cagctacatg ctcgcttctt gaccacggcc agggcatggc agctgccctc  66600
ctctagacat gagcagctaa ggccttgtgt tgggggtccc agctcagggc agaaccaaga  66660
gatgcccacc ttgaggggtg tacacataga gggcgactcc agccatcccc atgagaccag  66720
agctccccag ccttcaccgg ccgcatttct tggtgttgca ttcctggctc tatctcttct  66780
gagtttatga agtttccccc tcagcaacac cccactcttt ctgtagaaga aactctcctg  66840
ttcttaaaat tcttaggagg ccagtgcagc ctggaggcag cggcccttg tctgctctcc  66900 ttcatttctg attcctcttc ccaggcactg acccacctcg ctgcttcccg acctcactca  66960
```

-continued

```
cctccacttc tcagccccgc attcctcagt tctgacttgc atcccgctgc tgcccaggcc   67020
tgacttctac cctgccagag ctccccagct ctggcccttc cctgcccctt gcttcctaat   67080
ccaggcctcc cgccctcact caccccctaac acgggcctct ccgctgcttt tgtttcctag   67140
cctaaccatg ccagggtccc gggcctccac ggcttctgct tctgccgcag tctctgcggc   67200
ccggccccgc cagcaccaga aatccatgtc ggcctccgtg caccccaaca aggcctctgg   67260 gctgccccc acggagagta actgtgaggt gccgcggccc aggcaagtgt gctggggcag   67320
ctggtgcacc tgctgccctc agcccaccct acccccttgc cccaacaatt tcttcttccc   67380
acttgggggt cctgctgtgt tcttgtcatc ttagccacaa gaaatgggtc tgtcccctgc   67440
ggccaggaag tggagggaac aaaaaagagc attaatgccc ctcttttcca gttctccctc   67500
tcagaacagg tatgcaggaa gctgtcctaa ggctccaaag ggaaaccttt ttgttctgaa   67560
ccttccaggt tttccttagg gaccccgggg atagtcggca tcacagggac tcaatcctca   67620
agggttggtc cccattgccg ccttgagggt ccagtctgcc cggctcccag ggagcccgct   67680
gtctccagcc taaaccacac tccacacagg ggtccttcct tgcctccctc cctcccttcc   67740
caaaccatct ccttccactt ccacgagact tccttctcac cactgtcctc agtagtcaca   67800
cccttccttc tgtgtcctcg tgatggctgc ctctgcccta gcatccccct ccctgtcccc   67860
accacagggt gtccaggtgc ccagtgatgg ctgtcctgta ccctaattcg tcccctcaa   67920 ccccacttct cttcccacag cacagccccc cagcgtgtcc ctgttgcctc ccatccgcc   67980 cacaacatca gcagcagtgg tggagcccca gaccgaacta acttccccg gggtgtgtcc   68040 agccgaagca ccttccatgc tgggcagctc cgacaggtgc gggaccagca gaatttgccc   68100
tacggtgtga ccccagcctc tccctctggc cacagccagg gccggcgggg ggcctctggg   68160
agcatcttca gcaagttcac ctccaagttt gtacgcaggt aagcaaggag ctttgggtgg   68220
cagagaggct caggccaggc cttcctgctt tactcggggt gggttgggg ttgggggttg   68280 gggtttggga cactctgtac cggtattggg tcctggggtt agaagaggct tcaggaagca   68340
caagaaatta ggtctttgtc aacaccttat gtgcccaggc ccaccctct taggcctctc   68400 cccaactcct cacaggcacc cctcattctc tggccccaag cagatggccg atgccgcctc   68460
ctctctagga gagtgtgaac tcagatgcta aaataaaagc ccccccttct ctcctgggtt   68520
cccatggaaa cttatatttg gtgacgcagc tgcaaagtca tgaggcatga gccaggctgg   68580
ggccagcaag gaaaatttg tcctggtctc ttgccccttt gactgcctct cccactagtt   68640
ggttctgttt ctggctgcag gcgcagccat gcccttctgc ccggggggttt tagggtgaaa   68700 cctataaatg aaatcactgg cgagggccta cagtggcctc ttccctaacc taactccgat   68760
gtgccaaagg tttcctgtgt tggacccagg gtggggatct cttcacgggg tttctcacac   68820
ctgagccccc agccaccaca gaggtgcagc ttgaagtgca tccagccaac tggctggcct   68880
cctgggatgc tccgcatccc catcctgcca ttcctctccc tgccttggag tagcagctca   68940
ggaagcagca gggctttga gagaacaggc tcgcctgccc ttcctctacg tttcactcca   69000
ctctgctgga ggagccaaag ccactgcccc atccgagccc cagaatgcaa gtgtgaggcc   69060
tgcagagagt gtgggcaggt ctgaaagcct gggactctag tctcgctgag cggctcttcc   69120
gaaaatggga tgacccttga acctgtaaag ccacctcccc cacctgctta ccacataacc   69180
gtcttgttgg tttttttttt atttctttt ttattttgtc ttttttttgt ttgttttttt   69240
agaaatctgt ctttcaggtt tgccagaagg taggcgttga gcccgctgtg tgtgtgtgtg   69300
tgtgtgtgtg tgtctgtgtc ctgtgtcctg cctccatcac taactcccct tttctggctc   69360
```

```
ttactctcct ccatctgctt aaccaagtct gtgtggccct cctctctctg ccatcttaaa   69420
gggatgaaga ctgcctctga ttgggcatca gcacaaggcc tgccctccgt gcccccagta   69480
caaacaggca gggctaagag gccacattgg cccactcagg gcaaatggct ttaaaaatga   69540
gggccttcct tgggcccaca gttaacgcct gtcctcaagt aaggggagac tgtctcaggg   69600
aagcctccct ttaagattgt ctcctctcac ccacccacc ccaccccac tccctctcac    69660 cccaggtttt ggtcacaagt gttgggatcc tttcctgccc tttcccttgt catgtgcatg   69720
cgctatgagg aagctccagg gttacaagtg catctgggat ggtatcttgt ttgttgtctc   69780
ctgggtttcc tgaacttcag agctatgtga cctcttcccc gtggcctatg ggatcgcagg   69840
actttggaga cactacgggg accctggggc cccaaggttt cagtctggct cccccagacc   69900
ttaggagctt ttgtctcaca aatggagcac agcacccct cctggcagct cctgcagaac    69960
tagccccacc cacccgcacc cctgcccag caccccgcc accagcagca tctggataaa     70020
tcaagcctct tctcctctag gctgtttct ccagatatgg cctgtctctt ccaaagtgcg    70080
gggagctggg acattctagg gcaacggcca ttctacccca agccgtagca aaacaacagg   70140
agatctctgc acccttactc aggggtctcc cttcacagtc cccttcctgg ctctttcacc   70200
cctggcctta tgctcatcct ctctgcaggc ctcggggacc aaataccaag ctgaagacca   70260
agggccaggt taagagtgct tgttcccaa ggctgtctgc tcaggccctg cattgggact    70320
gggatgcctg gcaggcacat tggtgccaca gctgatggag gaacgtccag acagggtctt   70380 caggcttttcc ctatcccctc ctcctcccac ccagctgttg actgcatgac tggctgctgc  70440 ctcaagggc cccagcaggg ggctgcccca caggggtct ggagagagca gggagggtgc     70500
cttcctcgca cagccgggct ccctgctcgc agtgcgcttg tgtgcacccc tgtgttggtt   70560
gtgtcttcct gtttatttct atgtgctgct gctcttcctc cttcctctca catccttcct   70620
cctctgcaat cccagttc ctagctccag acacccatct tccagccagg agctggagaa     70680
gccgctcagc ggggccagac ctcttcccca cccacccaac caaggtgtct gccctgccct   70740
gccccacccc acccctcatcc tccctgcgta tgagcagatg gcctggcagg ccagcaggta  70800
ggggagttgg gaaaggtcgg aggaggccgc cttttccact cagcagcagg aagccatccc   70860
caggtgccta ccatgcagac ccaggccttg gcactttgag tctcctgaca ggcccttgcg   70920
tagccacggc cctcctcct acagagattc aaagcattgc agccccttc ctccaaaagg     70980 actgcagtcc tgagaccta gcgtgtggct ccaaaaacgc actcacacct gcaacccca     71040 gaacagcgcg tgagccctgg ctgtggggga gcagcctcgt gccgggccgt gtgctcagtg   71100
tgctcagtga agtgcgtgca cagccactcc ccctcctccc ccagagcaga ggctccttct   71160
ccccggcaca gatctgggaa tgtggggagg acaagcccc atgtgctggg ctccctgctg    71220
gaaaggaatg gttgagccgc cagtgtgagg tgctgcagag ccctgttggc ttgccaggtg   71280
atgggcagag ggccctgggc ttgggtcctg cccacccact ggtggcacct ccccagaccc   71340
actctcatct gggtctgtgg cggcggaagg agcgagagat cccagcacta aactctccct   71400
cgctctgttt tttgaggaac ctgaatgaac ctgaaagcaa agaccgagtg gagacgctca   71460
ggtgagaggg ctggagccag cactggccct gcccggcca ccgggcttgc cacagcctcc    71520
tgctcctctc ttccttctgc cacttggctc ttcctcccgt ggttctgccc tgtccctacc   71580
ctctggggcc tcccttcct cagagagttt cccttccca aacccaattg caggagttac     71640
gggcccttct cctcaggtct ggtatattct ggaagtcgga gttctgggtc gggtggttgg   71700
ggctacagat tcctaccct ggactatccc acctccctgt gctcggaggc tgctttctgg    71760
```

```
agagagagtc tgtgctcgtg ctgttgaggg cactggtgtc ttccctgacc ccacccgcc    71820
taccccaagg ctggcttctc ctcccctcg ctgtcctgag agatgggggt tggaggactg    71880
ccaccctccg cccccgcagg ccaggggcca cgcctggctg ctcctgctcc ctcccgctct   71940
cctctctggg ctcaggggct gtctgccagg gtggctctcc tggggtgggg tgcctcagcc   72000
cccccgtgac gcccgcctct gccctctcca cagacctcac gtggtgggca gtggcggcaa   72060
cgacaaagaa aaggaagaat tcgggaggc caagccccgc tccctccgct tcacgtggag    72120
tatgaagacc acgagctcca tggagcccaa cgagatgatg cgggagatcc gcaaggtgct   72180
ggacgcgaac agctgccaga gcgagctgca tgagaagtac atgctgctgt gcatgcacgg   72240
cacgccgggc cacgaggact tcgtgcagtg ggagatggag gtgtgcaaac tgccgcggct   72300
ctctctcaac ggggttcgat ttaagcggat atcgggcacc tccatggcct tcaaaaacat   72360
tgcctccaaa atagccaacg agctgaagct ttaacaggct gccaggagcg ggggcggcgg   72420
gggcgggcca gctggacggg ctgccggccg ctgcgccgcc ccacctgggc gagactgcag   72480
cgatggattg gtgtgtctcc cctgctggca cttctcccct cctggccct tctcagtttt    72540
ctcttacatg tttgtggggg gtgggagatt gttctccagc accccacatt caccctgcc    72600
cagagattcc cccttctcct ctccctact ggaggcaaag gaaggggagg gtggatgggg    72660
gggcagggct cccctcggt actgcggttg cacagagtat ttcgcctaaa ccaagaaatt    72720
ttttattacc aaaagaaaa agaaaaaaa aatcccagc ggccaccttt cctccctgcc     72780
ccattgggac agtcgagact ggatctgtgg ggtttccgg gaggtggct cagggctgga    72840
acactctcag gcaagagtgg tggagctccc gtcaggccct ccgccaggcc cactgtgggc   72900
ttctcccctc tcctccctcc ttcccctcca agcaaaccac cagaggtggc cttcccctga   72960
cctcaggccc ctgggctgga ggcctgggcg gtggggcagg gggcggggggt gctgcgcagc   73020
cctgcagtgg gtggggctgg gggctgctcc ggggctgctg aggctggagg gccggcacaa   73080
ggctccgcct ccctccacac tgtaccctct gcccctcctc cccagagctg gcatttcct    73140
tccacaagct gctgtgggga cgtgtgttcc ctcaaagtct gtgccatctt ctcccacccc   73200
tcccgggtag aaggaggggc tgaccccagg gctgggagag gggaggggac tggagggcag   73260
actggcttct cggtccccag ggggccgctt ggctgttgg tctccagagc agggccactg    73320
ggcactctgt gatggggag cctttgtctg aaagcacagc cccctcgccc ttcctctccc   73380
catggcttcc ccttcattgg cattaatctg ggcaccagct ctctccatag cagtgacttc   73440
cctcaccact ctcatctctc agccttgcct tttcttcctg acactgtcgc cccctcctct   73500
caggagacac tgccgagggc cacctggcag aaggctgagt taggcagcag ggccgggagc   73560
gtctgccctc cacagggtgg gggacagata ggctaagcga ctcccagctt gctaccctca   73620
gtggccagtg tgggcgtggg cggtttgggg cgcttggctg gtggtggcca ctgcatccct   73680
taatttattt ctctgctgtt tctgttcttg agaaattggg ggtgggagtc ctacacagag   73740
gctgccccta ccctcacctg agttgtacat tttttgtga tgggttttat tttttattat   73800
tttattttat tttttttttt ttttgattta tgatgactcc ccccctcttc atcacccccg   73860
ctcccaggcc aggctcagcg attaagccga gcccttgcgt cctaggaagg ggccttgcca   73920
acctcagccc tcctgcccca cactcctact gcggctcaga ccaagggctc cccctccctc   73980
ccttcccccc tcctgcccta tggaacagcc cgggtgctct gaggggctg ggagggcatg    74040
gcttggctcc caagggggt aggggcccgg ggcacccagg caaggtggcc cctccccgtc    74100
tagccccctc ctccccaacc ctgcacttag tttctcctct ggatcaaaca cgtaataaag   74160
```

-continued

```
agaatgtttg gaatctgagc tgcctcctcc tgtctcttct cccagccagg cagggaccca    74220
gtctcctgtg ggcaagatgt ggcctagccc acctgccttg caggagagac ttgattcctg    74280
tctggggcca gtgctgggtg ggcccagctc cccacttacc cacagggcac agacaggaag    74340
caaagcccag ggcccttgca ccaaaaggga agaaaactc agtaagctta gattttattt     74400
tttttaattt ttaaaaaatg ttgaaaaata aatccatgtc tgcataagtt cccaaccccc    74460
atttctccaa gtttctggaa ggtgggcttg gtgggcaccc tcagctcctt agcatttccc    74520
agctggcccc tgaagacaga gcttctcttc cagcctctgc tgctgtaagg ccctctgcc     74580 cacctccccc cctgcagcct ccctccccac ctcacccag acttattgct aaaagaaggg     74640
aaagaggaat gagaacagcc agcacaccca actgccctct ccccactcca cgctaaggtc    74700 actacccgg acacacaaag ggcaggaccc agaggccaag ccccagcaga ctaggacaca     74760
gccattccag taccggccag gaagcgaaag tgccctcagg ccagctcaaa ggcccctgag    74820
cccggccatg gccccaggag acaggcccag ctgccaggaa cacatgcaga acccaaaggg    74880
cggggctggg ctgtccgaaa ctctggtctt acaaagaccc cgccagagcc ctagtccctt    74940
ctgtcctcag tgacaccaga gatgcctggg gatggccagc aaagggtcc tggagcccgt     75000 ggttggtgga ggacgtcagg gctcagagtg agggtgctgg gggctccaga ggggttccaa    75060
tcagggtggg tgggggctga gggccagggc gggcgctgtg gcgggggca gccagagcgg     75120 ggcggatgag aggcggtggg ggctggttgg gggccagccg gggctggagg aagcggccct    75180
gctgcagtgg gggtggctgt cggagcagag tgggagccgt gggcaaaggt ggcctcagca    75240 gcggggggtgg ctgggacagc gaggtgggag gtggaggggg tggtggcgca gggggcactg    75300
atcggggcac ggacgtggag accgatgtaa tctggacctg aggggagagg aaagagtgag    75360
aagccaggct cttcccgccc tcagcccagt ctaag                              75395
```

<210> SEQ ID NO 4
<211> LENGTH: 722
<212> TYPE: PRT
<213> ORGANISM: Rattus norvegicus

<400> SEQUENCE: 4

```
Met Ser Ser Ala Arg Thr Pro Leu Pro Thr Leu Asn Glu Arg Asp Thr
1               5                   10                  15

Glu Gln Pro Thr Leu Gly His Leu Asp Ser Lys Pro Ser Ser Lys Ser
            20                  25                  30

Asn Met Leu Arg Gly Arg Asn Ser Ala Thr Ser Ala Asp Glu Gln Pro
        35                  40                  45

His Ile Gly Asn Tyr Arg Leu Leu Lys Thr Ile Gly Lys Gly Asn Phe
    50                  55                  60

Ala Lys Val Lys Leu Ala Arg His Ile Leu Thr Gly Lys Glu Val Ala
65                  70                  75                  80

Val Lys Ile Ile Asp Lys Thr Gln Leu Asn Ser Ser Ser Leu Gln Lys
                85                  90                  95

Leu Phe Arg Glu Val Arg Ile Met Lys Val Leu Asn His Pro Asn Ile
            100                 105                 110

Val Lys Leu Phe Glu Val Ile Glu Thr Glu Lys Thr Leu Tyr Leu Val
        115                 120                 125

Met Glu Tyr Ala Ser Gly Gly Glu Val Phe Asp Tyr Leu Val Ala His
    130                 135                 140

Gly Arg Met Lys Glu Lys Glu Ala Arg Ala Lys Phe Arg Gln Ile Val
145                 150                 155                 160
```

-continued

```
Ser Ala Val Gln Tyr Cys His Gln Lys Phe Ile Val His Arg Asp Leu
            165                 170                 175
Lys Ala Glu Asn Leu Leu Leu Asp Ala Asp Met Asn Ile Lys Ile Ala
            180                 185                 190
Asp Phe Gly Phe Ser Asn Glu Phe Thr Phe Gly Asn Lys Leu Asp Thr
            195                 200                 205
Phe Cys Gly Ser Pro Pro Tyr Ala Ala Pro Glu Leu Phe Gln Gly Lys
    210                 215                 220
Lys Tyr Asp Gly Pro Glu Val Asp Val Trp Ser Leu Gly Val Ile Leu
225                 230                 235                 240
Tyr Thr Leu Val Ser Gly Ser Leu Pro Phe Asp Gly Gln Asn Leu Lys
            245                 250                 255
Glu Leu Arg Glu Arg Val Leu Arg Gly Lys Tyr Arg Ile Pro Phe Tyr
            260                 265                 270
Met Ser Thr Asp Cys Glu Asn Leu Leu Lys Lys Phe Leu Ile Leu Asn
            275                 280                 285
Pro Ser Lys Arg Gly Thr Leu Glu Gln Ile Met Lys Asp Arg Trp Met
            290                 295                 300
Asn Val Gly His Glu Asp Asp Glu Leu Lys Pro Tyr Val Glu Pro Leu
305                 310                 315                 320
Pro Asp Tyr Lys Asp Pro Arg Arg Thr Glu Leu Met Val Ser Met Gly
            325                 330                 335
Tyr Thr Arg Glu Glu Ile Gln Asp Ser Leu Val Gly Gln Arg Tyr Asn
            340                 345                 350
Glu Val Met Ala Thr Tyr Leu Leu Leu Gly Tyr Lys Ser Ser Glu Leu
            355                 360                 365
Glu Gly Asp Thr Ile Thr Leu Lys Pro Arg Pro Ser Ala Asp Leu Thr
            370                 375                 380
Asn Ser Ser Ala Pro Ser Pro Ser His Lys Val Gln Arg Ser Val Ser
385                 390                 395                 400
Ala Asn Pro Lys Gln Arg Arg Ser Ser Asp Gln Ala Val Pro Ala Ile
            405                 410                 415
Pro Thr Ser Asn Ser Tyr Ser Lys Lys Thr Gln Ser Asn Asn Ala Glu
            420                 425                 430
Asn Lys Arg Pro Glu Glu Glu Thr Gly Arg Lys Ala Ser Ser Thr Ala
            435                 440                 445
Lys Val Pro Ala Ser Pro Leu Pro Gly Leu Asp Arg Lys Lys Thr Thr
            450                 455                 460
Pro Thr Pro Ser Thr Asn Ser Val Leu Ser Thr Ser Thr Asn Arg Ser
465                 470                 475                 480
Arg Asn Ser Pro Leu Leu Asp Arg Ala Ser Leu Gly Gln Ala Ser Ile
            485                 490                 495
Gln Asn Gly Lys Asp Ser Thr Ala Pro Gln Arg Val Pro Val Ala Ser
            500                 505                 510
Pro Ser Ala His Asn Ile Ser Ser Ser Gly Ala Pro Asp Arg Thr
            515                 520                 525
Asn Phe Pro Arg Gly Val Ser Ser Arg Ser Thr Phe His Ala Gly Gln
            530                 535                 540
Leu Arg Gln Val Arg Asp Gln Asn Leu Pro Phe Gly Val Thr Pro
545                 550                 555                 560
Ala Ser Pro Ser Gly His Ser Gln Gly Arg Arg Gly Ala Ser Gly Ser
            565                 570                 575
```

```
Ile Phe Ser Lys Phe Thr Ser Lys Phe Val Arg Arg Asn Leu Asn Glu
            580                 585                 590

Pro Glu Ser Lys Asp Arg Val Glu Thr Leu Arg Pro His Val Val Gly
            595                 600                 605

Gly Gly Gly Thr Asp Lys Glu Lys Glu Glu Phe Arg Glu Ala Lys Pro
            610                 615                 620

Arg Ser Leu Arg Phe Thr Trp Ser Met Lys Thr Thr Ser Ser Met Glu
625                 630                 635                 640

Pro Asn Glu Met Met Arg Glu Ile Arg Lys Val Leu Asp Ala Asn Ser
                    645                 650                 655

Cys Gln Ser Glu Leu His Glu Arg Tyr Met Leu Leu Cys Val His Gly
                660                 665                 670

Thr Pro Gly His Glu Asn Phe Val Gln Trp Glu Met Glu Val Cys Lys
            675                 680                 685

Leu Pro Arg Leu Ser Leu Asn Gly Val Arg Phe Lys Arg Ile Ser Gly
        690                 695                 700

Thr Ser Met Ala Phe Lys Asn Ile Ala Ser Lys Ile Ala Asn Glu Leu
705                 710                 715                 720

Lys Leu
```